(12) United States Patent
Ikeda et al.

(10) Patent No.: US 9,508,939 B2
(45) Date of Patent: Nov. 29, 2016

(54) COMPOUND AND ORGANIC ELECTROLUMINESCENT ELEMENT PRODUCED USING SAME

(71) Applicant: IDEMITSU KOSAN CO., LTD., Tokyo (JP)

(72) Inventors: Kiyoshi Ikeda, Sodegaura-shi (JP); Akinori Yomogita, Sodegaura-shi (JP); Masahiro Kawamura, Sodegaura-shi (JP); Hidetoshi Ono, Sodegaura-shi (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 0 days.

(21) Appl. No.: 14/906,824

(22) PCT Filed: Jul. 23, 2014

(86) PCT No.: PCT/JP2014/003885
§ 371 (c)(1),
(2) Date: Jan. 21, 2016

(87) PCT Pub. No.: WO2015/011924
PCT Pub. Date: Jan. 29, 2015

(65) Prior Publication Data
US 2016/0172604 A1    Jun. 16, 2016

(51) Int. Cl.
C07D 403/14 (2006.01)
C09K 11/02 (2006.01)
C09K 11/06 (2006.01)
H01L 51/00 (2006.01)
H01L 51/50 (2006.01)

(52) U.S. Cl.
CPC ......... *H01L 51/0072* (2013.01); *C07D 403/14* (2013.01); *C09K 11/025* (2013.01); *C09K 11/06* (2013.01); *C09K 2211/1011* (2013.01); *C09K 2211/1029* (2013.01); *C09K 2211/1037* (2013.01); *C09K 2211/1044* (2013.01); *C09K 2211/1059* (2013.01); *C09K 2211/1088* (2013.01); *C09K 2211/1092* (2013.01); *C09K 2211/185* (2013.01); *H01L 51/0059* (2013.01); *H01L 51/0085* (2013.01); *H01L 51/5016* (2013.01)

(58) Field of Classification Search
CPC .. C07D 403/14; C09K 11/025; C09K 11/06; C09K 2211/1011; C09K 2211/1029; C09K 2211/1037; C09K 2211/1044; C09K 2211/1059; C09K 2211/1088; C09K 2211/1092; C09K 2211/185
See application file for complete search history.

(56) References Cited

U.S. PATENT DOCUMENTS

| | | | |
|---|---|---|---|
| 7,723,722 B2 | 5/2010 | Kawakami et al. |
| 8,134,147 B2 | 3/2012 | Kawakami et al. |
| 8,278,655 B2 | 10/2012 | Kawakami et al. |
| 8,530,672 B2 | 9/2013 | Kawakami et al. |
| 8,803,134 B2 | 8/2014 | Inoue et al. |
| 8,816,098 B2 | 8/2014 | Kawakami et al. |
| 9,136,479 B2 | 9/2015 | Kawakami et al. |
| 9,373,802 B2 | 6/2016 | Inoue et al. |
| 2004/0076853 A1 | 4/2004 | Jarikov |
| 2008/0242871 A1 | 10/2008 | Kawakami et al. |
| 2010/0200847 A1 | 8/2010 | Kawakami et al. |
| 2012/0104379 A1 | 5/2012 | Kawakami et al. |
| 2012/0211736 A1 | 8/2012 | Kim et al. |
| 2012/0223295 A1 | 9/2012 | Inoue et al. |

(Continued)

FOREIGN PATENT DOCUMENTS

| | | |
|---|---|---|
| CN | 101270075 A | 9/2008 |
| JP | 2009-246097 A | 10/2009 |

(Continued)

OTHER PUBLICATIONS

International Search Report issued in corresponding application No. PCT/JP2014/003885 dated Oct. 21, 2014.

(Continued)

*Primary Examiner* — Erich A Leeser
(74) *Attorney, Agent, or Firm* — Foley & Lardner LLP

(57) ABSTRACT

A compound represented by the following formula (1): wherein in the formula, $L_1$ is a single bond or a linking group, A is a group represented by the following formula (A), B is a group represented by the following formula (B), m is an integer of 1 to 3, and n is an integer of 1 to 4.

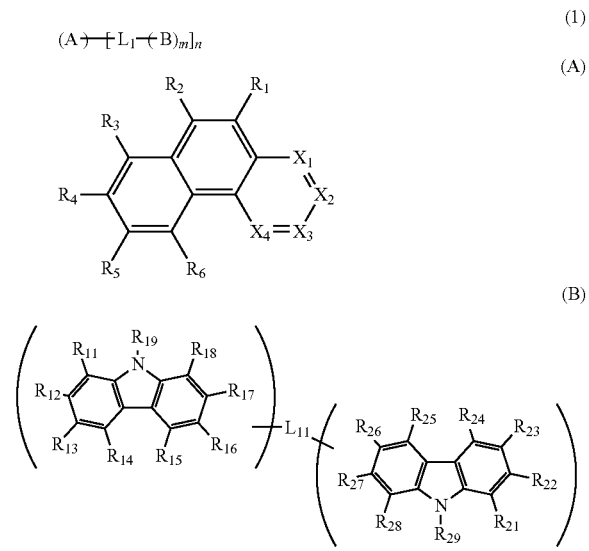

29 Claims, 1 Drawing Sheet

(56) References Cited

U.S. PATENT DOCUMENTS

| | | |
|---|---|---|
| 2012/0309984 A1 | 12/2012 | Kawakami et al. |
| 2013/0323870 A1 | 12/2013 | Kawakami et al. |
| 2014/0048784 A1 | 2/2014 | Inoue et al. |
| 2014/0191225 A1 | 7/2014 | Inoue et al. |
| 2014/0306207 A1 | 10/2014 | Nishimura et al. |
| 2014/0312331 A1 | 10/2014 | Inoue et al. |
| 2015/0004731 A1 | 1/2015 | Kawakami et al. |
| 2015/0249219 A1 | 9/2015 | Inoue et al. |

FOREIGN PATENT DOCUMENTS

| | | | |
|---|---|---|---|
| KR | 10-2012-0117693 A | | 10/2012 |
| KR | 2012/117693 | * | 10/2012 |
| TW | 201237140 A1 | | 9/2012 |
| WO | WO-2004/039786 A1 | | 5/2004 |
| WO | WO-2006/104118 A1 | | 10/2006 |
| WO | WO-2012/108388 A1 | | 8/2012 |
| WO | WO-2012/121561 A1 | | 9/2012 |
| WO | WO-2013/024872 A1 | | 2/2013 |
| WO | WO-2013/062075 A1 | | 5/2013 |

OTHER PUBLICATIONS

Translation of the Written Opinion of the International Searching Authority issued in corresponding application No. PCT/JP2014/003885 dated Feb. 4, 2016.

Office Action issued in Chinese Patent Application No. 201480037395.0 dated Jul. 25, 2016.

* cited by examiner

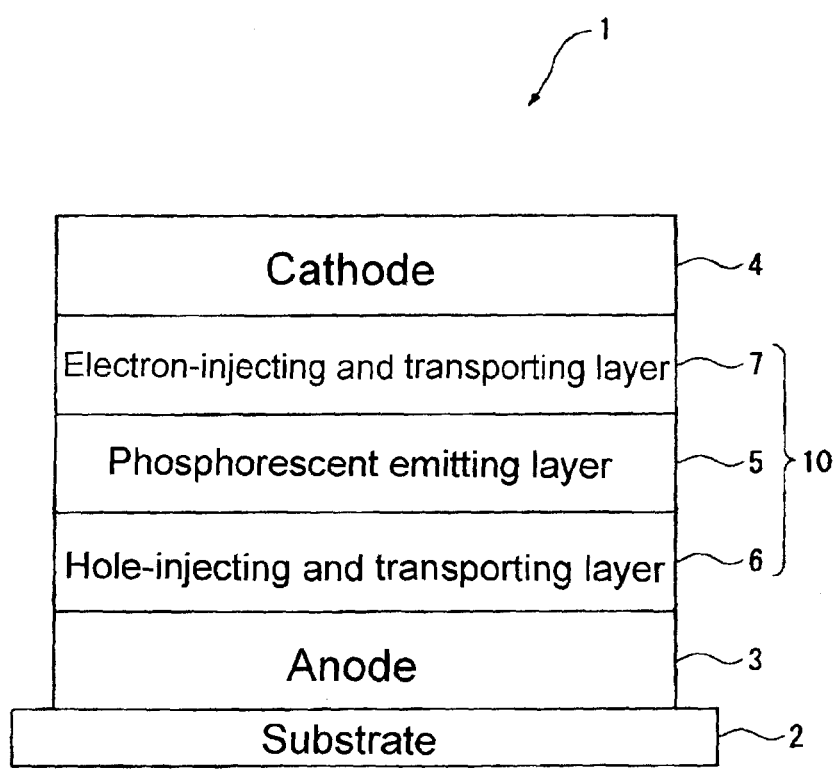

COMPOUND AND ORGANIC ELECTROLUMINESCENT ELEMENT PRODUCED USING SAME

TECHNICAL FIELD

The invention relates to a novel compound and an organic electroluminescence device obtained by using the same.

BACKGROUND ART

In general, an organic electroluminescence (EL) device comprises an anode, a cathode and one or more organic thin film layers disposed between the anode and the cathode. When a voltage is applied between the electrodes, electrons and holes are injected from the cathode and the anode, respectively, to an emission region. The electrons and the holes injected are recombined in the emitting region to form an exited state, and light is emitted when the excited state is returned to the ground state.

Since an organic EL device can provide various emission colors by using various emitting materials in the emitting layer, practical application thereof to a display or the like has been actively studied. In particular, researches on emitting materials of the three primary colors of red, green and blue are conducted most actively, and extensive studies have been made in order to attain improvement in properties.

For examples as a material for an organic EL device, Patent Documents 1 to 5 disclose a compound having a benzoquinazoline structure. In the field of an organic EL device, in order to further improve device performance, development of new materials has been required.

RELATED ART DOCUMENT

Patent Documents

Patent Document 1: Korean Patent Publication No. 10-2012-0117693
Patent Document 2: JP-A-2009-246097
Patent Document 3: U.S. Unexamined Patent Application Publication No. 2004/076853
Patent Document 4: WO2004/039786
Patent Document 5: WO2006/104118

SUMMARY OF THE INVENTION

An object of the invention is to provide a novel compound that is useful as a material for an organic EL device.

According to one embodiment of the invention, a compound represented by the following formula (1) is provided.

(1)

wherein in the formula, $L_1$ is a single bond or a linking group, A is a group represented by the following formula (A), B is a group represented by the following formula (B), m is an integer of 1 to 3, and n is an integer of 1 to 4;

when m is 2 or more, plural Bs may be the same as or different from each other;

when n is 2 or more, plural $L_1$s may be the same as or different from each other, and plural Bs may be the same as or different from each other; and when $L_1$ is a single bond, it means that A and B are directly bonded, and m is 1;

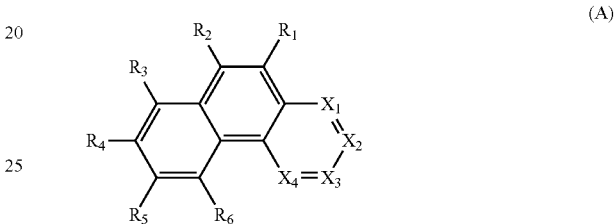
(A)

wherein in the formula (A), $X_1$ to $X_4$ are independently a nitrogen atom (N) or CRa, and two of $X_1$ to $X_4$ are a nitrogen atom;

"n" of Ra and $R_1$ to $R_6$ are a single bond that allows a carbon atom in the formula (A) for which they are substituted to be directly bonded to $L_1$ (or B when $L_1$ is a single bond); and among Ra and $R_1$ to $R_6$, Ra and $R_1$ to $R_6$ that are not a single bond are independently a hydrogen atom or a substituent;

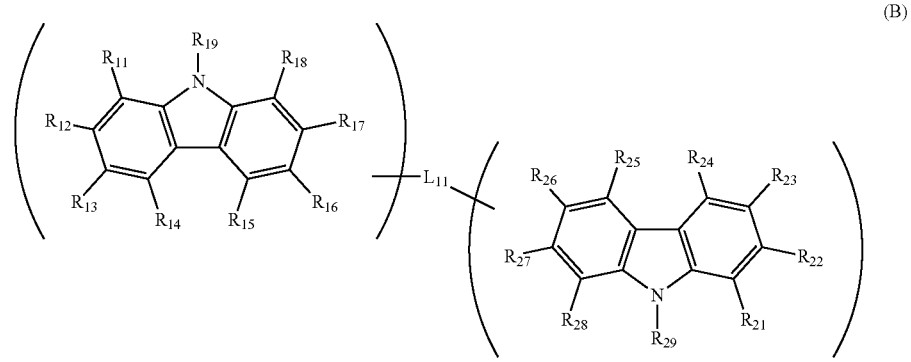
(B)

wherein in the formula (B), $L_{11}$ is a single bond or a linking group;

one of $R_{11}$ to $R_{19}$ is a single bond that allows a carbon atom in the formula (B) for which it is substituted to be directly bonded to $L_1$ (or A when $L_1$ is a single bond) and the other one of $R_{11}$ to $R_{19}$ is a single bond that allows a carbon atom in the formula (B) for which it is substituted to be directly bonded to $L_{11}$;

among $R_{11}$ to $R_{19}$, $R_{11}$ to $R_{19}$ that are not a single bond are independently a hydrogen atom or a substituent;

one of $R_{21}$ to $R_{29}$ is a single bond that allows a carbon atom in the formula (B) for which it is substituted to be directly bonded to $L_{11}$;

among $R_{21}$ to $R_{29}$, $R_{21}$ to $R_{29}$ that are not a single bond are independently a hydrogen atom or a substituent; and when $L_{11}$ is a single bond, one of $R_{11}$ to $R_{19}$ and one of $R_{21}$ to $R_{29}$ are independently a single bond that allows carbon atoms in the formula (B) for which they are substituted to be directly bonded with each other.

According to the invention, it is possible to provide a novel compound that is useful as a material for an organic EL device.

BRIEF DESCRIPTION OF THE DRAWINGS

FIG. 1 is a schematic cross-sectional view showing one example of an organic EL device according to the invention.

MODE FOR CARRYING OUT THE INVENTION

In this specification, the number of carbon atoms that form a ring (hereinafter referred to as "ring carbon atoms") means the number of carbon atoms among atoms that constitute a ring itself of a compound having a structure in which atoms or molecules are bonded in a ring form (e.g. monocyclic compounds, fused ring compounds, cross-linked compounds, spiro-ring compounds, carbocyclic compounds, heterocyclic compounds). When the ring is substituted by a substituent, carbon atoms included in the substituent is not included in the number of the ring carbon atoms. The same is applied to the "ring carbon atoms" mentioned below unless otherwise indicated.

For example, a benzene ring has 6 ring carbon atoms, a naphthalene ring has 10 ring carbon atoms, a pyridinyl group has 5 ring carbon atoms, and a furanyl group has 4 ring carbon atoms. Further, when a benzene ring or a naphthalene ring is substituted by an alkyl group as a substituent, for example, the number of carbon atoms in the alkyl group is not included in the number of the ring carbon atoms. Further, when a fluorene ring is bonded, as a substituent, to a fluorene ring, for example (including a spiro-fluorene ring), the number of carbon atoms of a fluorene ring as a substituent is not included in the number of the ring carbon atoms.

The number of atoms that form a ring (hereinafter referred to as "ring atoms") means the number of atoms that constitute a ring itself of a compound having a structure in which atoms or molecules are bonded in a ring form (for example, a monocycle, a fused ring, an assembly of rings) (for example, monocyclic compounds, fused ring compounds, cross-linked compounds, spiro-ring compounds, carbocyclic compounds, heterocyclic compounds). Atoms that do not constitute a ring (for example, a hydrogen atom that terminates an atomic bonding of atoms constituting a ring) or an atom included in a substituent when the ring is substituted by a substituent are not included in the number of the ring atoms. The same can be applied to the "ring atoms" mentioned below unless otherwise indicated.

For example, a pyridine ring has 6 ring atoms, a quinazoline ring has 10 ring atoms, and a furan ring has 5 ring atoms. Hydrogen atoms that are independently bonded to carbon atoms of a pyridine ring or a quinazoline ring or atoms that constitute a substituent are not included in the number of ring atoms. Further, if a fluorene ring is bonded, as a substituent, to a fluorene ring (including a spirofluorene ring), for example, the number of atoms of a fluorene ring as a substituent is not included in the number of ring atoms.

If a ring is formed by adjacent substituents, a structure is included in which the ring is separated at a point where the number of carbon atoms of one substituent becomes minimum within the above-mentioned range, and the number of carbon atoms of the other substituent falls in the above-mentioned range. The same is applied to the number of carbon atoms of a substituent mentioned below, unless otherwise indicated.

The "aromatic hydrocarbon ring" means a ring that is formed only of carbon atoms and hydrogen atoms and has aromaticity (including a monocycle, a fused ring and a ring formed by bonding of these plural rings through a single bond). The "heterocyclic aromatic ring" means a ring that contains one or more hetero atoms in addition to carbon atoms and hydrogen atoms and have aromaticity (including a monocycle, a fused ring and a ring formed by bonding of these plural rings through a single bond). The "heterocyclic aliphatic ring" means a ring that contains one or more hetero atoms in addition to carbon atoms and hydrogen atoms and does not have aromaticity (including a monocycle, a fused ring and a ring formed by bonding of these plural rings through a single bond).

The "XX to YY carbon atoms" in the "substituted or unsubstituted ZZ group including XX to YY carbon atoms" means the number of carbon atoms in the ZZ group which is unsubstituted, and does not include the number of carbon atoms of a substituent when the ZZ group is substituted. Here, the "YY" is larger than "XX" and "XX" and "YY" are independently an integer of 1 or more.

The "XX to YY atoms" in the "substituted or unsubstituted ZZ group including XX to YY atoms" means the number of atoms in the ZZ group which is unsubstituted, and does not include the number of atoms of a substituent when the ZZ group is substituted. Here, the "YY" is larger than "XX", and "XX" and "YY" are independently an integer of 1 or more.

The "unsubstituted" in the "substituted or unsubstituted . . . " means that a group or an atom is not substituted by the above-mentioned substituent and a hydrogen atom is bonded thereto.

In the invention, the "hydrogen atom" includes isomers differing in number of neutrons, i.e. protium, deuterium and tritium.

The compound according to one embodiment of the invention is represented by the following formula (1):

In the formula (1), $L_1$ is a single bond or a linking group, A is a group represented by the following formula (A), B is a group represented by the following formula (B), m is an integer of 1 to 3, and n is an integer of 1 to 4.

When m is 2 or more, plural Bs may be the same as or different from each other.

When n is 2 or more, plural $L_1$s may be the same as or different from each other, and plural Bs may be the same as or different from each other.

When $L_1$ is a single bond, it means that A and B are directly bonded, and m is 1.

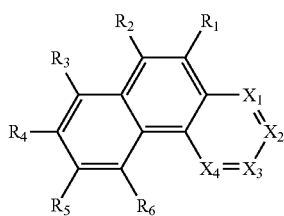

(A)

wherein in the formula (A), $X_1$ to $X_4$ are independently a nitrogen atom (N) or CRa, and two of $X_1$ to $X_4$ are nitrogen atoms.

"n" of Ra and $R_1$ to $R_6$ mean a single bond that allows a carbon atom in the formula (A) for which they are substituted to be directly bonded to $L_1$ (or B when $L_1$ is a single bond).

Among Ra and $R_1$ to $R_6$, Ra and $R_1$ to $R_6$ that are not a single bond are independently a hydrogen atom or a substituent.

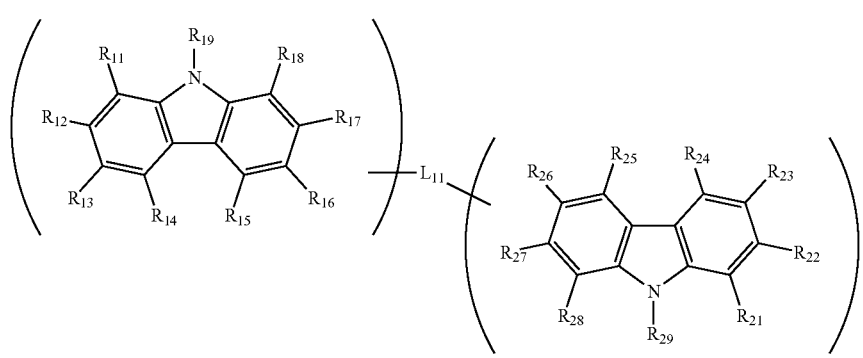

(B)

wherein in the formula (B), $L_{11}$ is a single bond or a linking group.

One of $R_{11}$ to $R_{19}$ means a single bond that allows a carbon atom in the formula (B) for which it is substituted to be directly bonded to $L_1$ (or A when $L_1$ is a single bond), and the other one is a single bond that allows a carbon atom in the formula (B) for which it is substituted to be directly bonded to $L_{11}$.

Among $R_{11}$ to $R_{19}$, $R_{11}$ to $R_{19}$ that are not a single bond are independently a hydrogen atom or a substituent.

One of $R_{21}$ to $R_{29}$ is a single bond that allows a carbon atom in the formula (B) for which it is substituted to be directly bonded to $L_{11}$.

Among $R_{21}$ to $R_{29}$, $R_{21}$ to $R_{29}$ that are not a single bond are independently a hydrogen atom or a substituent.

When $L_{11}$ is a single bond, one of $R_{11}$ to $R_{19}$ and one of $R_{21}$ to $R_{29}$ are independently a single bond that allows carbon atoms in the formula (B) for which they are substituted to be directly bonded to each other.

The compound represented by the formula (1) has a structure represented by the A mentioned above and the biscarbazole structure represented by the B mentioned above. Due to such structure, the hole-transporting properties of the compound are improved. Therefore, an organic EL device obtained by using this compound can have a low driving voltage.

Carrier balance is improved by using the above-mentioned compound. Therefore, an organic EL device obtained by using this compound as a host material in the emitting layer has an improved luminous efficiency.

Further, the above-mentioned compound has high durability. Therefore, an organic EL device obtained by using this compound has a long luminous life.

As the compound represented by the above formula (1), a compound represented by the following formula (2) can be given, for example.

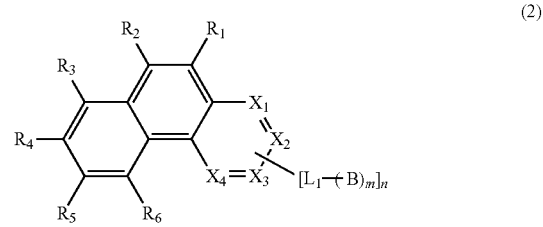

(2)

wherein in the formula, $R_1$ to $R_6$, $X_1$ to $X_4$, $L_1$, B and m are as defined in the formula (1). n is 1 or 2, and "n" of the Ra is (are) a single bond that allows carbon atoms in the formula (2) for which it (they) is (are) substituted to be directly bonded to $L_1$ (or B if $L_1$ is a single bond).

As the structure represented by A, for example, a benzoquinazoline structure represented by the following formula (A1) or (A2) is preferable. By this structure, an excellent carrier balance is attained to improve luminous efficiency.

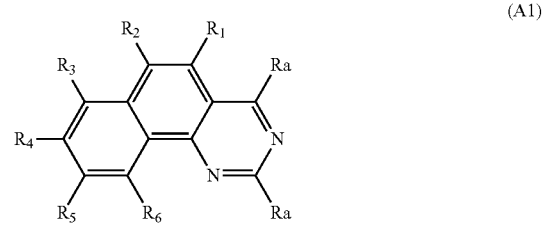

(A1)

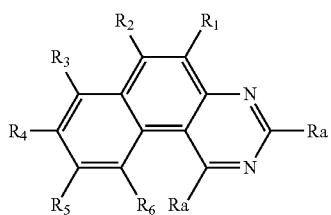

(A2)

wherein in the formula, Ra and $R_1$ to $R_6$ are as defined in the formula (A).

The compound having a group represented by the above formula (A1) is represented by the following formula (A1-1) or (A1-2).

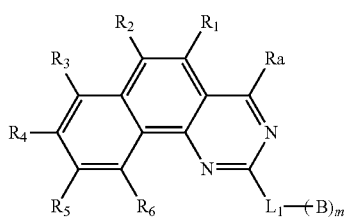

(A1-1)

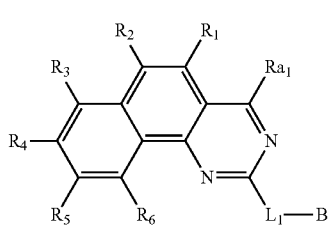

(A1-2)

wherein in the formula, Ra, $R_1$ to $R_6$, $L_1$, B and m are as defined in the formulas (1) and (A1).

Further, as a compound having a group represented by the above formula (A1), a compound represented by the following formulas (A1-3) to (A1-6) can be given, for example.

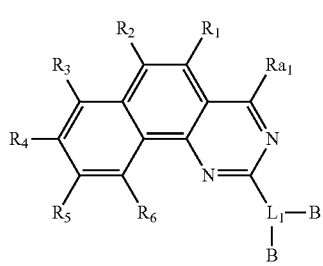

(A1-3)

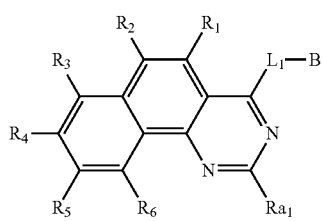

(A1-4)

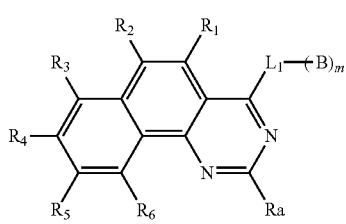

(A1-5)

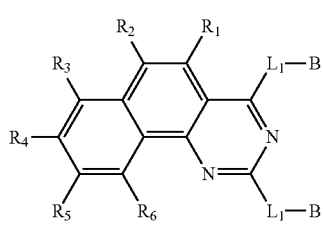

(A1-6)

wherein in the formula, $R_1$ to $R_6$, L and B are the same as defined in the formulas (1) and (A1). Two Bs may be the same as or different from each other. $Ra_1$ is a substituted or unsubstituted aryl group including 6 to 60 ring carbon atoms or a substituted or unsubstituted heteroaryl group including 5 to 60 ring atoms.

Among the compounds having a group represented by the above formula (A1), in respect of improvement of hole-transporting properties, a compound represented by the following formula (A1-7) or (A1-8) is preferable.

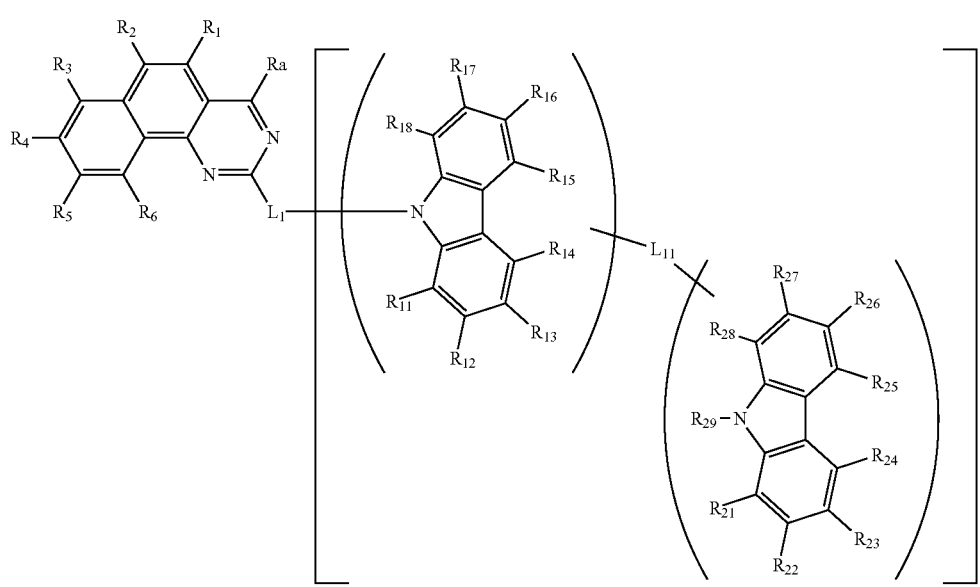

(A1-7)

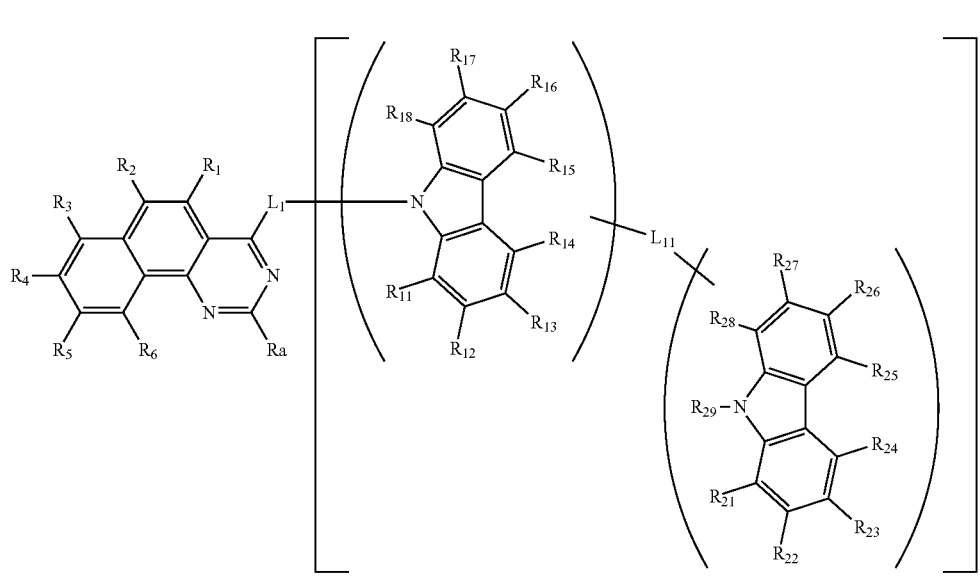

(A1-8)

wherein in the formula, $L_1$, m, Ra, $R_1$ to $R_6$, $R_{11}$ to $R_{18}$, $R_{21}$ to $R_{29}$ and $L_{11}$ are as defined in the formula (1).

In order to attain hole-transporting properties and electron-transporting properties in combination, as well as to attain excellent carrier balance, in the biscarbazole, it is preferred that two carbazoles be bonded at the 3-positions. For example, a compound represented by the following formula (A1-9) or (A1-10) is preferable.

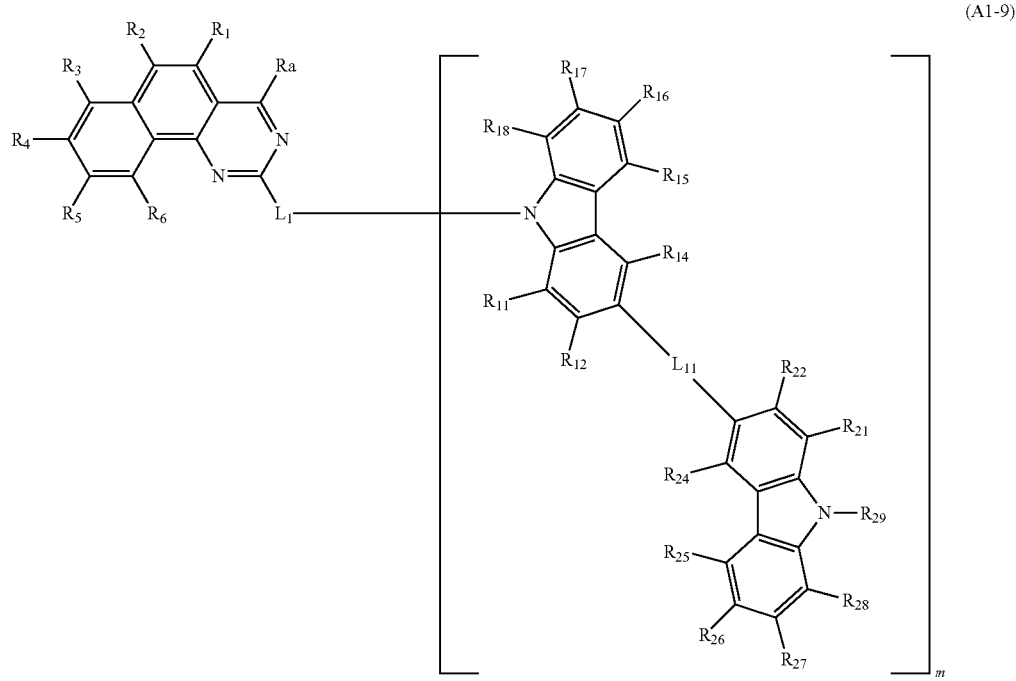

(A1-9)

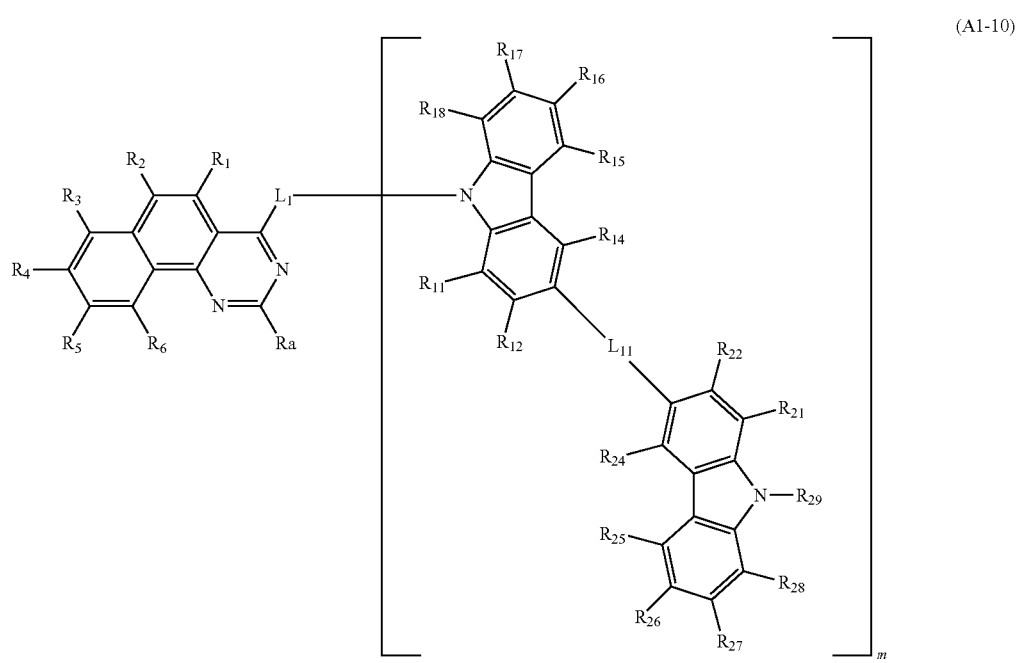

(A1-10)

wherein in the formula, $L_1$, m, Ra, $R_1$ to $R_6$, $R_{11}$ to $R_{16}$, $R_{21}$ to $R_{29}$ and $L_{11}$ are as defined in the formula (1).

In order to attain hole-transporting properties and electron-transporting properties in combination, as well as to attain excellent carrier balance, in the biscarbazole, it is preferred that two carbazoles be bonded at the 2-position and the 3-position. For example, a compound represented by the following formula (A1-11) or (A1-12) is preferable.

(A1-11)

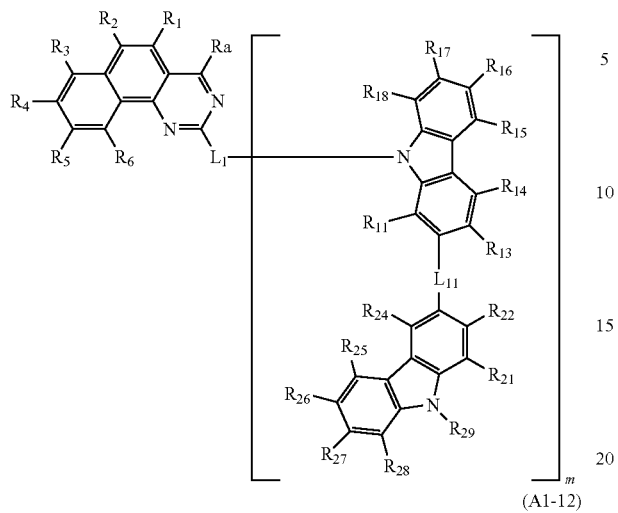

(A1-12)

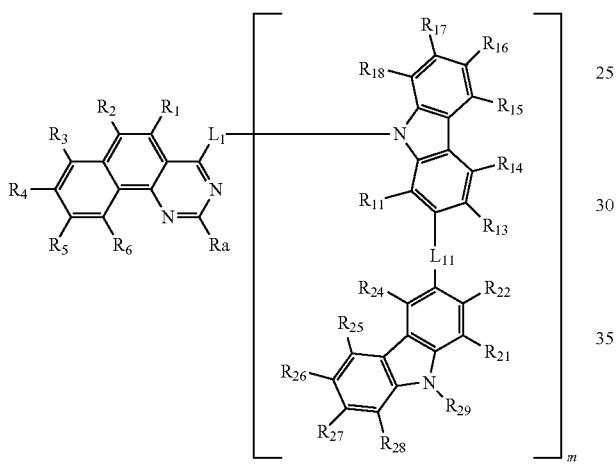

wherein in the formula, $L_1$, m, Ra, $R_1$ to $R_6$, $R_{11}$ to $R_{16}$, $R_{21}$ to $R_{29}$, and $L_{11}$ are as defined in the formula (1).

A compound having a group represented by the above formula (A2) is represented by the following formula (A2-1) or (A2-2), for example.

(A2-1)

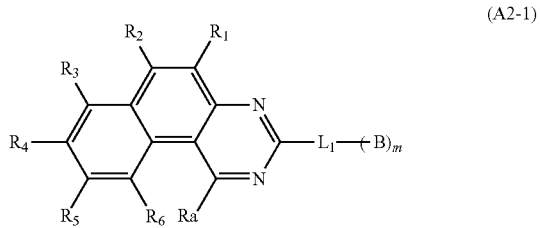

(A2-2)

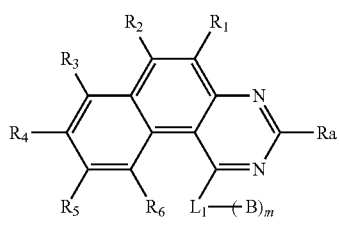

wherein in the formula, Ra, $R_1$ to $R_6$, $L_1$, B and m are as defined in the formulas (1) and (A2).

In respect of improvement of hole-transporting properties, a compound represented by the following formula (A2-3) or (A2-4) is preferable.

(A2-3)

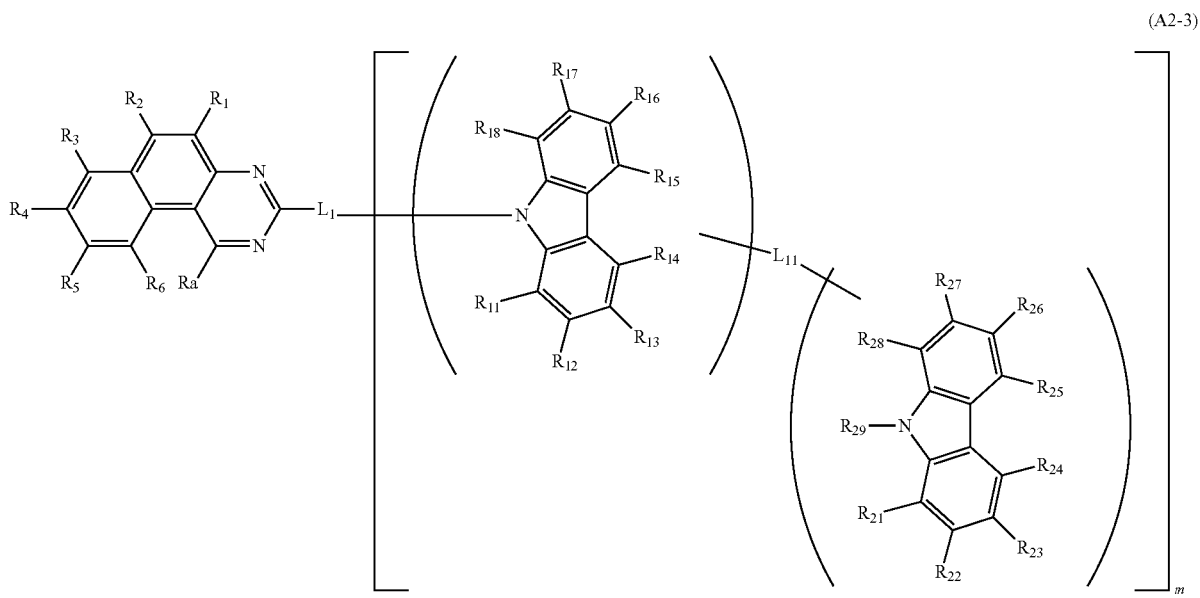

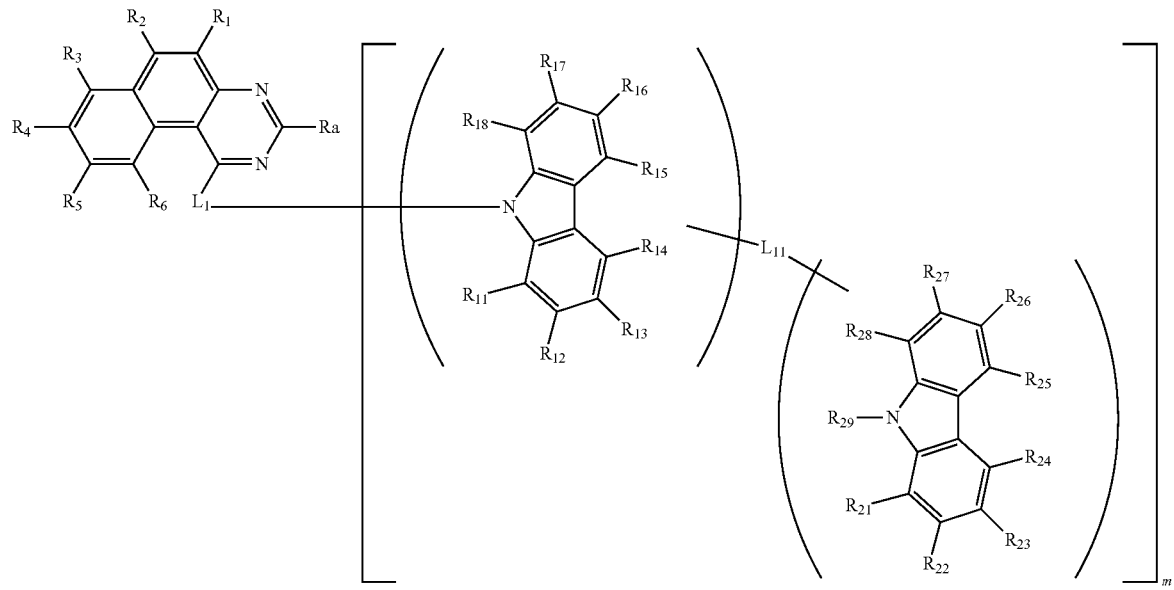
(A2-4)
wherein in the formula, $L_1$, m, Ra, $R_1$ to $R_6$, $R_{11}$ to $R_{18}$, $R_{21}$ to $R_{29}$ and $L_{11}$ are as defined in the formula (1).
As in the case of the above-mentioned formulas (A1-9) to (A1-12), in the biscarbazole, it is preferred that two carbazoles be bonded at the 2-position and the 3-position or at the 3-positions. Specifically, compounds represented by the following formulas (A2-5) to (A2-8) are preferable.
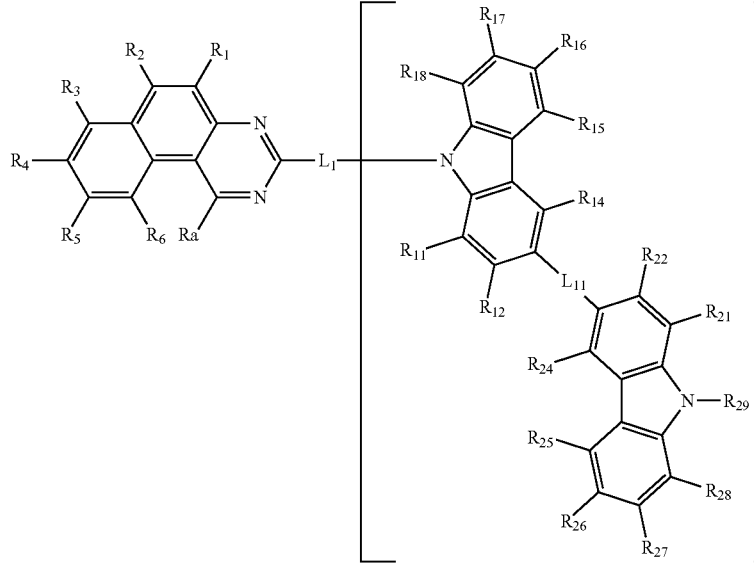
(A2-5)

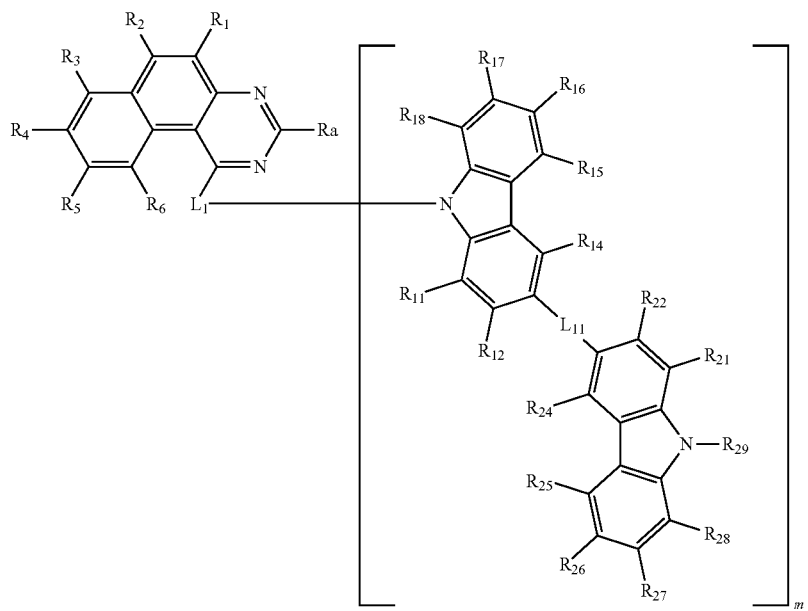
(A2-6)
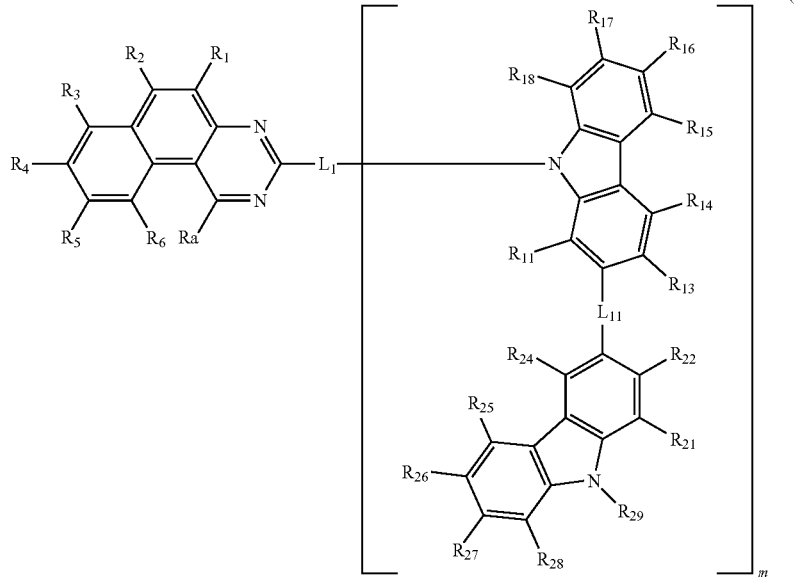
(A2-7)

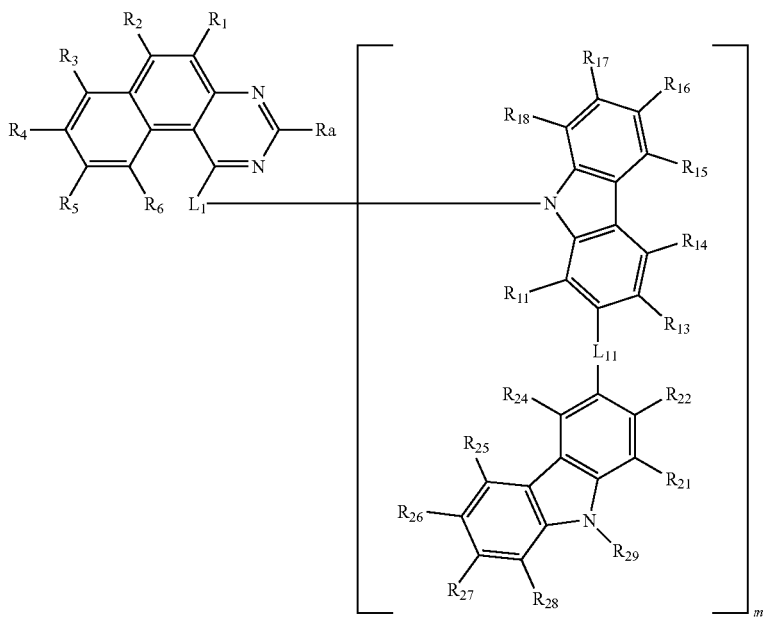

(A2-8)

wherein in the formula, $L_1$, m, Ra, $R_1$ to $R_6$, $R_{11}$ to $R_{18}$, $R_{21}$ to $R_{29}$ and $L_{11}$ are as defined in the formula (1).

In the above formulas (A1-1) to (A1-12) and (A2-1) to (A2-8), it is preferred that the substituent represented by $R_1$ to $R_{29}$ and Ra be independently selected from the following group (A). It is more preferred that the substituent be selected from the following group (B), with a substituent selected from the following group (C) being further preferable.

The group (A) is a group consisting of a substituted or unsubstituted alkyl group including 1 to 50 carbon atoms, a substituted or unsubstituted cycloalkyl group including 3 to 50 ring carbon atoms, a substituted or unsubstituted aryl group including 6 to 60 ring carbon atoms (the same meaning as the "aromatic hydrocarbon group", the same is applied hereinbelow), a substituted or unsubstituted aralkyl group including 7 to 51 carbon atoms, an amino group, a mono- or di-substituted amino group having a substituent selected from a substituted or unsubstituted alkyl group including 1 to 50 carbon atoms and a substituted or unsubstituted aryl group including 6 to 60 ring carbon atoms, a substituted or unsubstituted alkoxy group including 1 to 50 carbon atoms, a substituted or unsubstituted aryloxy group including 6 to 50 ring carbon atoms, a mono-, di- or tri-substituted silyl group having a substituent selected from a substituted or unsubstituted alkyl group including 1 to 50 carbon atoms and a substituted or unsubstituted aryl group including 6 to 60 ring carbon atoms, a substituted or unsubstituted heteroaryl group including 5 to 60 ring atoms (the same meaning as the "heterocyclic group", the same is applied hereinbelow), a substituted or unsubstituted haloalkyl group including 1 to 50 carbon atoms, a halogen atom, a cyano group, a nitro group, a sulfonyl group having a substituent selected from a substituted or unsubstituted alkyl group including 1 to 50 carbon atoms and a substituted or unsubstituted aryl group including 6 to 60 ring carbon atoms, a di-substituted phosphoryl group having a substituent selected from a substituted or unsubstituted alkyl group including 1 to 50 carbon atoms and a substituted or unsubstituted aryl group including 6 to 60 ring carbon atoms, an alkylsulfonyloxy group, an arylsulfonyloxy group, an alkylcarbonyloxy group, an arylcarbonyloxy group, a boron-containing group, a zinc-containing group, a tin-containing group, a silicon-containing group, a magnesium-containing group, a lithium-containing group, a hydroxyl group, an alkyl-substituted or aryl-substituted carbonyl group, a carboxyl group, a vinyl group, a (meth)acryloyl group, an epoxy group and an oxetanyl group.

The group (B) is a group consisting of a substituted or unsubstituted alkyl group including 1 to 50 carbon atoms, a substituted or unsubstituted cycloalkyl group including 3 to 50 ring carbon atoms, a substituted or unsubstituted aryl group including 6 to 60 ring carbon atoms, a substituted or unsubstituted aralkyl group including 7 to 51 carbon atoms, an amino group, a mono- or di-substituted amino group having a substituent selected from a substituted or unsubstituted alkyl group including 1 to 50 carbon atoms and a substituted or unsubstituted aryl group including 6 to 60 ring carbon atoms, a substituted or unsubstituted alkoxy group including 1 to 50 carbon atoms, a substituted or unsubstituted aryloxy group including 6 to 50 ring carbon atoms, a mono-, di- or tri-substituted silyl group having a substituent selected from a substituted or unsubstituted alkyl group including 1 to 50 carbon atoms and a substituted or unsubstituted aryl group including 6 to 60 ring carbon atoms, a substituted or unsubstituted heteroaryl group including 5 to 60 ring atoms, a substituted or unsubstituted haloalkyl group including 1 to 50 carbon atoms, a halogen atom, a cyano group, a nitro group, a sulfonyl group having a substituent selected from a substituted or unsubstituted alkyl group including 1 to 50 carbon atoms and a substituted or unsubstituted aryl group including 6 to 60 ring carbon atoms, and a di-substituted phosphoryl group having a substituent selected from a substituted or unsubstituted alkyl group including 1 to 50 carbon atoms and a substituted or unsubstituted aryl group including 6 to 60 ring carbon atoms.

The group (C) is a group consisting of a substituted or unsubstituted alkyl group including 1 to 50 carbon atoms, a substituted or unsubstituted cycloalkyl group including 3 to 50 ring carbon atoms, a substituted or unsubstituted aryl group including 6 to 60 ring carbon atoms, a substituted or unsubstituted aralkyl group including 7 to 51 carbon atoms, an amino group, a mono- or di-substituted amino group having a substituent selected from a substituted or unsubstituted alkyl group including 1 to 50 carbon atoms and a substituted or unsubstituted aryl group including 6 to 60 ring carbon atoms, a substituted or unsubstituted alkoxy group including 1 to 50 carbon atoms, a substituted or unsubstituted aryloxy group including 6 to 50 ring carbon atoms, a mono-, di- or tri-substituted silyl group having a substituent selected from a substituted or unsubstituted alkyl group including 1 to 50 carbon atoms and a substituted or unsubstituted aryl group including 6 to 60 ring carbon atoms, a substituted or unsubstituted heteroaryl group including 5 to 60 ring atoms, a substituted or unsubstituted haloalkyl group including 1 to 50 carbon atoms, a halogen atom, a cyano group and a nitro group.

As examples of the alkyl group including 1 to 50 (preferably 1 to 18, more preferably 1 to 8) carbon atoms, a methyl group, an ethyl group, a n-propyl group, an isopropyl group, a n-butyl group, an isobutyl group, a s-butyl group, a t-butyl group, a pentyl group (including isomers), a hexyl group (including isomers), a heptyl group (including isomers), an octyl group (including isomers), a nonyl group (including isomers), a decyl group (including isomers), an undecyl group (including isomers), a dodecyl group (including isomers), a tridecyl group, a tetradecyl group, an octadecyl group, a tetracosanyl group, a tetracontanyl group or the like can be given. A methyl group, an ethyl group, a n-propyl group, an isopropyl group, a n-butyl group, an isobutyl group, a s-butyl group, a t-butyl group, a pentyl group (including isomers), a hexyl group (including isomers), a heptyl group (including isomers), an octyl group (including isomers), a nonyl group (including isomers), a decyl group (including isomers), a undecyl group (including isomers), a dodecyl group (including isomers), a tridecyl group, a tetradecyl group and an octadecyl group are preferable. A methyl group, an ethyl group, a n-propyl group, an isopropyl group, a n-butyl group, an isobutyl group, a s-butyl group, a t-butyl group, a pentyl group (including isomers), a hexyl group (including isomers), a heptyl group (including isomers), and octyl group (including isomers) are further preferable.

As the cycloalkyl group including 3 to 50 (preferably 3 to 10, more preferably 3 to 8, and further preferably 5 or 6) ring carbon atoms, a cyclopropyl group, a cyclobutyl group, a cyclopentyl group, a cyclohexyl group, a cycloheptyl group, a cyclooctyl group, an adamantyl group or the like can be given, with a cyclopentyl group and a cyclohexyl group being preferable.

As the aryl group including 6 to 60 (preferably 6 to 25, more preferably 6 to 18) ring carbon atoms, a phenyl group, a naphthyl group, a naphthylphenyl group, a biphenylyl group, a terphenylyl group, an acenaphthylenyl group, an anthryl group, a benzoanthryl group, an aceanthryl group, a phenanthryl group, a benzophenanthryl group, a phenalenyl group, a fluorenyl group, a 9,9'-spirobifluorenyl group, a benzofluorenyl group, a dibenzofluorenyl group, a picenyl group, a pentaphenyl group, a pentacenyl group, a pyrenyl group, a chrysenyl group, a benzochrysenyl group, an s-indacenyl group, an as-indacenyl group, a fluoranthenyl group, a benzofluoranthenyl group, a tetracenyl group, a triphenylenyl group, a benzotriphenylenyl group, a perylenyl group, a coronyl group and a dibenzoanthryl group can be given, for example. A phenyl group, a biphenyl group, a naphthyl group, a phenathryl group, a triphenylenyl group and a fluorenyl group are preferable.

As the substituted or unsubstituted aralkyl group including 7 to 51 carbon atoms, an aralkyl group having the above-mentioned aryl group including 6 to 50 (preferably 6 to 25, more preferably 6 to 18) ring carbon atoms can be given.

As the mono- or di-substituted amino group having a substituent selected from a substituted or unsubstituted alkyl group including 1 to 50 (preferably 1 to 18, more preferably 1 to 8) carbon atoms and a substituted or unsubstituted aryl group including 6 to 60 (preferably 6 to 25, more preferably 6 to 18) ring carbon atoms, a mono- or di-substituted amino group having a substituent selected from the above-mentioned alkyl group and the above-mentioned aryl group can be given.

As the substituted or unsubstituted alkoxy group including 1 to 50 carbon atoms, an alkoxy group having the above-mentioned alkyl group including 1 to 50 (preferably 1 to 18, more preferably 1 to 8) carbon atoms can be given.

As the substituted or unsubstituted aryloxy group including 6 to 50 ring carbon atoms, an aryloxy group having the above-mentioned aryl group including 6 to 50 (preferably 6 to 25, more preferably 6 to 18) ring carbon atoms can be given.

As the mono-, di- or tri-substituted silyl group having a substituent selected from an alkyl group including 1 to 50 (preferably 1 to 18, more preferably 1 to 8) carbon atoms and a substituted or unsubstituted aryl group including 6 to 50 (preferably 6 to 25, more preferably 6 to 18) ring carbon atoms, a mono-, di- or tri-substituted silyl group having a substituent selected from the above-mentioned alkyl group and the above-mentioned aryl group can be given.

The heteroaryl group including 5 to 60 (preferably 5 to 24, more preferably 5 to 13) ring atoms includes at least one, preferably 1 to 5 (more preferably 1 to 3, further preferably 1 to 2) hetero atoms (for example, a nitrogen atom, a sulfur atom, an oxygen atom, a phosphorus atom).

As the heteroaryl group, a pyrrolyl group, a furyl group, a thienyl group, a pyridyl group, a pyridazinyl group, a pyrimidinyl group, a pyrazinyl group, a triazinyl group, an imidazolyl group, an oxazolyl group, a thiazolyl group, a pyrazolyl group, an isoxazolyl group, an isothiazolyl group, an oxadiazolyl group, a thiadiazolyl group, a triazolyl group, a tetrazolyl group, an indolyl group, an isoindolyl group, a benzofuranyl group, an isobenzofuranyl group, a benzothiophenyl group, an isobenzothiophenyl group, an indolizinyl group, a quinolizinyl group, a quinolyl group, an isoquinolyl group, a cinnolyl group, a phthalazinyl group, a quinazolinyl group, a quinoxalinyl group, a benzimidazolyl group, a benzoxazolyl group, a benzothiazolyl group, an indazolyl group, a benzisoxazolyl group, a benzisothiazolyl group, a dibenzofuranyl group, a dibenzothiophenyl group, a carbazolyl group, a phenanthridinyl group, an acridinyl group, a phenanthrolinyl group, a phenazinyl group, a phenothiazinyl group, a phenoxazinyl group, an azatriphenylenyl group, a diazatriphenylenyl group, a xanthenyl group, an azacarbazolyl group, an azadibenzofuranyl group, an azadibenzothiophenyl group, a benzofuranobenzothiophenyl group, a benzothienobenzothiophenyl group, a dibenzofuranonaphthyl group, a dibenzothienonaphthyl group, a dinaphthothienothiophenyl group or the like can be given, for example. A pyridyl group, a pyrimidinyl group, a triazinyl group, a quinazolinyl group, a carbazolyl group, a dibenzothiophenyl group and a dibenzofuranyl group are preferable.

The "carbazolyl group" mentioned above includes the following structures.

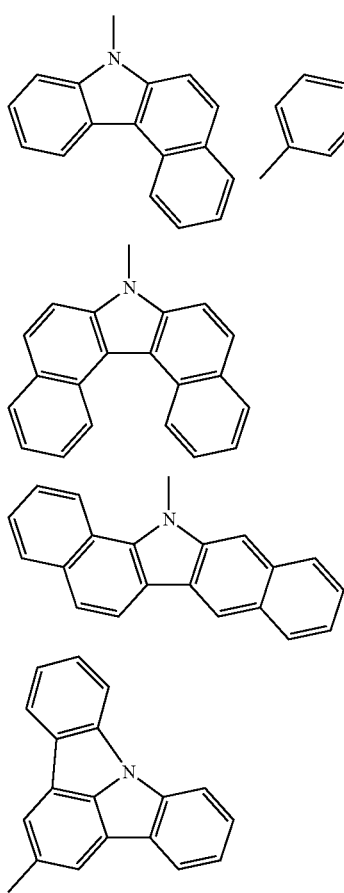
The heteroaryl group mentioned above includes the following structures.
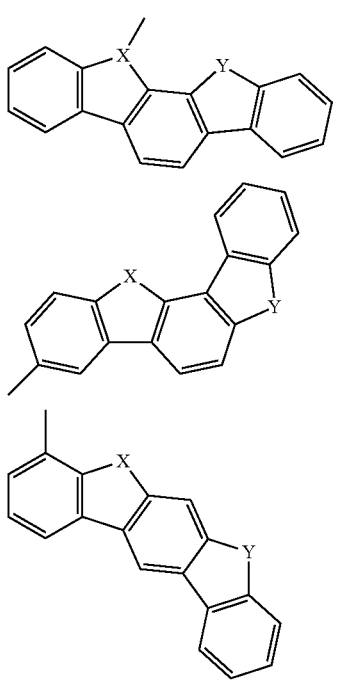
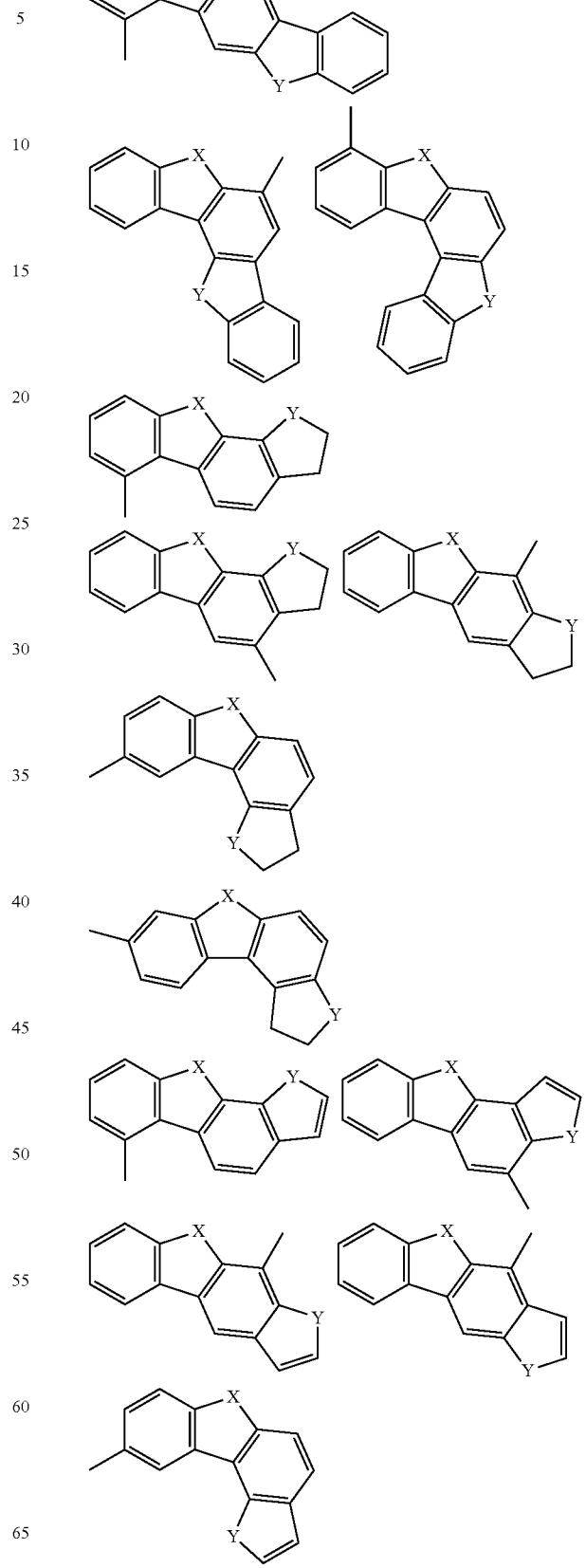

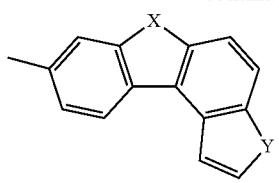

wherein in the formula, X and Y are independently an oxygen atom, a sulfur atom, a nitrogen atom or a —NH— group.

As specific examples of the heteroaryl group including 5 to 60 ring atoms, a monovalent group obtained by removing one hydrogen atom from any of compounds represented by the following formulas is also preferable.

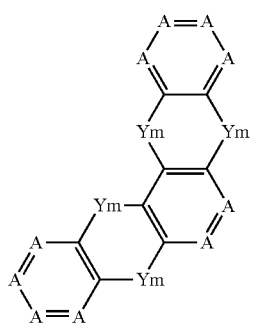

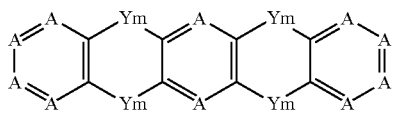

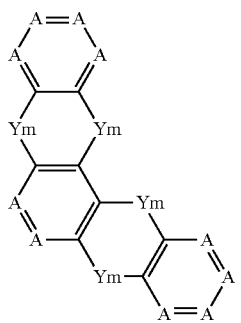

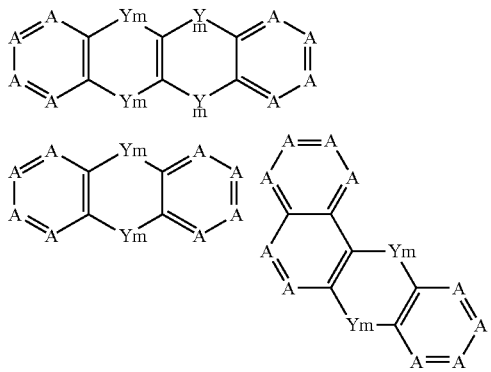

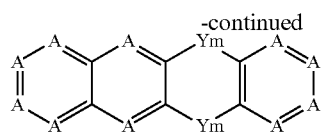

wherein in the formula, A is independently $CR^{100}$ or a nitrogen atom and $R^{100}$s are independently a hydrogen atom or a substituent;

Y is independently a single bond, $C(R^{101})(R^{102})$, an oxygen atom, a sulfur atom or $N(R^{103})$;

$R^{101}$, $R^{102}$ and $R^{103}$ are independently a hydrogen atom or a substituent and ms are independently 0 or 1.

As the substituent in the formula, the same as those mentioned above can be given.

As the substituted or unsubstituted haloalkyl group including 1 to 50 (preferably 1 to 18, more preferably 1 to 8) carbon atoms, one obtained by substituting one or more hydrogen atoms in the above-mentioned alkyl group by a halogen atom (a fluorine atom, a chlorine atom, a bromine atom, an iodine atom) can be given.

As the sulfonyl group having a substituent selected from a substituted or unsubstituted alkyl group including 1 to 50 (preferably 1 to 18, more preferably 1 to 8) carbon atoms and a substituted or unsubstituted aryl group including 6 to 50 (preferably 6 to 25, more preferably 6 to 18) ring carbon atoms, a sulfonyl group having a substituent selected from the above-mentioned alkyl group or the above-mentioned aryl group can be given.

As the di-substituted phosphoryl group having a substituent selected from a substituted or unsubstituted alkyl group including 1 to 50 (preferably 1 to 18, more preferably 1 to 8) carbon atoms and a substituted or unsubstituted aryl group including 6 to 50 (preferably 6 to 25, more preferably 6 to 18) ring carbon atoms, a di-substituted phosphoryl group having a substituent selected from the above-mentioned alkyl group and the above-mentioned aryl group can be given.

Among the above-mentioned substituents, a substituted or unsubstituted aryl group or a substituted or unsubstituted heteroaryl group is preferable.

As the substituent represented by Ra, a substituted or unsubstituted aryl group is preferable. For example, an aryl group selected from the group consisting of a phenyl group, a naphthyl group, a naphthylphenyl group, a biphenylyl group, a terphenylyl group, an acenaphthylenyl group, an anthryl group, a benzoanthryl group, an aceanthryl group, a phenanthryl group, a benzophenanthryl group, a phenalenyl group, a fluorenyl group, a 9,9'-spirobifluorenyl group, a benzofluorenyl group, a dibenzofluorenyl group, a picenyl group, a pentaphenyl group, a pentacenyl group, a pyrenyl group, a chrysenyl group, a benzochrysenyl group, an s-indacenyl group, an as-indacenyl group, a fluoranthenyl group, a benzofluoranthenyl group, a tetracenyl group, a triphenylenyl group, a benzotriphenylenyl group, a perylenyl group, a coronyl group and a dibenzoanthryl group can be given.

As the linking group represented by $L_1$ and $L_{11}$, a substituted or unsubstituted aromatic hydrocarbon ring is preferable. As the aromatic hydrocarbon ring group, a divalent group obtained by removing one hydrogen atom from the aryl group including 6 to 50 ring carbon atoms given above as a substituent represented by $R_1$ or the like can be given.

$L_1$ is preferably a substituted or unsubstituted arylene group including 6 to 30 ring carbon atoms. For example, a phenylene group, a biphenylene group or a naphthylene group is preferable. Among phenylene groups, m-phenylene is preferable.

$L_{11}$ is preferably a single bond. For example, the formula (B) is represented by the following formula (B').

selected from an alkyl group including 1 to 50 (preferably 1 to 18, more preferably 1 to 8) carbon atoms and an aryl group including 6 to 50 (preferably 6 to 25, more preferably 6 to 18) ring carbon atoms; an alkoxy group having an alkyl group including 1 to 50 (preferably 1 to 18, more preferably 1 to 8) carbon atoms; an aryloxy group having an aryl group including 6 to 50 (preferably 6 to 25, more preferably 6 to 18) ring carbon atoms; a mono-, di- or hi-substituted silyl group having a substituent selected from an alkyl group including 1 to 50 (preferably 1 to 18, more preferably 1 to 8) carbon atoms and an aryl group including 6 to 50 (preferably 6 to 25, more preferably 6 to 18) ring carbon atoms; a heteroaryl group including 5 to 50 (preferably 5 to 24, more preferably 5 to 13) ring atoms; a haloalkyl group including 1 to 50 (preferably 1 to 18, more preferably 1 to 8) carbon atoms; a halogen atom (a fluorine atom, a chlorine atom, a bromine atom, an iodine atom); a cyano group; a nitro group; a sulfonyl group having a substituent selected from an alkyl group including 1 to 50 (preferably 1 to 18, more preferably 1 to 8) carbon atoms and an aryl group including 6 to 50 (preferably 6 to 25, more preferably 6 to 18) ring carbon atoms; a di-substituted phosphoryl group having a substituent selected from an alkyl group including 1 to 50 (preferably 1 to 18, more preferably 1 to 8) carbon atoms and an aryl group including 6 to 50 (preferably 6 to 25, more preferably 6 to 18) ring carbon atoms; an alkylsulfonyloxy group; an arylsulfonyloxy group; an alkylcar-

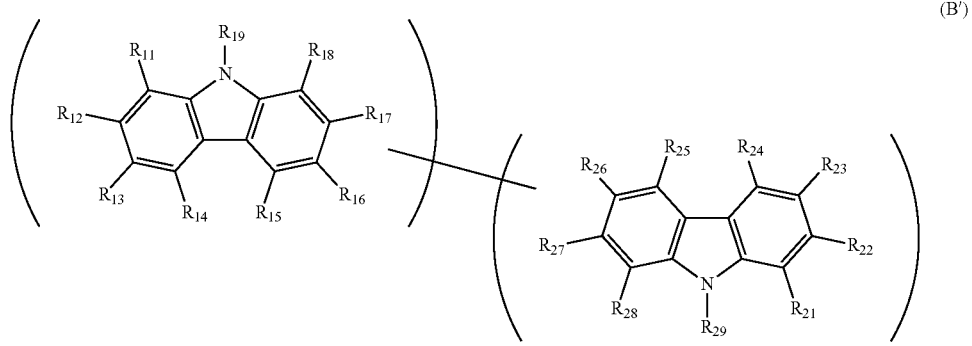

(B')

wherein $R_{11}$ to $R_{19}$ and $R_{21}$ to $R_{29}$ are as defined in the formula (B).

It is preferred that an arbitrary substituent in the "substituted or unsubstituted" be selected from the group consisting of an alkyl group including 1 to 50 (preferably 1 to 18, more preferably 1 to 8) carbon atoms; a cycloalkyl group including 3 to 50 (preferably 3 to 10, more preferably 3 to 8, and further preferably 5 or 6) ring carbon atoms; an aryl group including 6 to 50 (preferably 6 to 25, more preferably 6 to 18) ring carbon atoms; an aralkyl group that includes 7 to 51 (preferably 7 to 30, more preferably 7 to 20) carbon atoms and has an aryl group including 6 to 50 (preferably 6 to 25, more preferably 6 to 18) ring carbon atoms; an amino group; a mono- or di-substituted amino group having a substituent bonyloxy group; an arylcarbonyloxy group; a boron-containing group; a zinc-containing group; a tin-containing group; a silicon-containing group; a magnesium-containing group; a lithium-containing group; a hydroxy group; an alkyl-substituted or aryl-substituted carbonyl group; a carboxyl group; a vinyl group; a (meth)acryloyl group; an epoxy group; and an oxetanyl group.

These substituents may be further substituted by the above-mentioned arbitrary substituents. Further, a plurality of these substituents may be bonded to each other to form a ring.

One example of the compound according to one aspect of the invention is shown below.

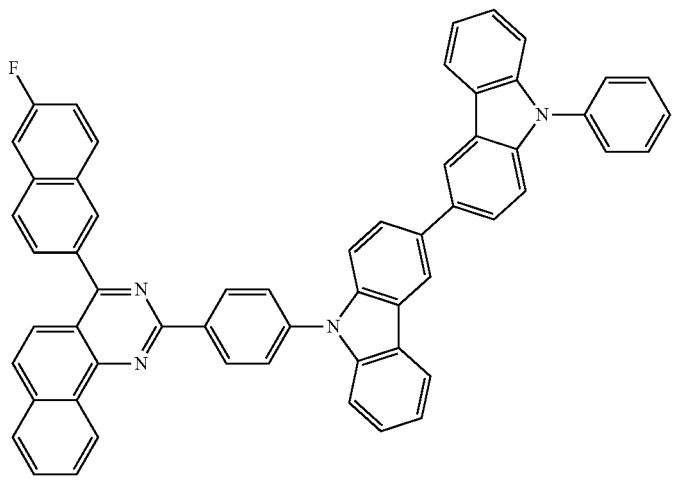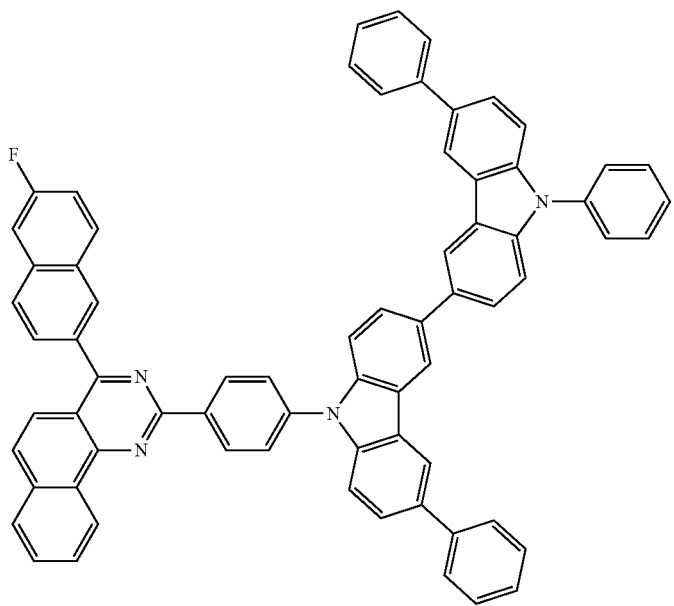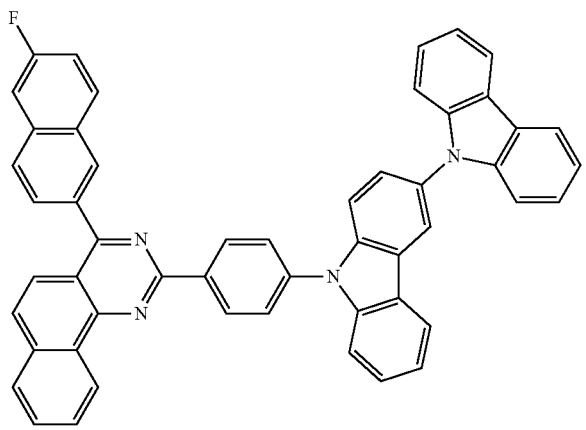

-continued
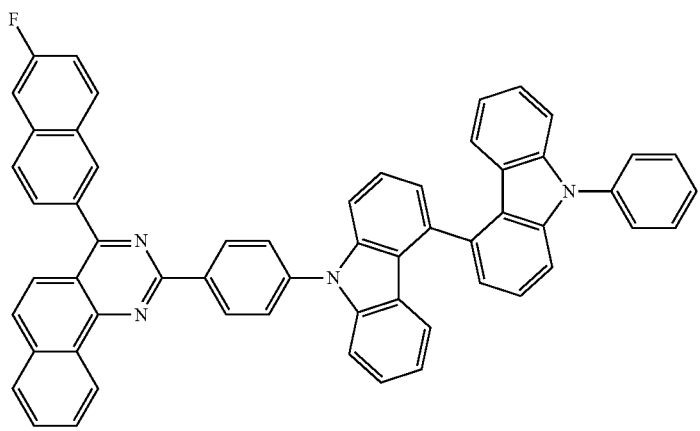
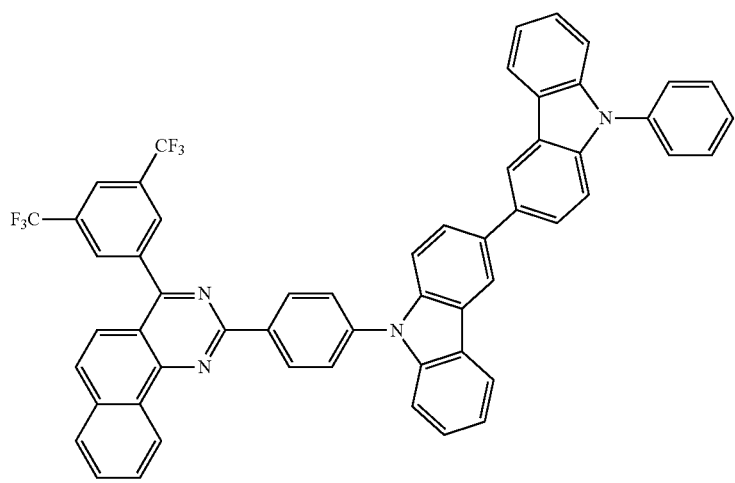
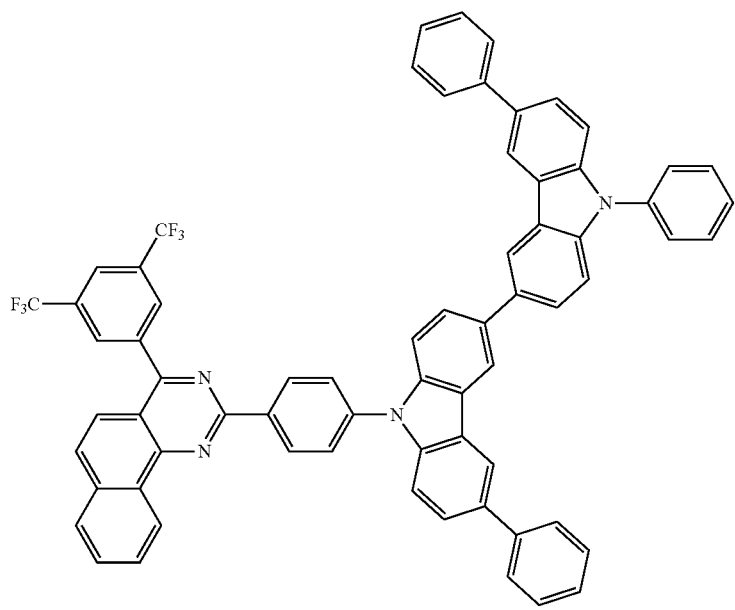

-continued
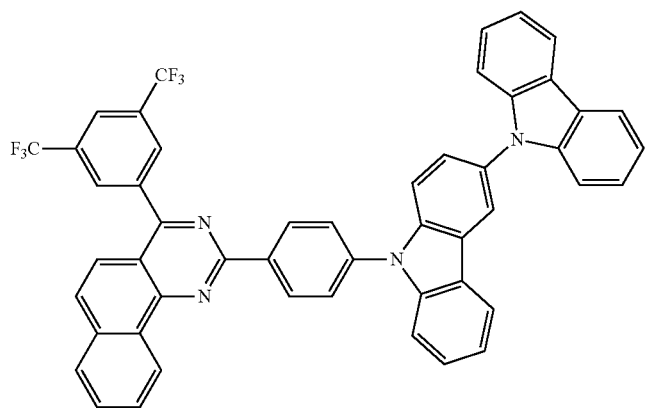
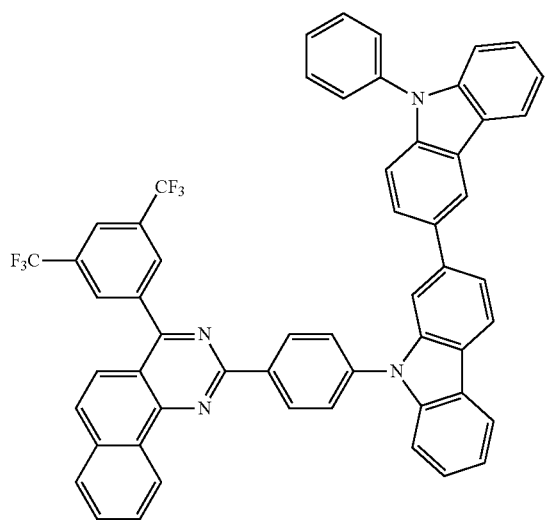
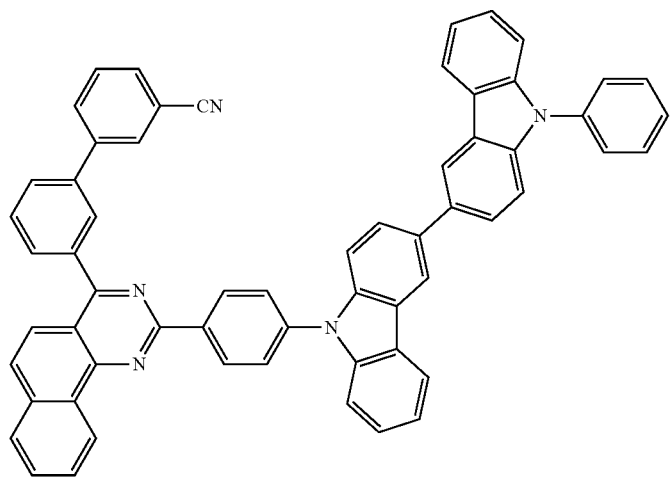

-continued
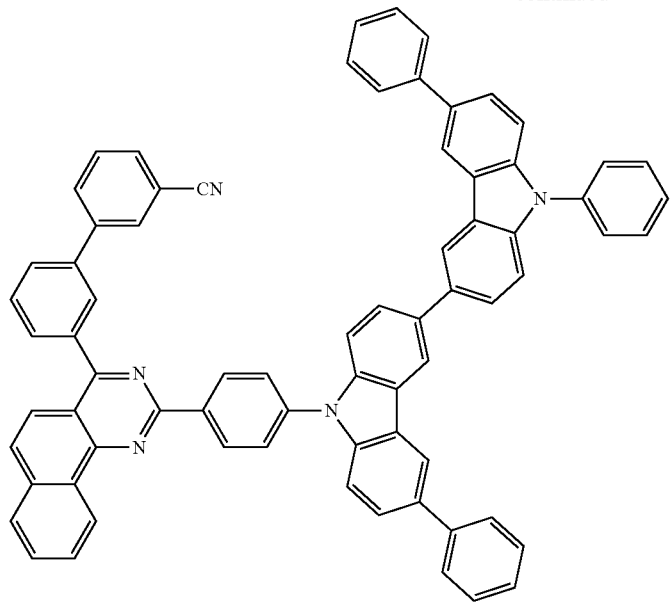
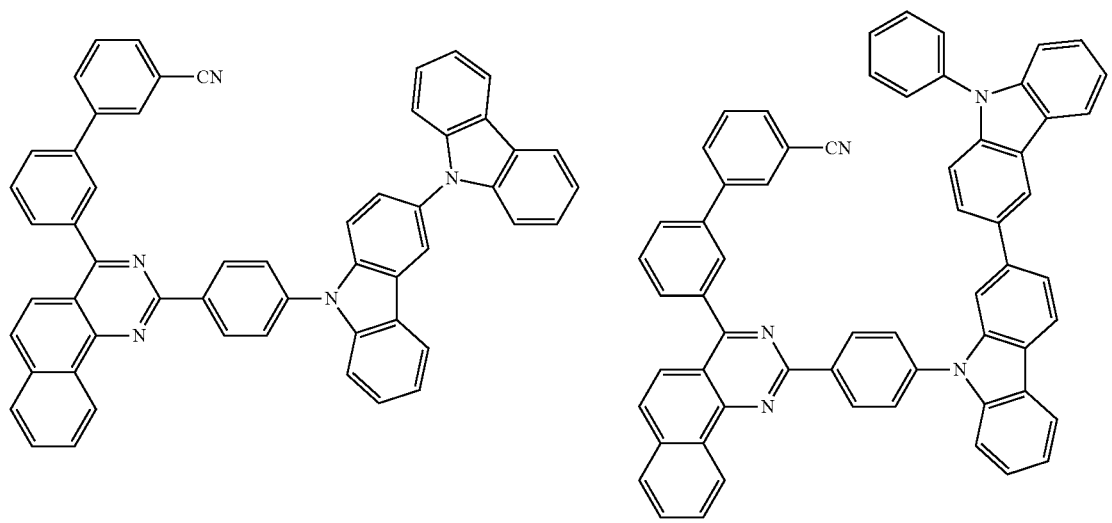
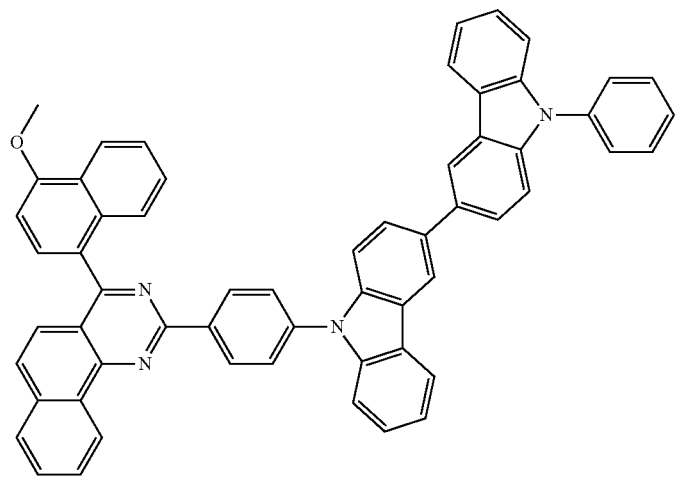

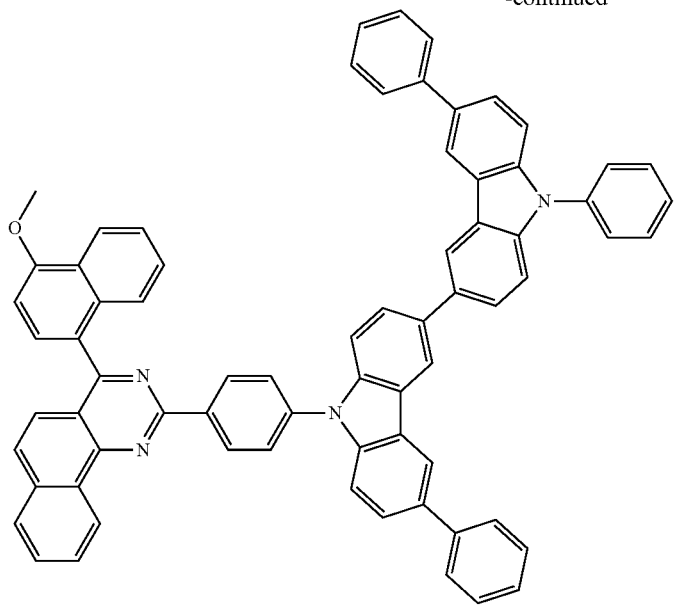
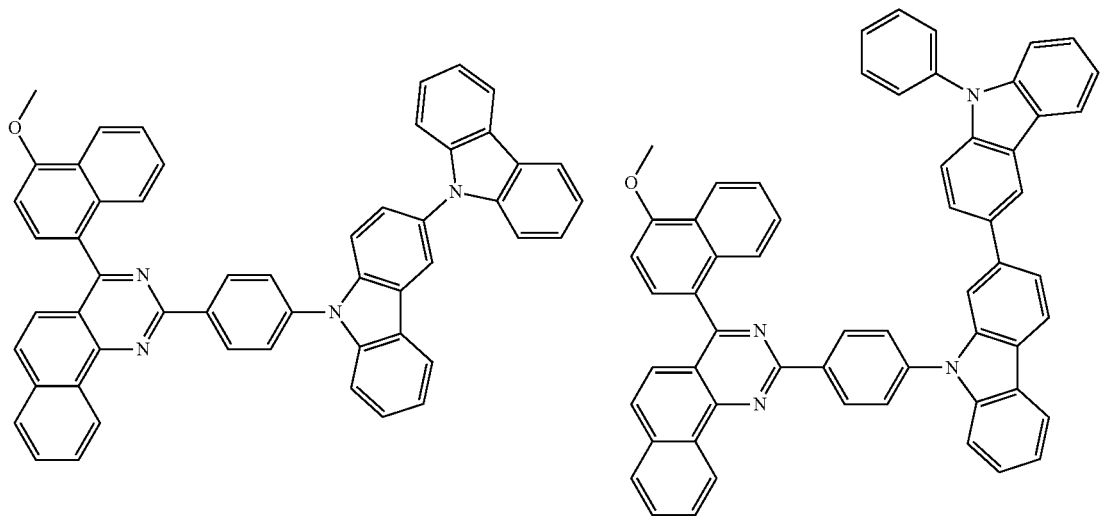
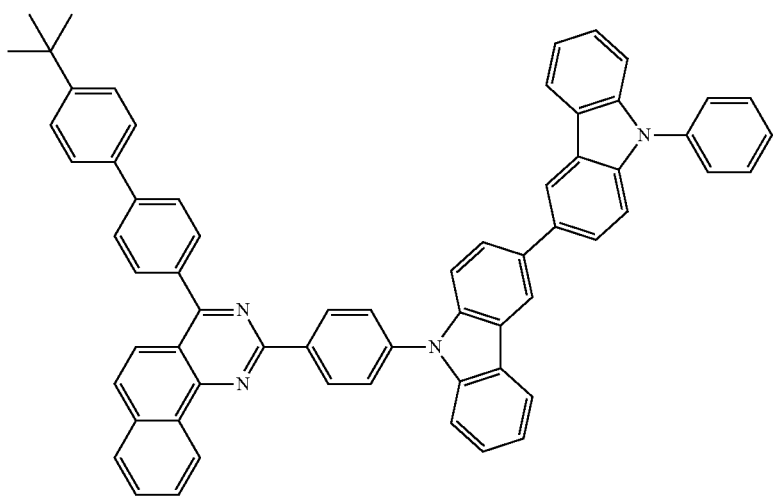

-continued
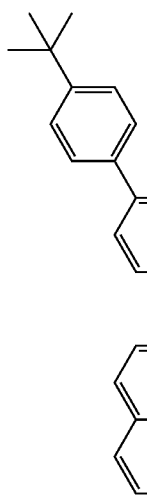 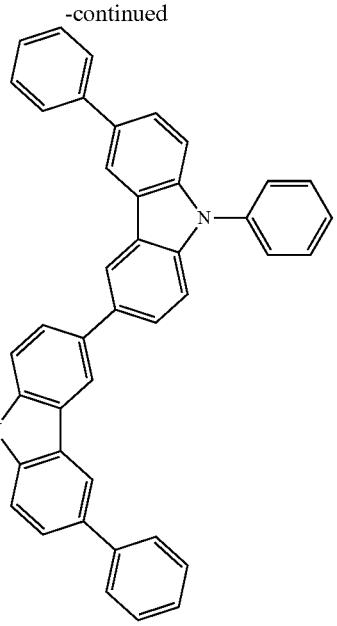
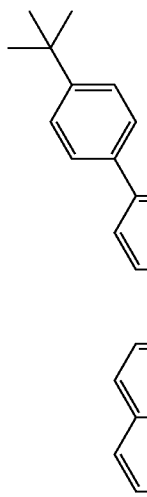 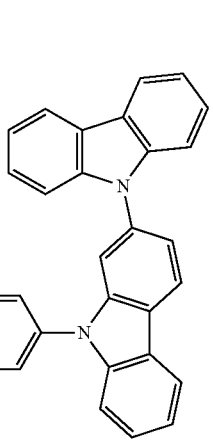 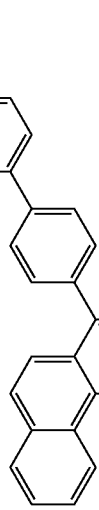 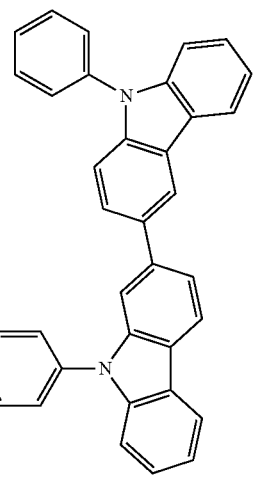
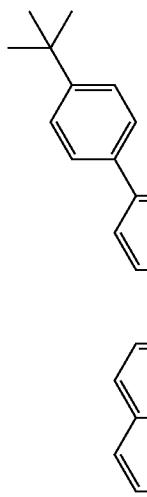 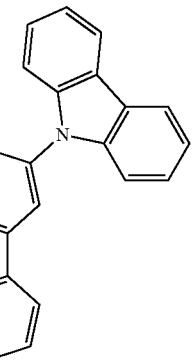

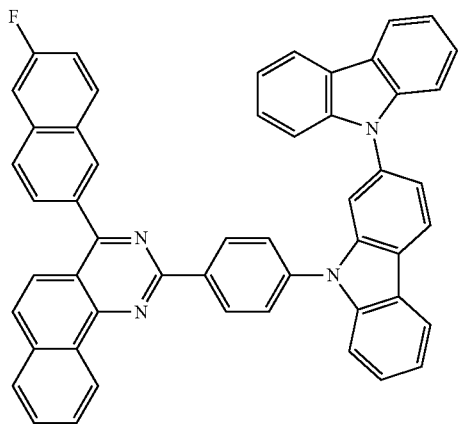
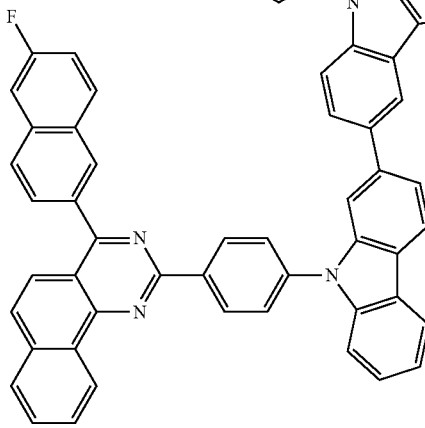
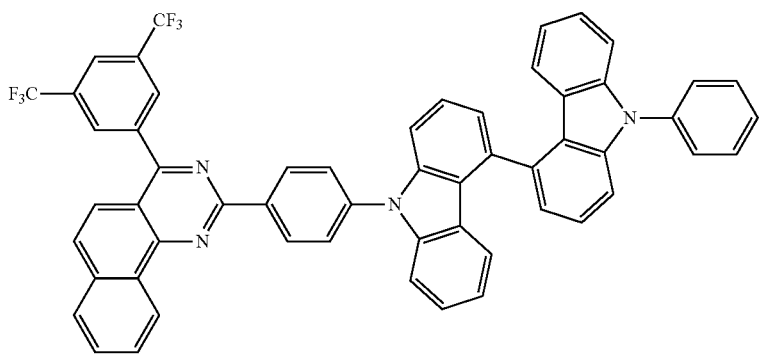
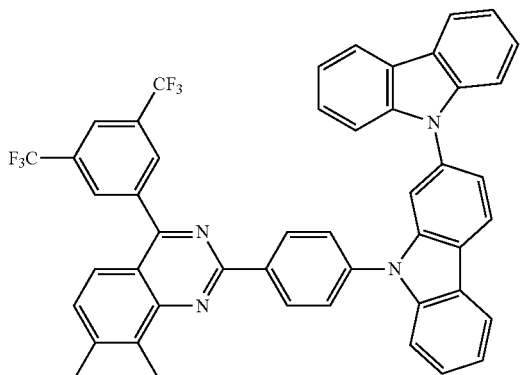
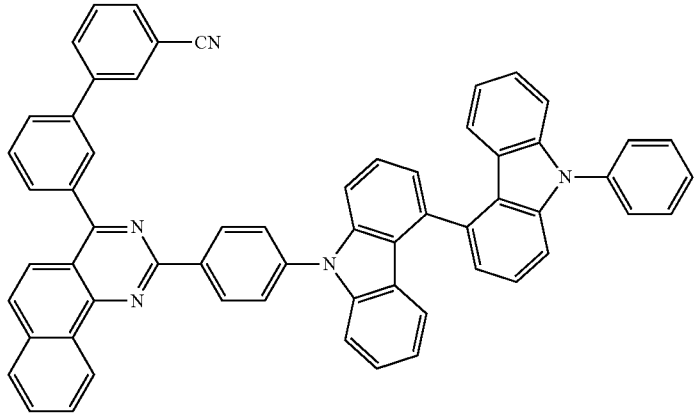

-continued
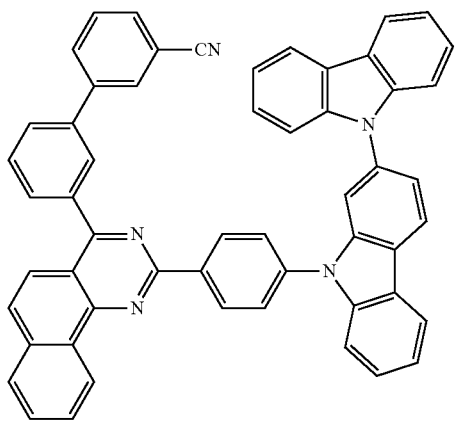
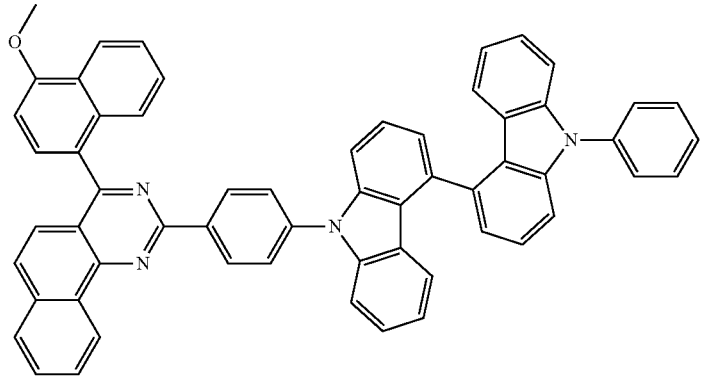
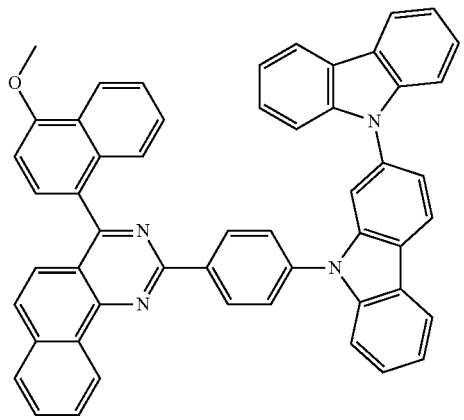
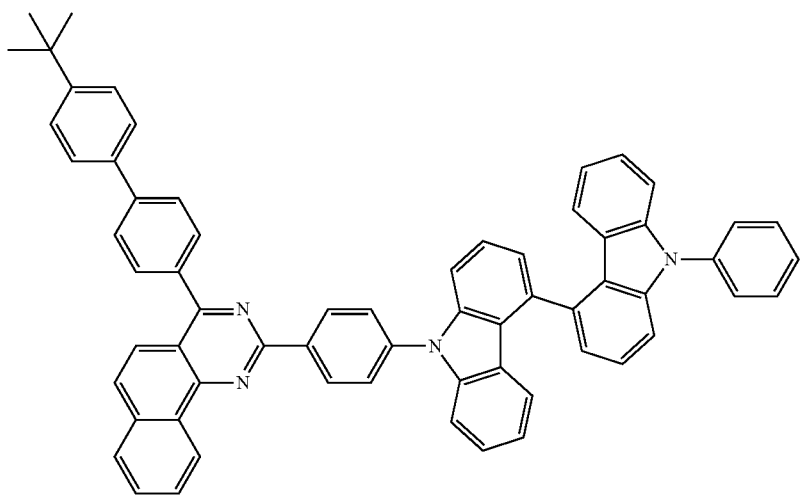

-continued
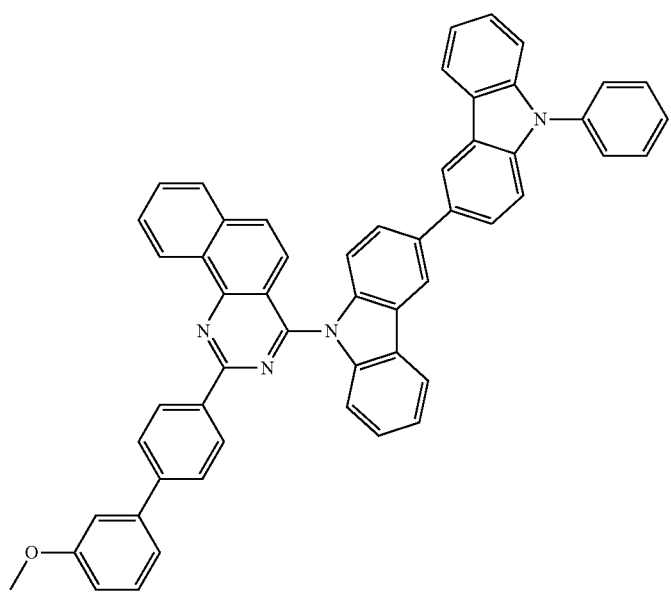
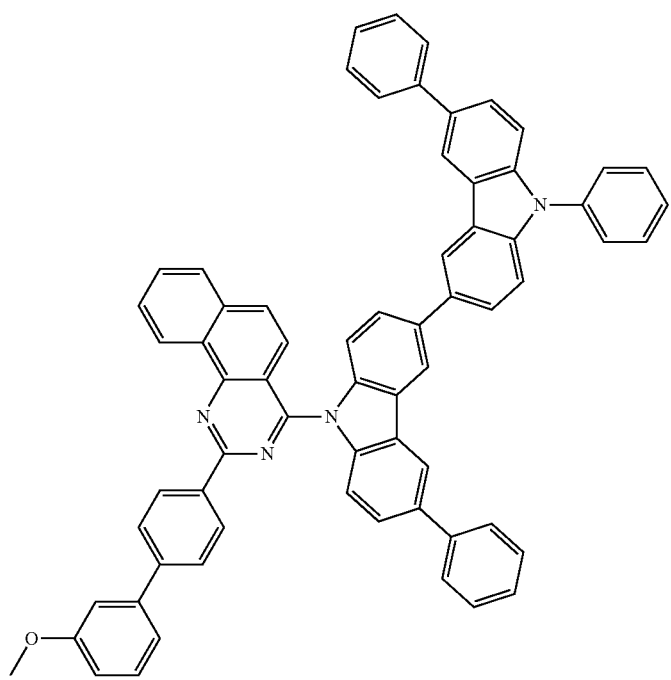

-continued
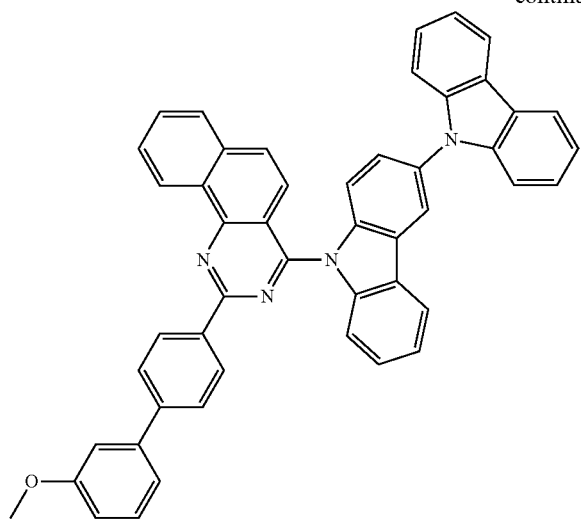
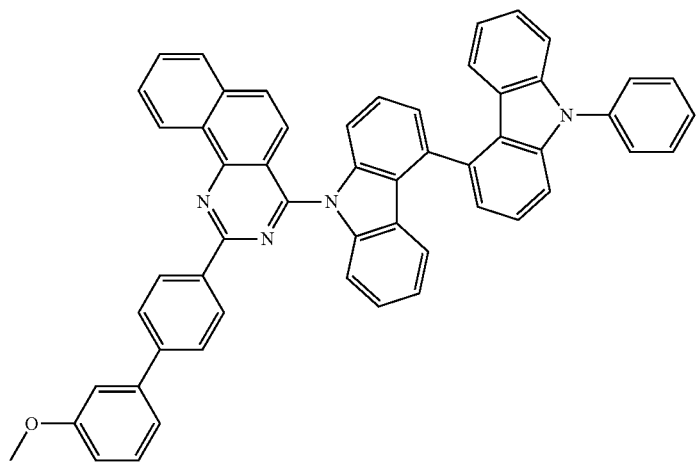
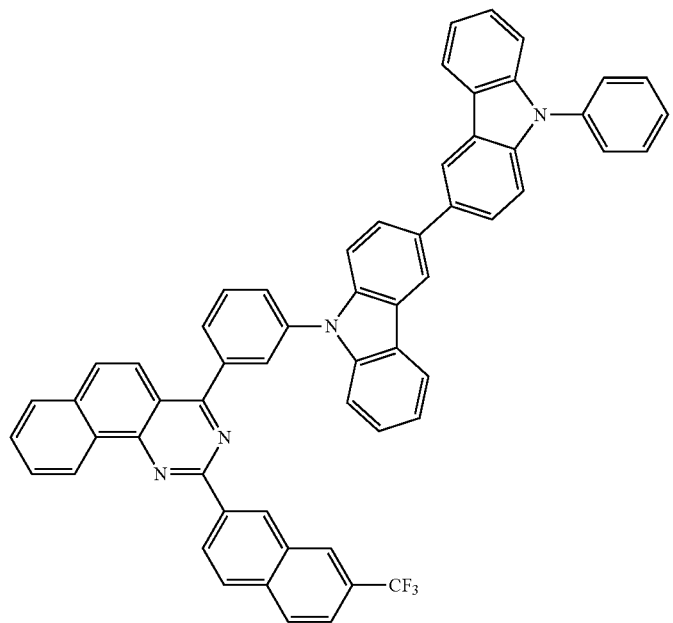

-continued
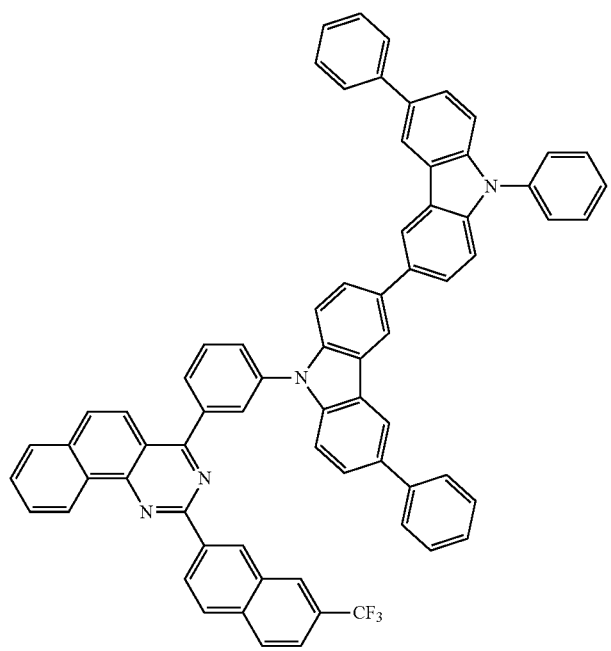
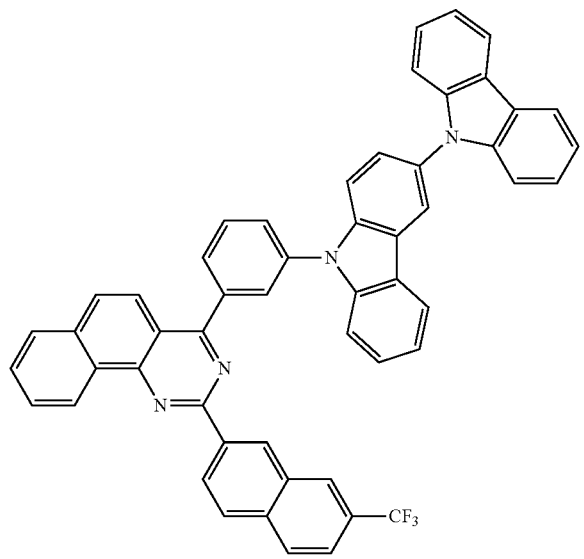
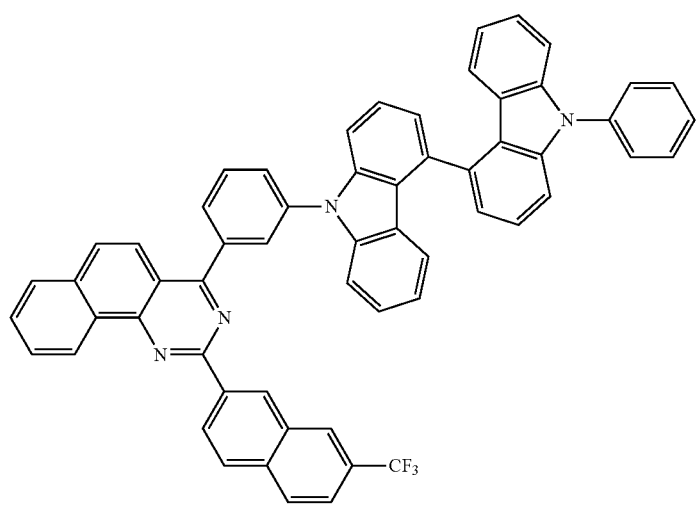

-continued
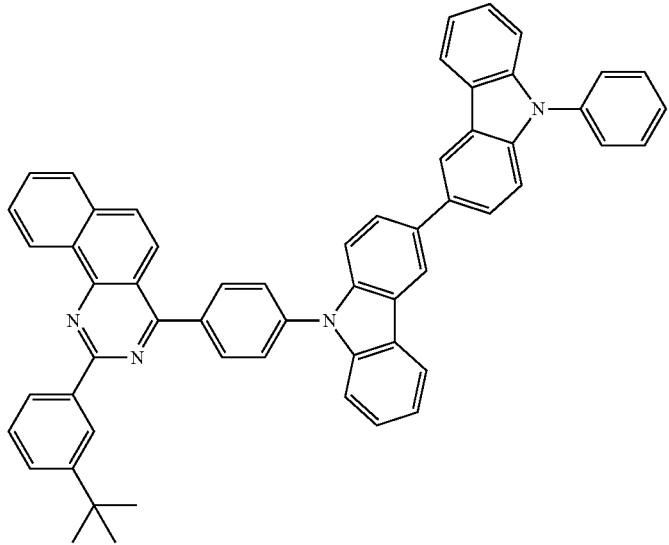
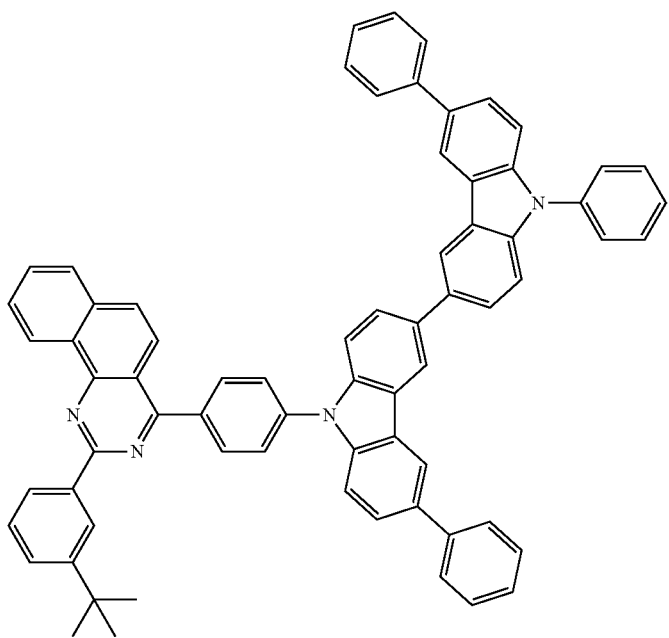
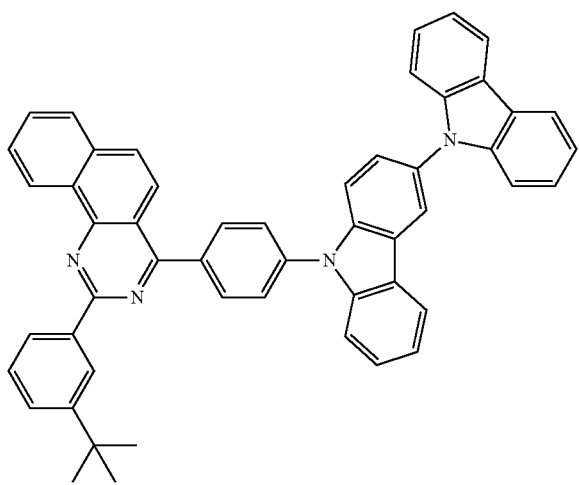

-continued
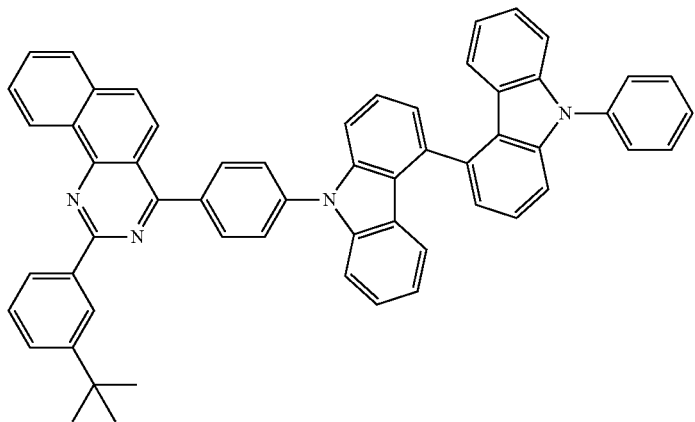
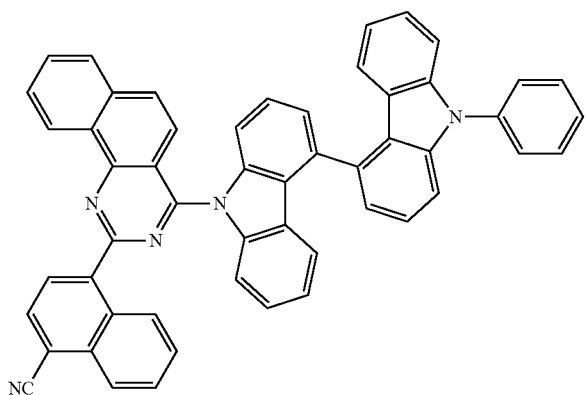
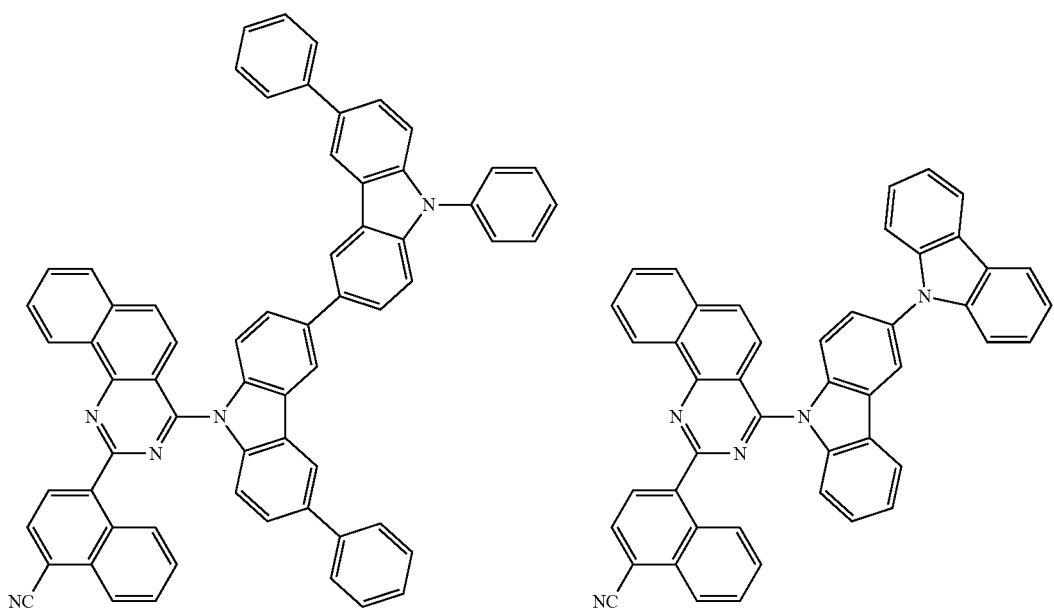

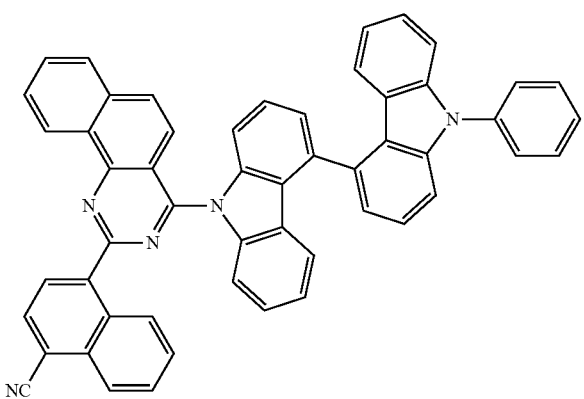
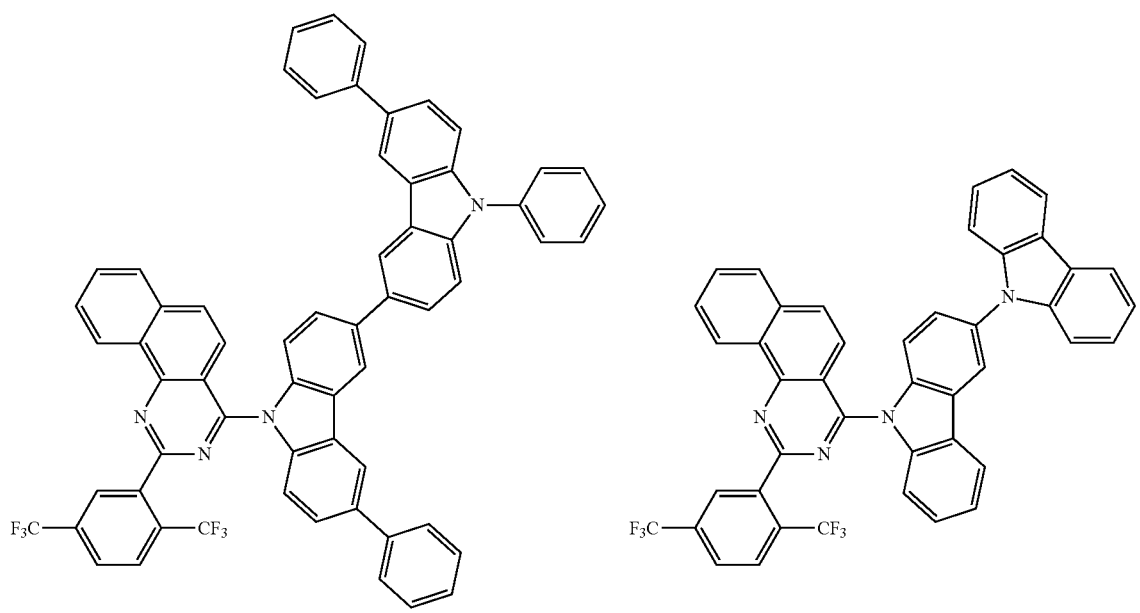
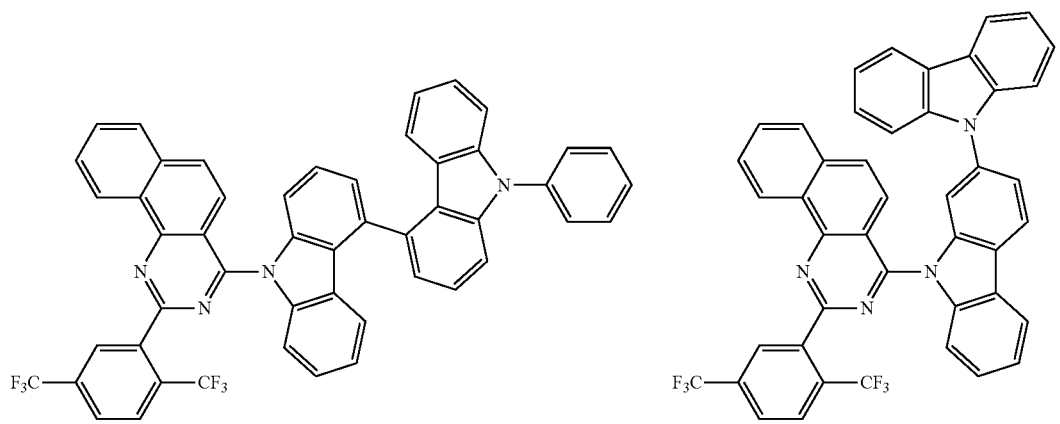

-continued
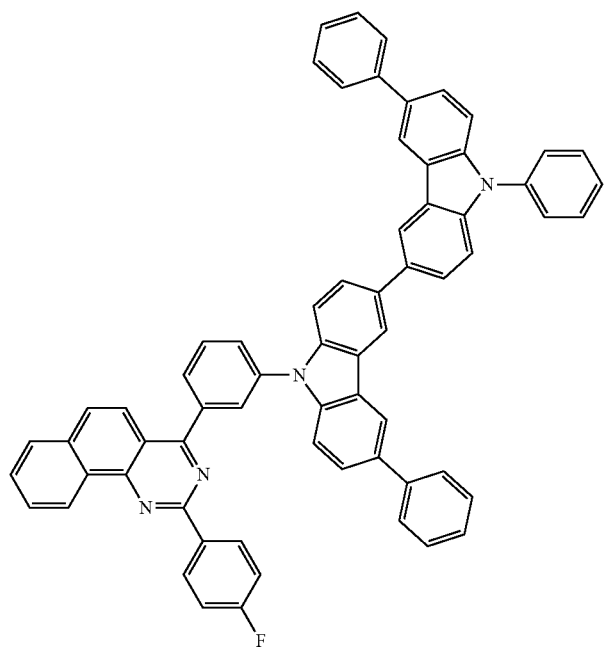
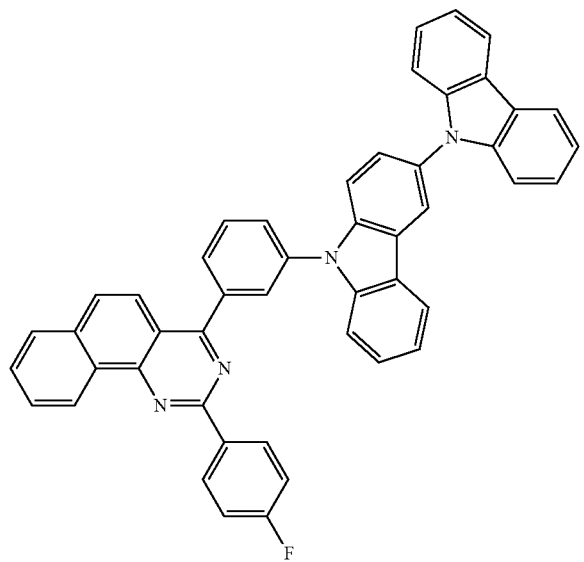
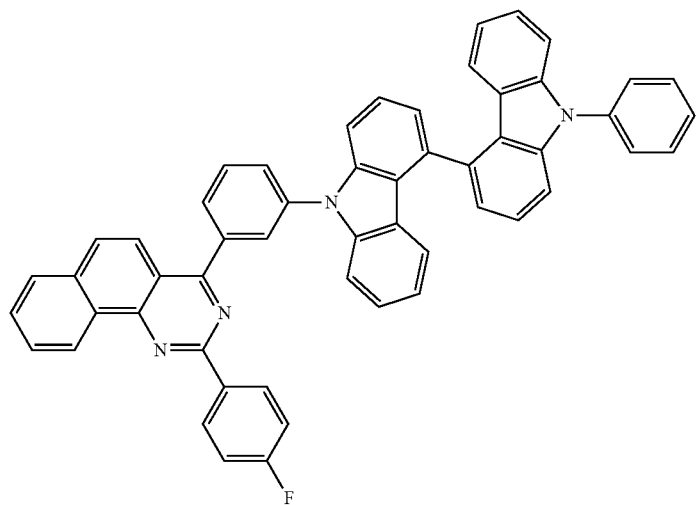

59 60
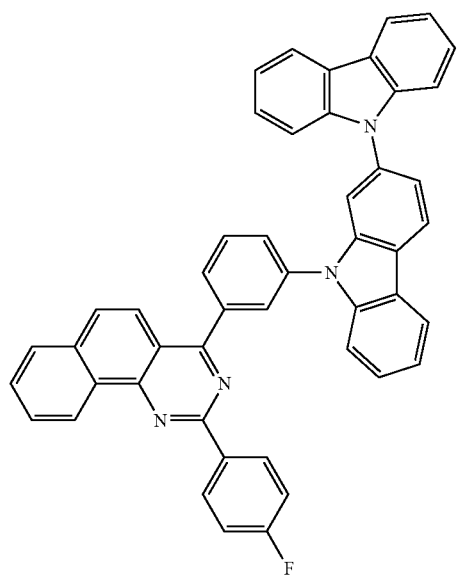 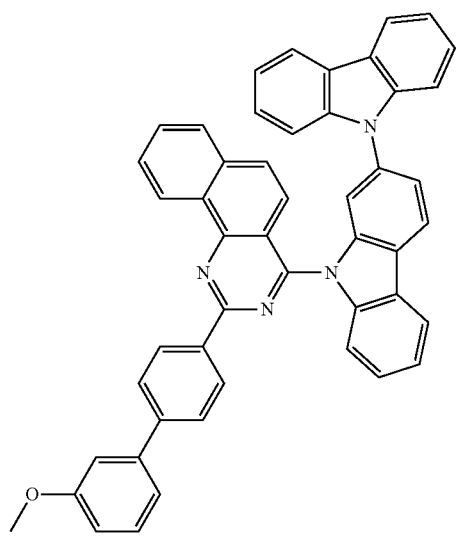
-continued
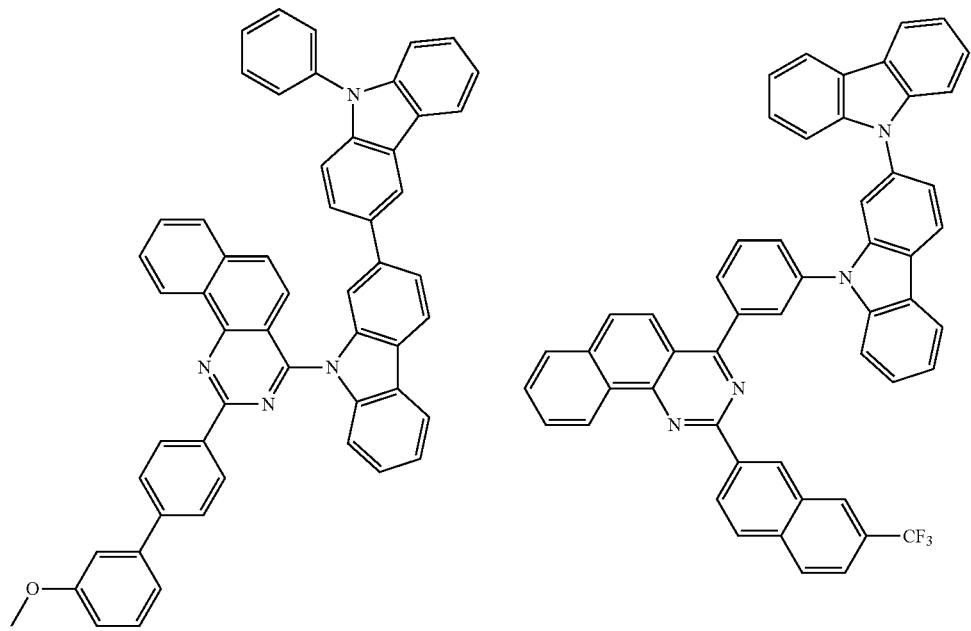

-continued
61
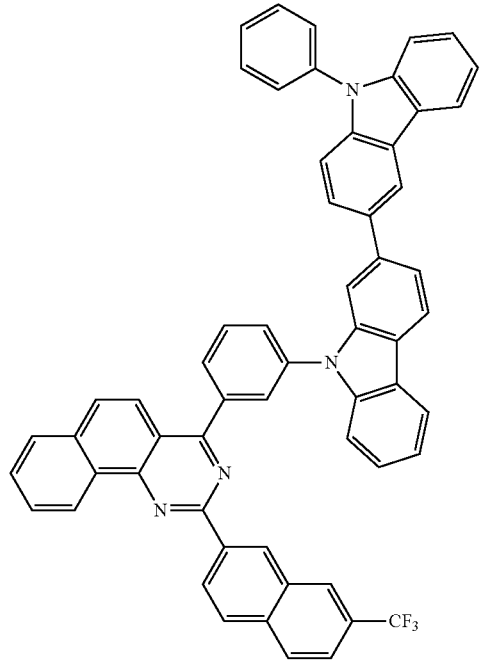
62
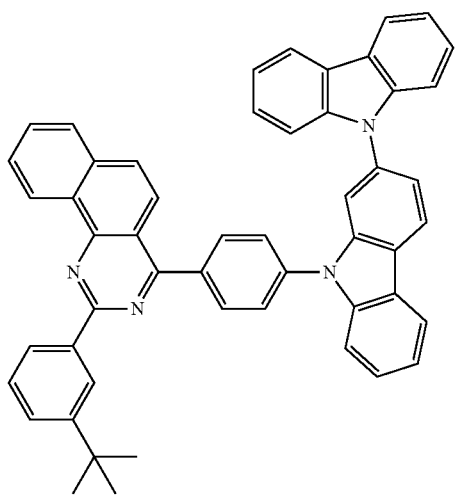
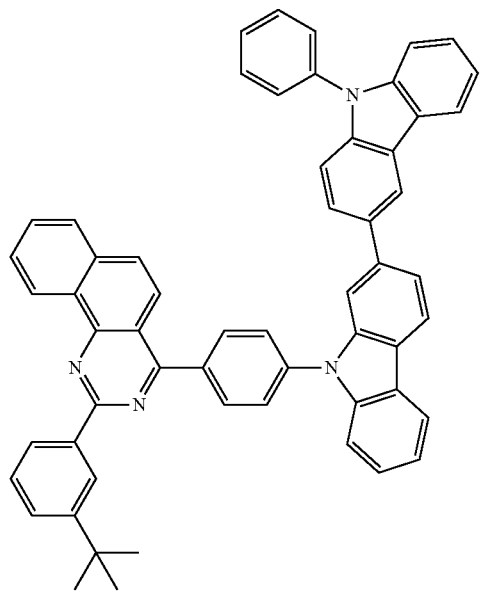
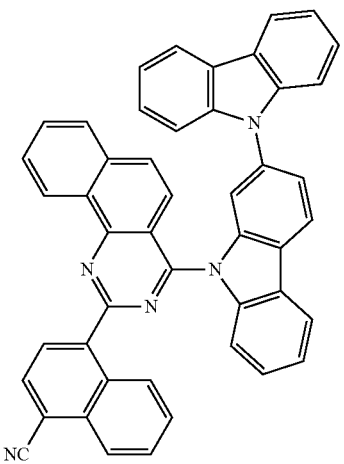

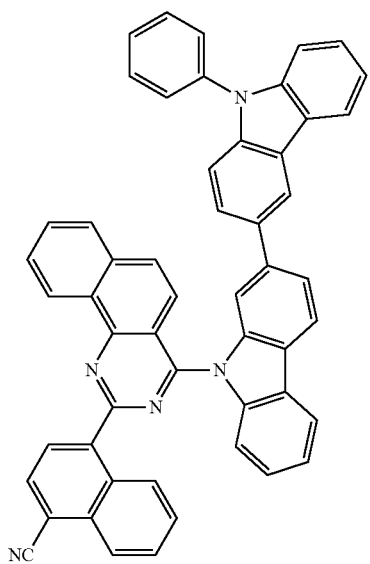
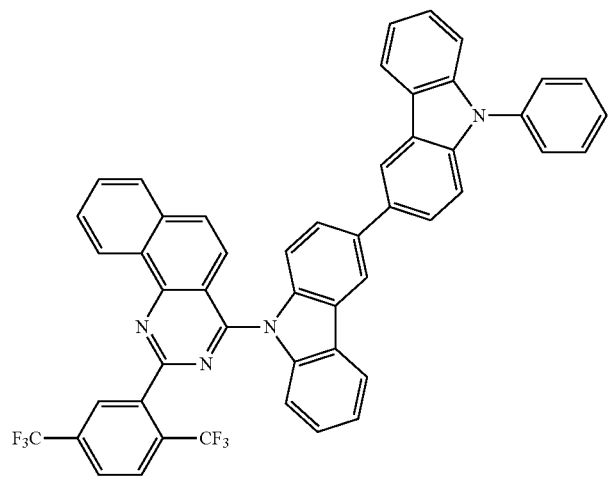
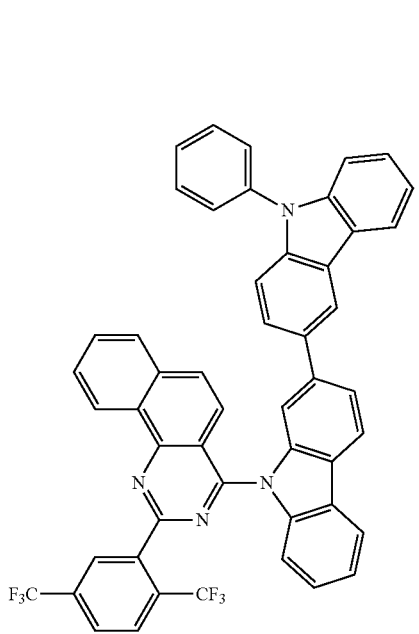
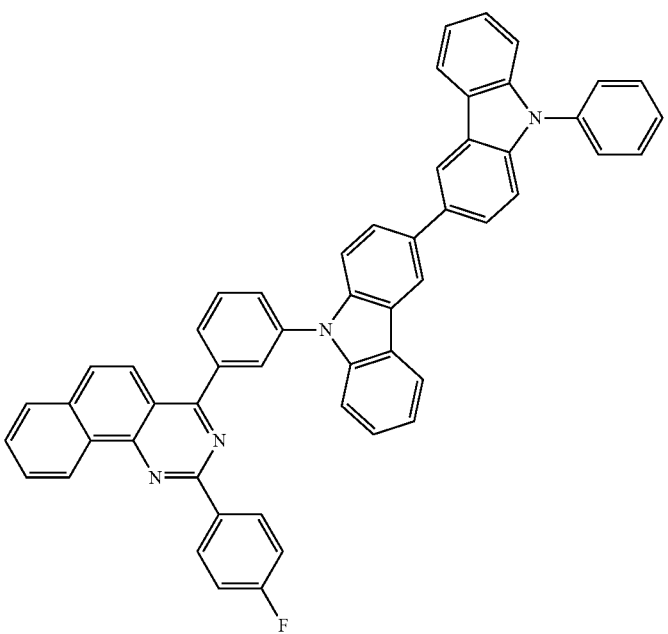

-continued
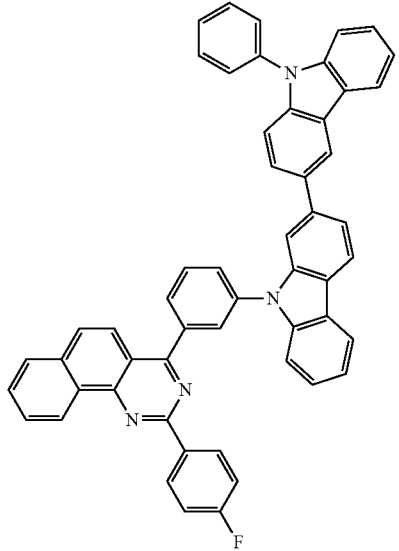
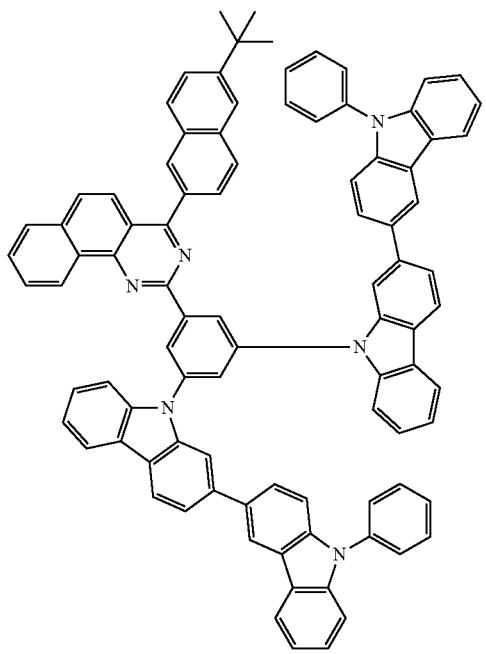
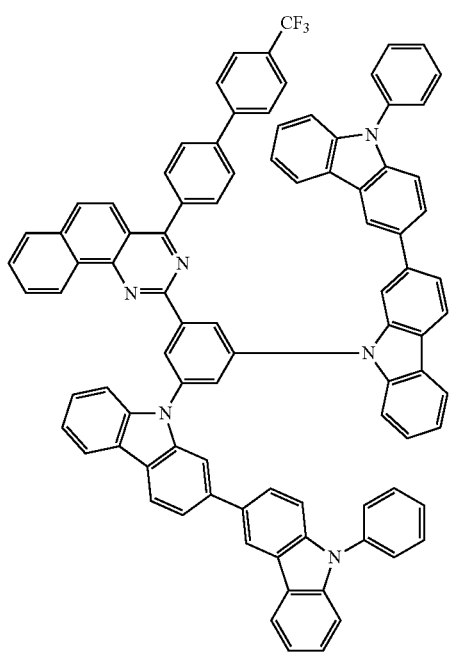
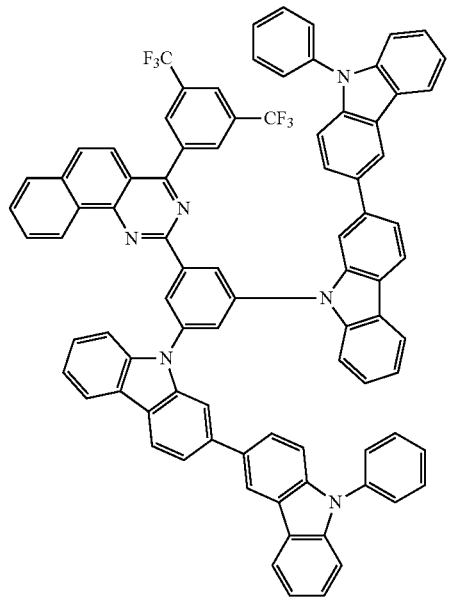

-continued
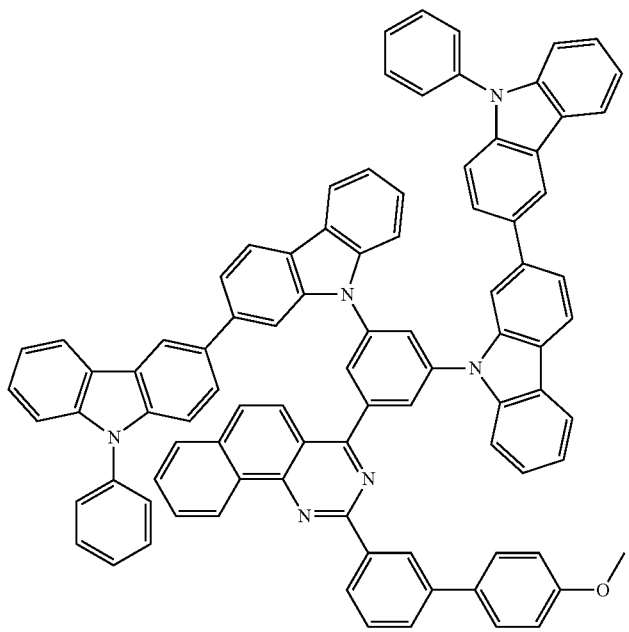
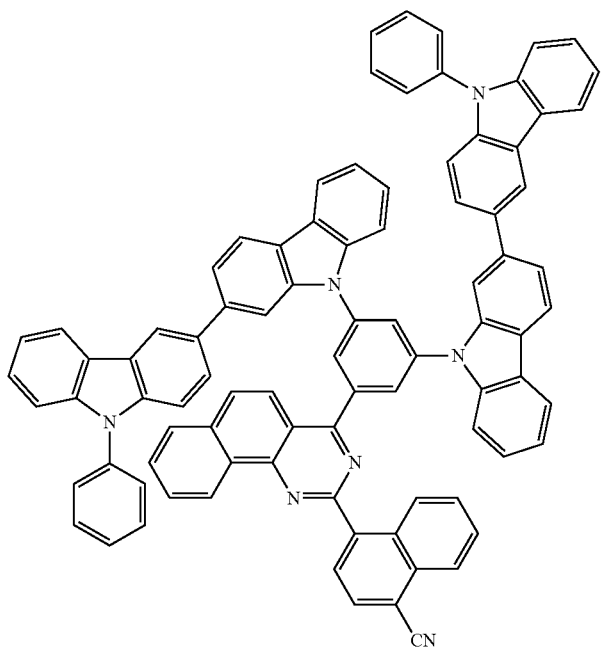

-continued
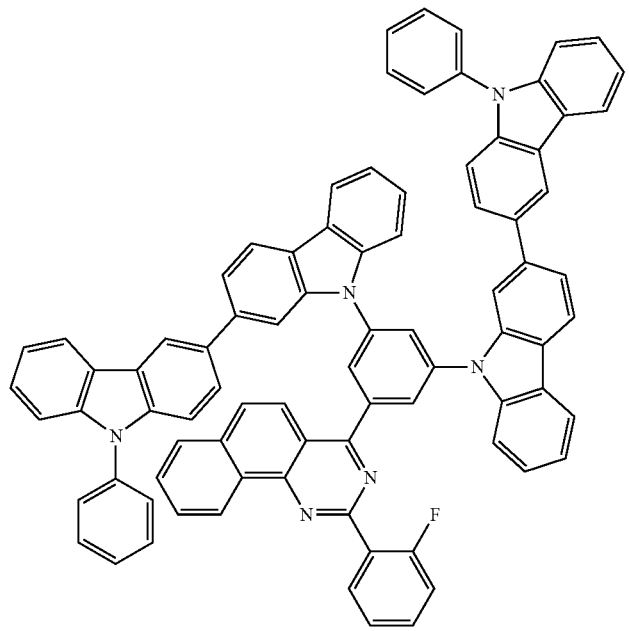
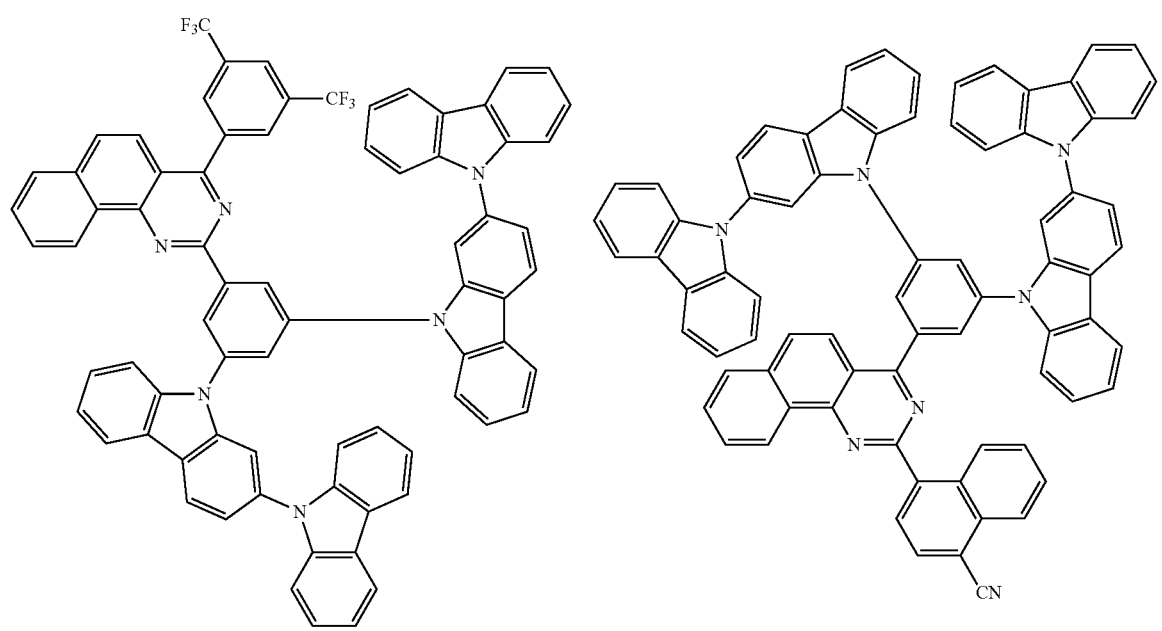

-continued
71
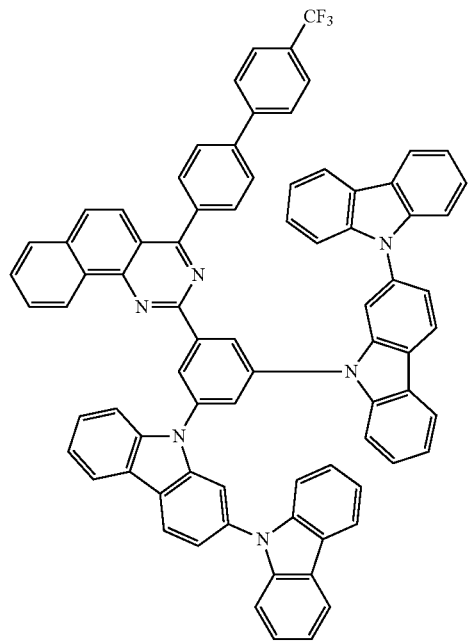
72
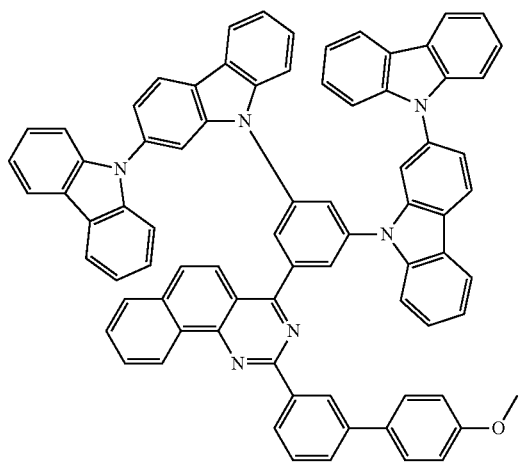
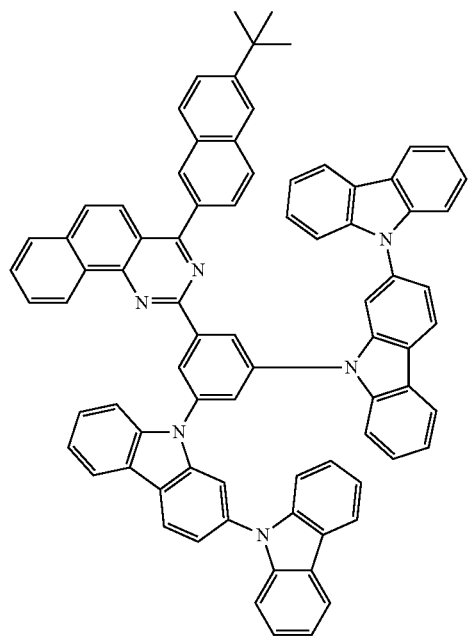
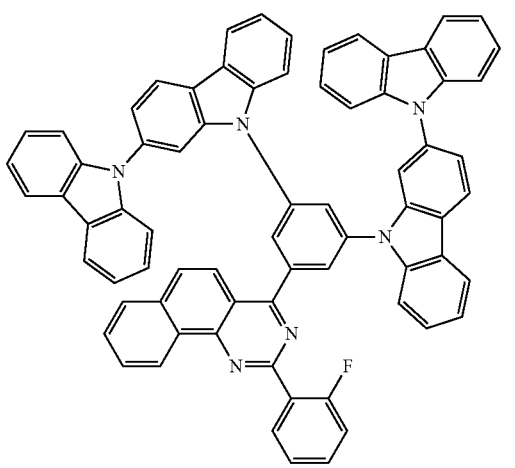

-continued
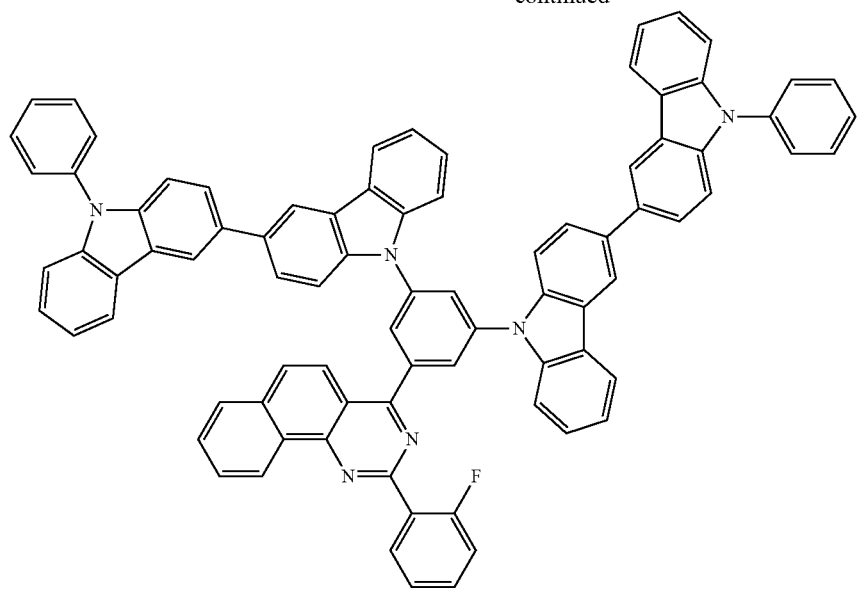
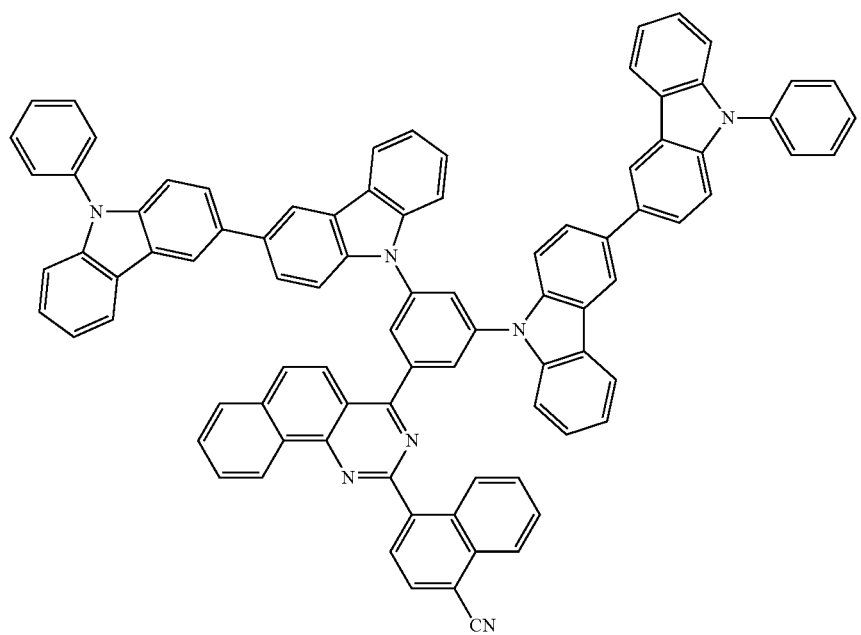

-continued
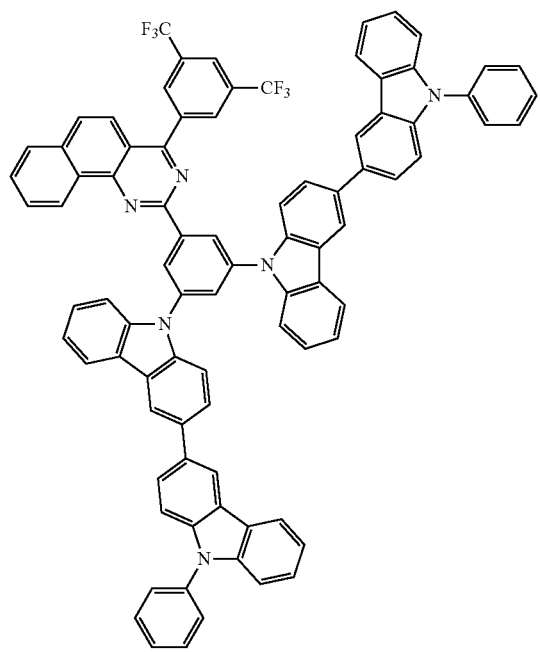
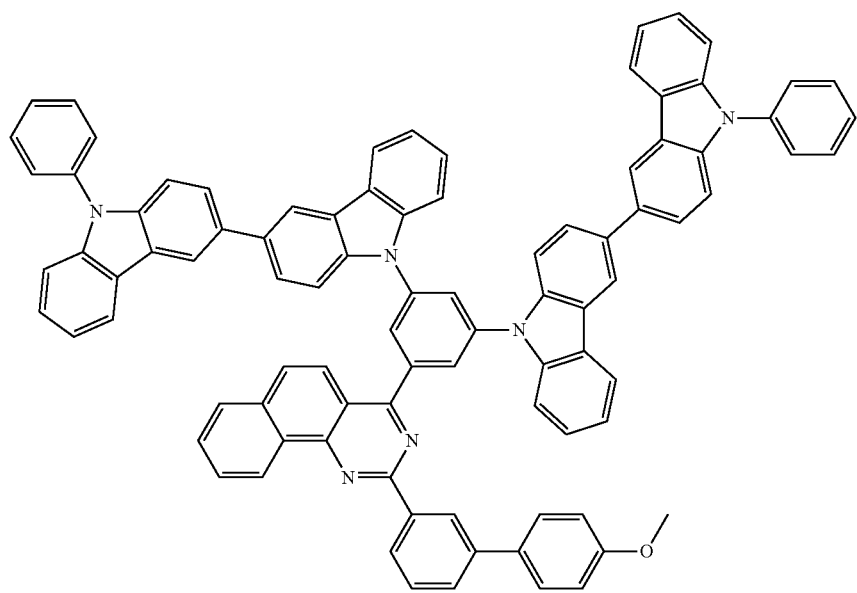

-continued
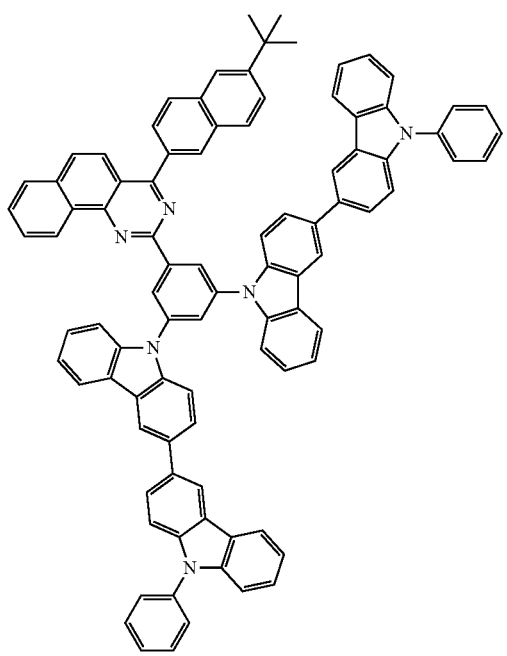
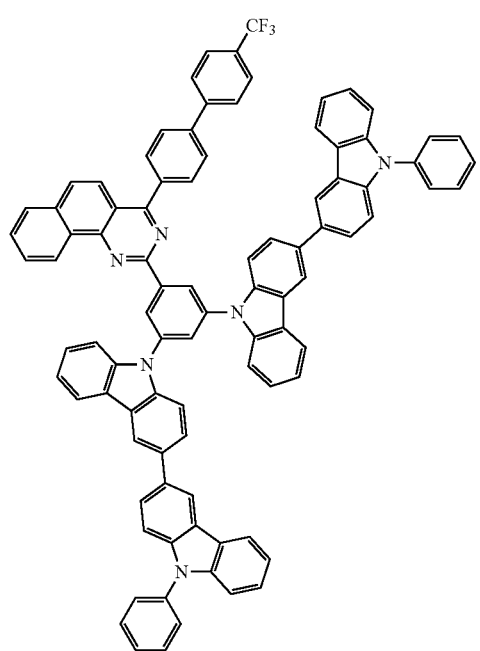

-continued
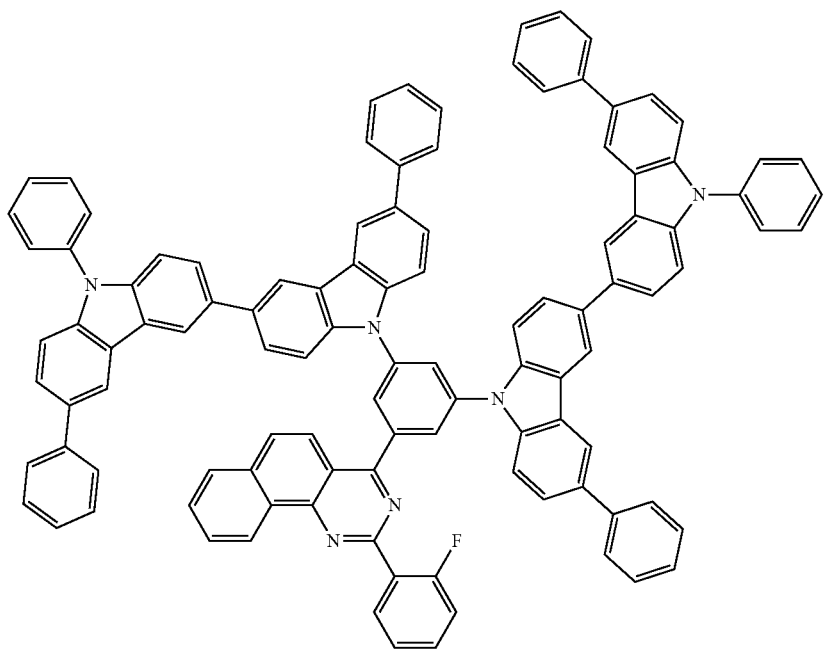
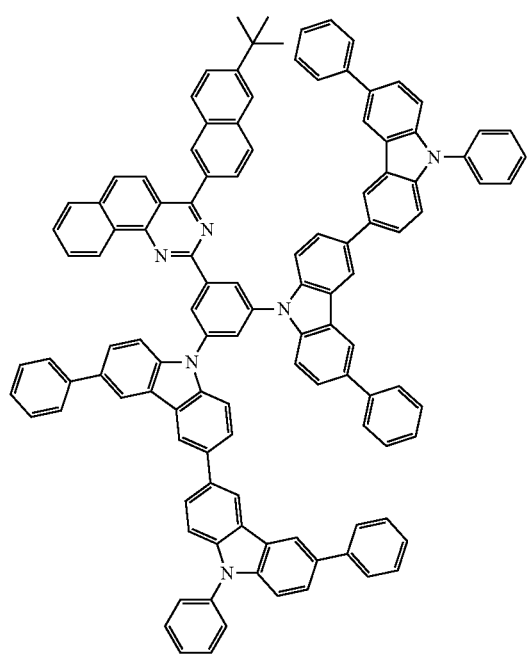

-continued
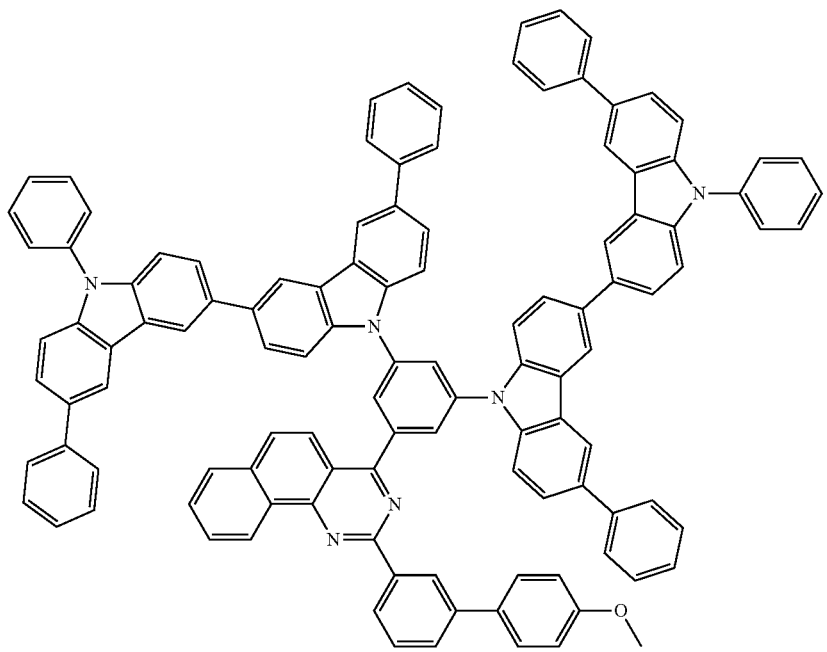

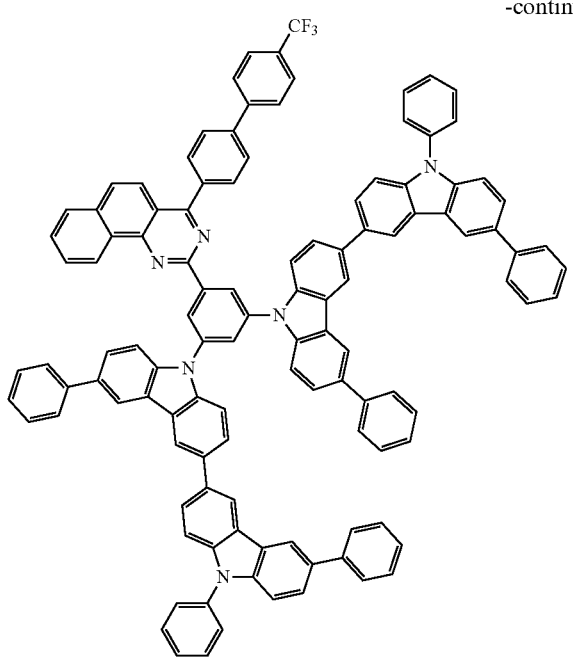
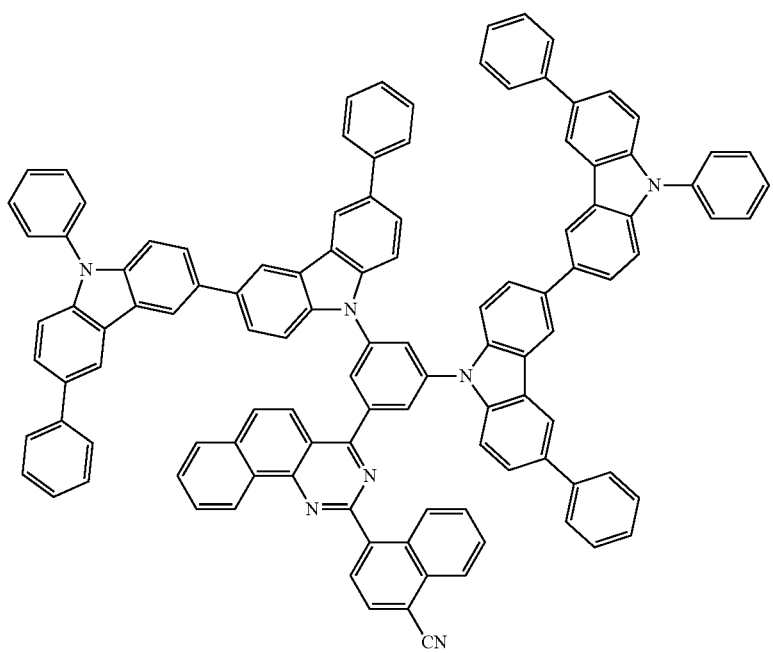

-continued
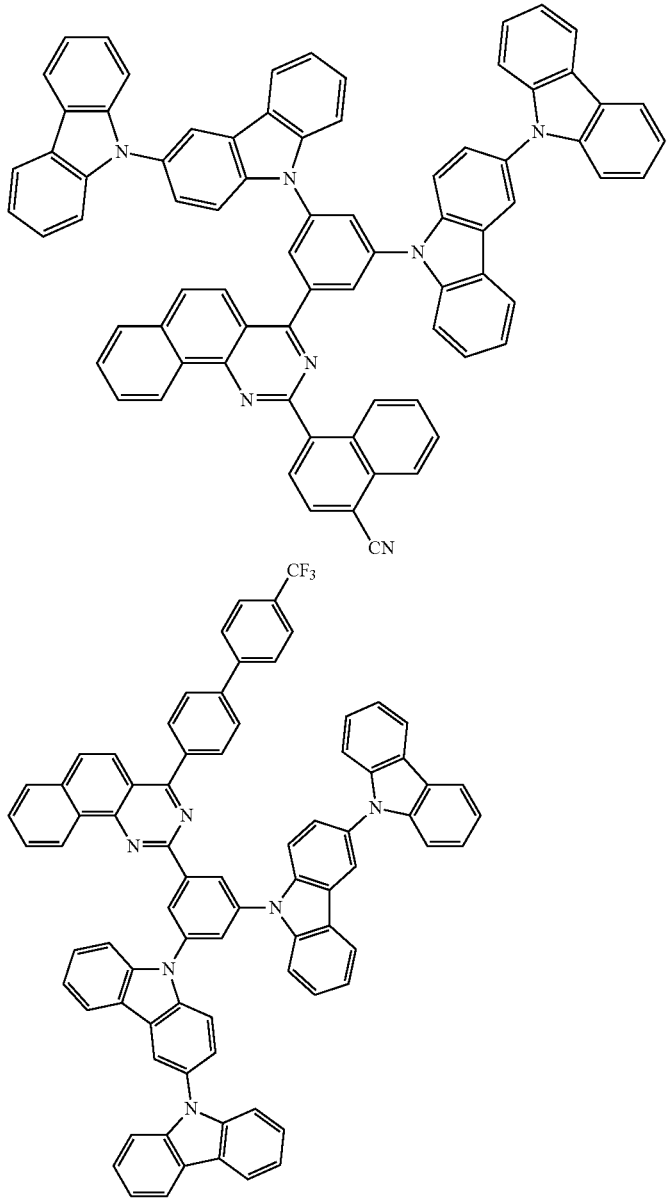
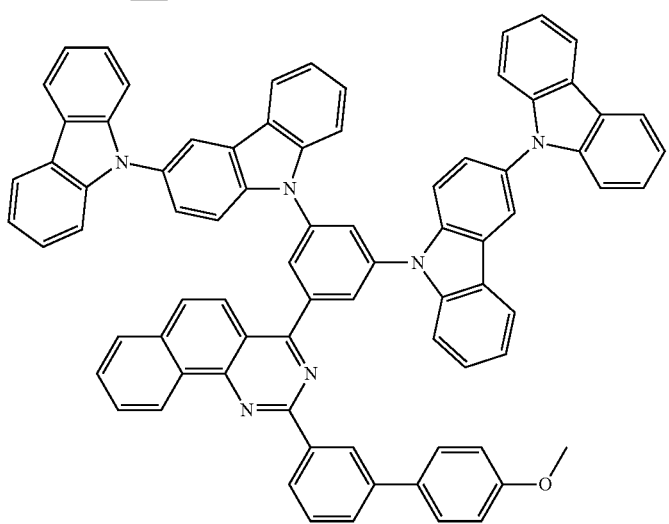

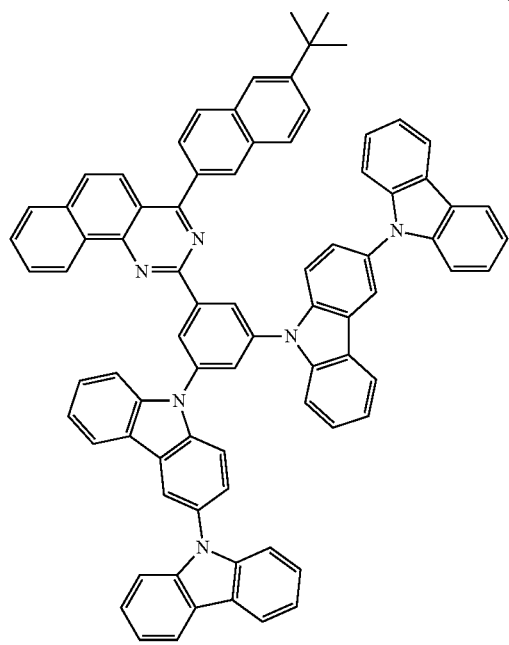
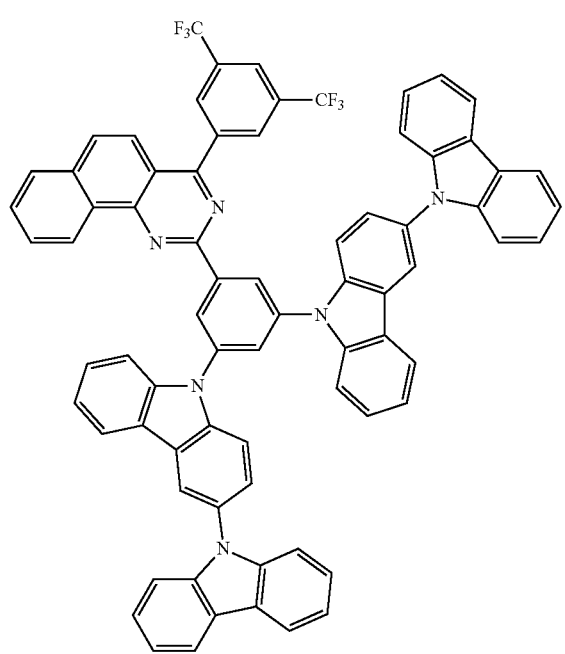

-continued
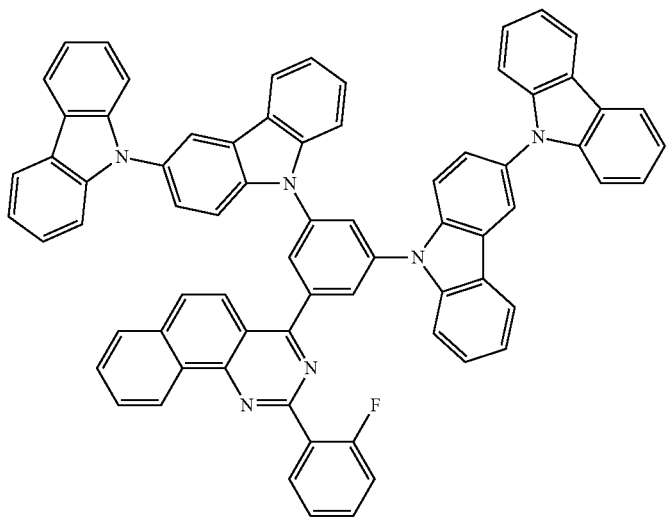
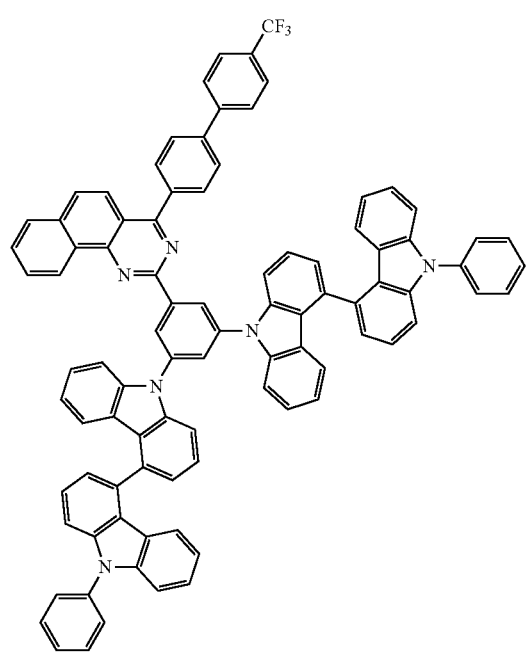

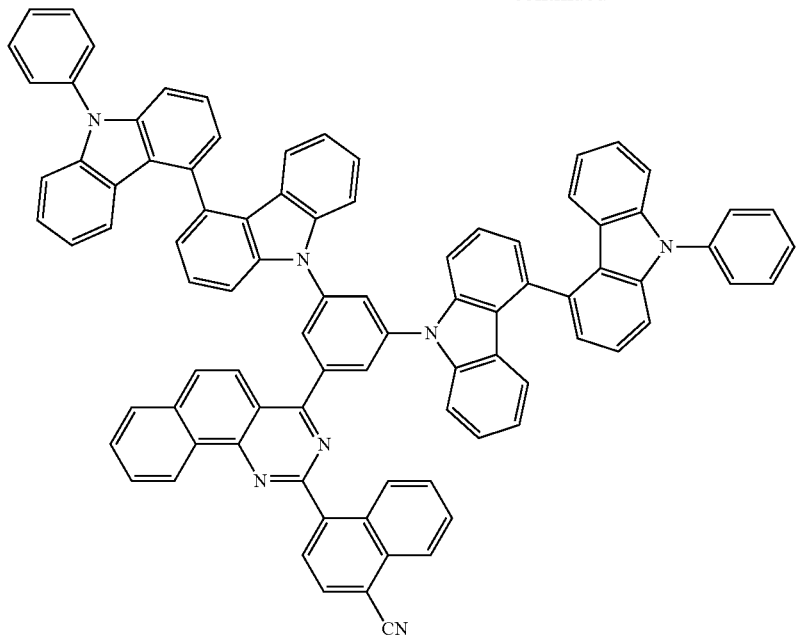
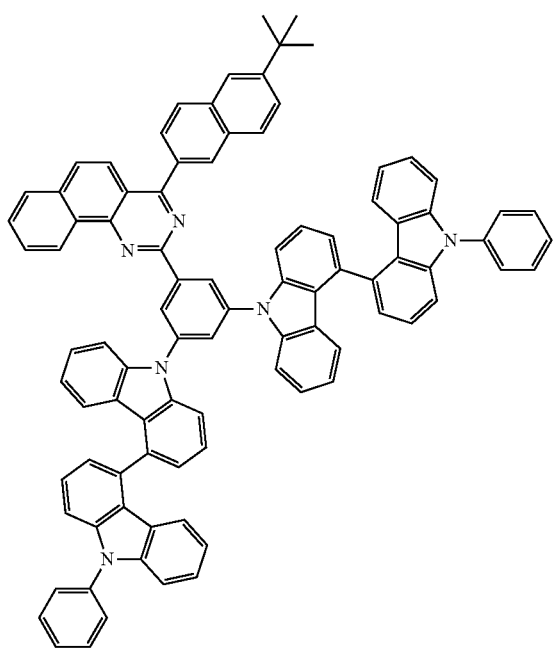

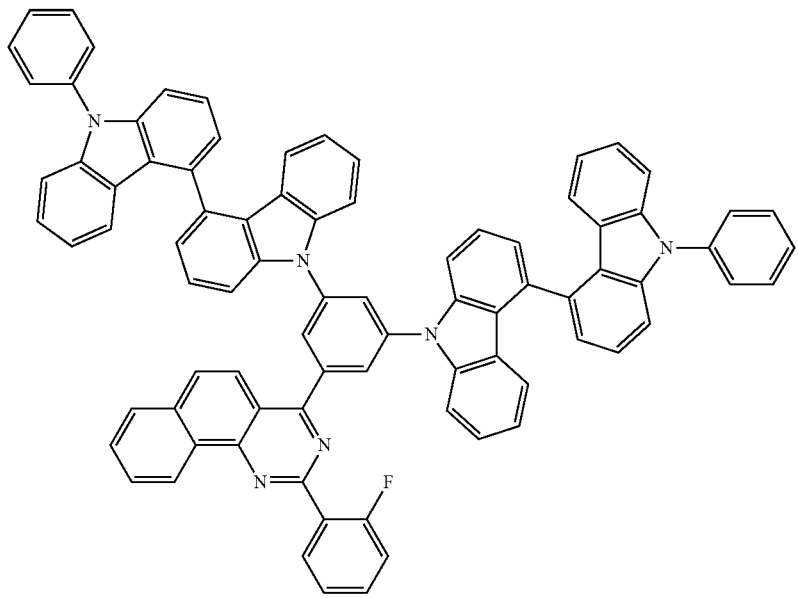
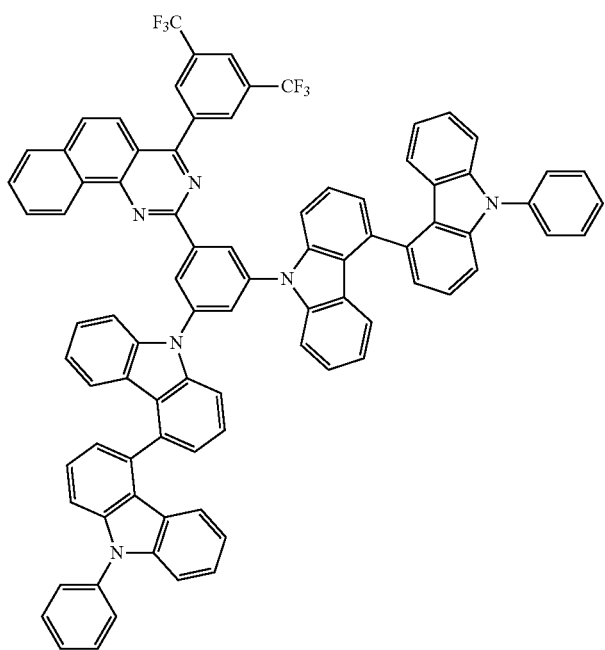

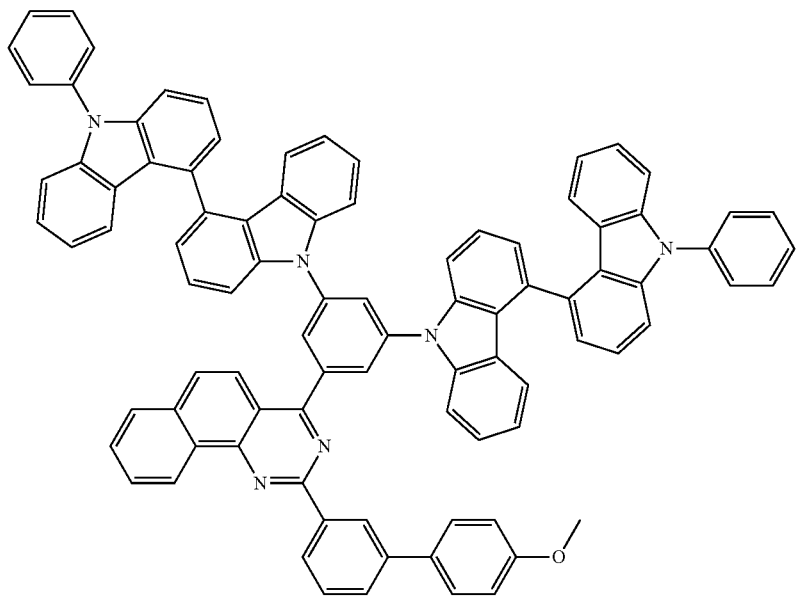
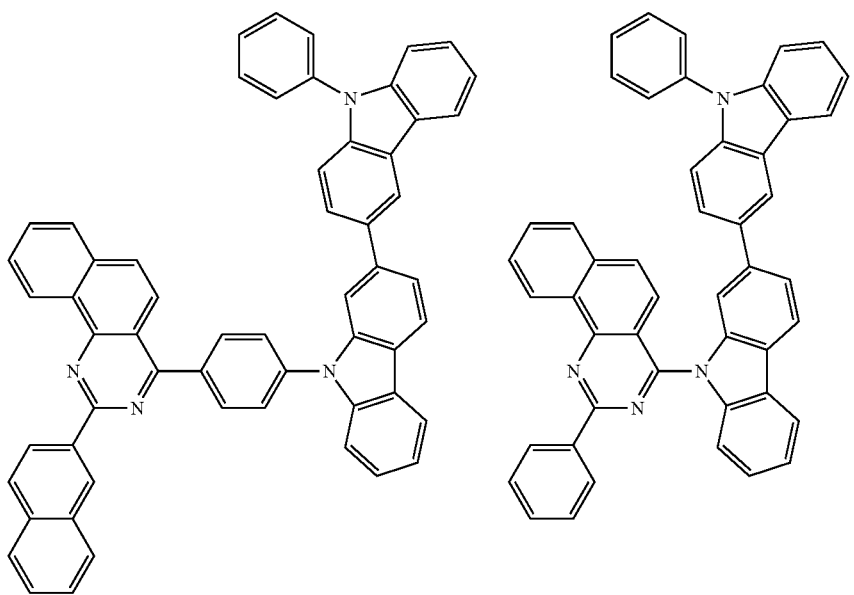

97
98
-continued
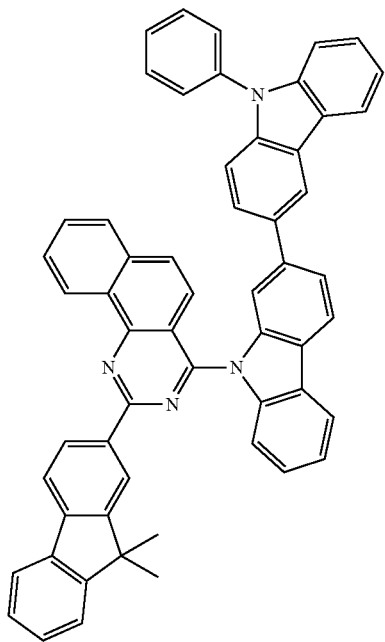
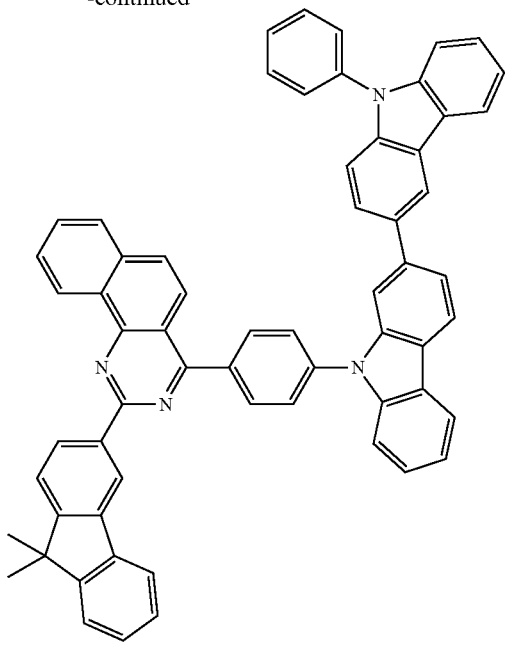
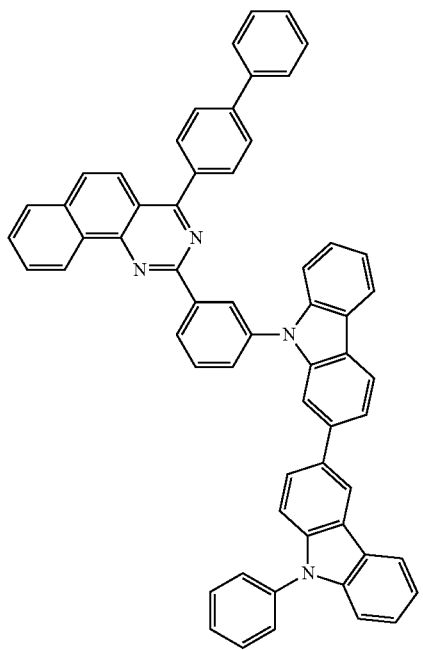
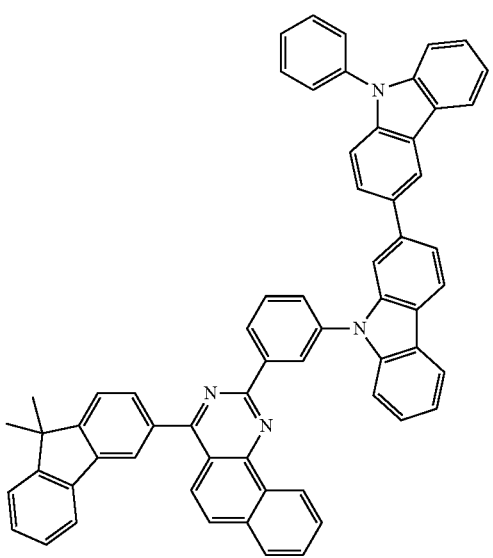

99 100
-continued
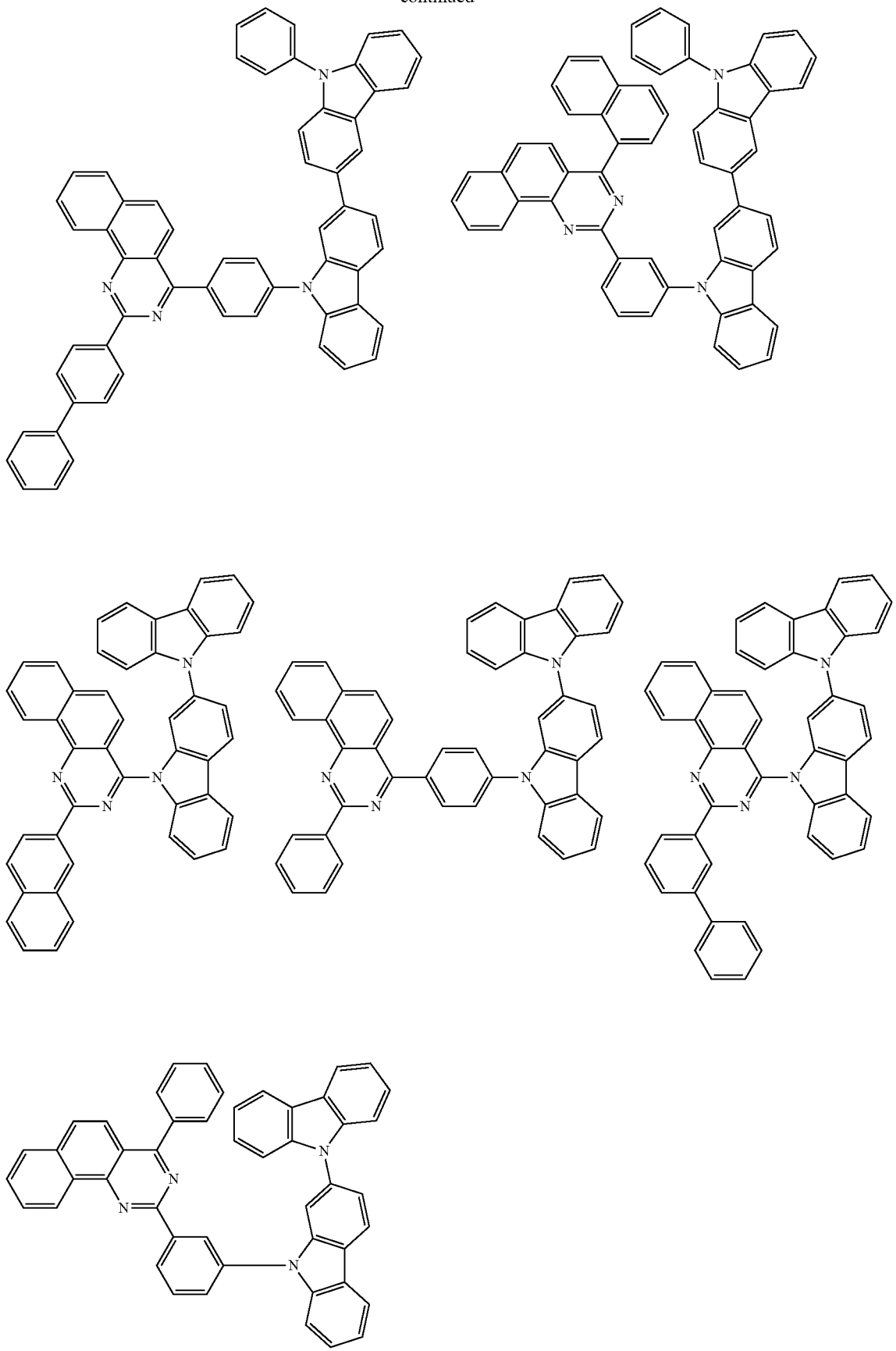

-continued
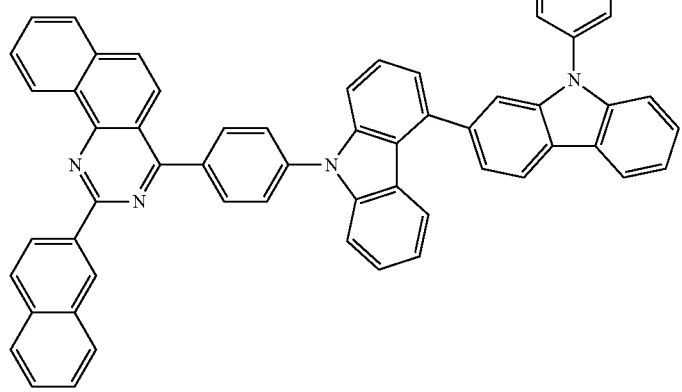
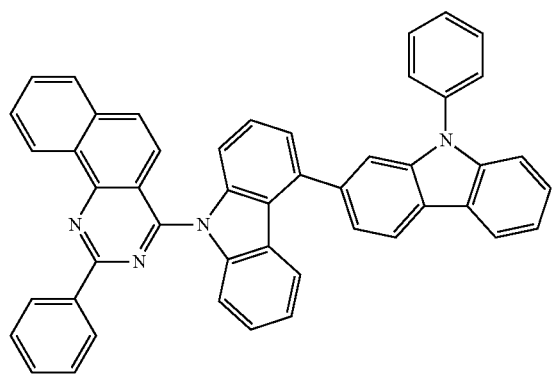
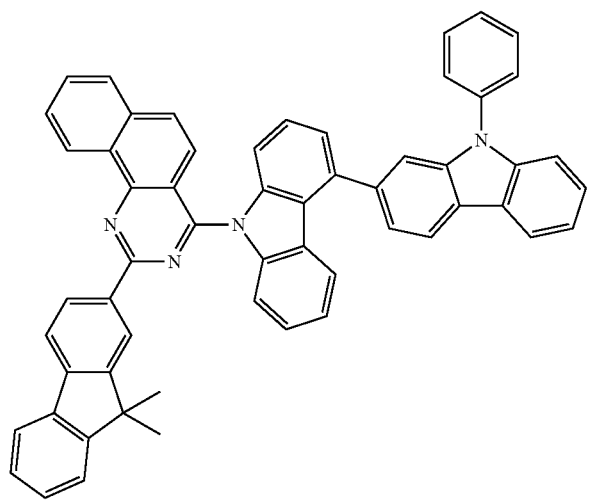

-continued
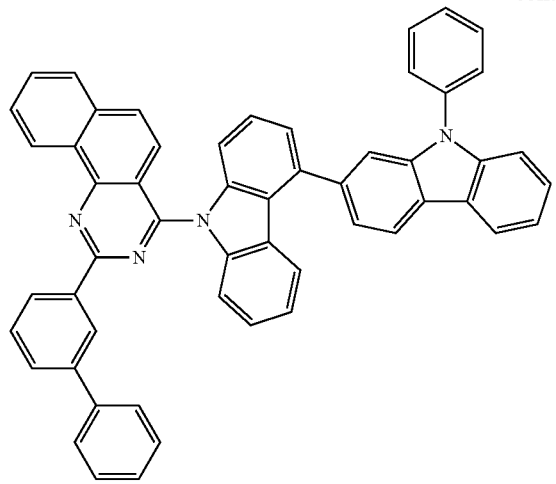
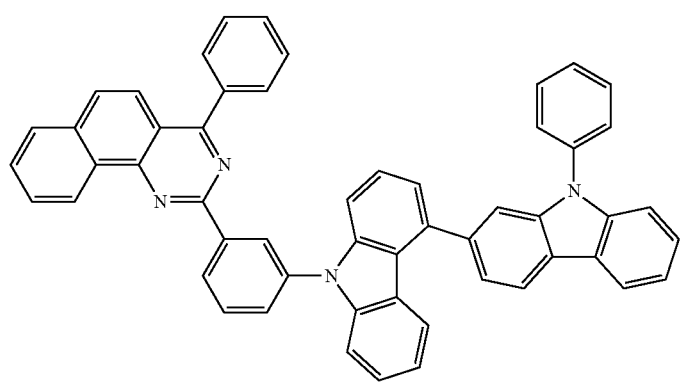
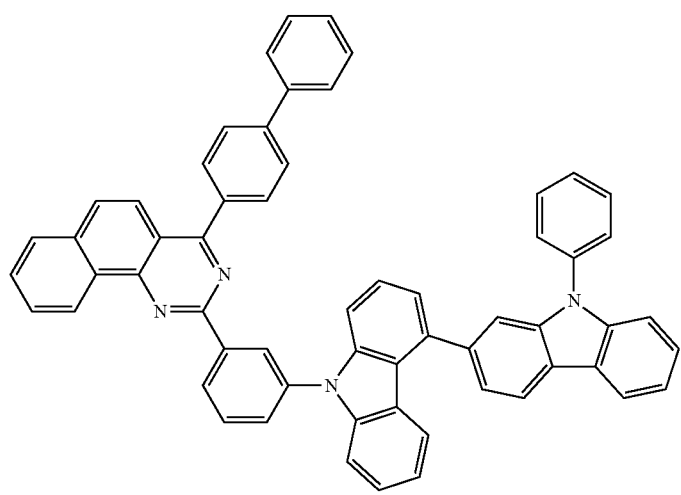

-continued
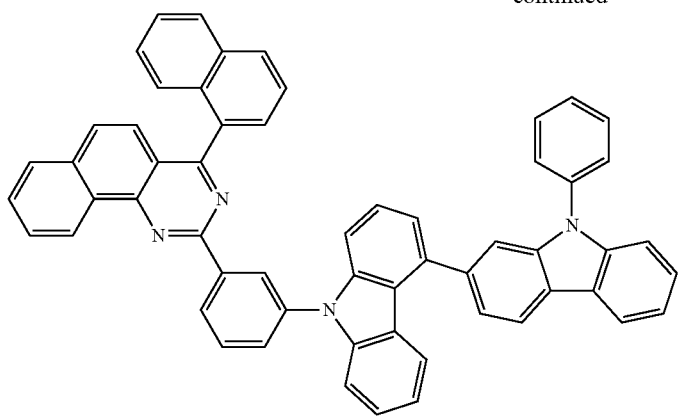
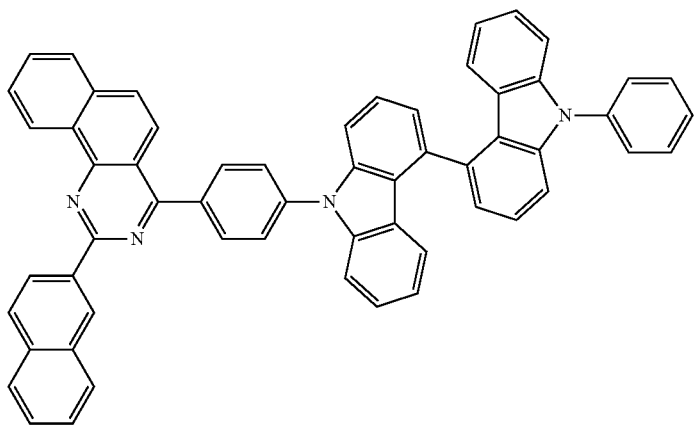
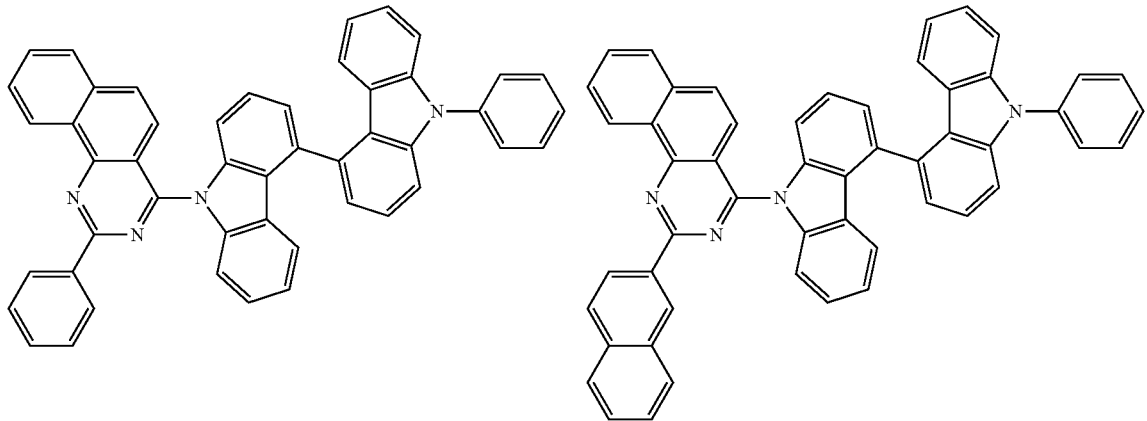
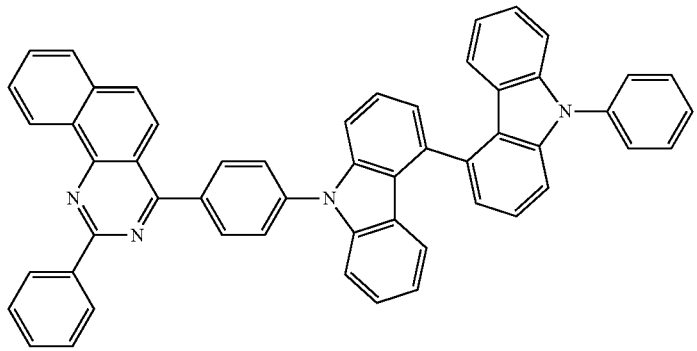

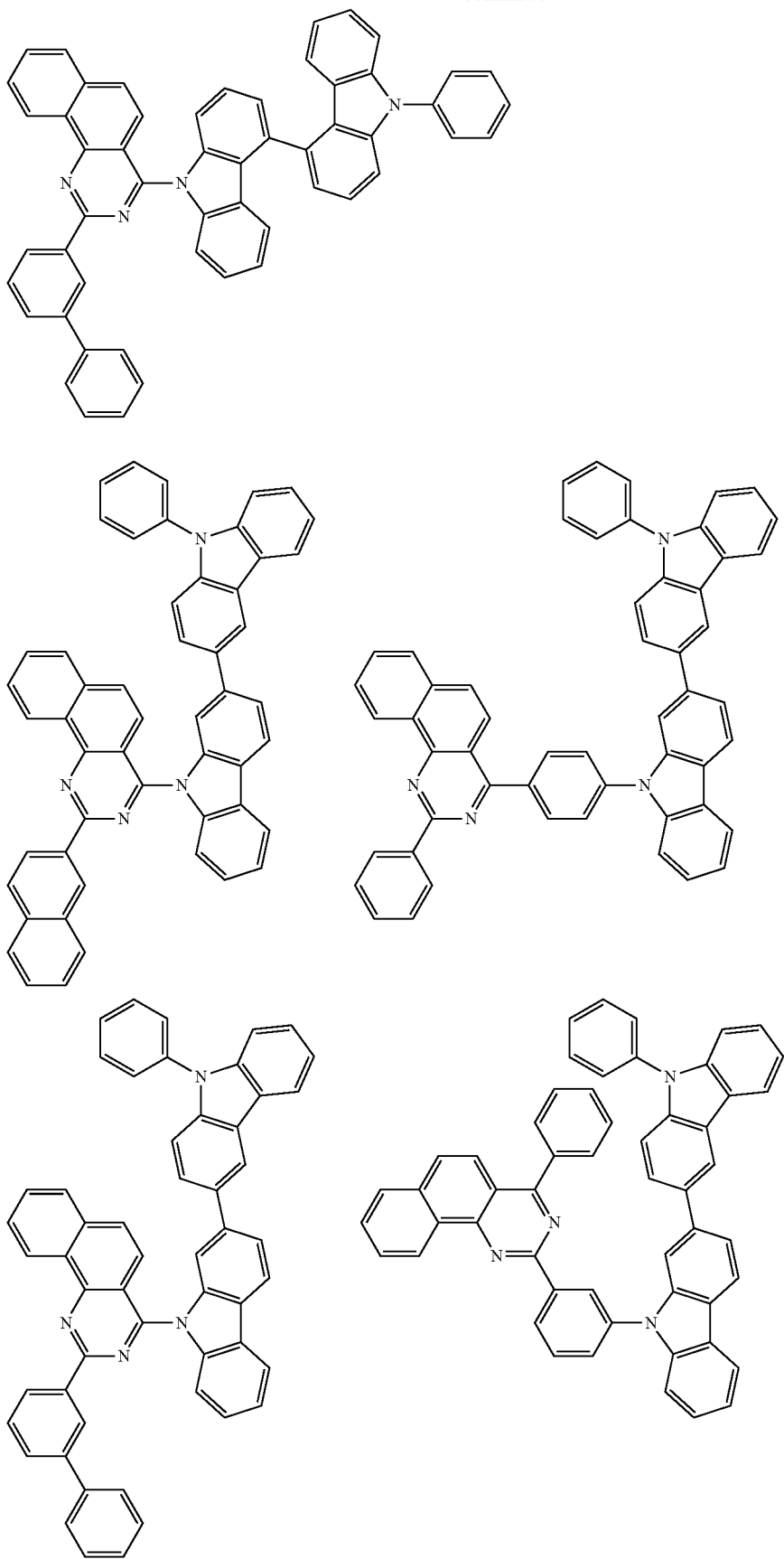

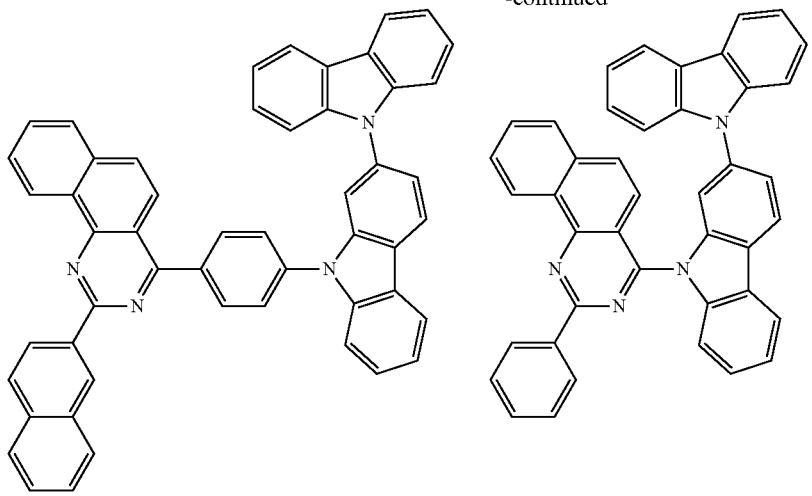
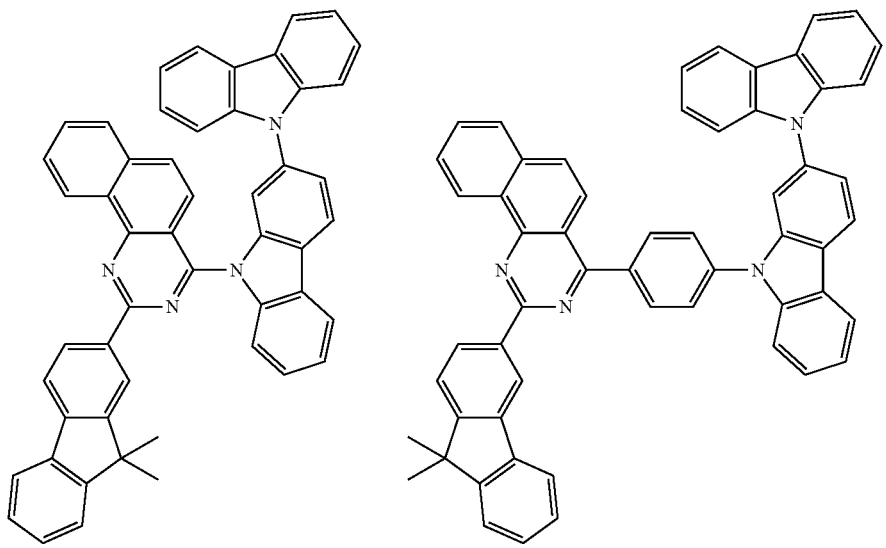
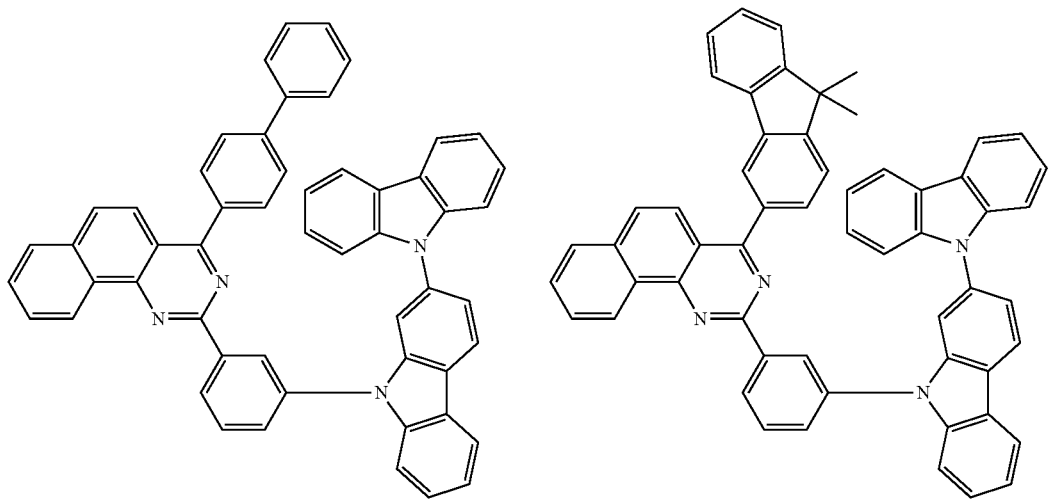

-continued
111
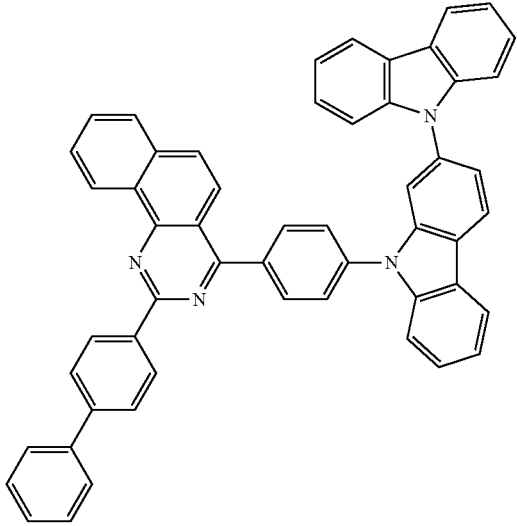
112
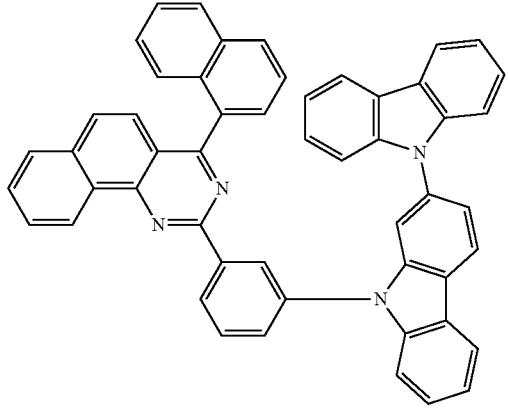
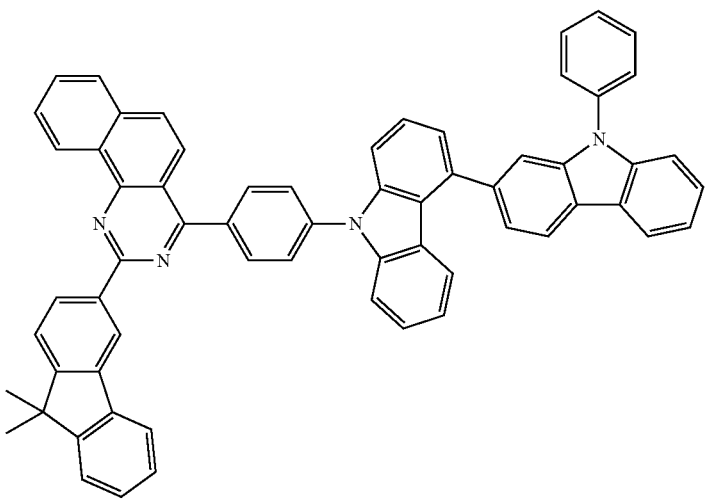
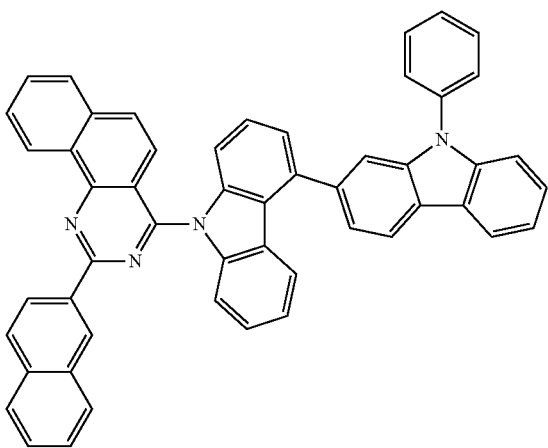

-continued
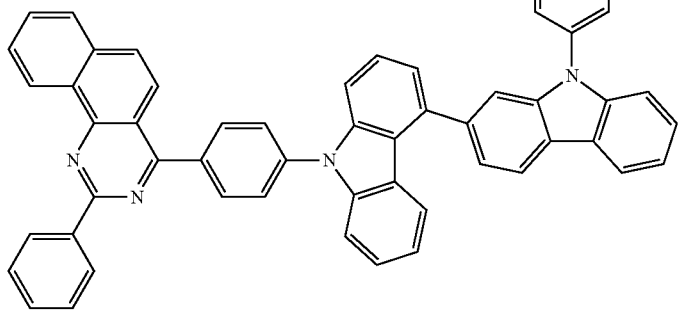
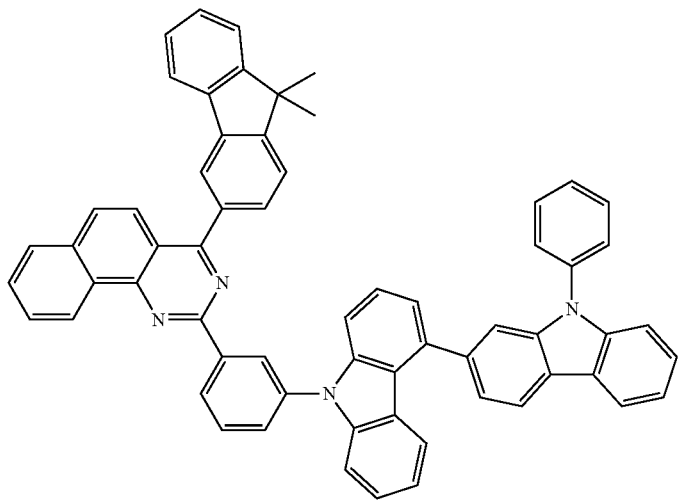
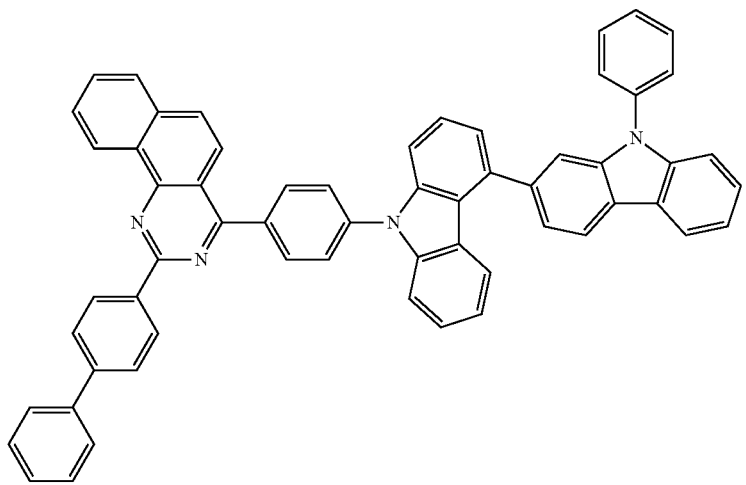

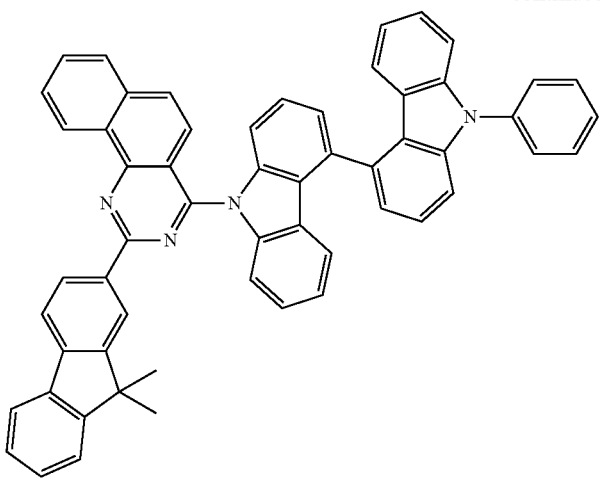
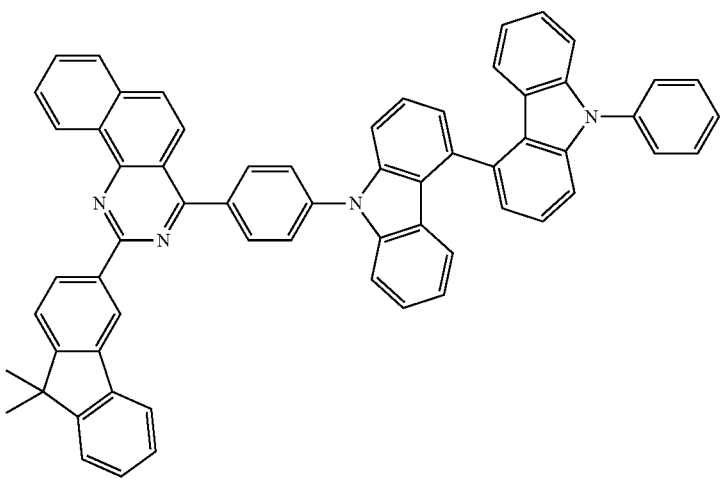
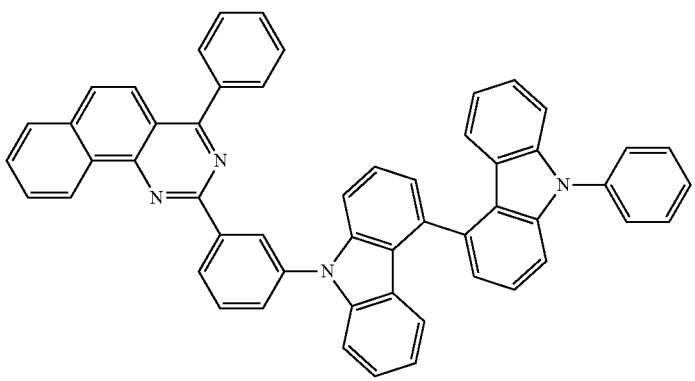

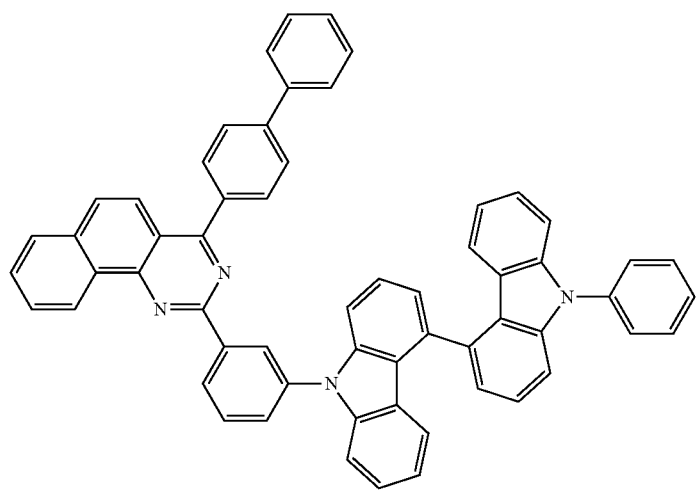
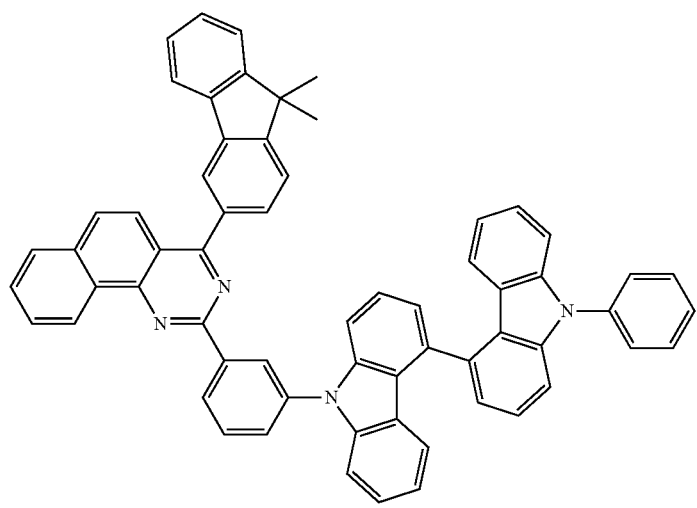
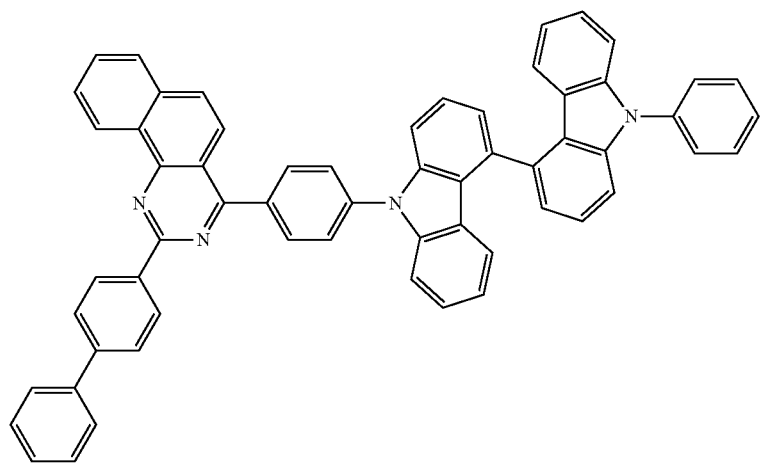

-continued
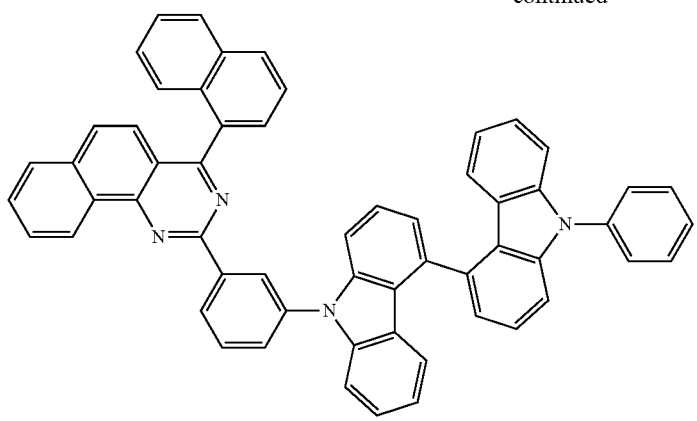
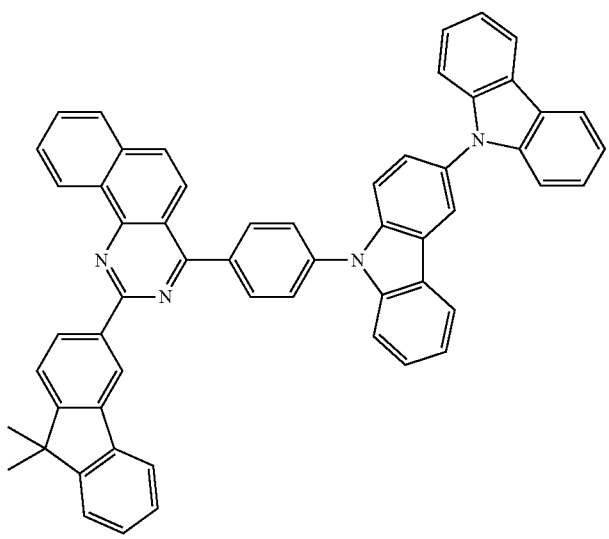
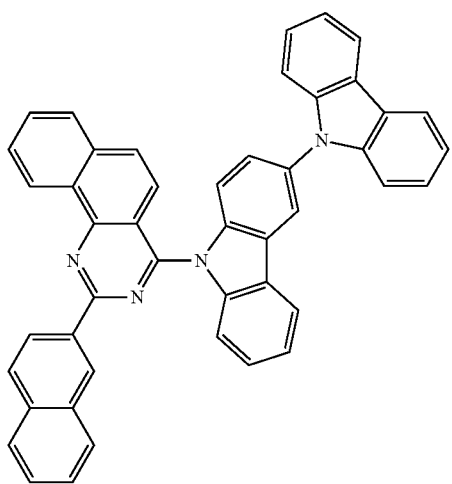

-continued
121
122
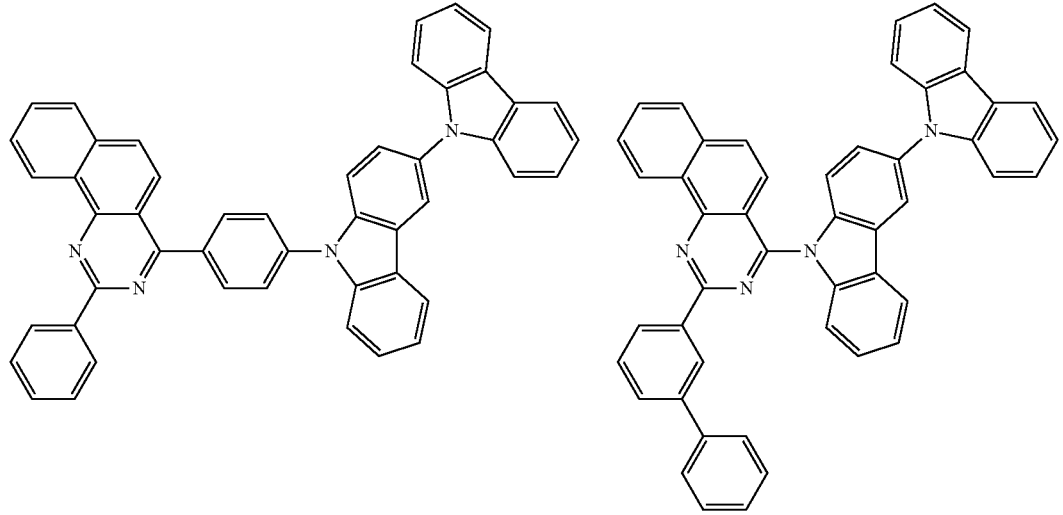
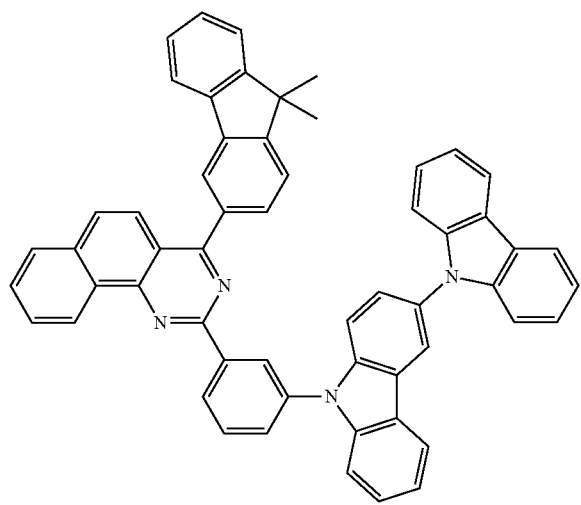
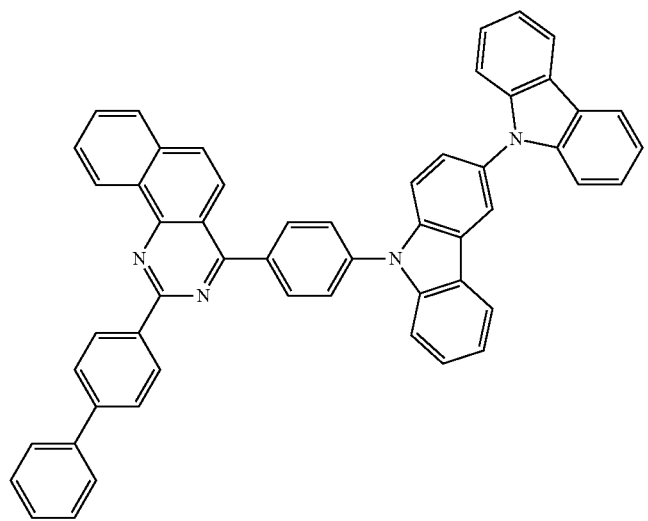

-continued
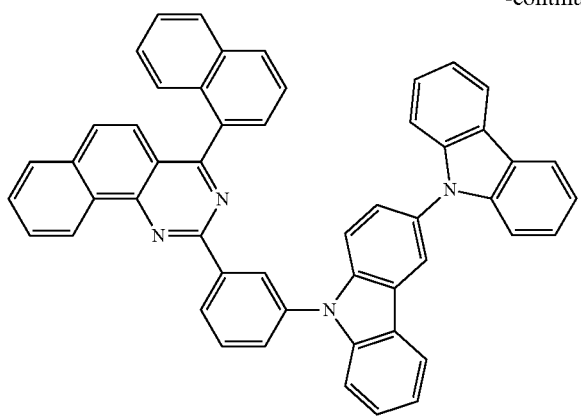
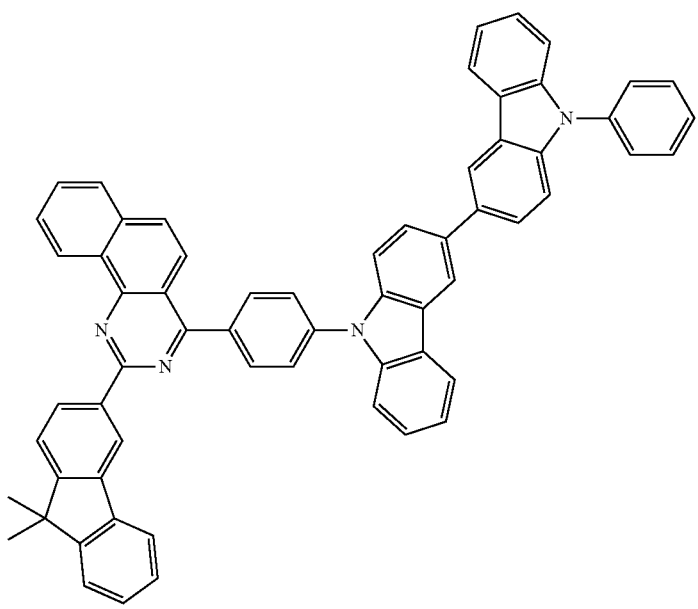
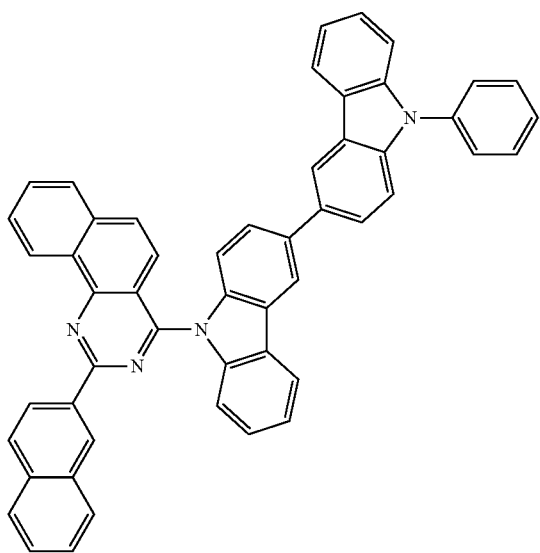

-continued
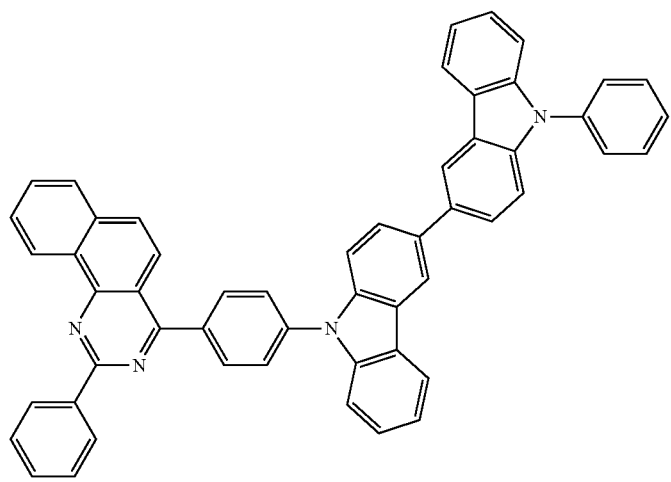
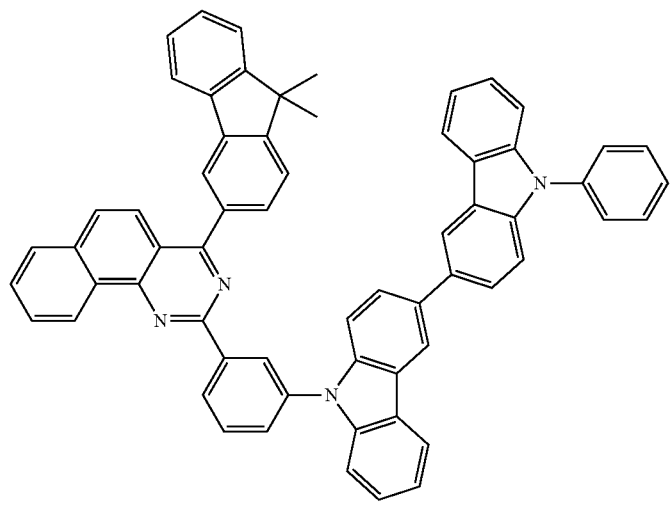
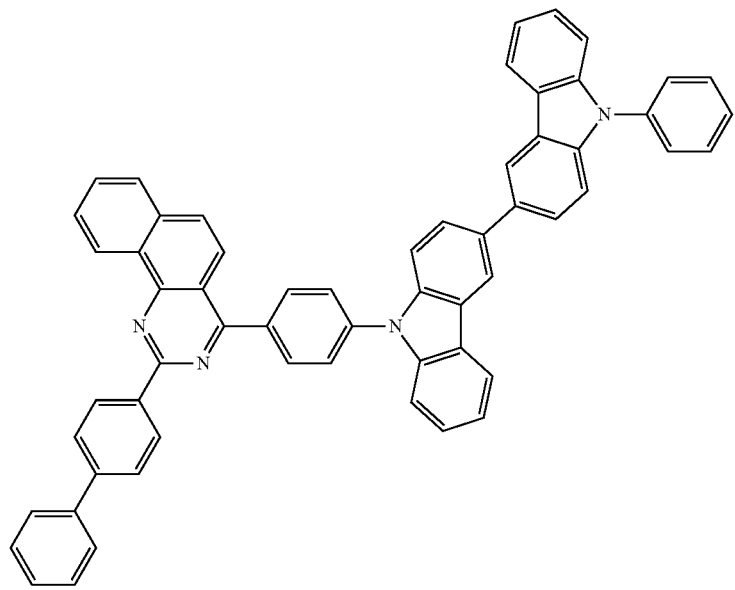

-continued
127
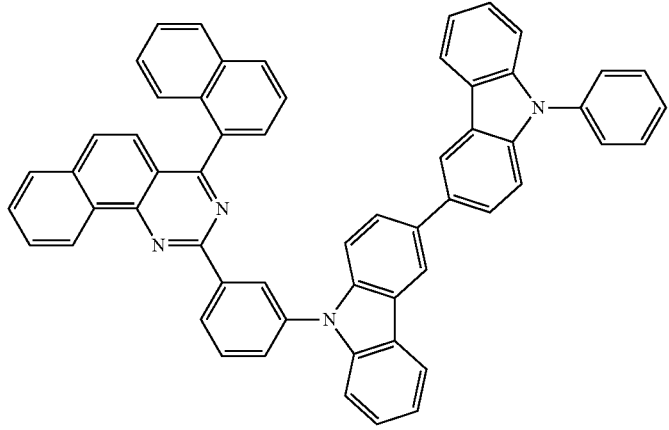
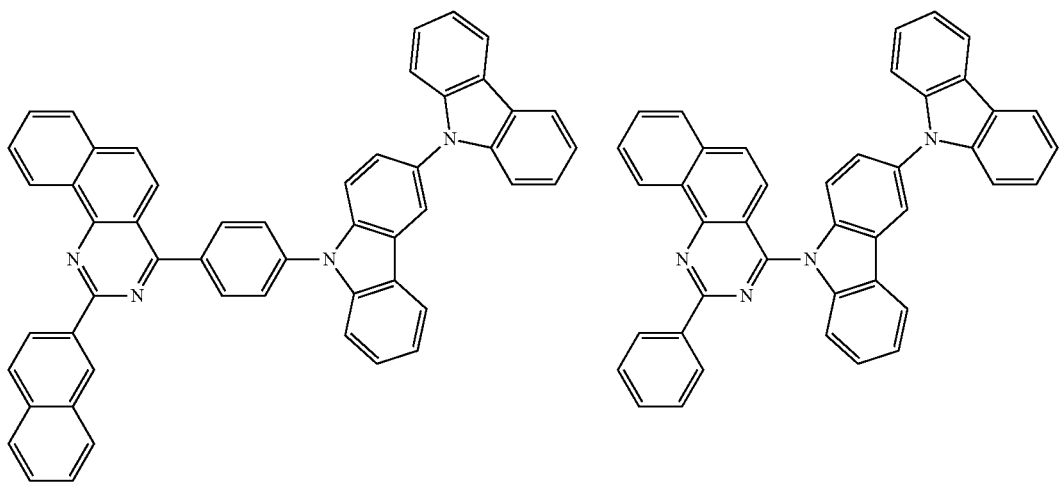
128
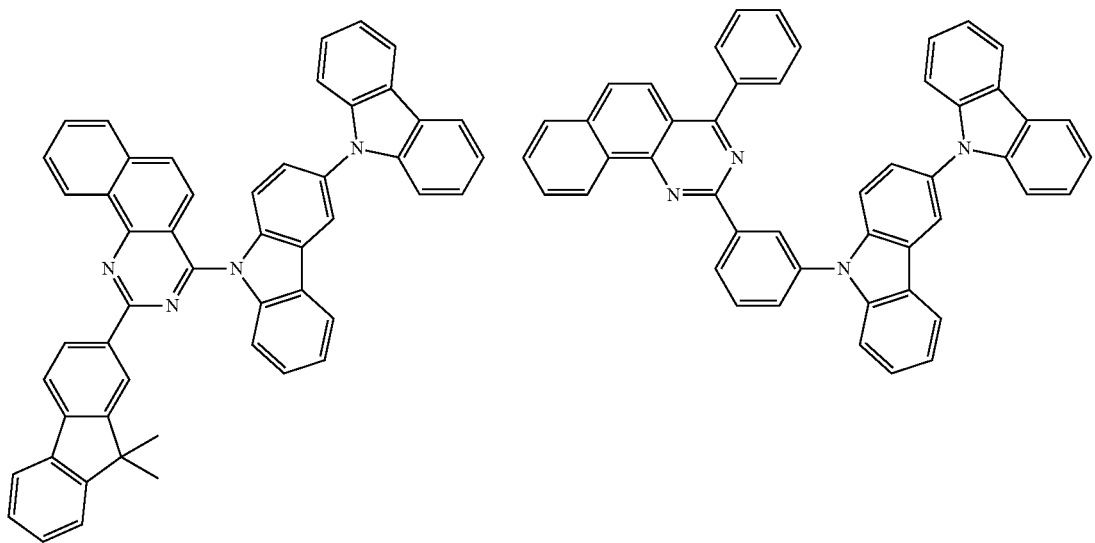

-continued
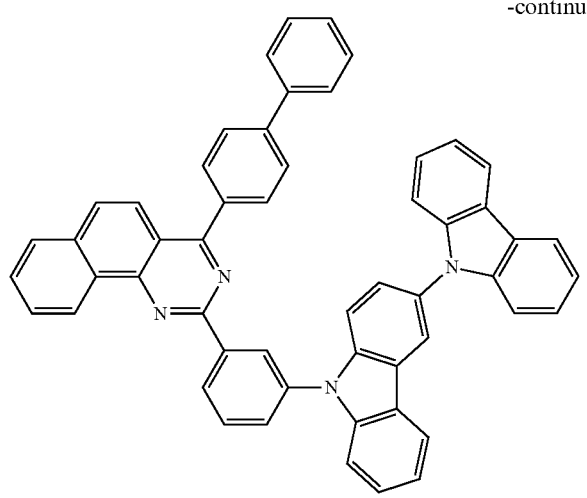

-continued
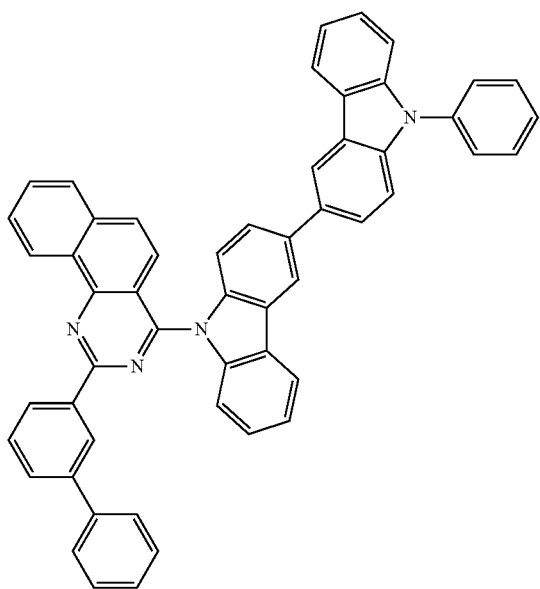
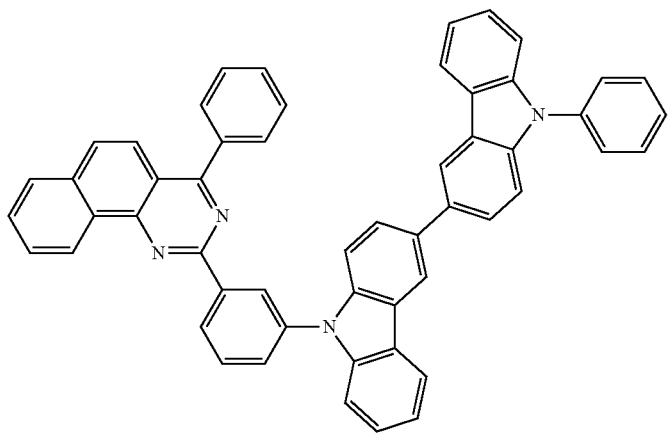
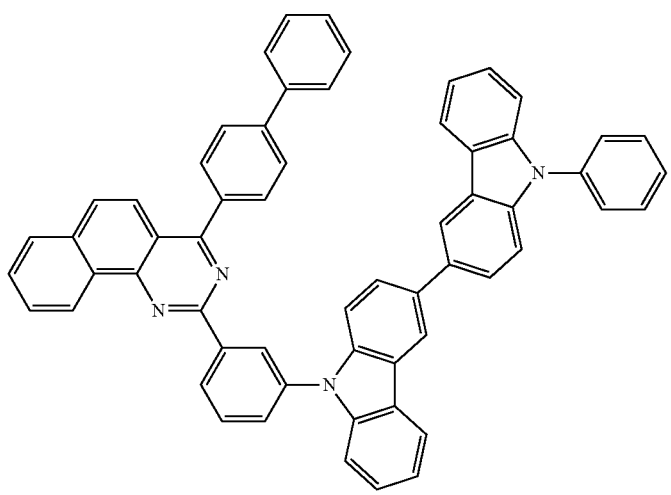

-continued
133 134
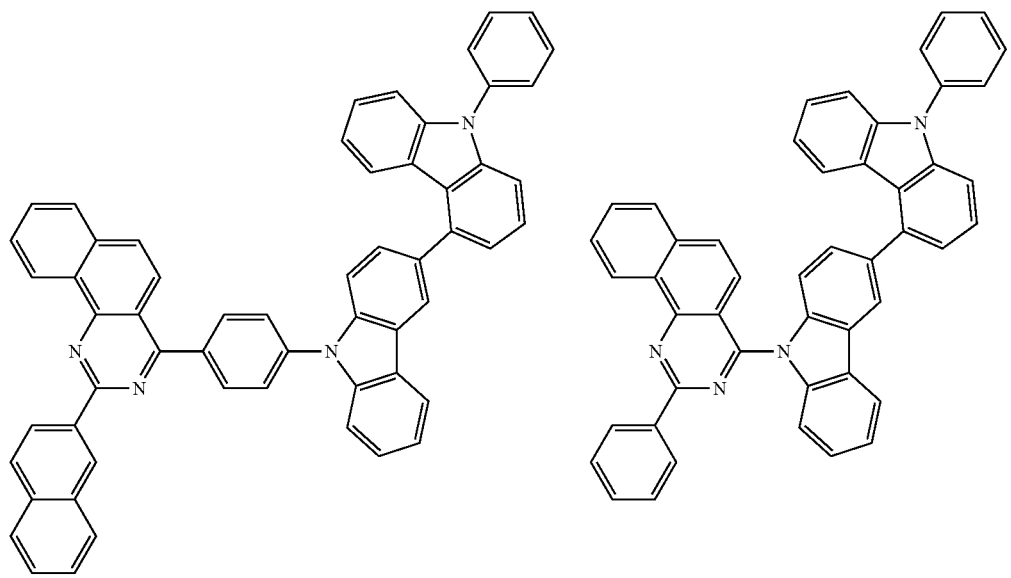
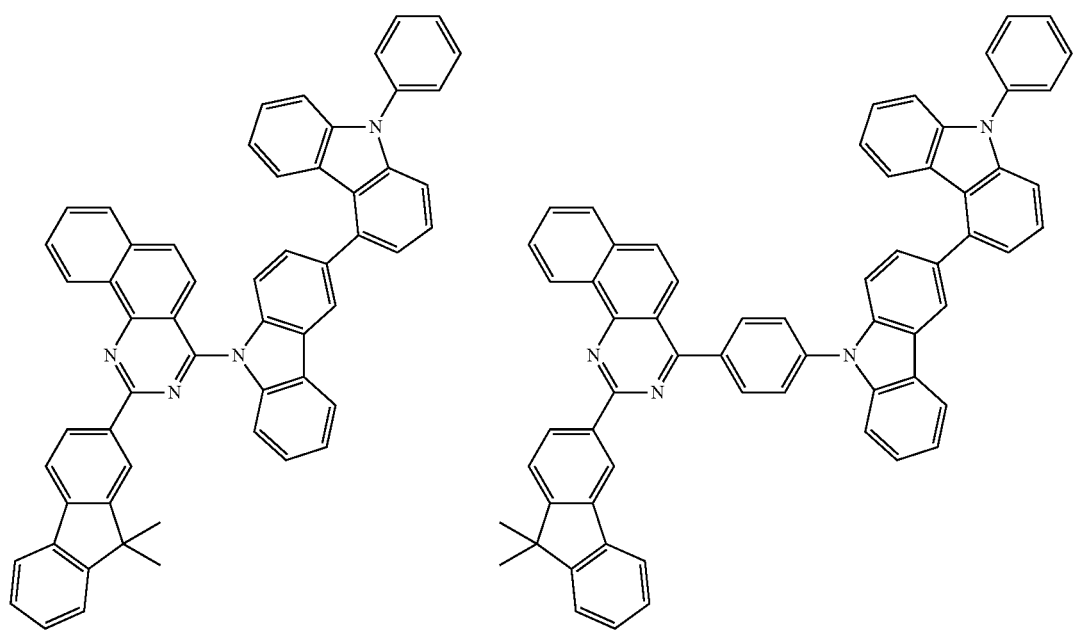

-continued
| 135 | 136 |
|---|---|
| 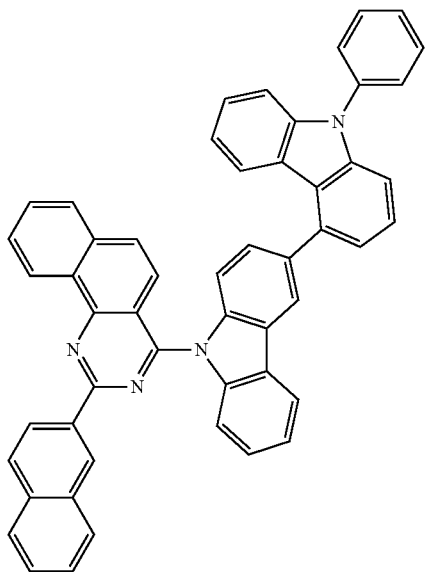 | 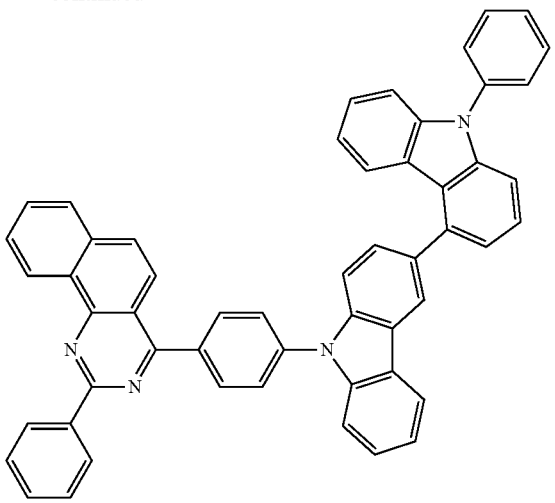 |
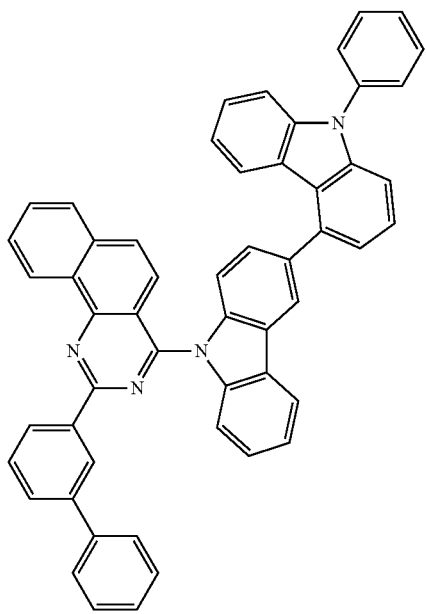

-continued
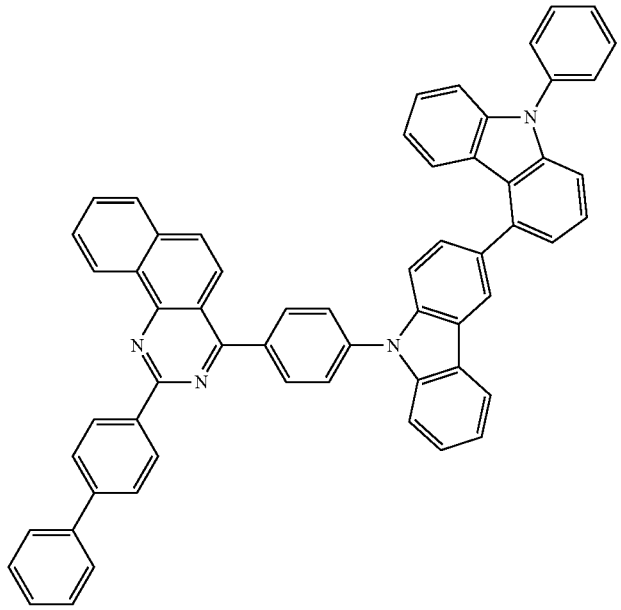
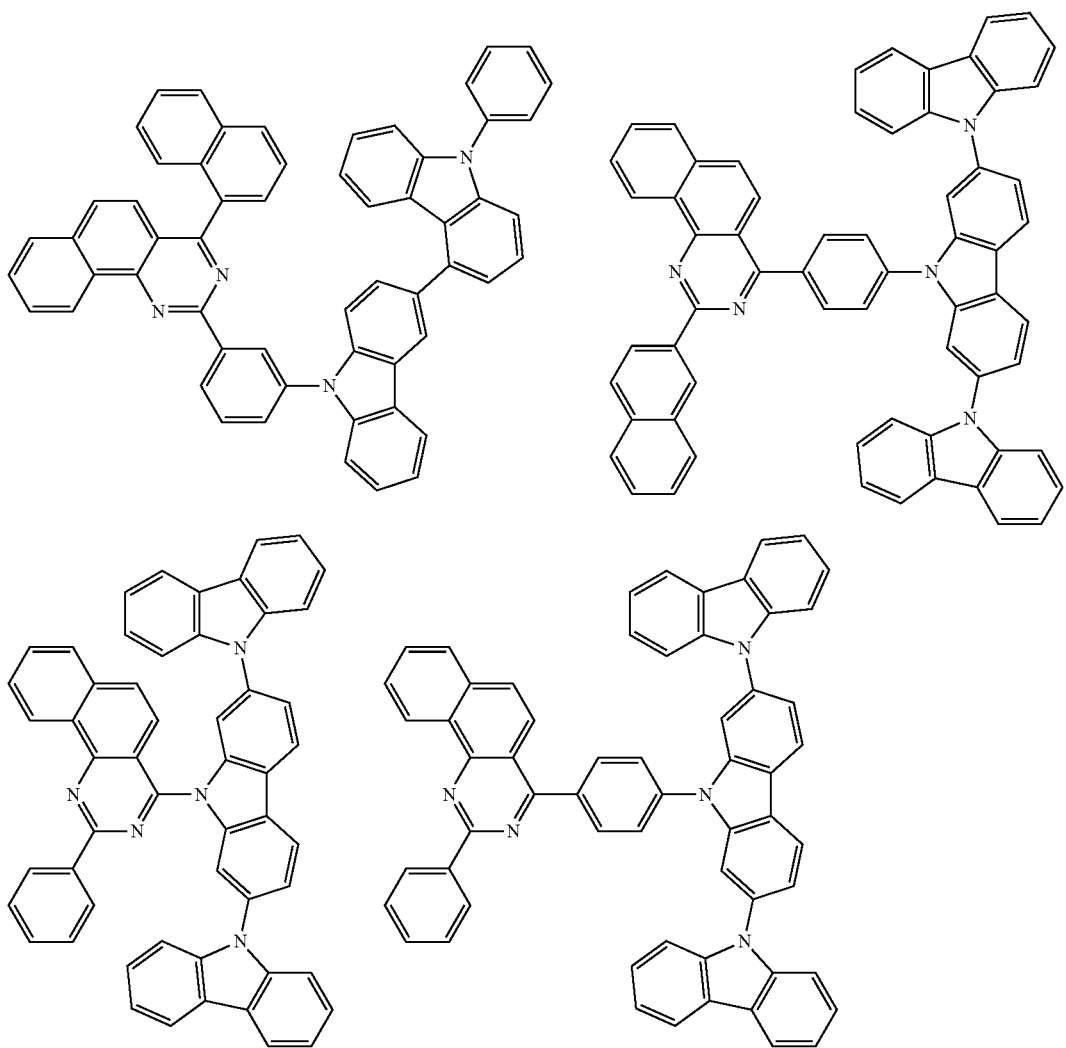

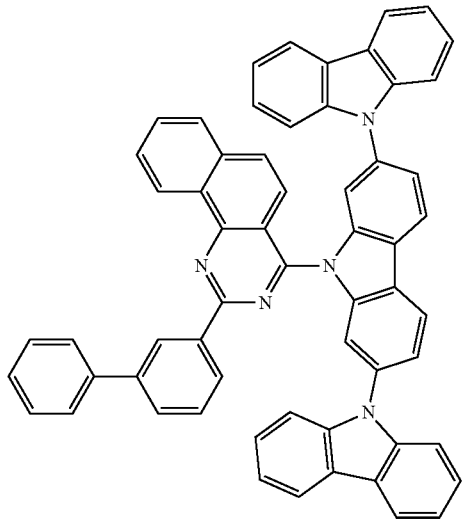
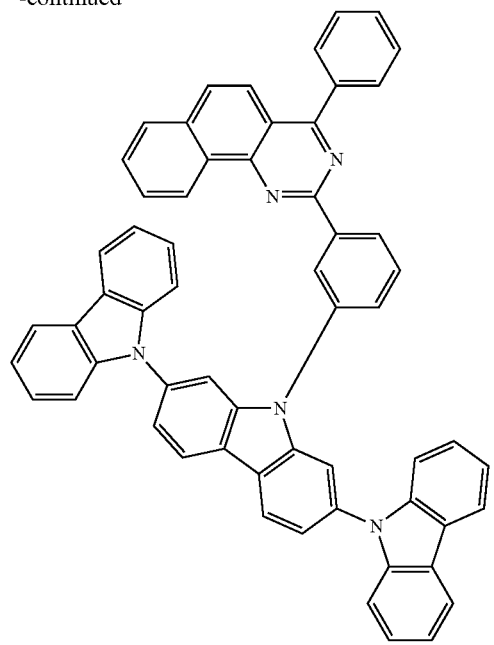
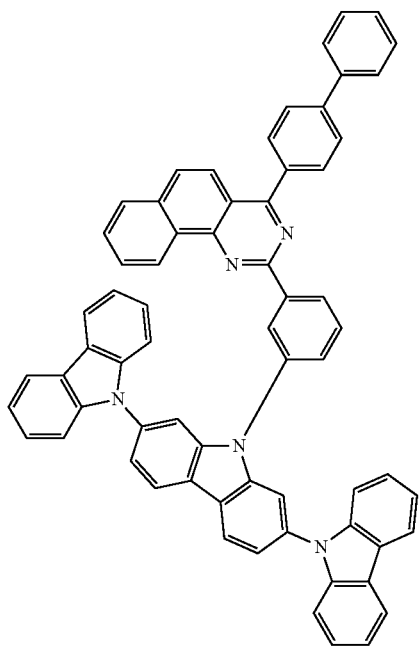
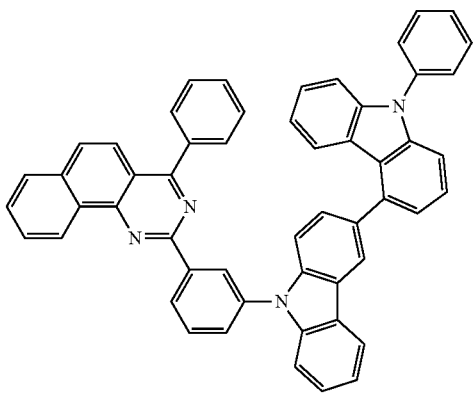

-continued
| 141 | 142 |
|---|---|
| 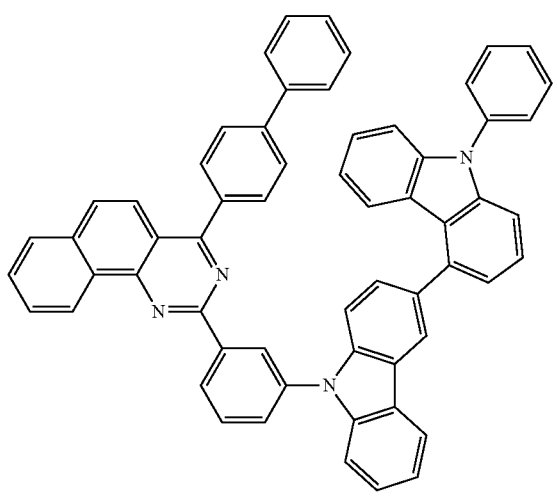 | 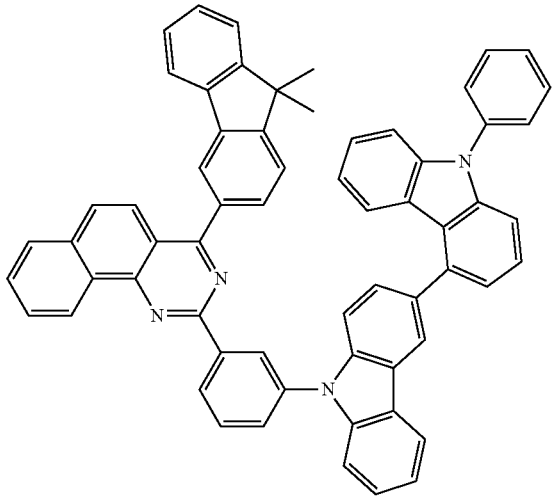 |
| 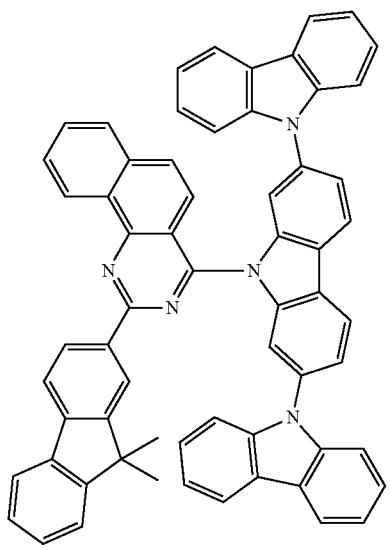 | 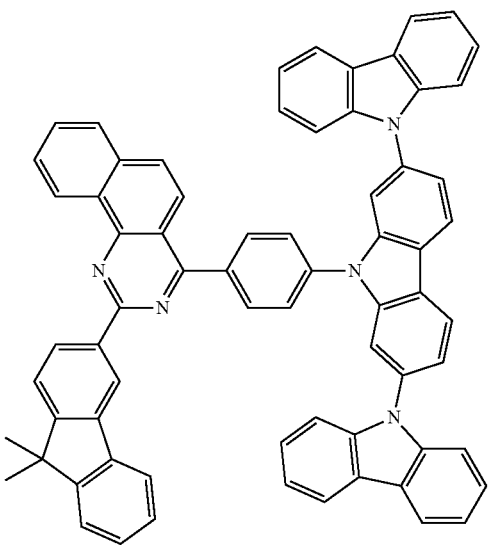 |
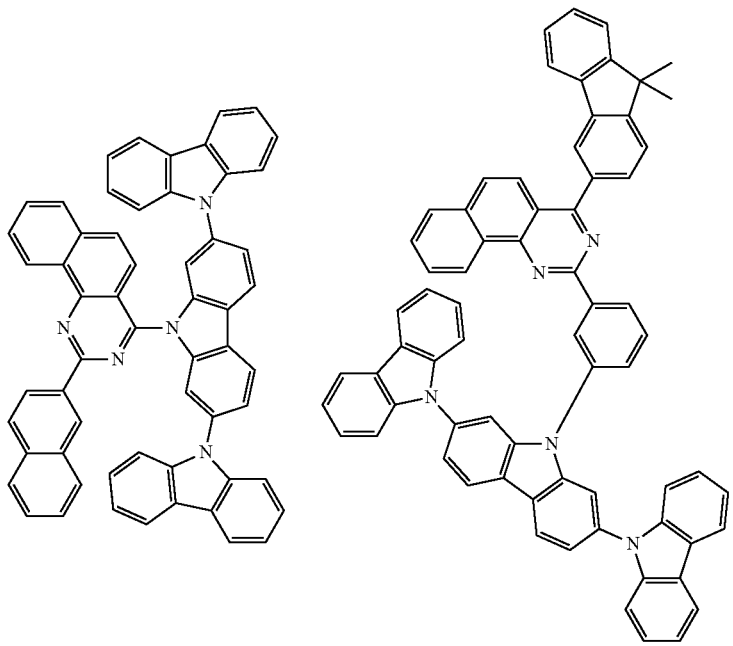

-continued
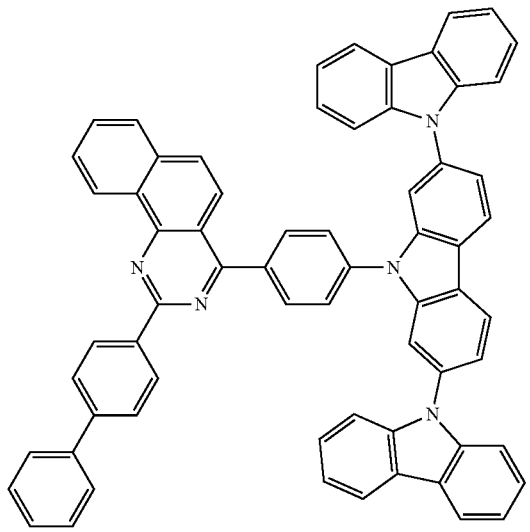
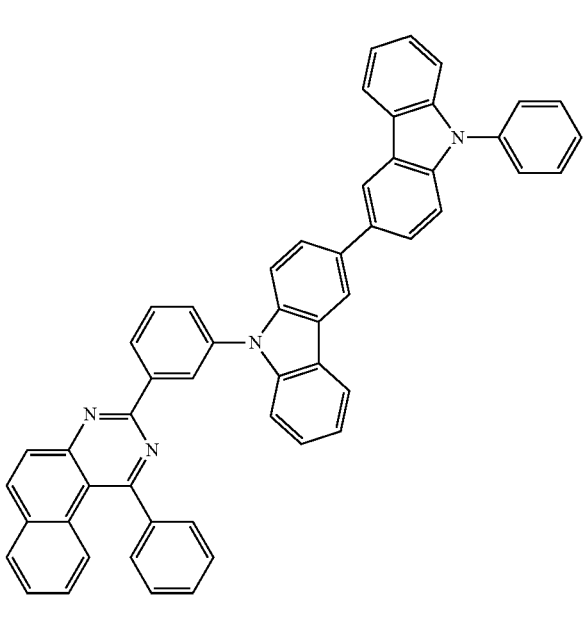

-continued
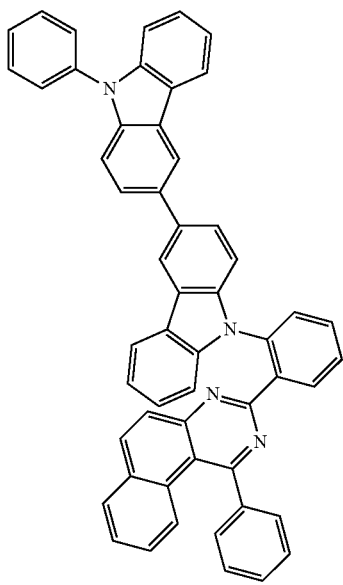
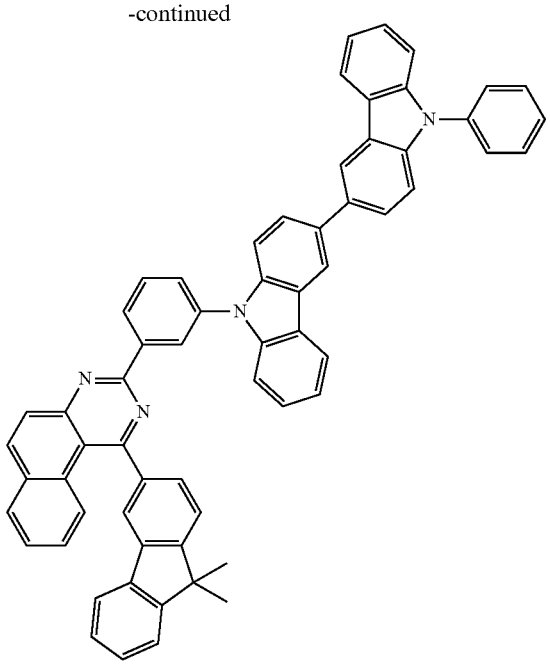
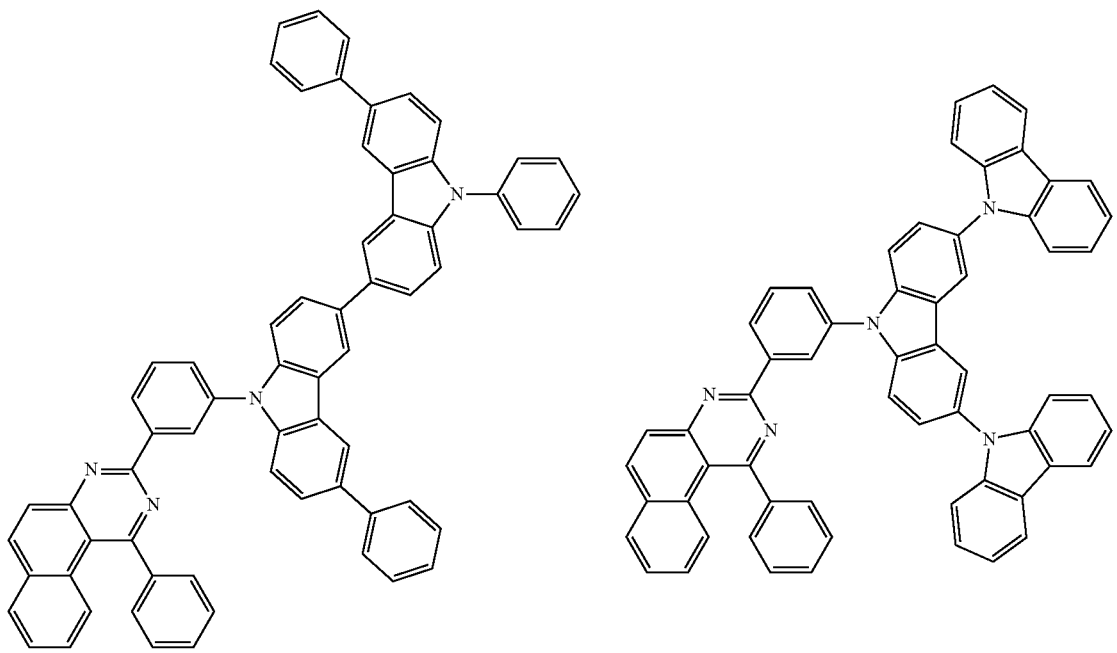

-continued
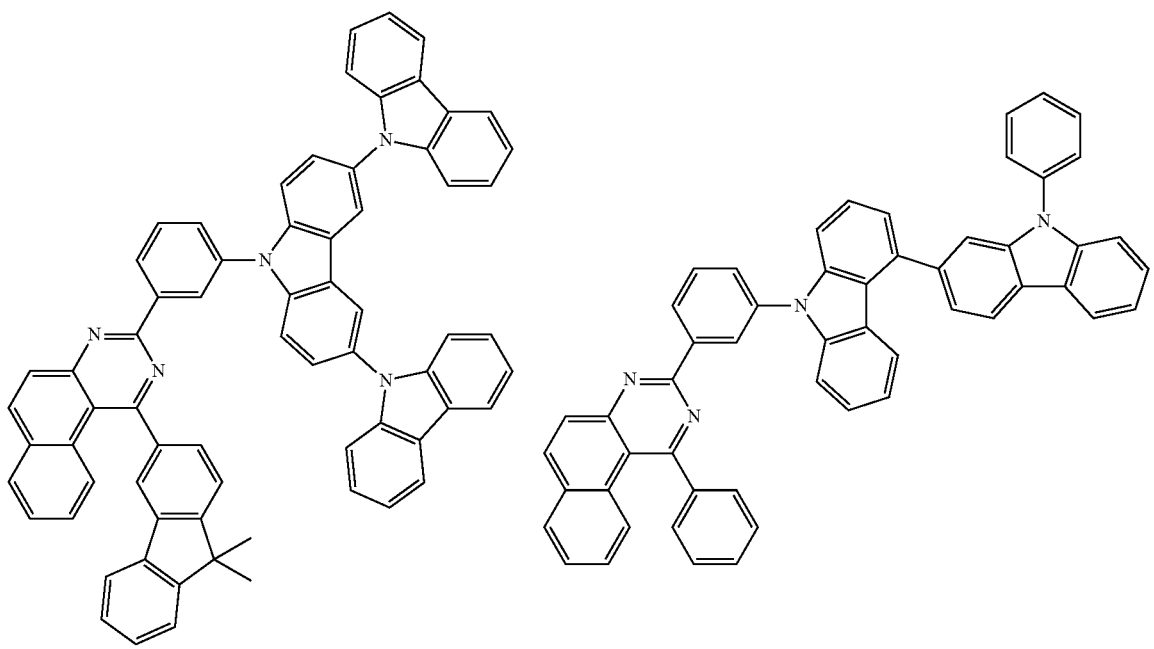
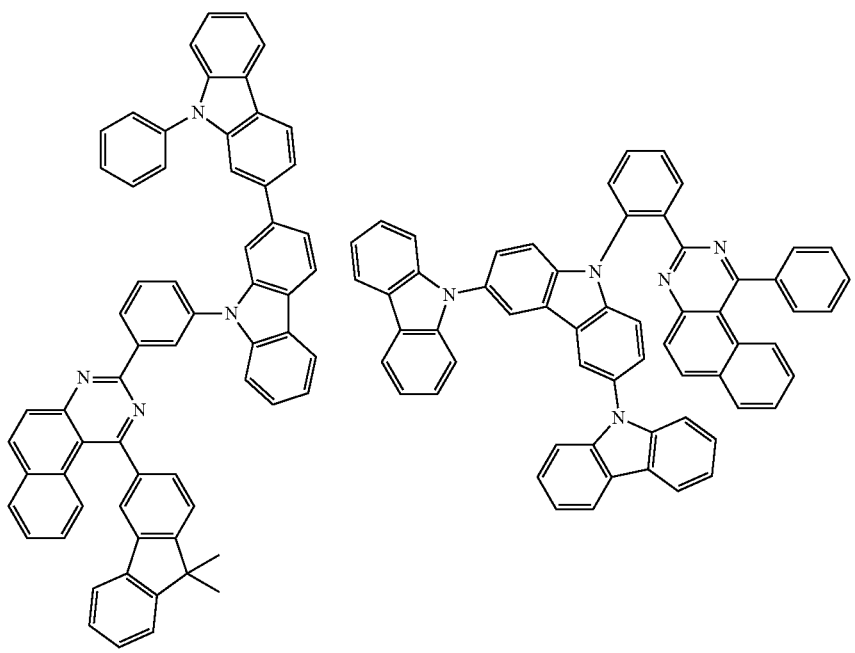
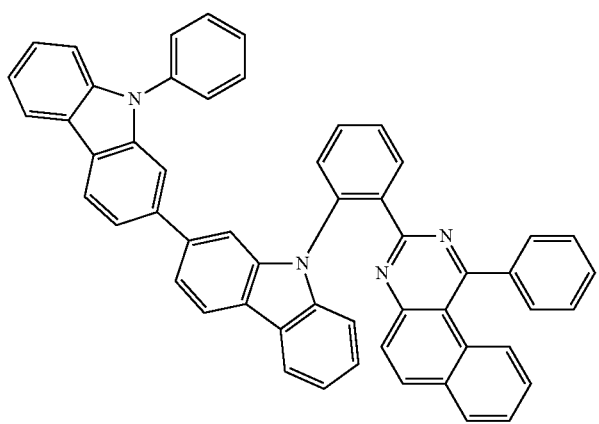

-continued
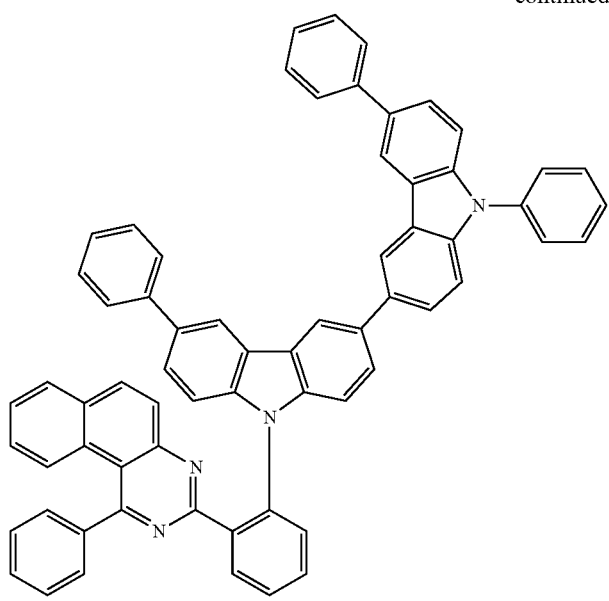
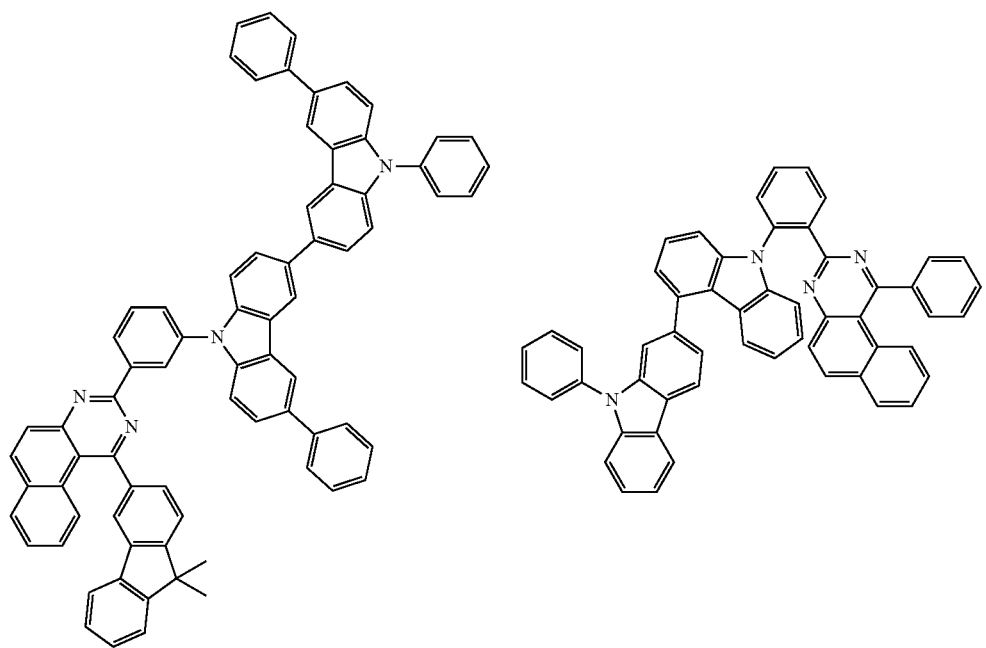

-continued
151
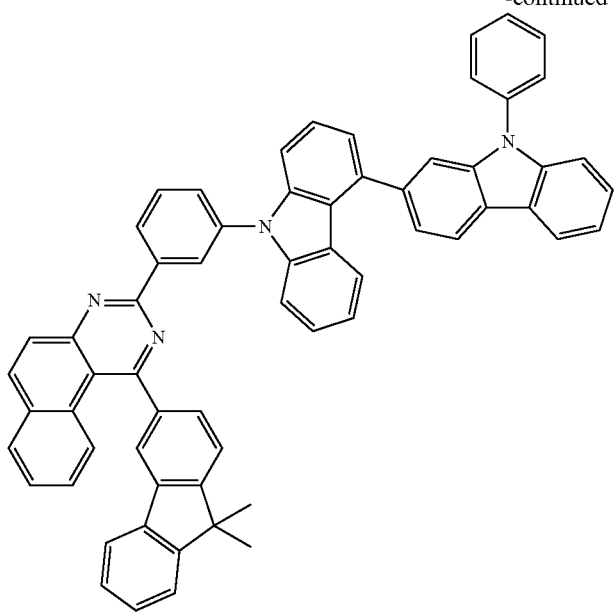
152
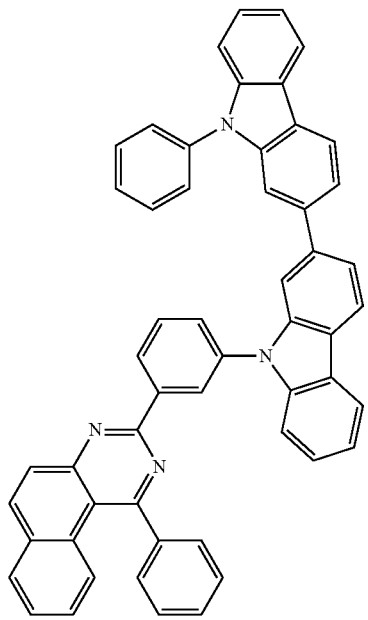
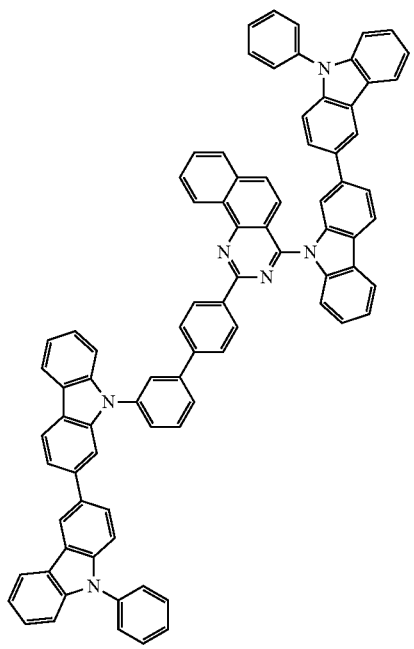

-continued
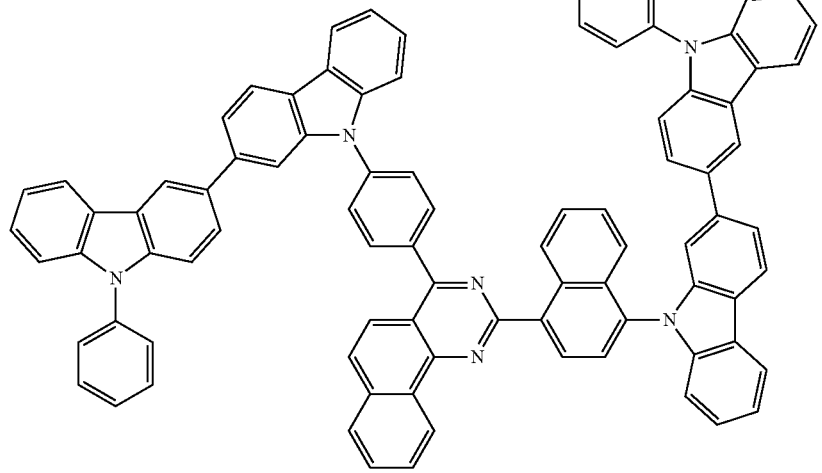
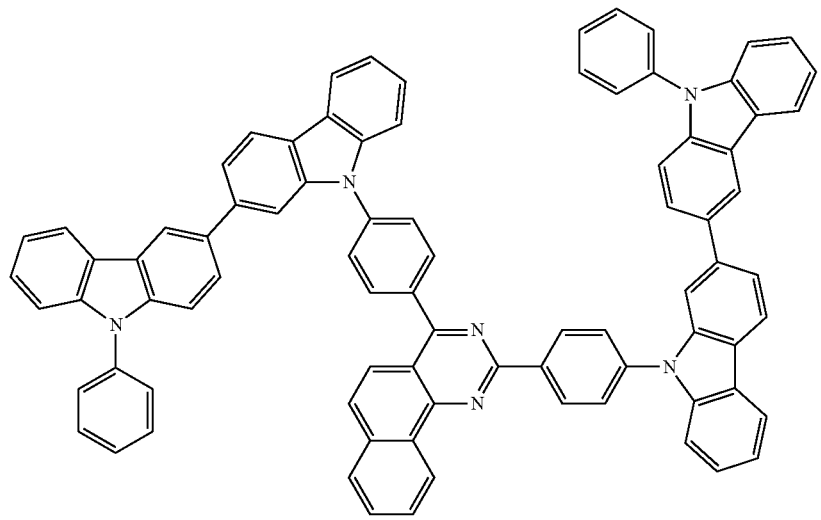
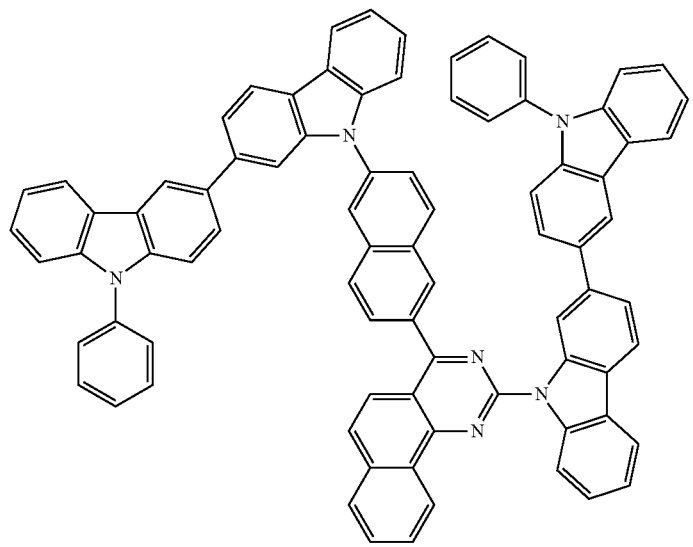

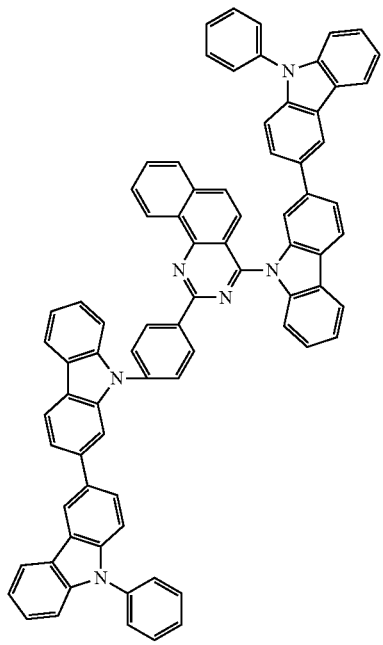
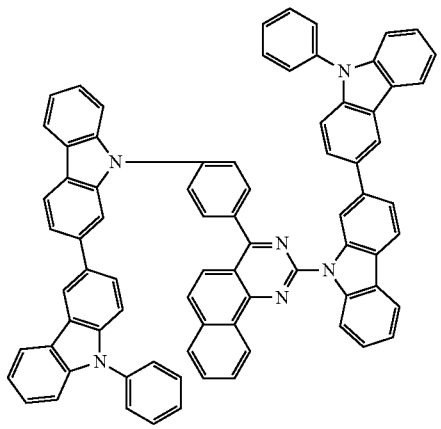
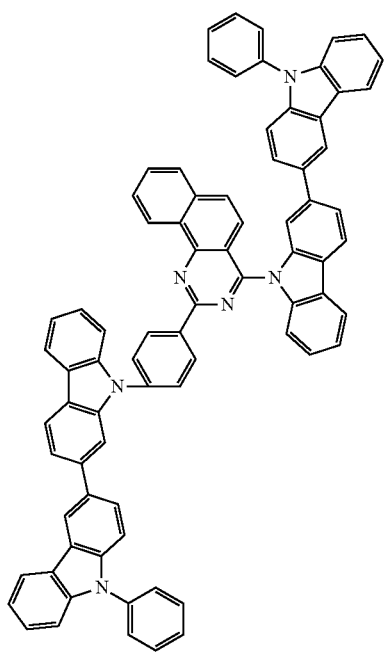
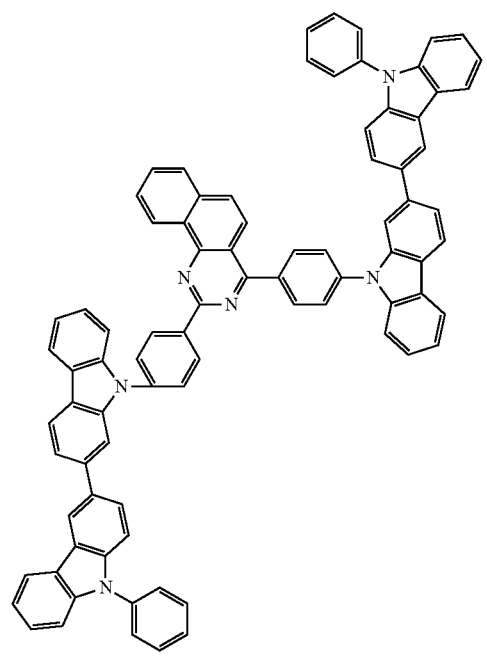

-continued
157
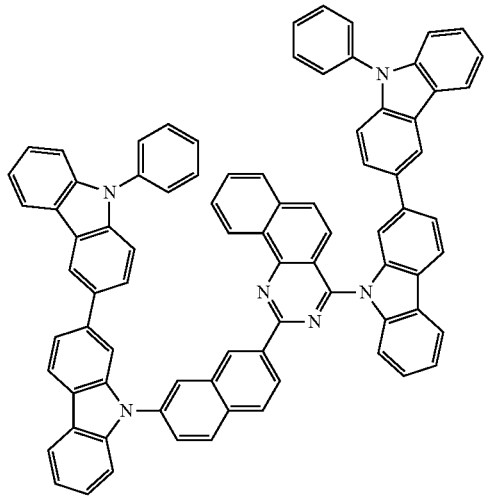
158
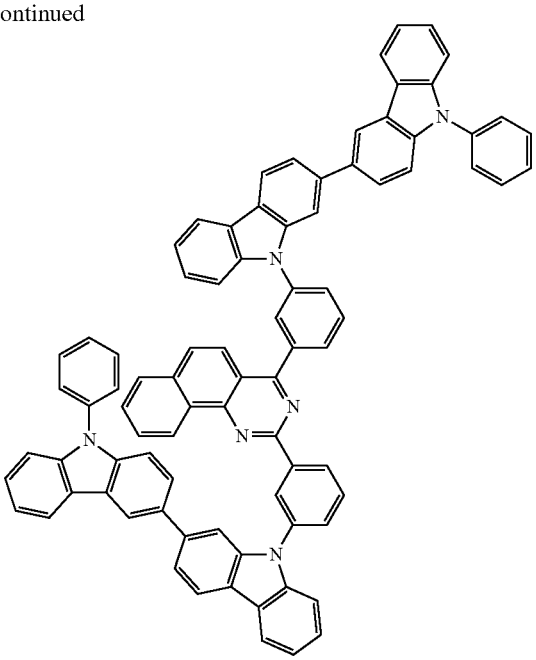
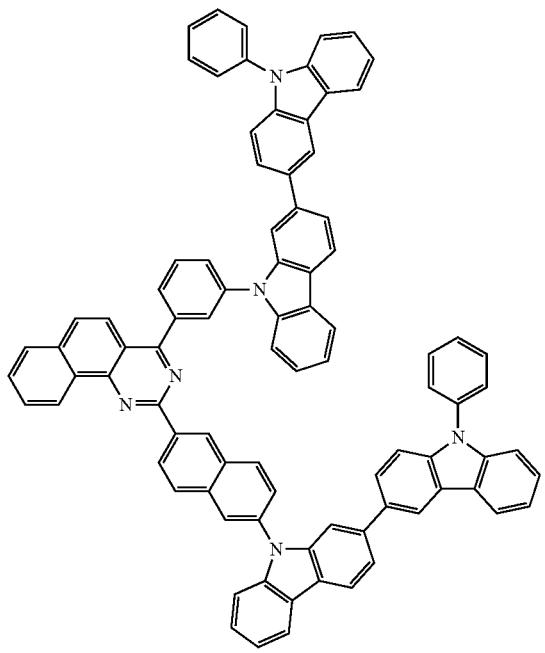

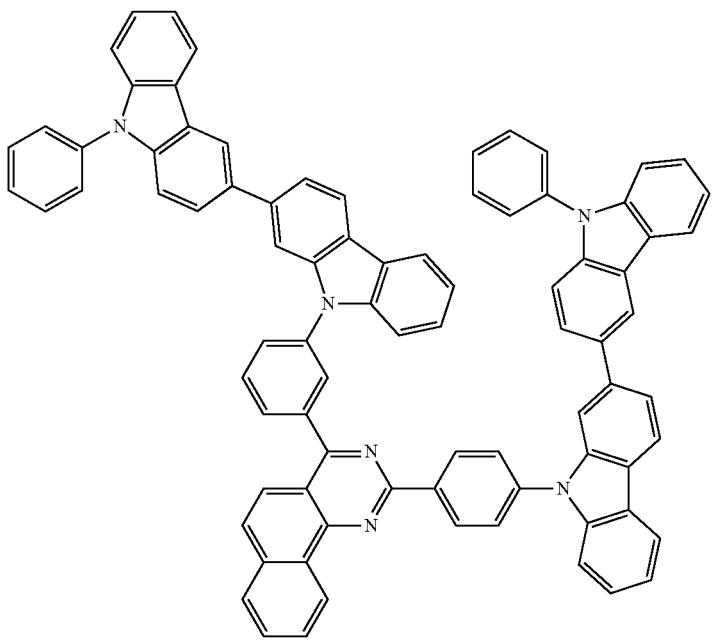
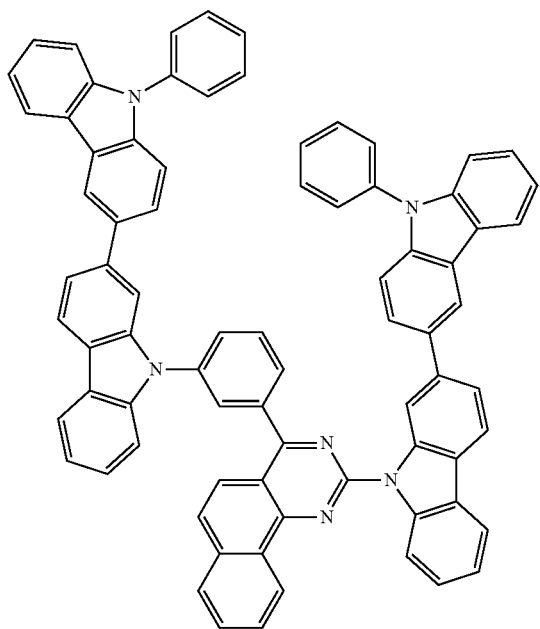

-continued
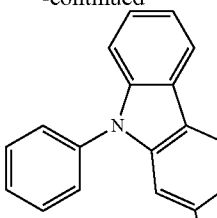
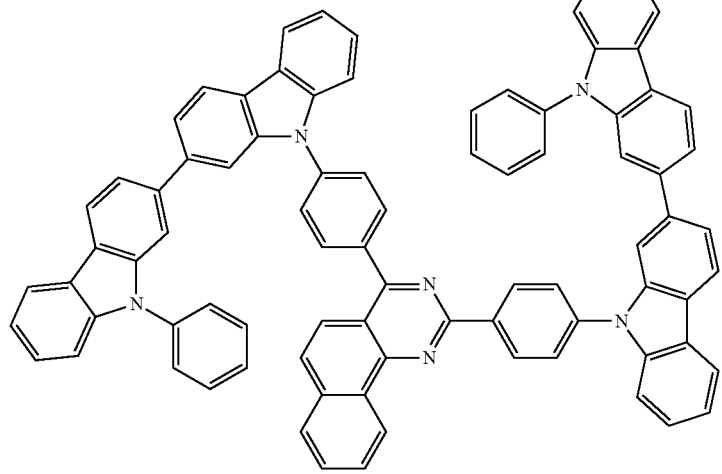
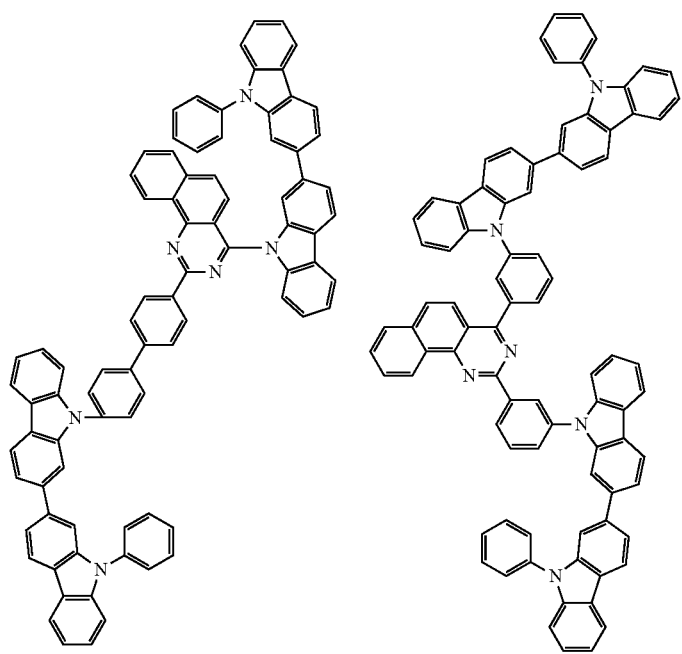

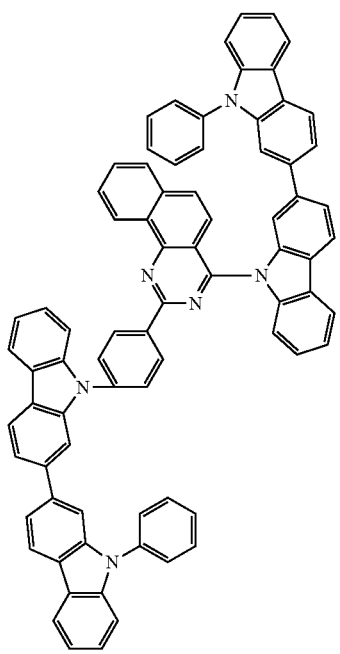
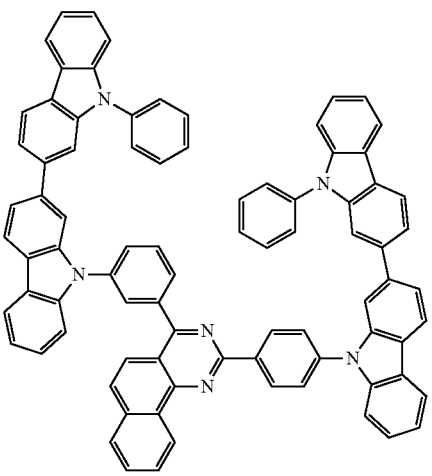
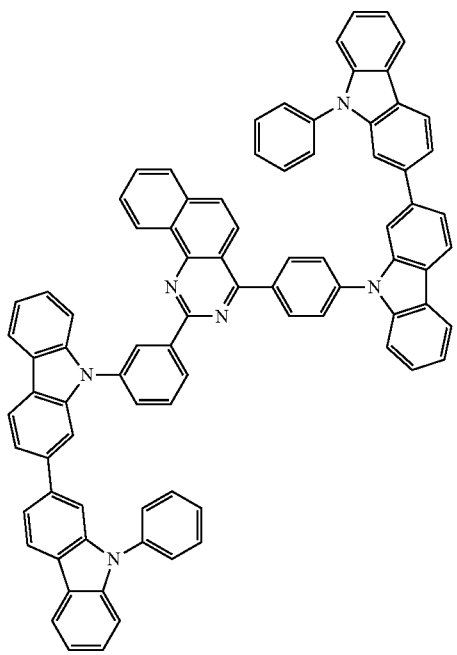
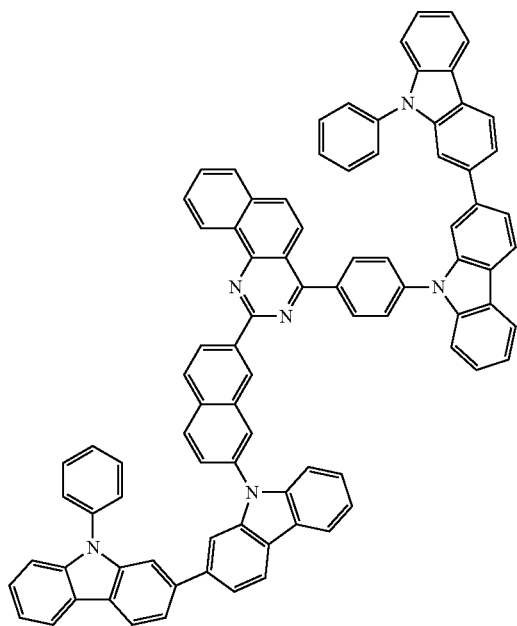

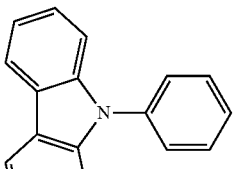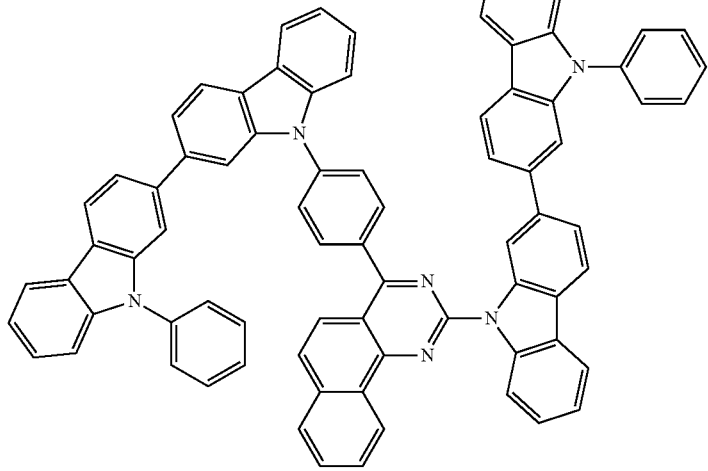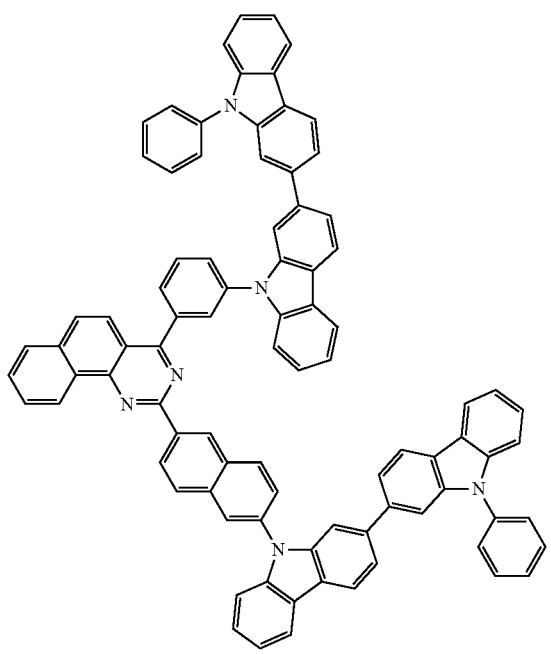

-continued
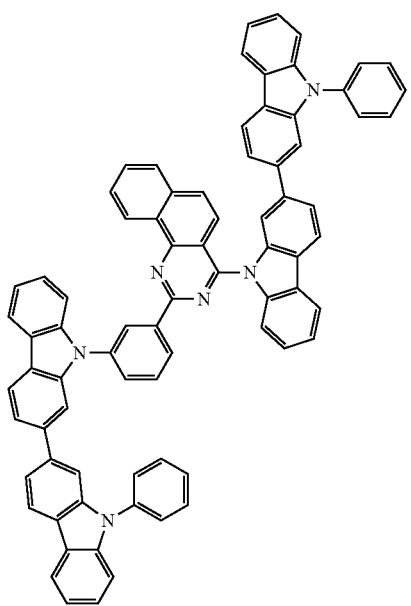
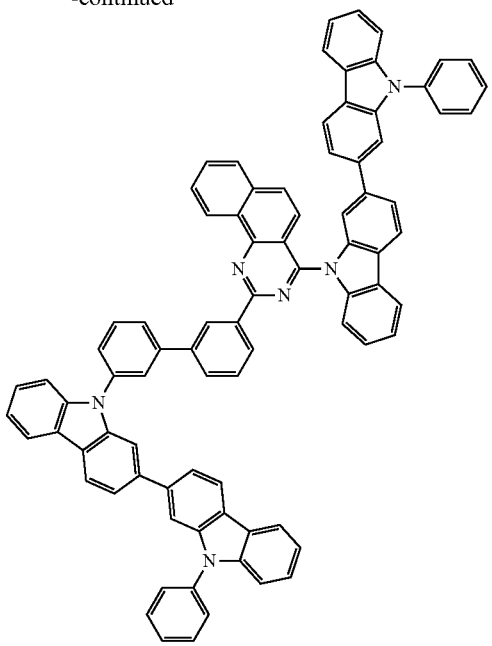
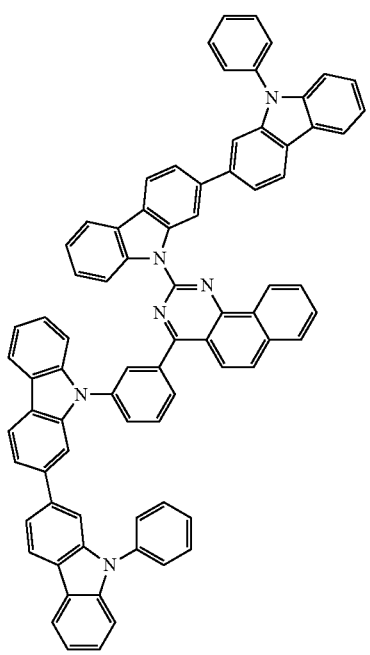
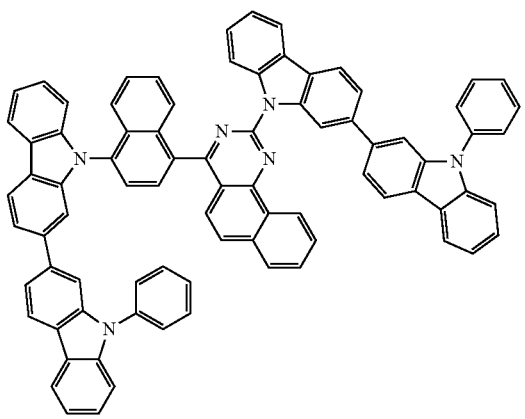

-continued
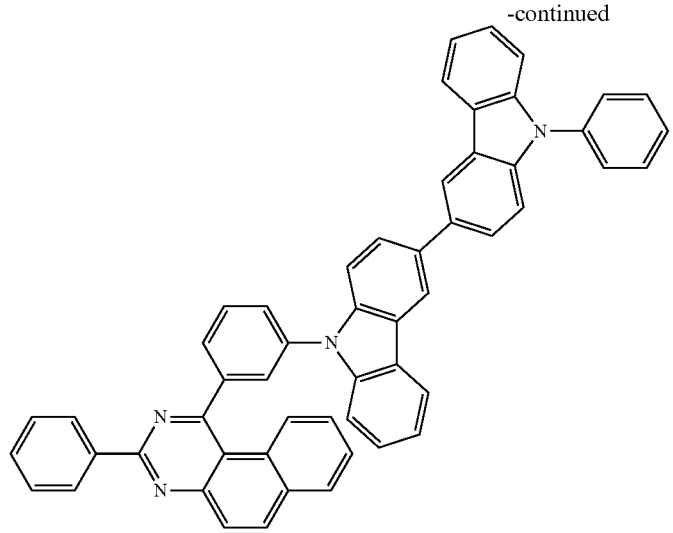
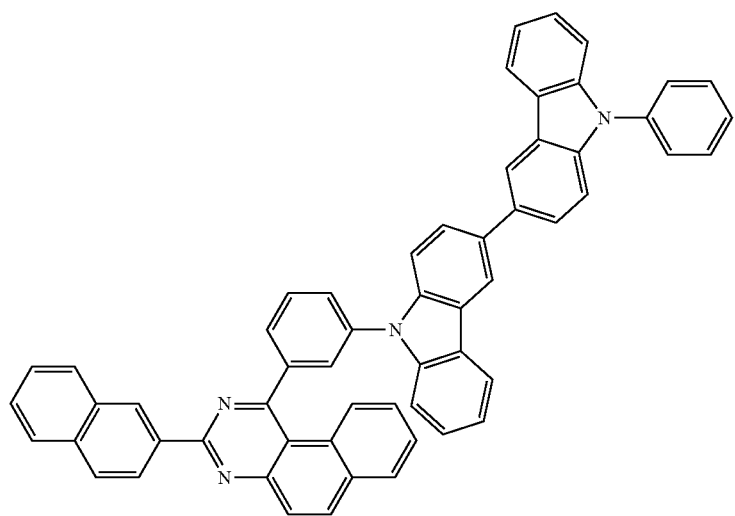
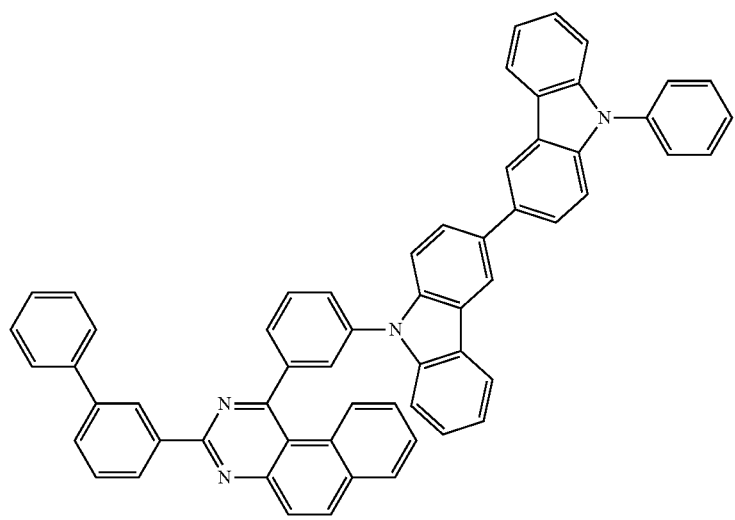

-continued
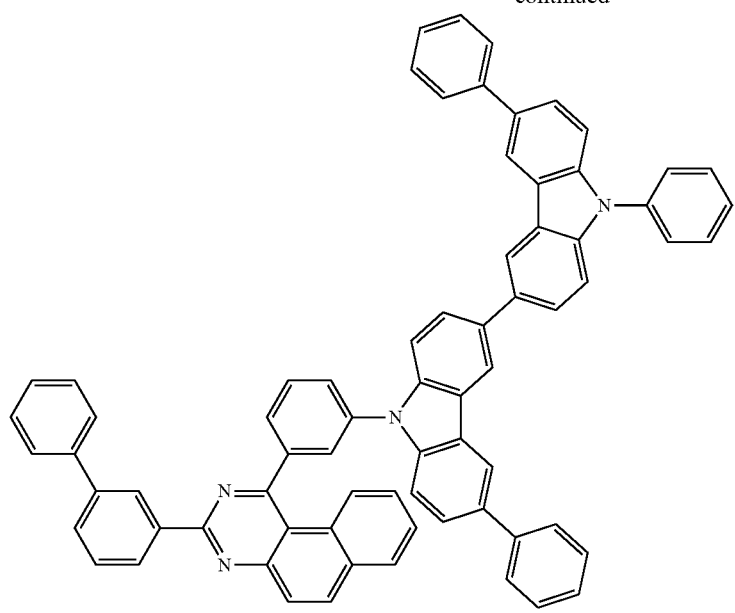
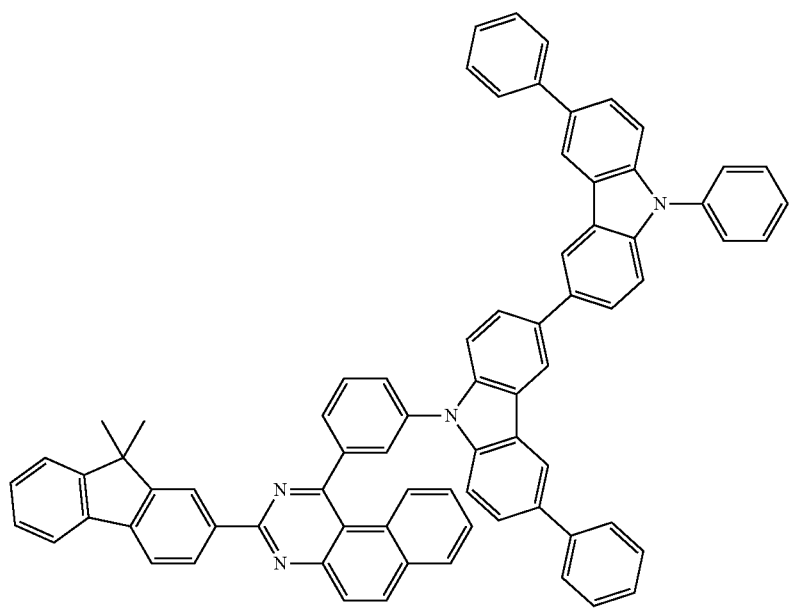

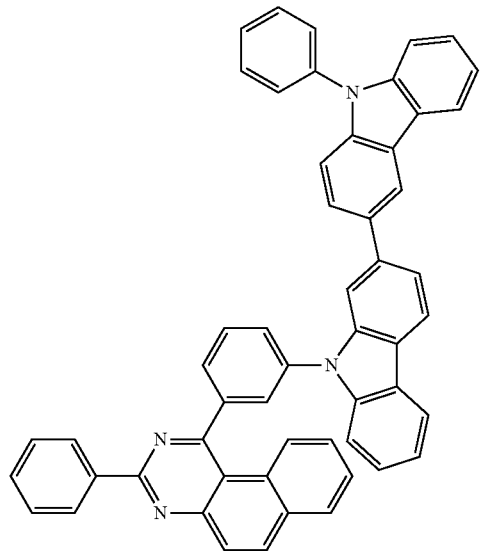
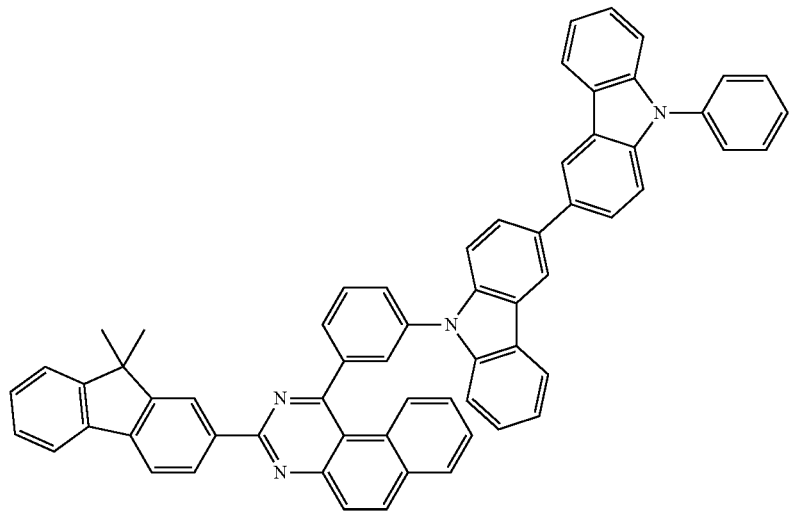
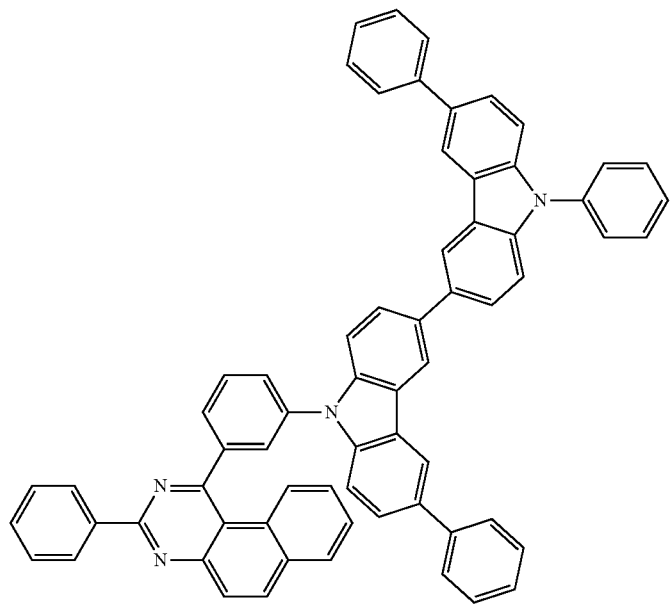

-continued
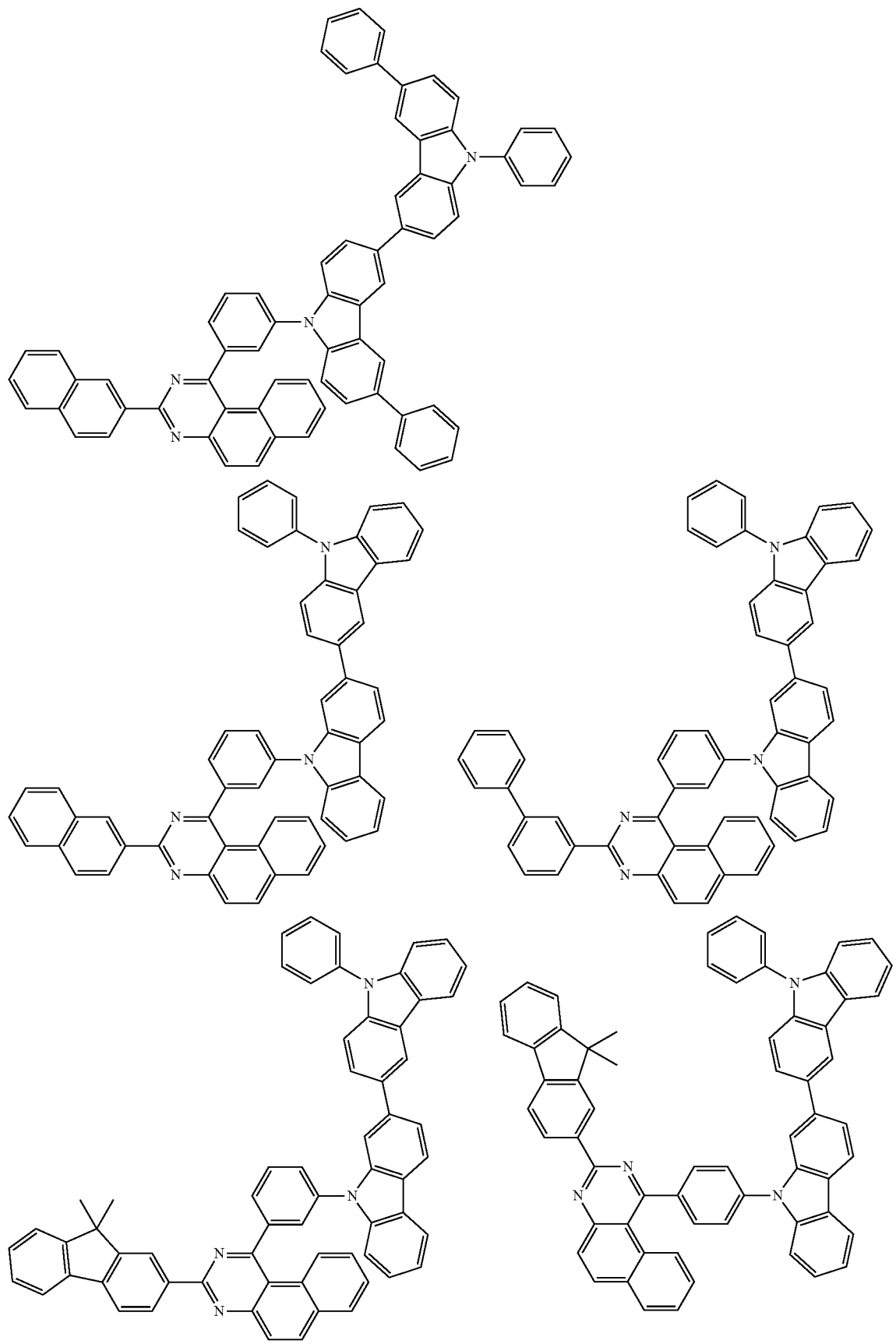

-continued
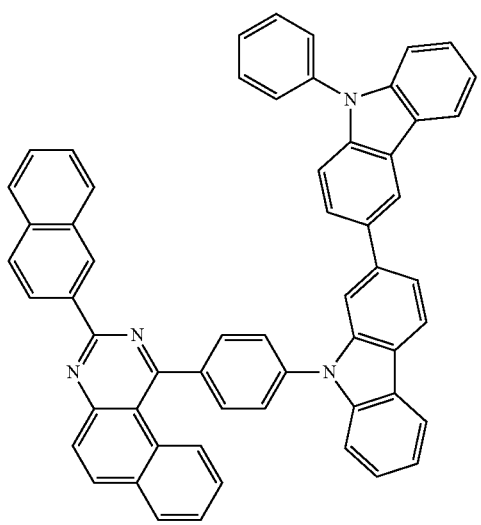 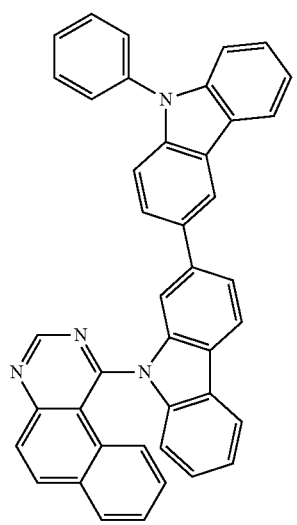
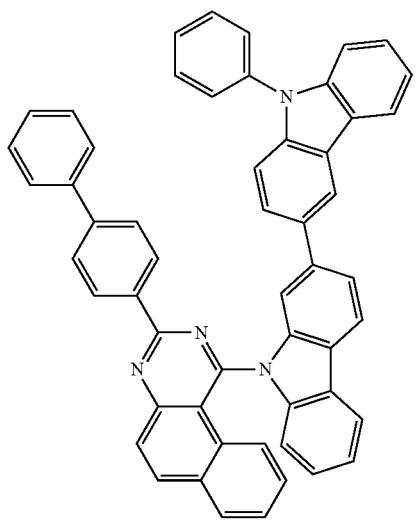 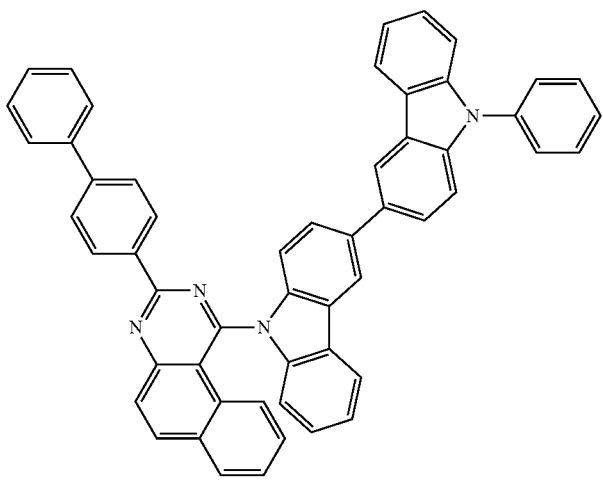
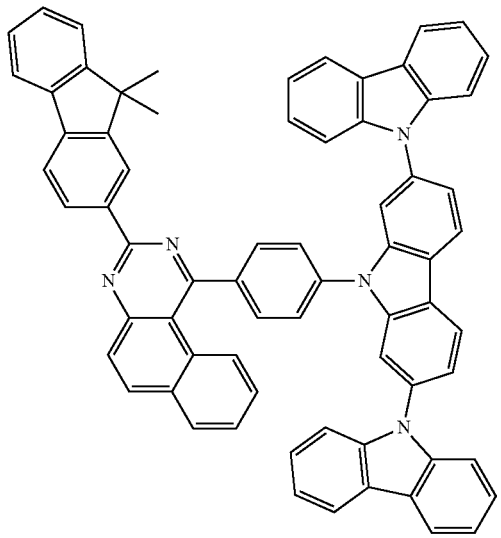 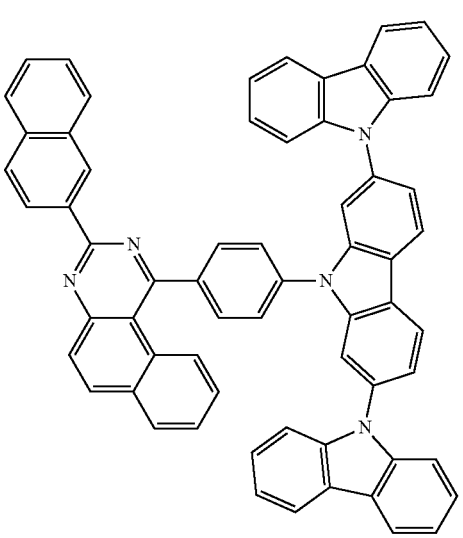

-continued
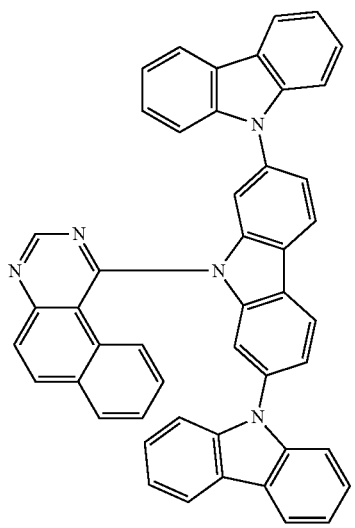
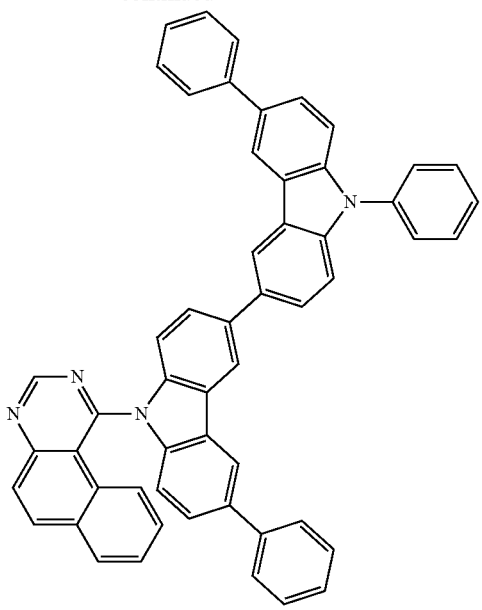
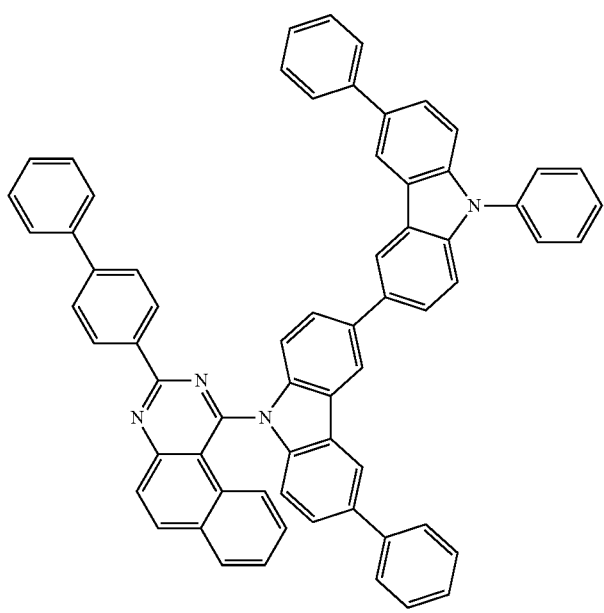
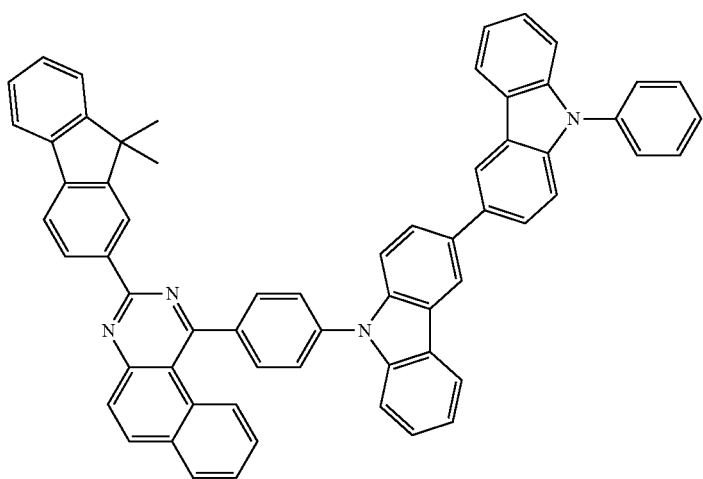

-continued
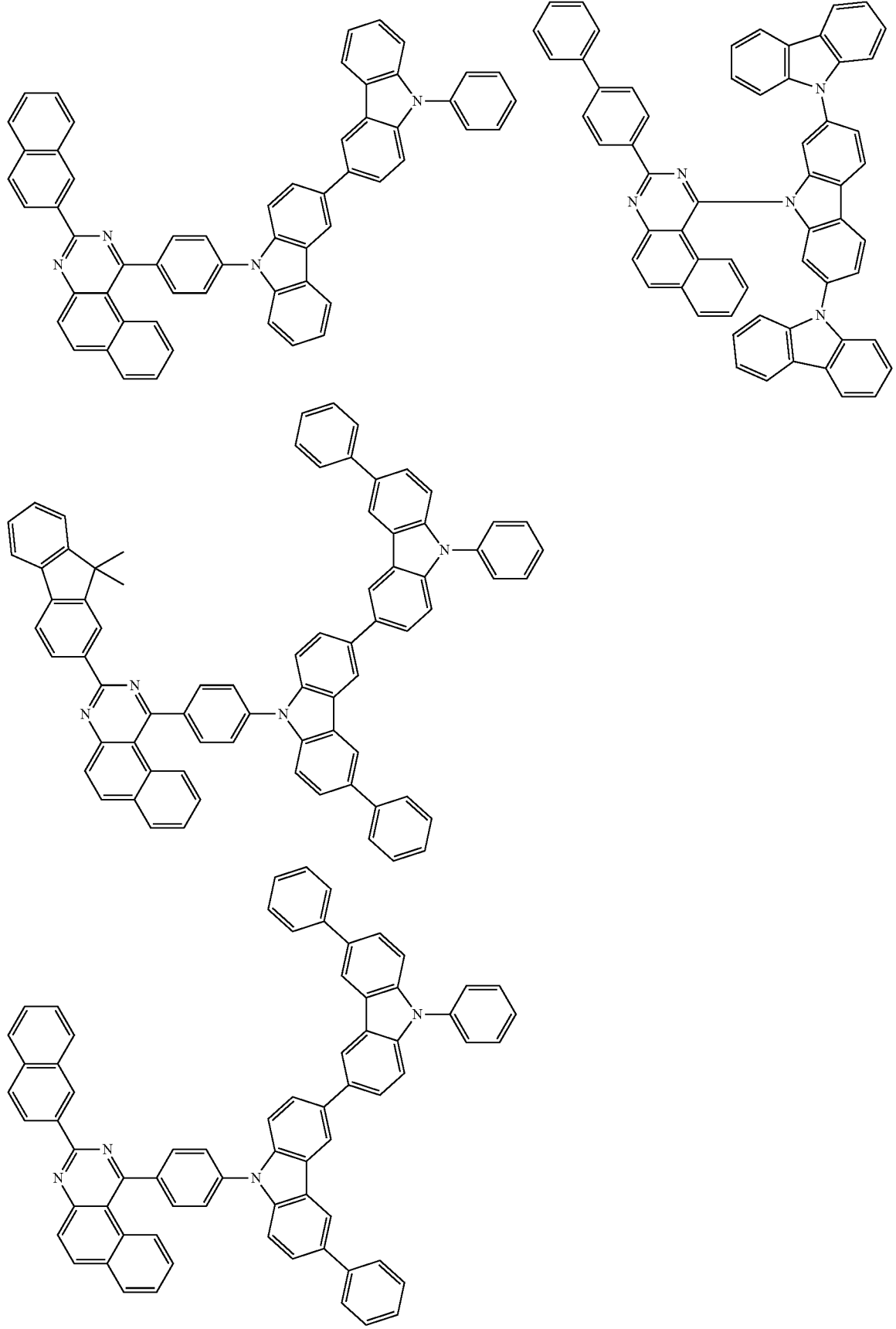

183
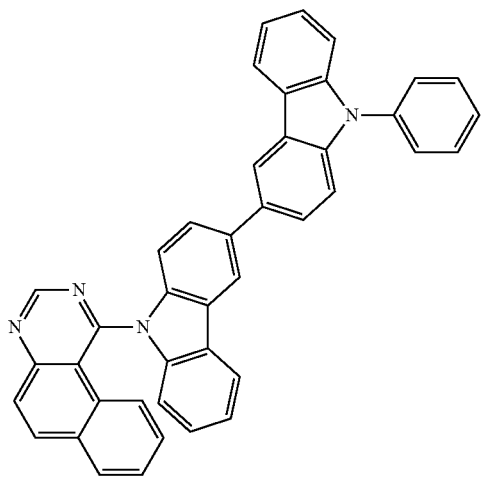
184
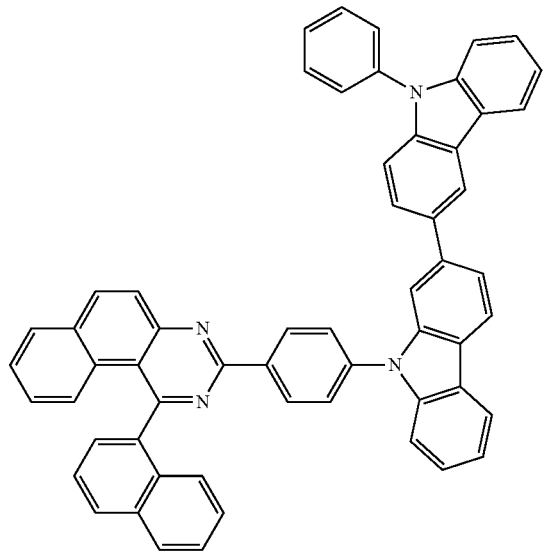
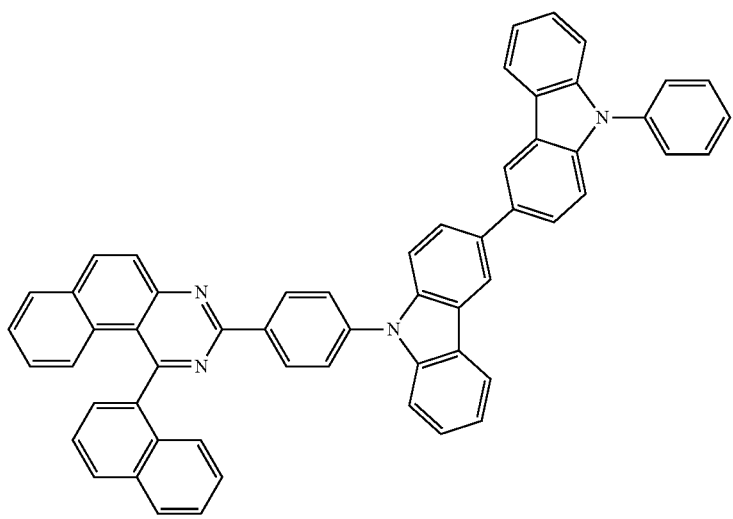
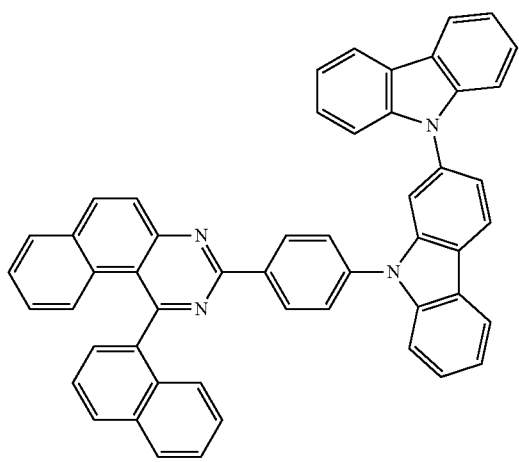

-continued
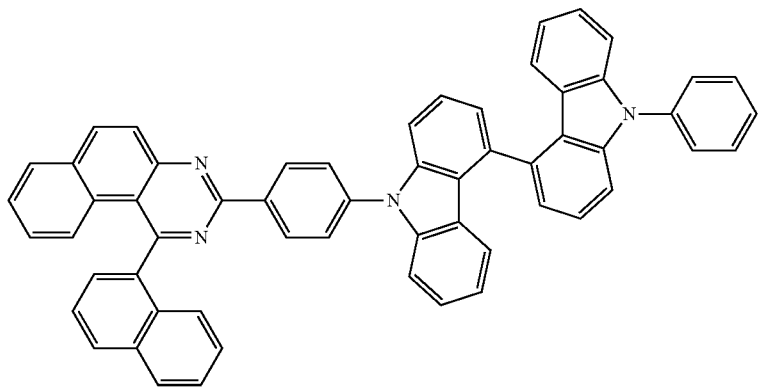
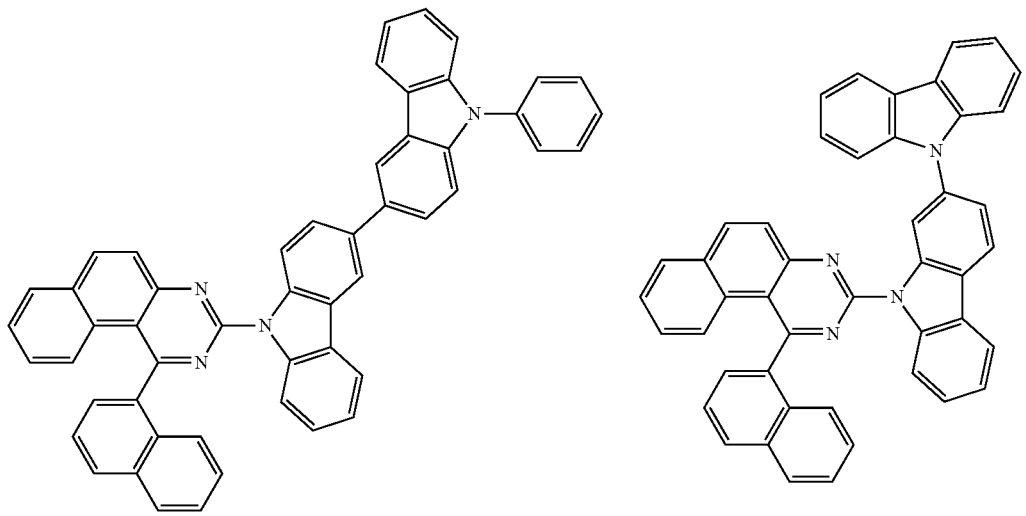
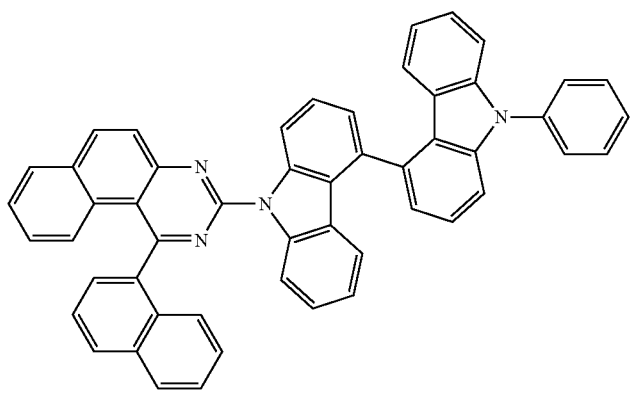
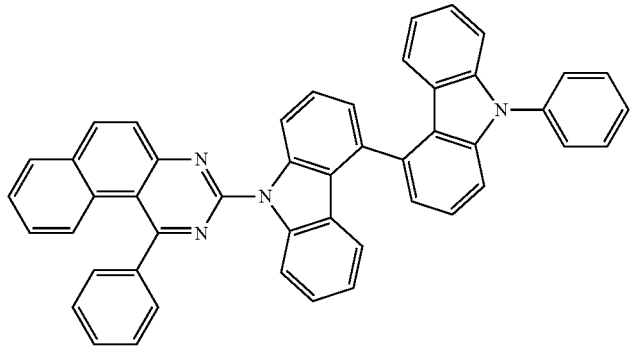

-continued
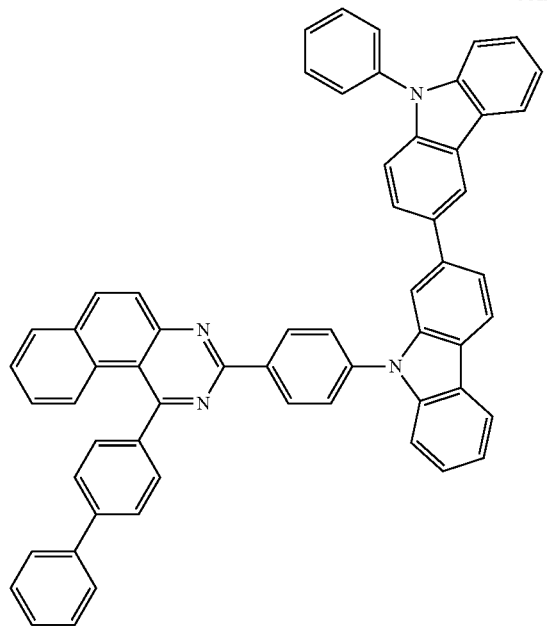
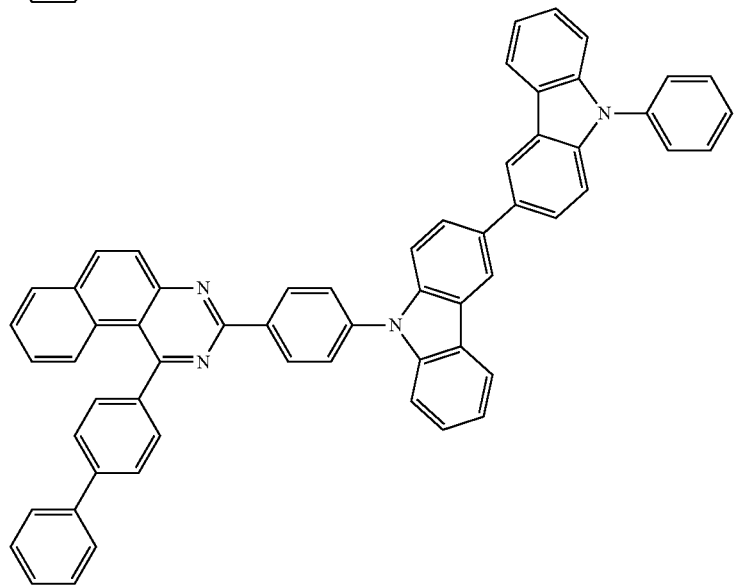
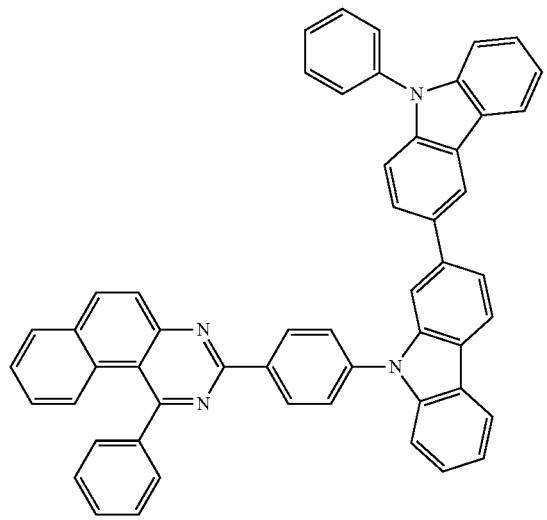

-continued
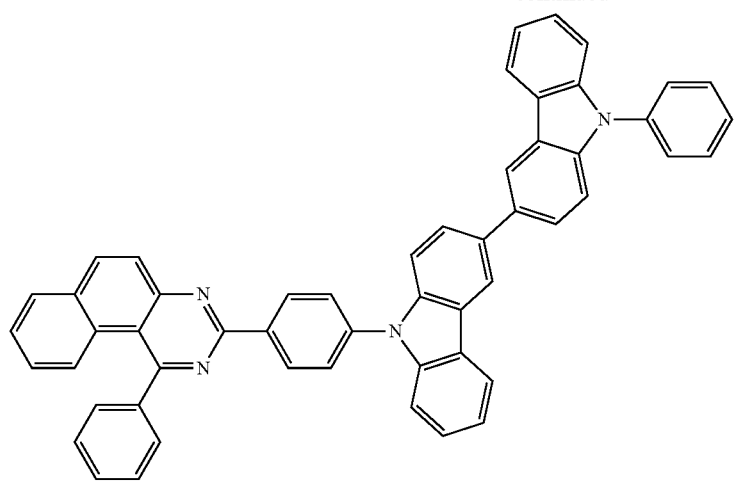
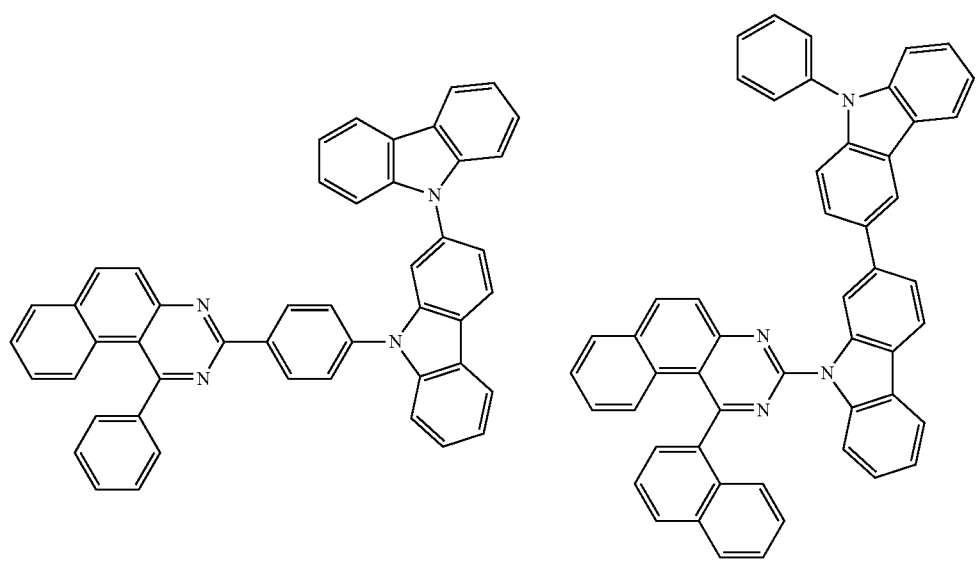
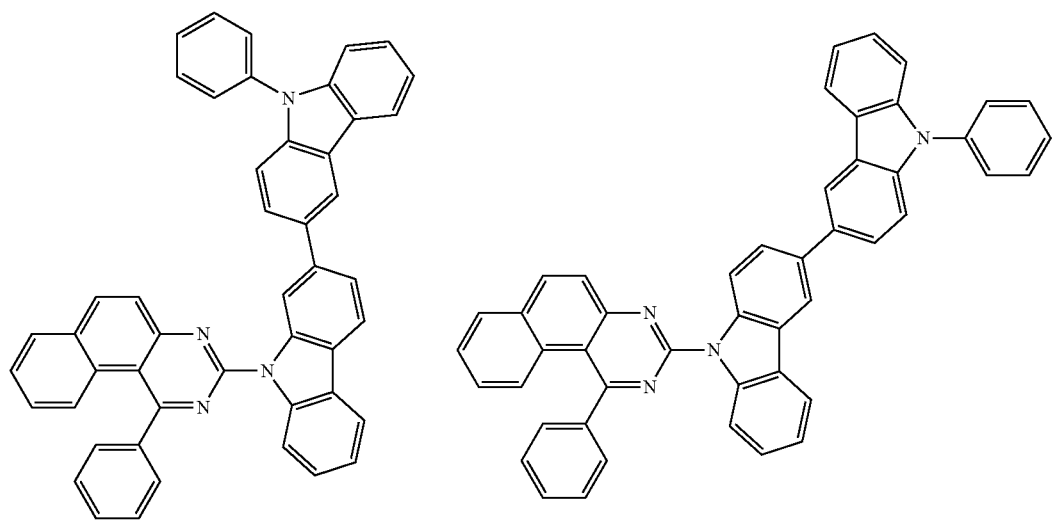

191 192
-continued
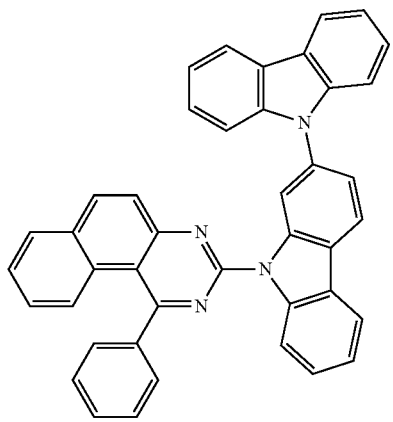
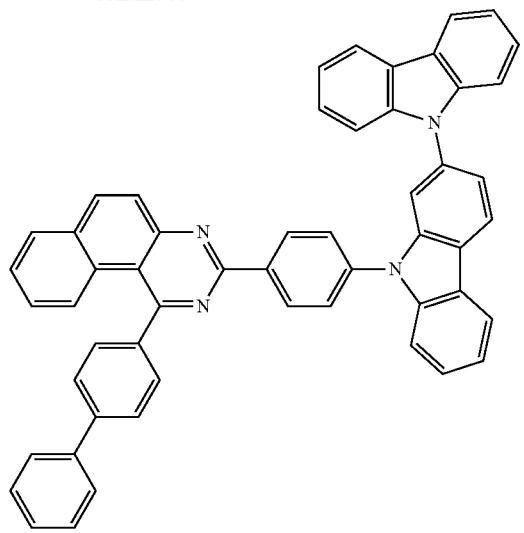
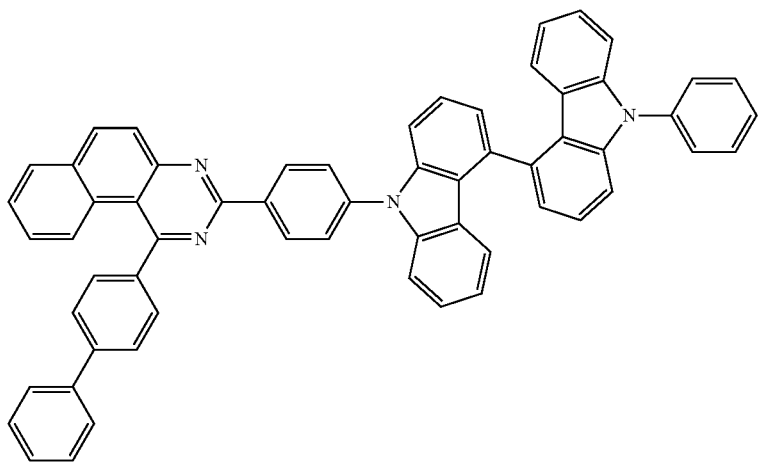
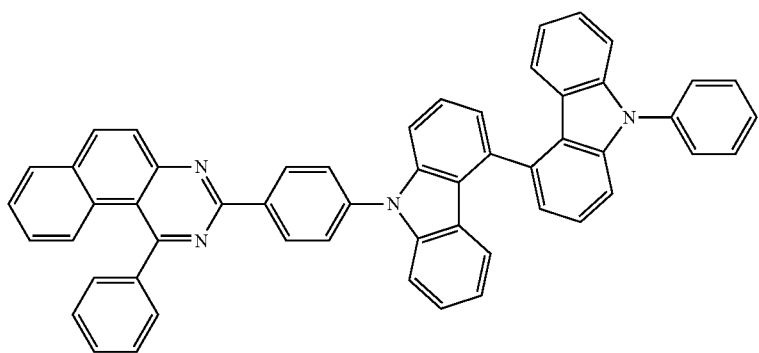

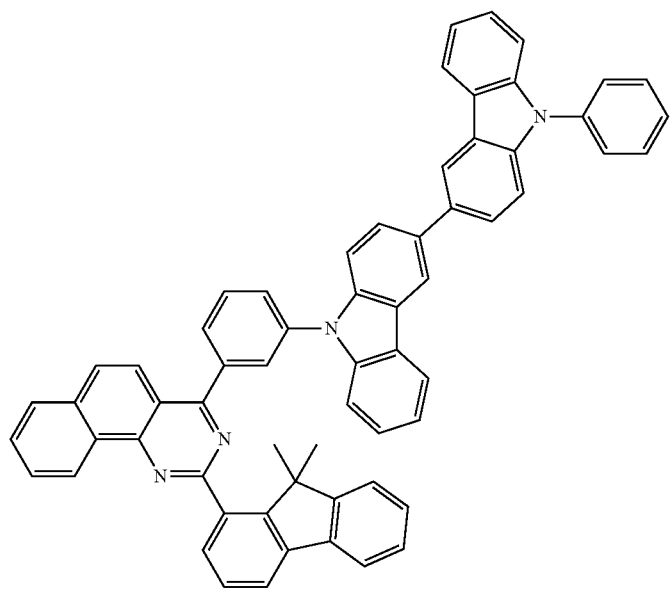
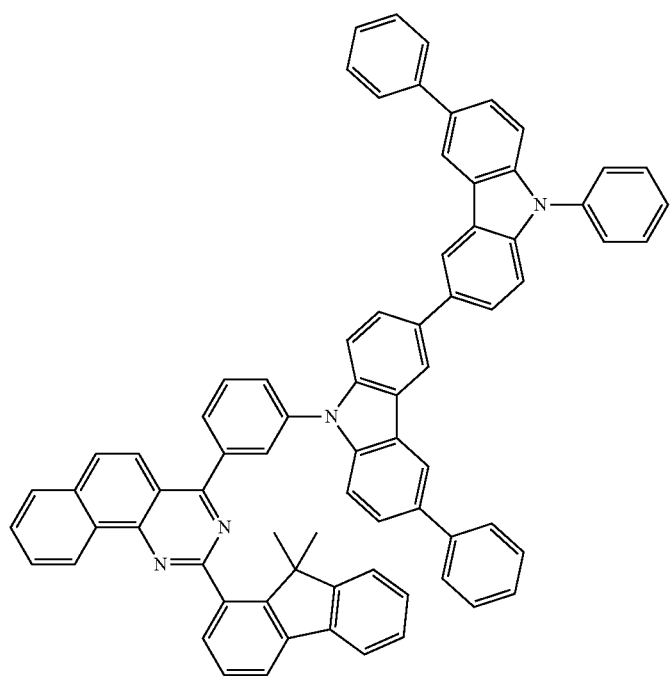

-continued
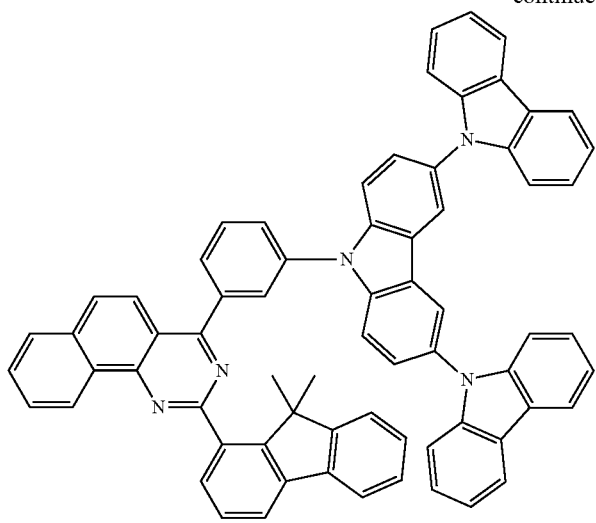
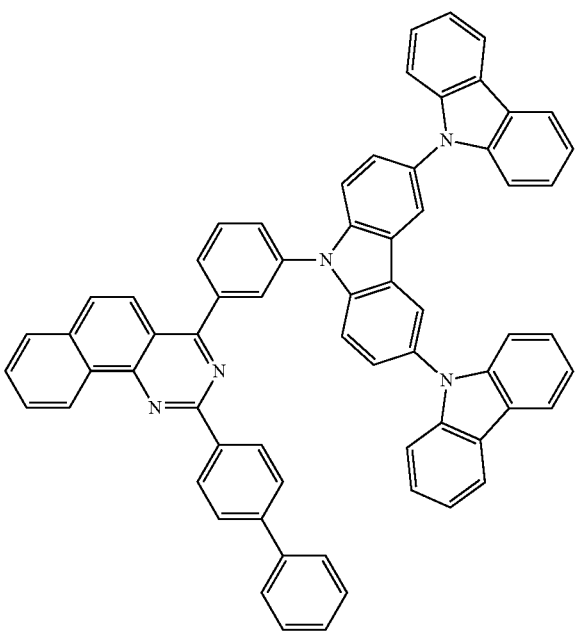

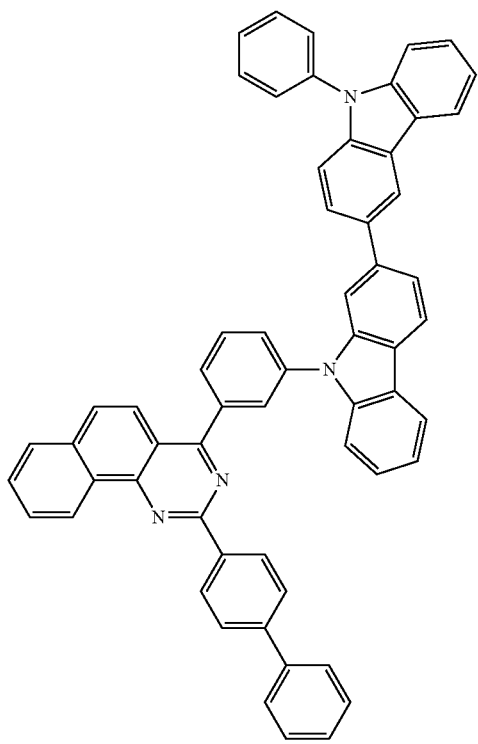
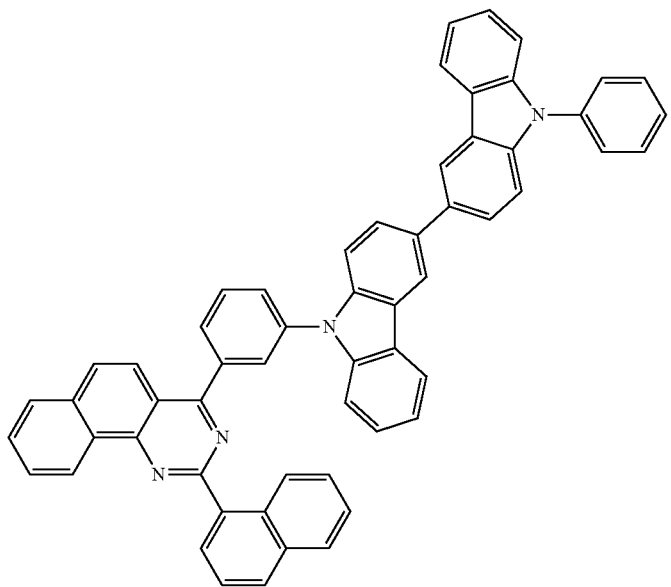

-continued
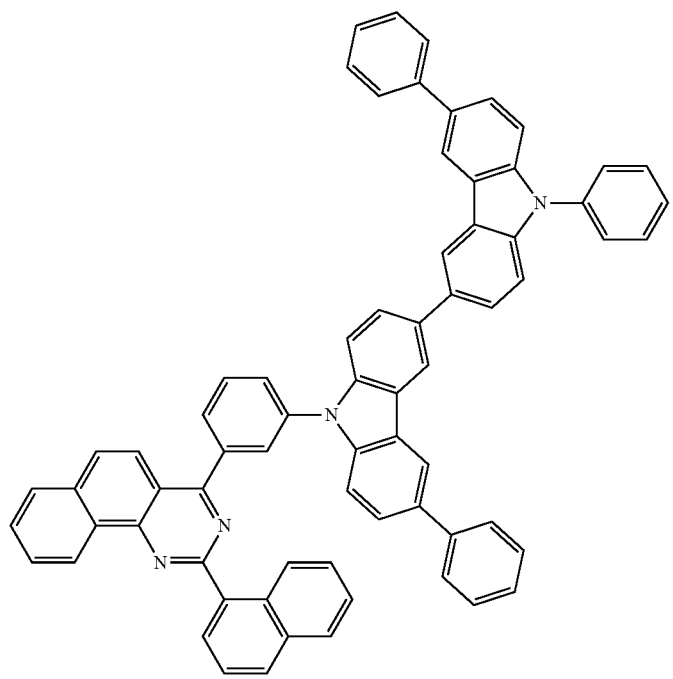
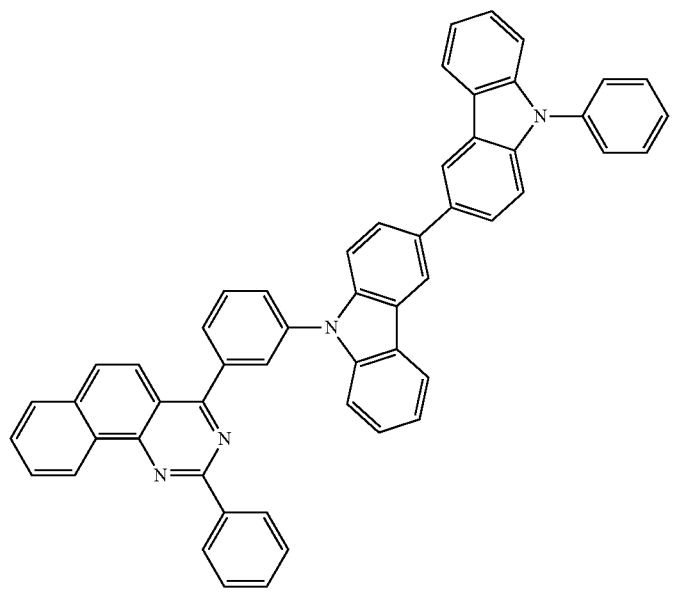

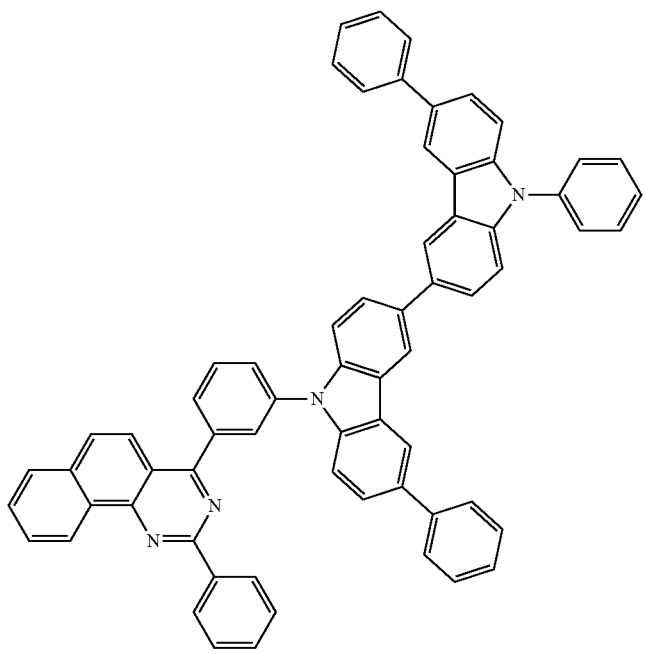
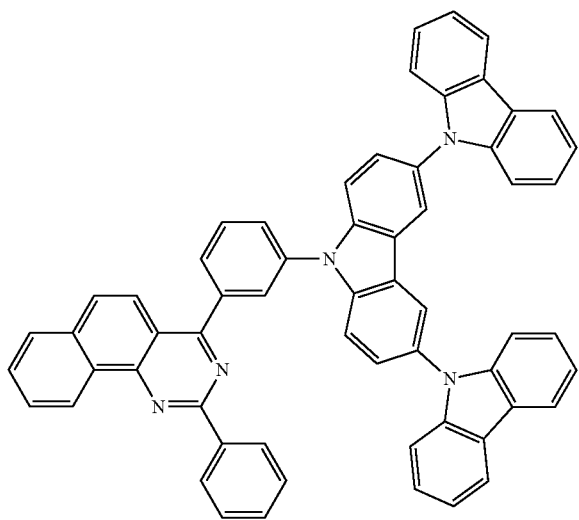

203 204
-continued
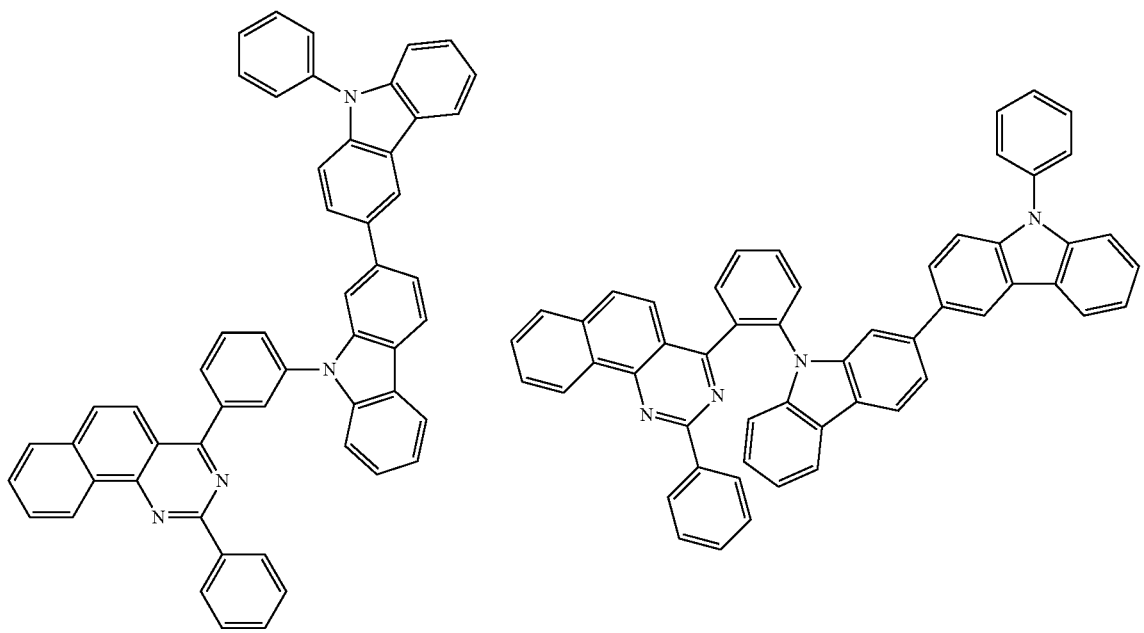
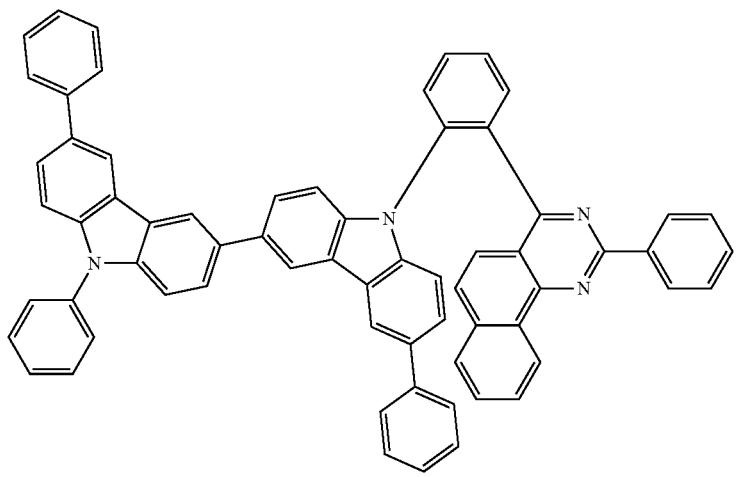

-continued
205
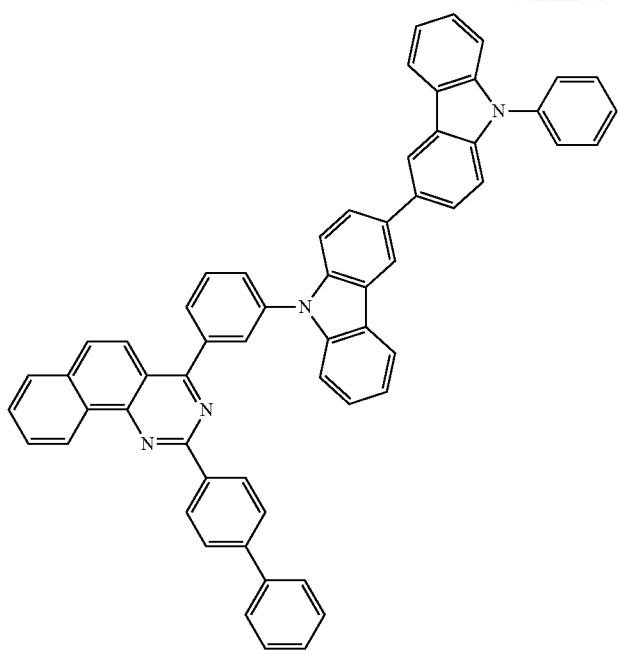
206
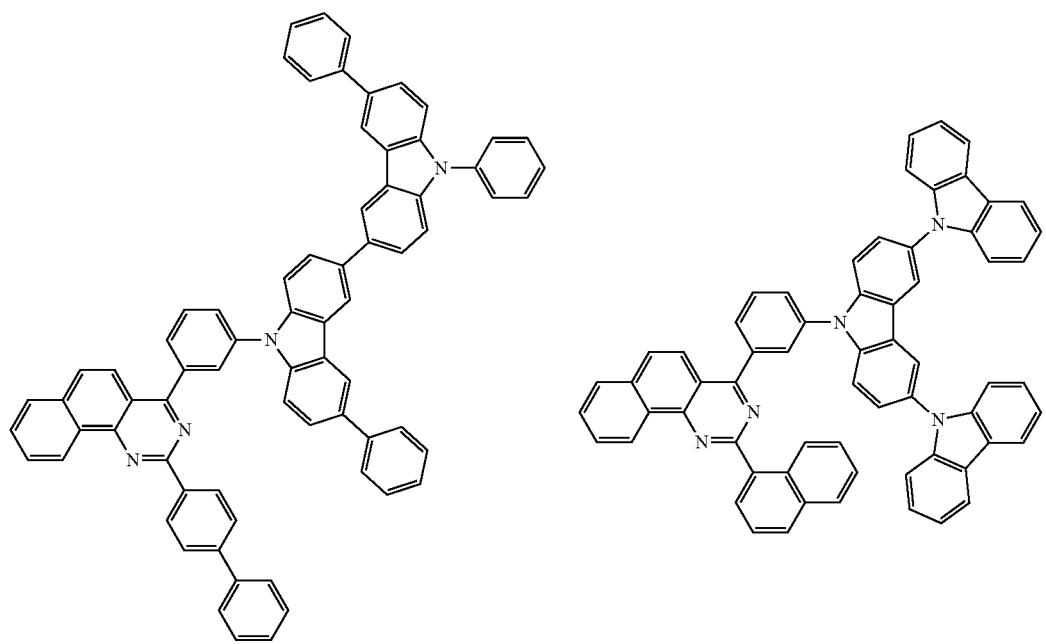

207
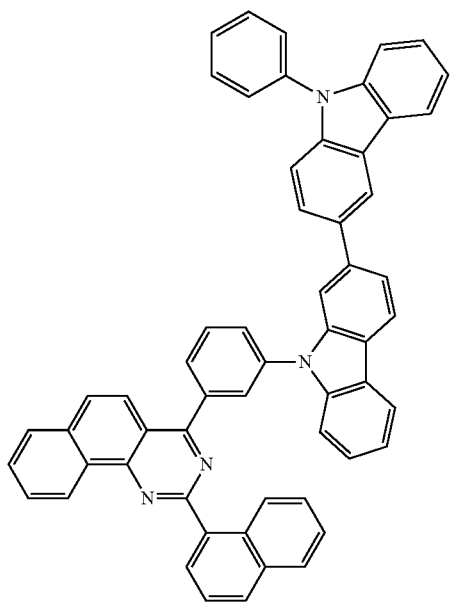
208
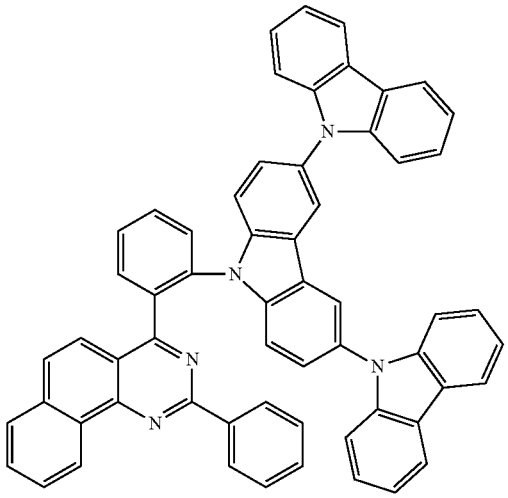
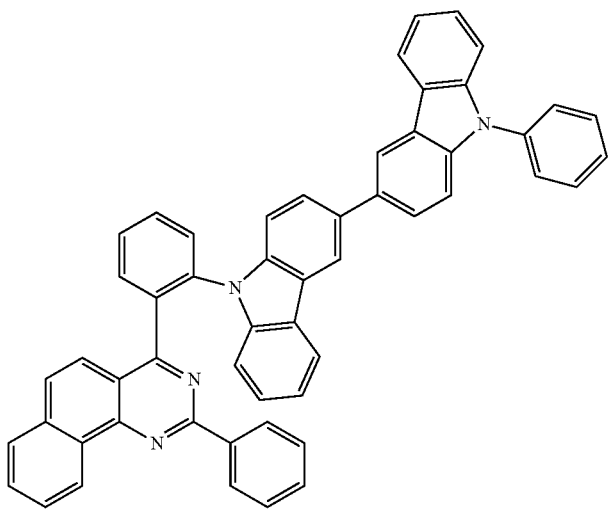
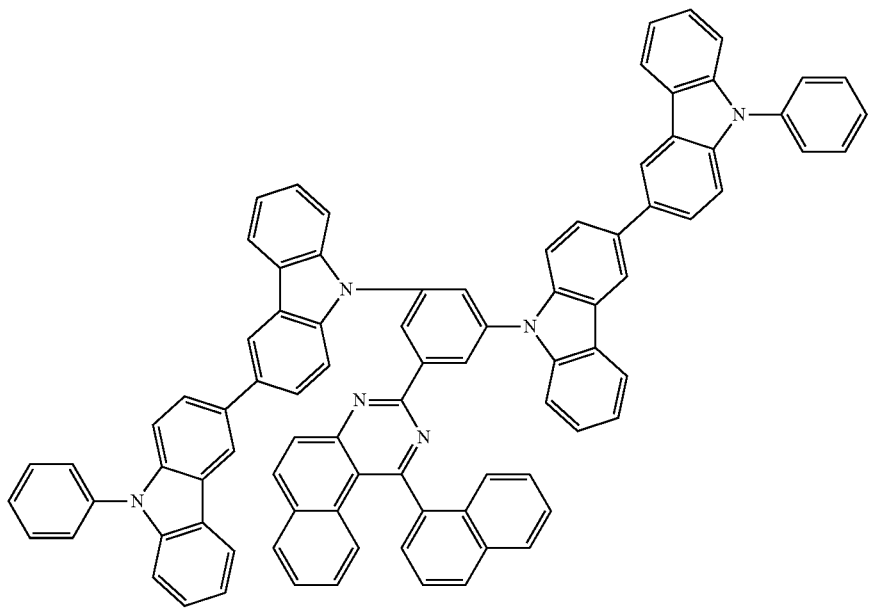

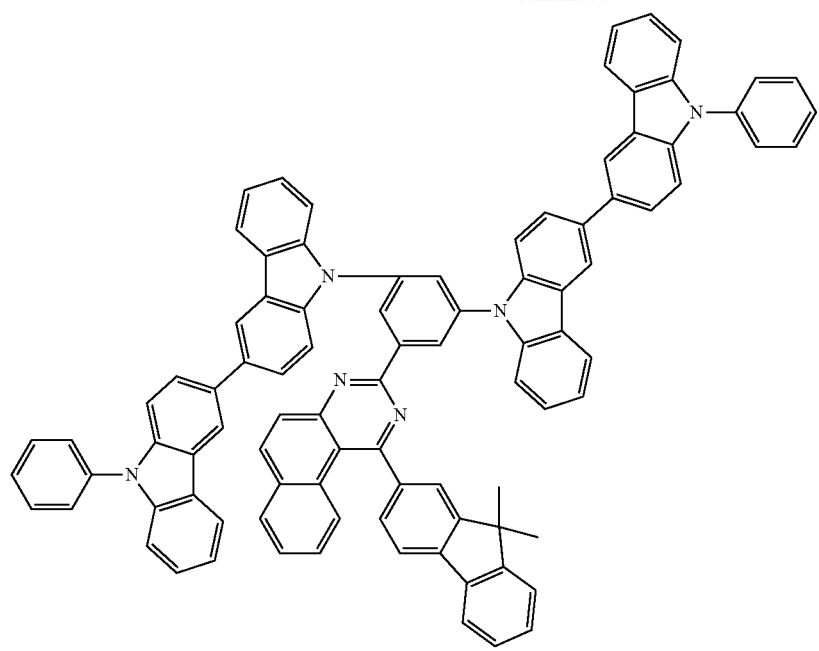
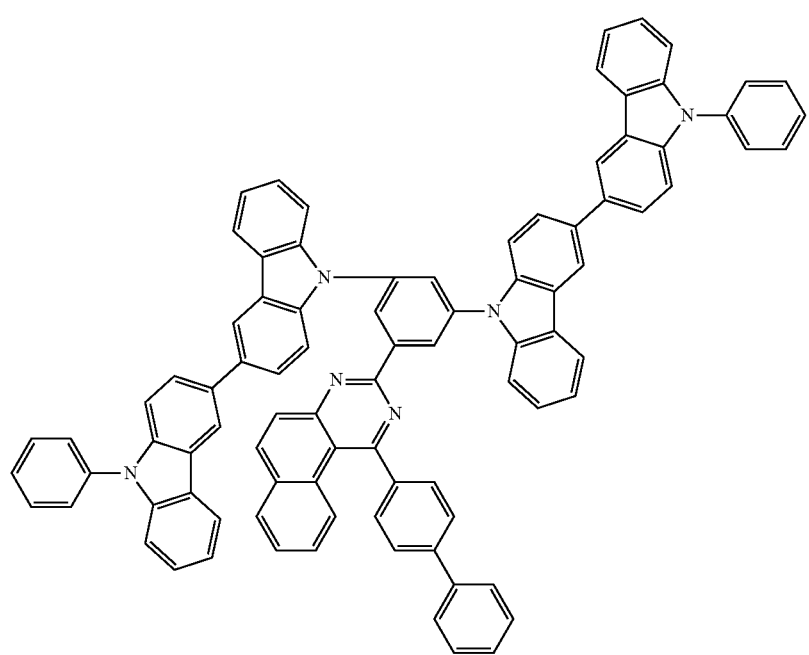

-continued
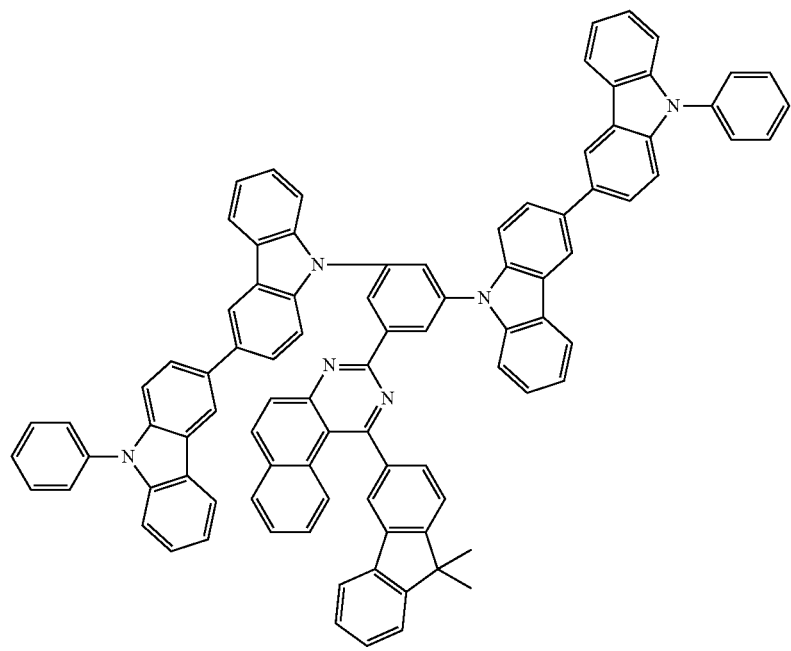
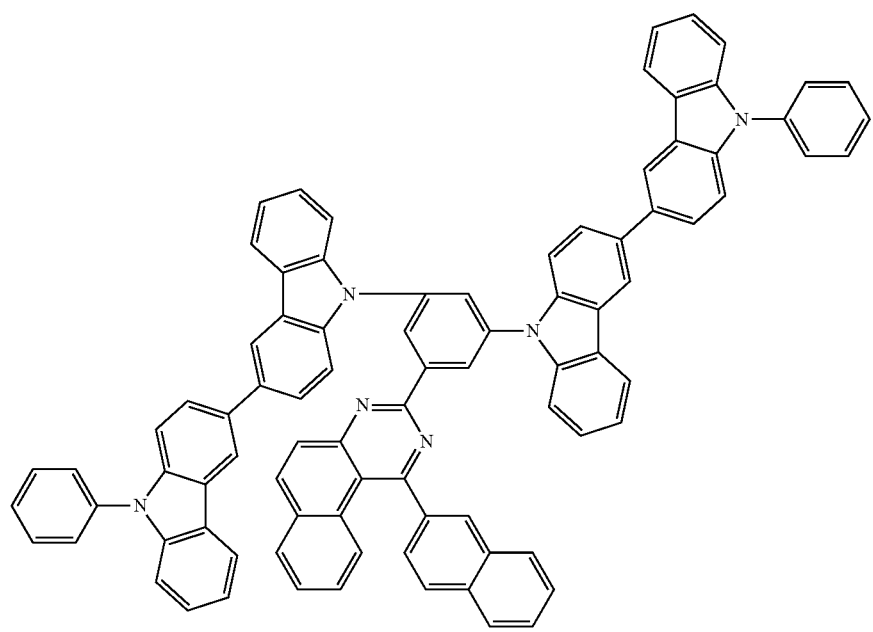

-continued
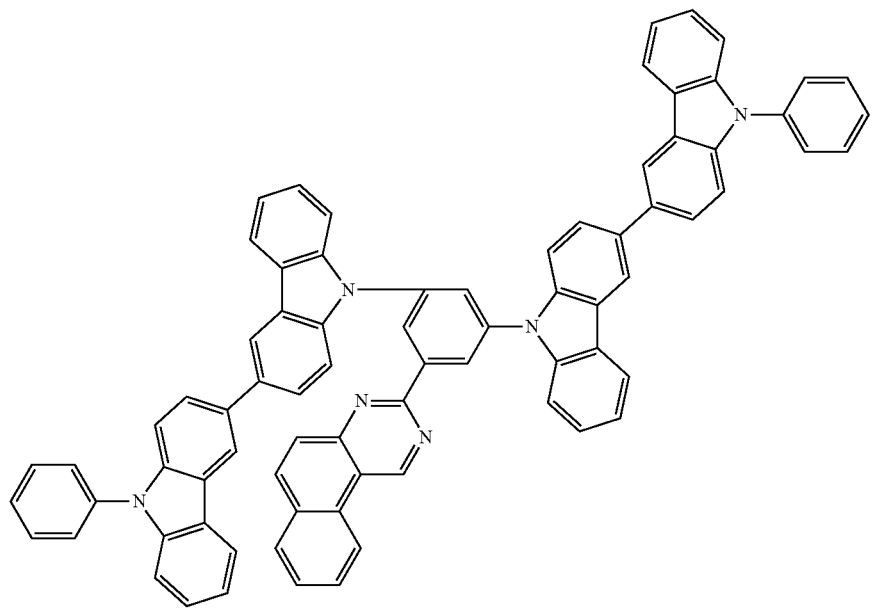
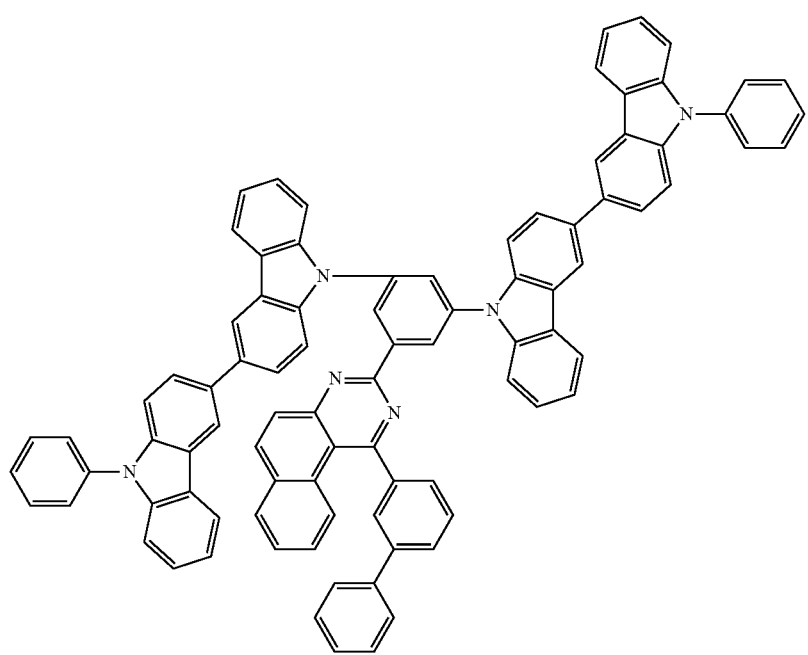

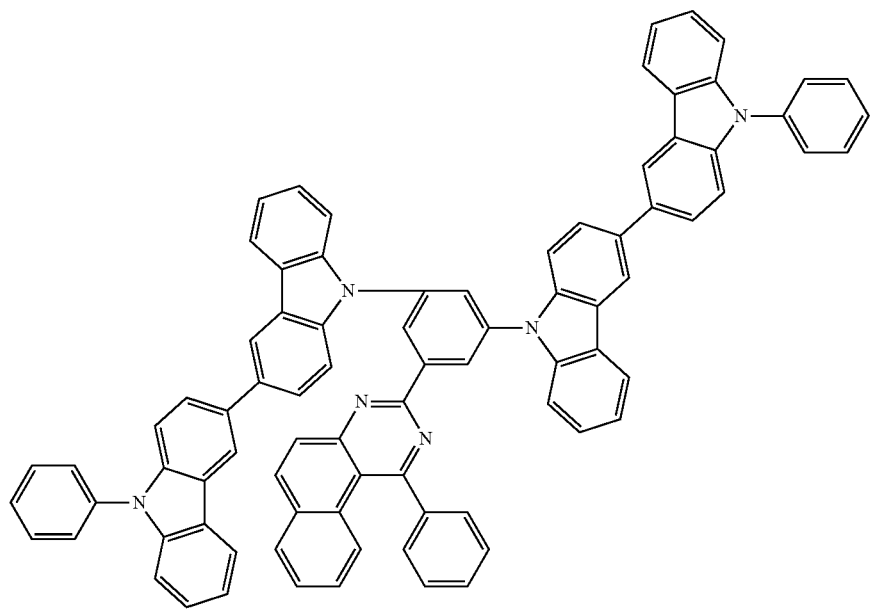
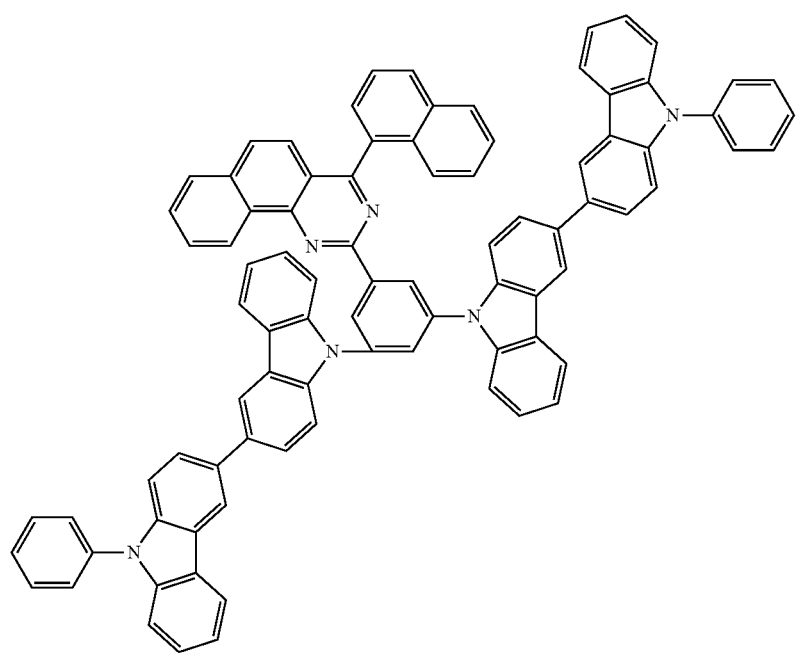

-continued
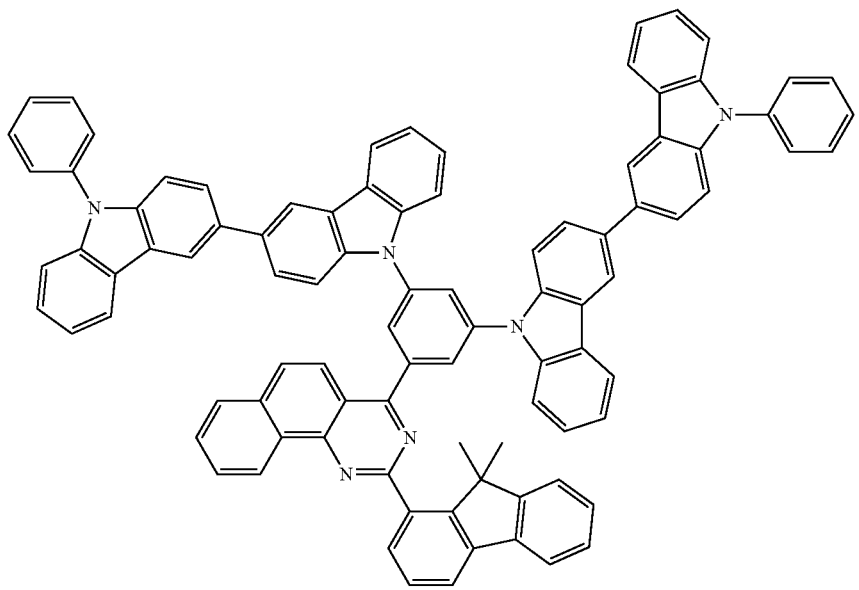
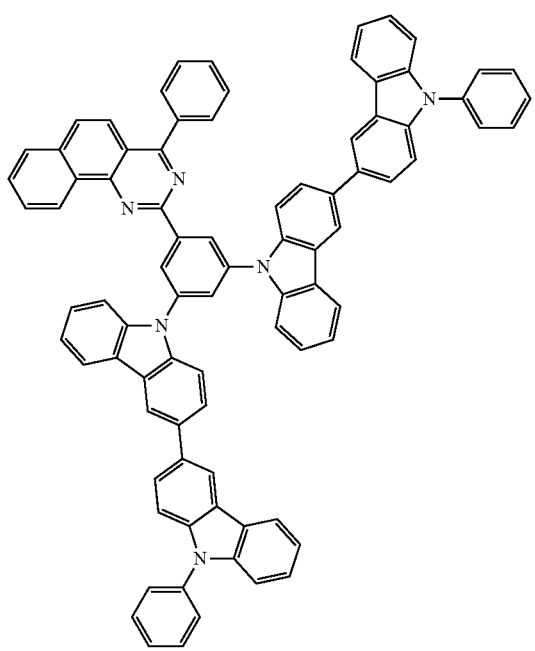

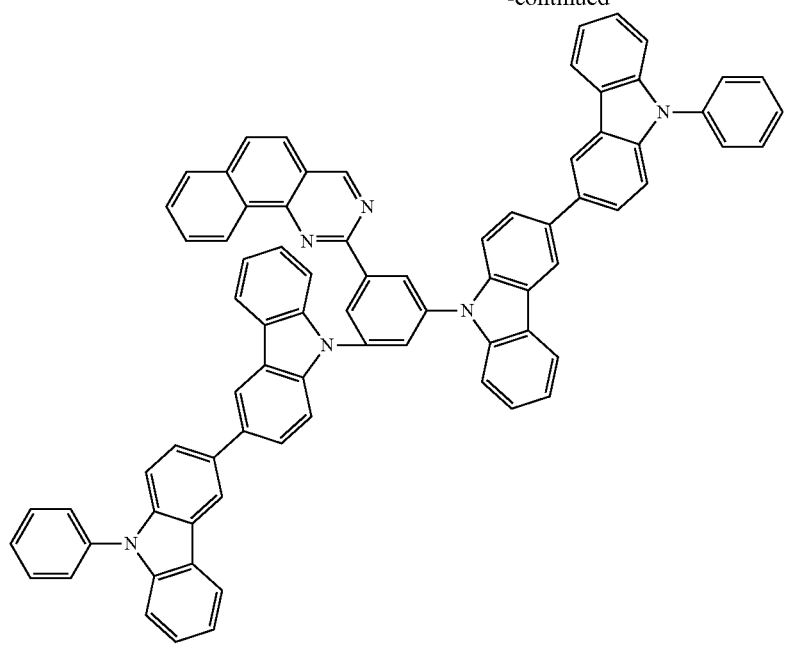
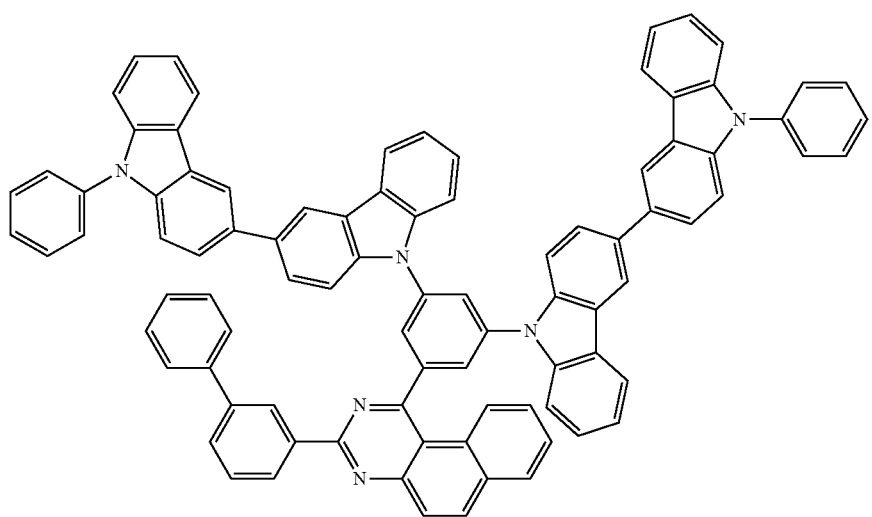

-continued
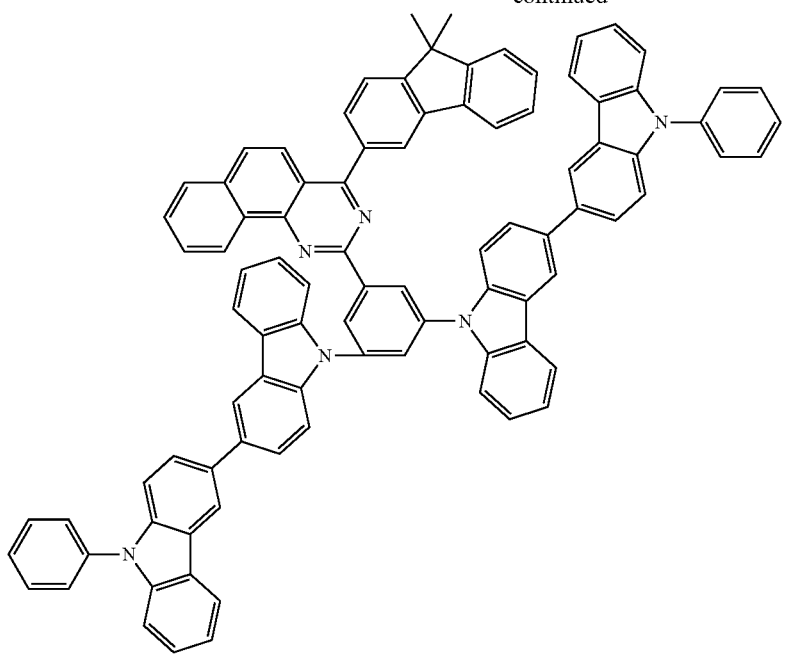
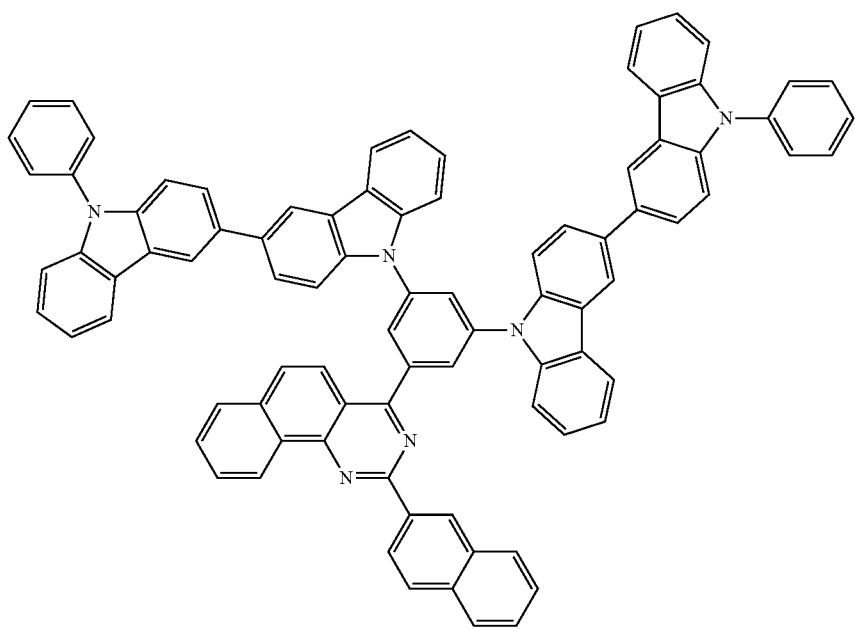

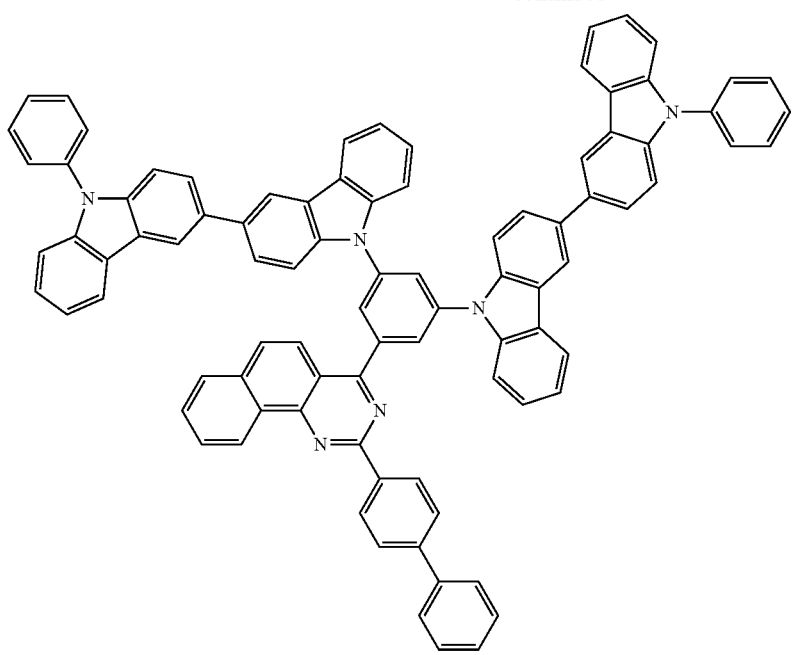
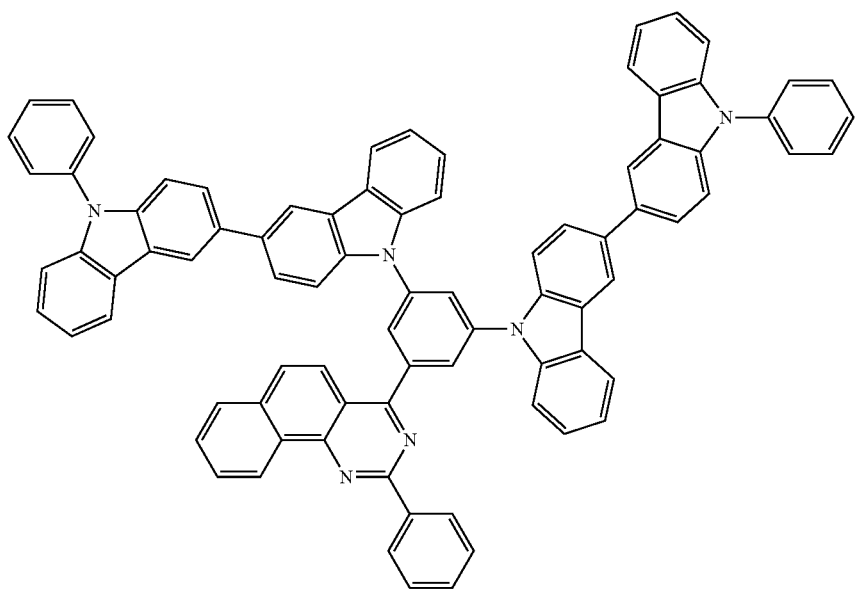

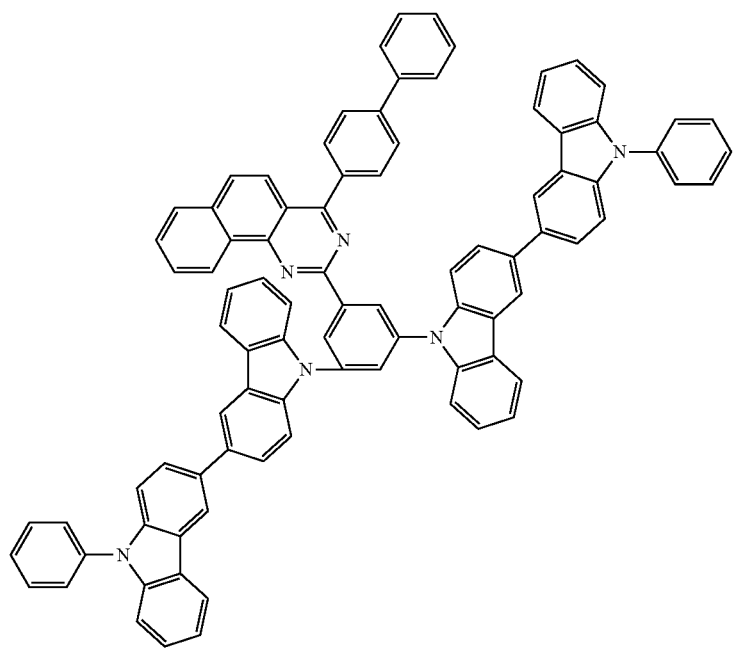
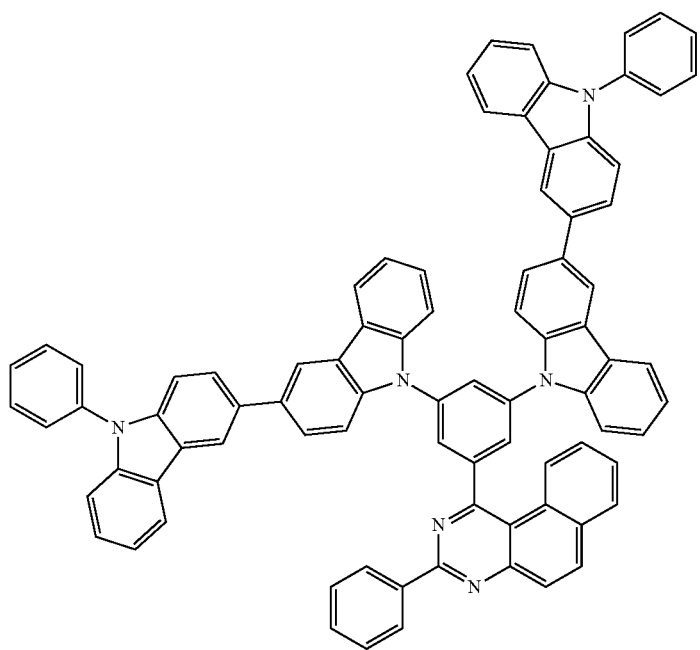 [SMILES: c1ccc(-c2nc(-c3cc(-n4c5ccccc5c5cc(-c6ccc7c(c6)c6ccccc6n7-c6ccccc6)ccc54)cc(-n4c5ccccc5c5cc(-c6ccc7c(c6)c6ccccc6n7-c6ccccc6)ccc54)c3)c3c(ccc4ccccc43)n2)cc1]

227 228
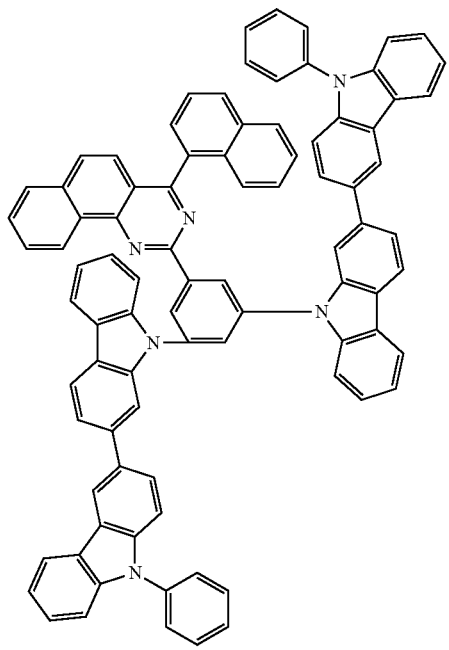
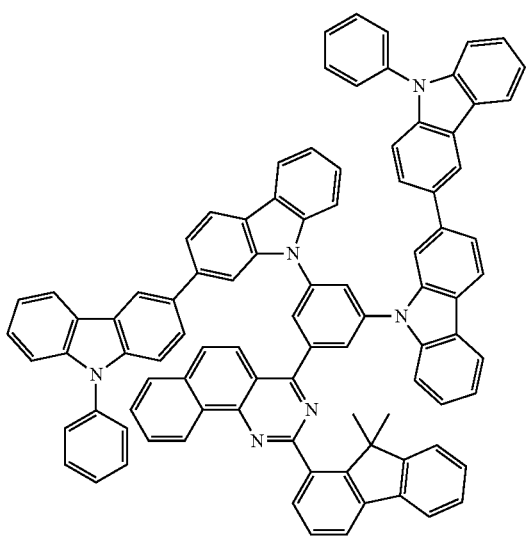
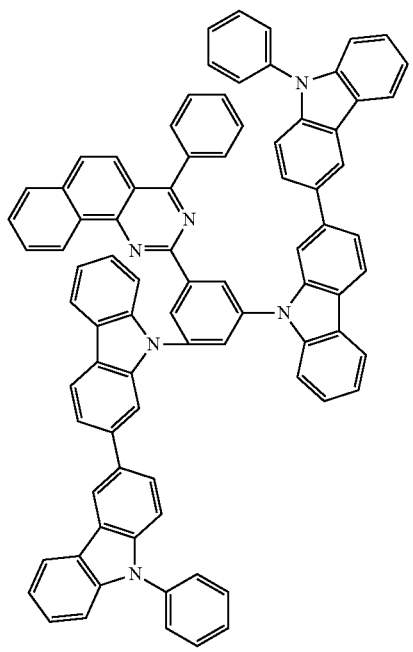
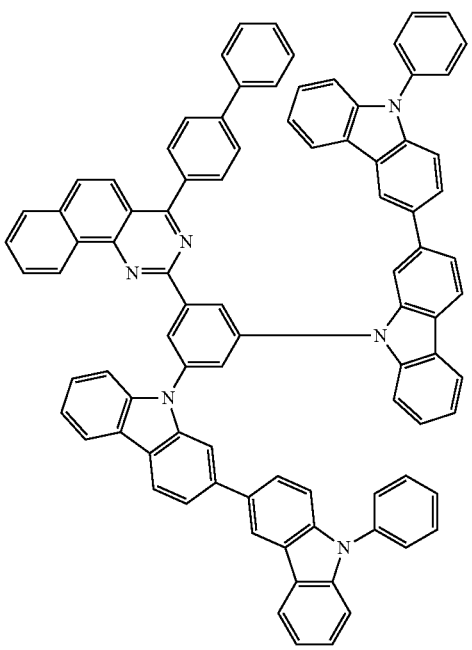

-continued
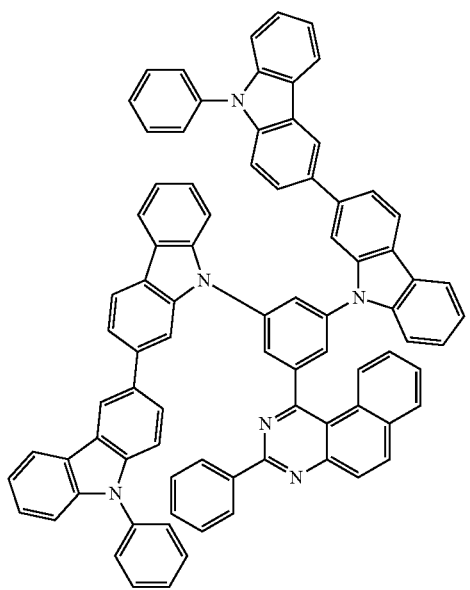
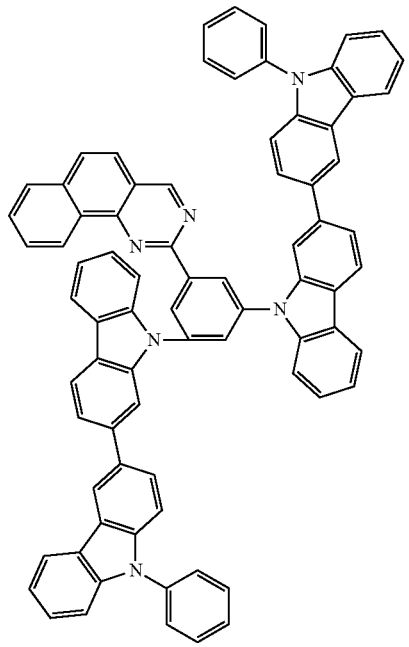
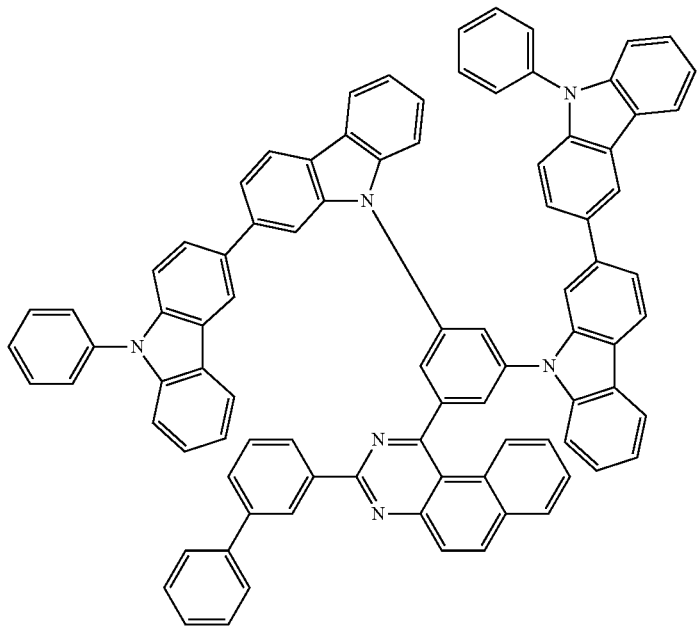

231
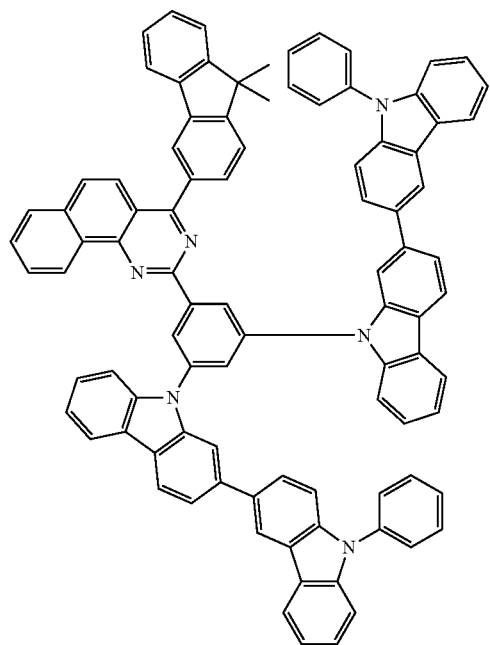
232
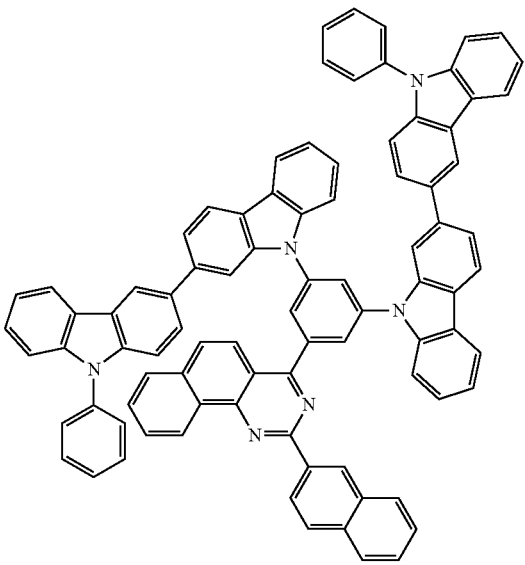
-continued
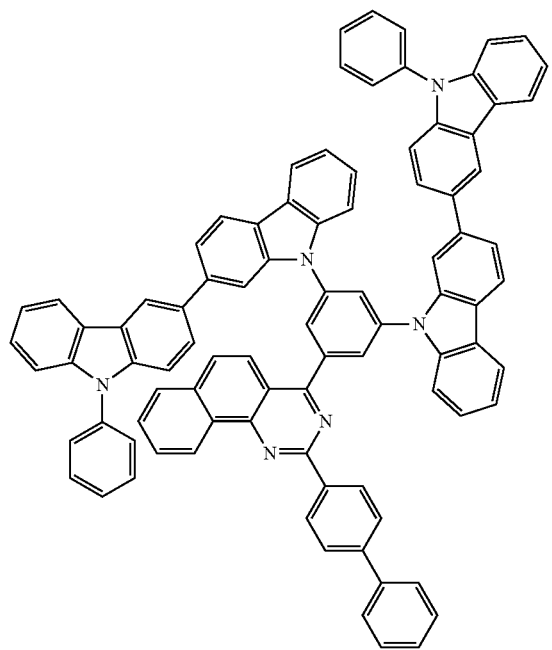

-continued
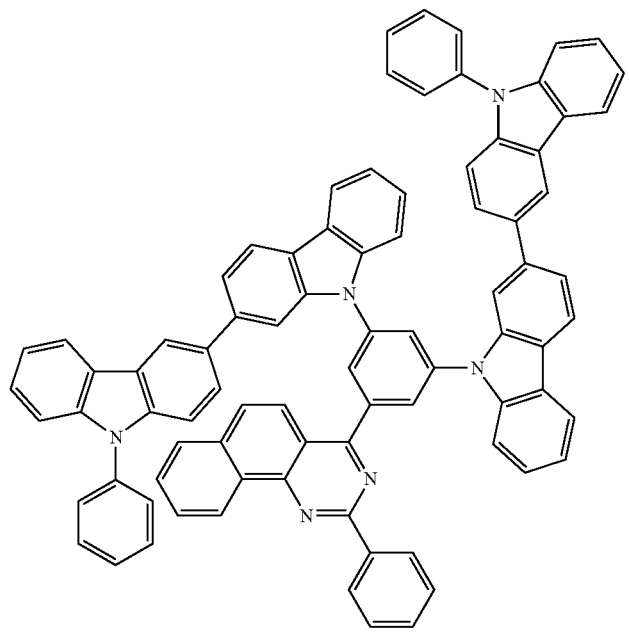
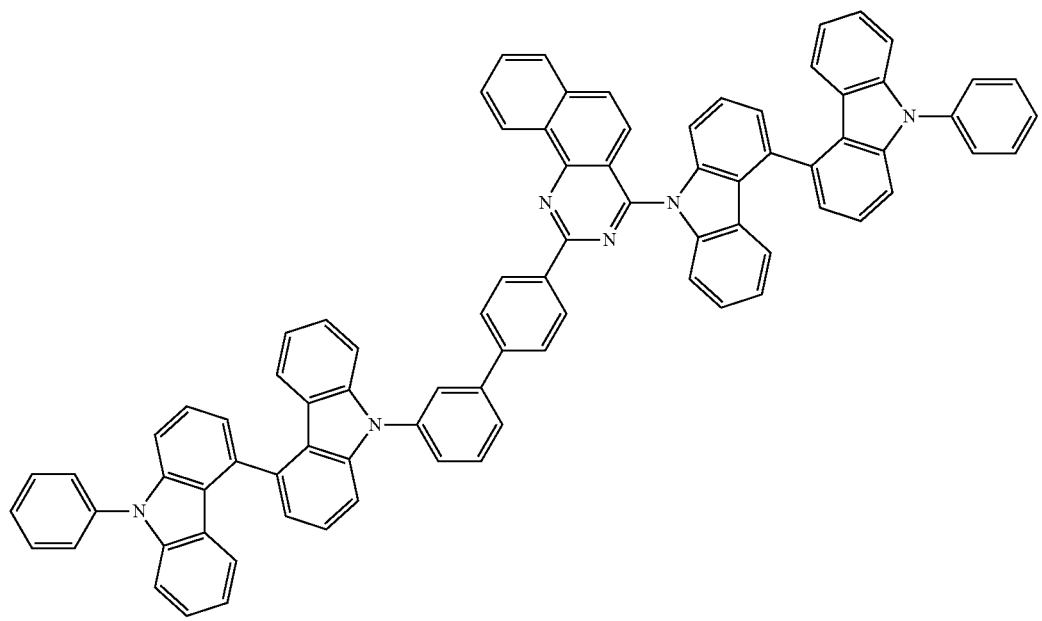
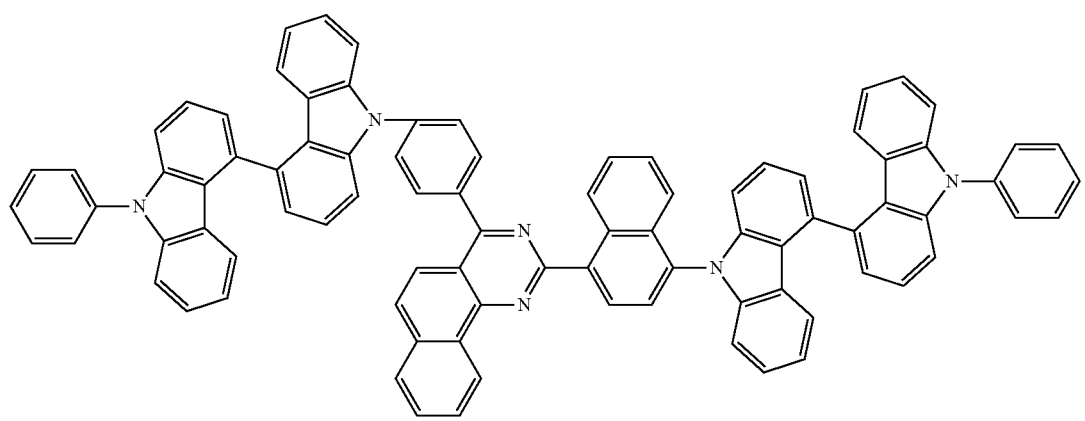

-continued
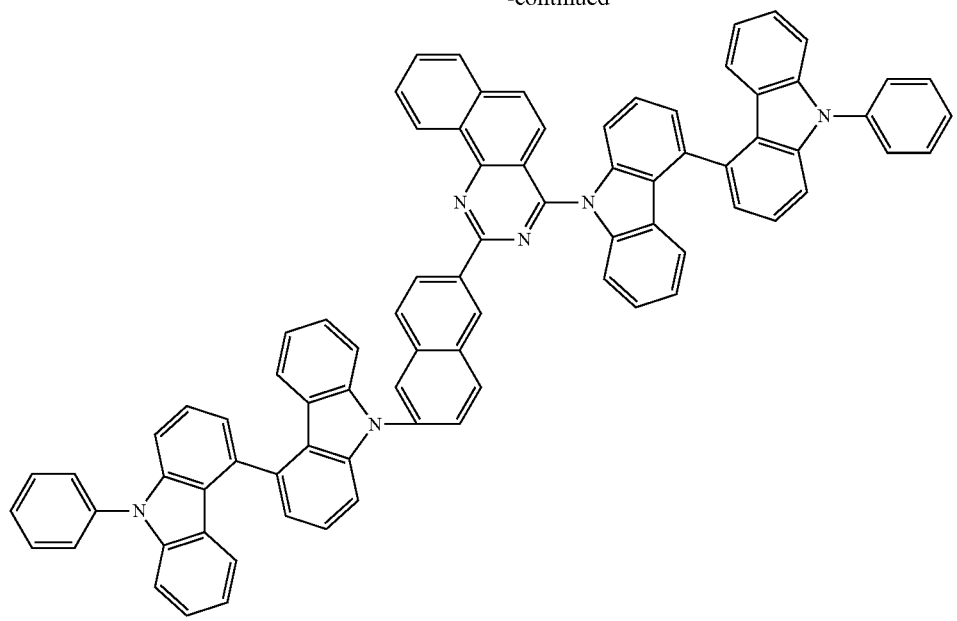
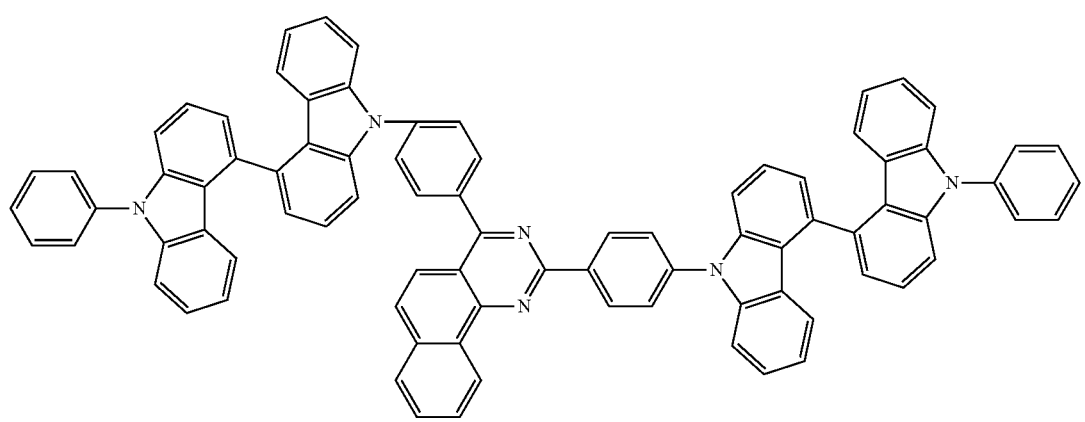
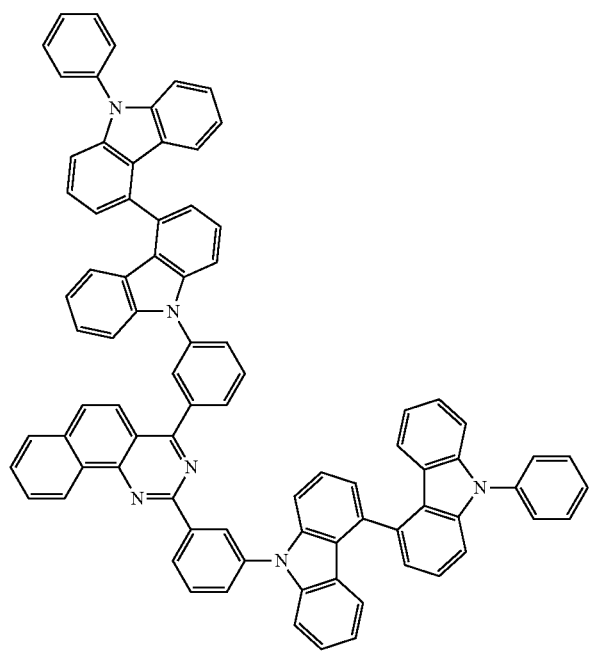

-continued
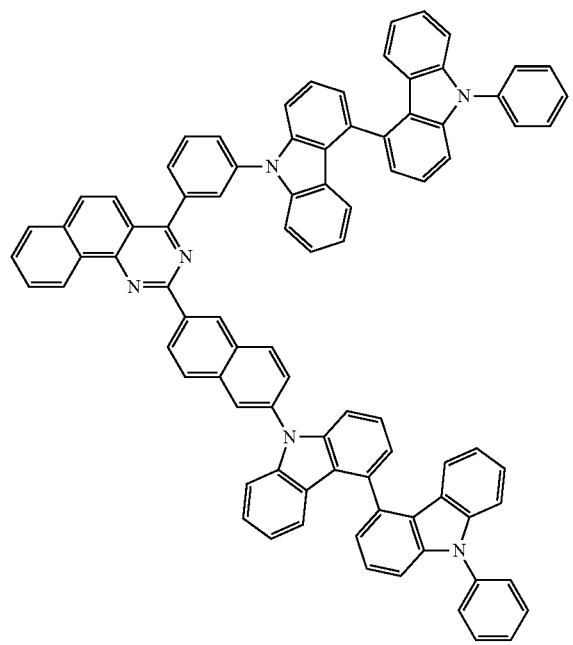
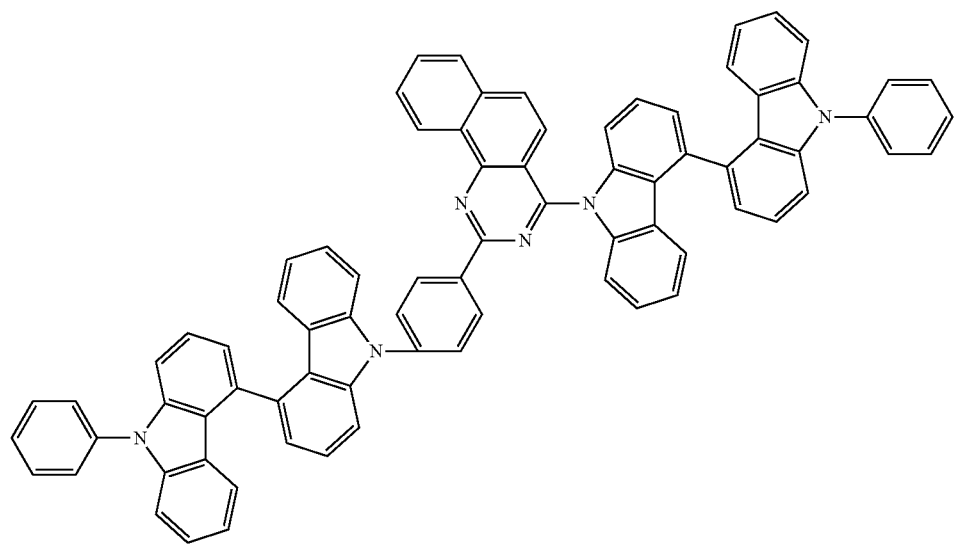
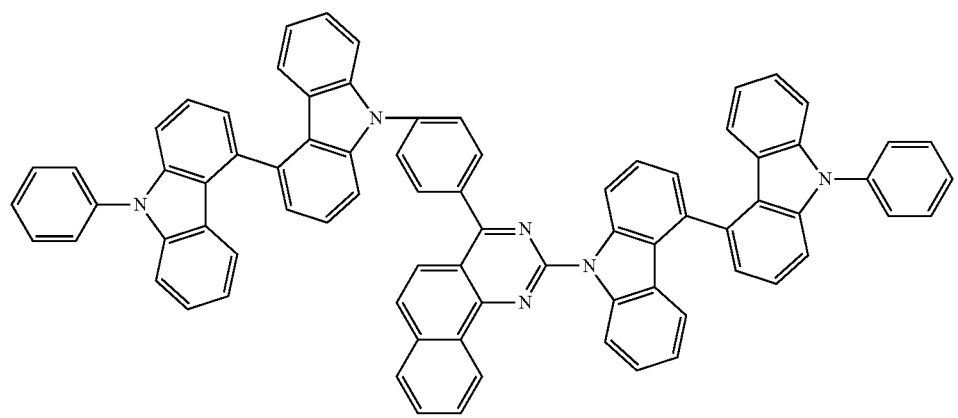

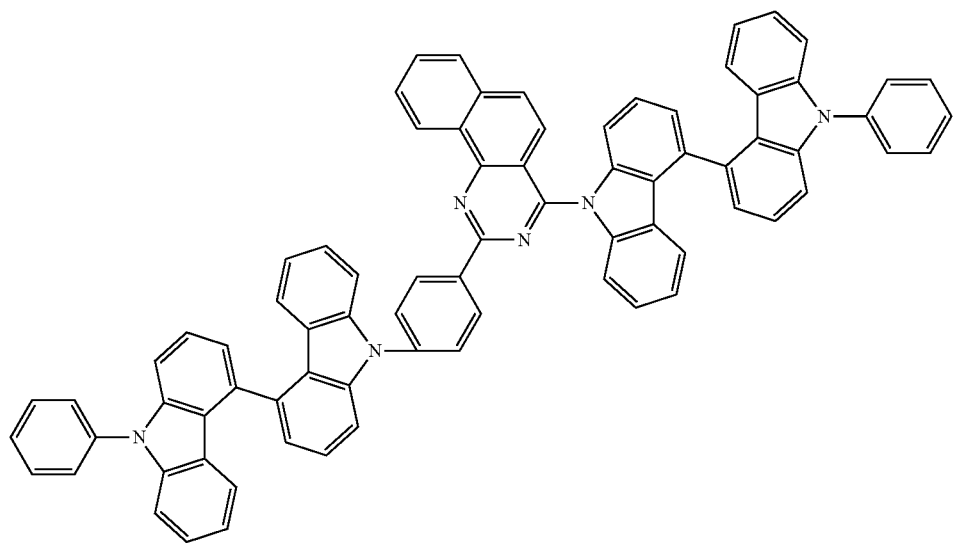
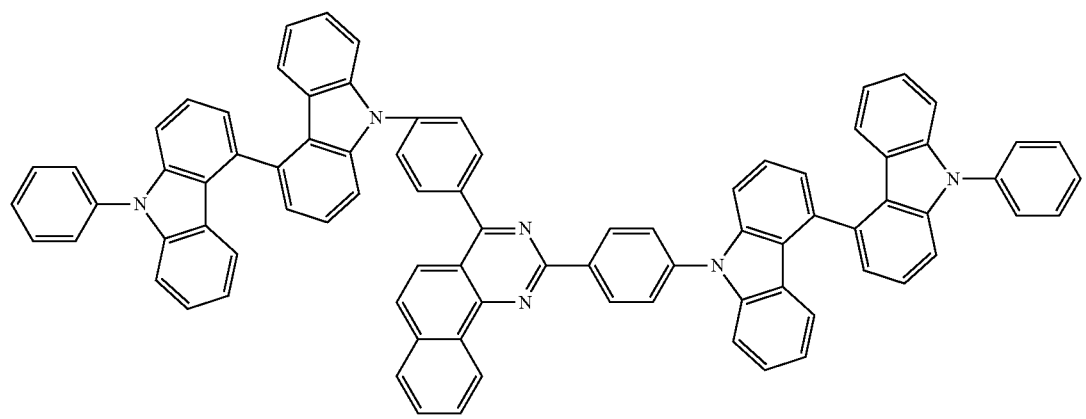
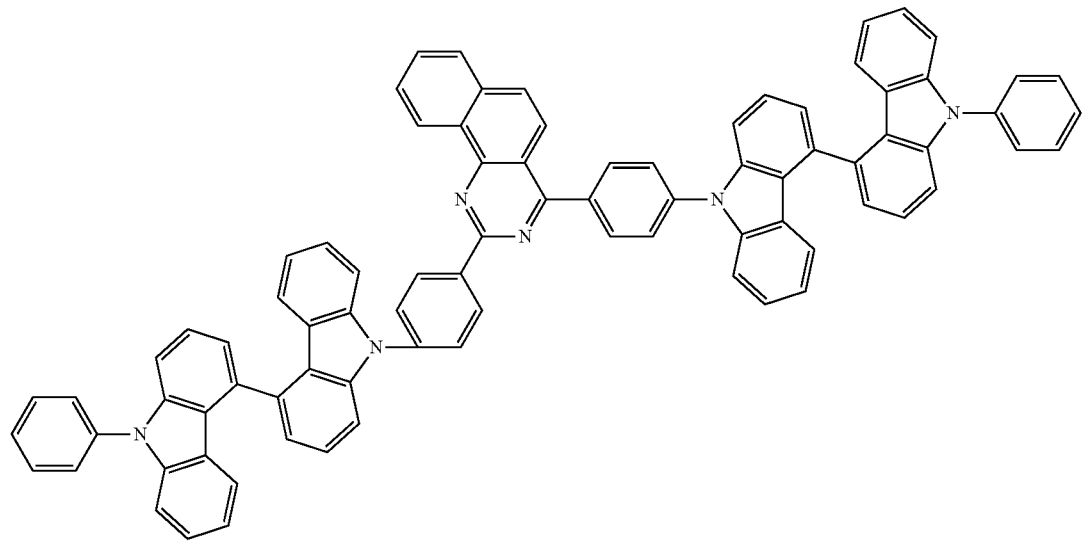

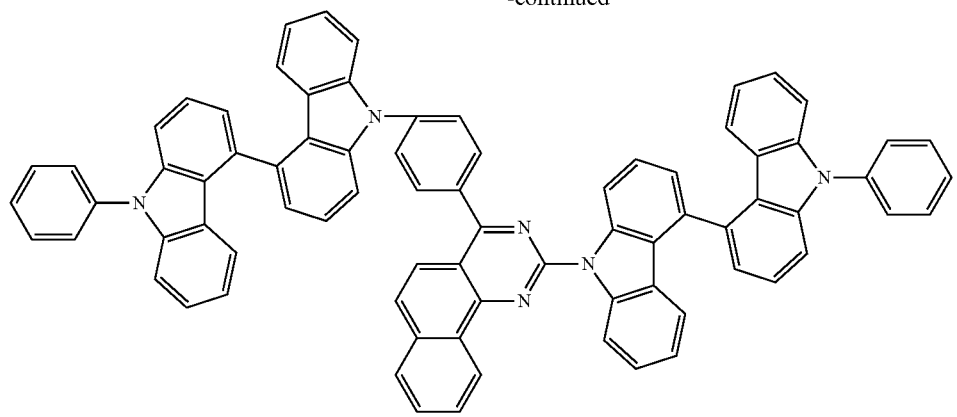
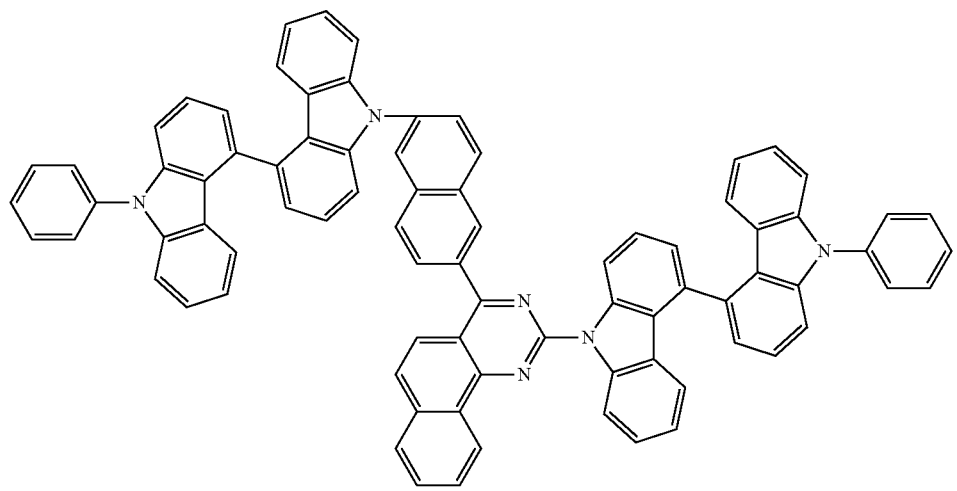
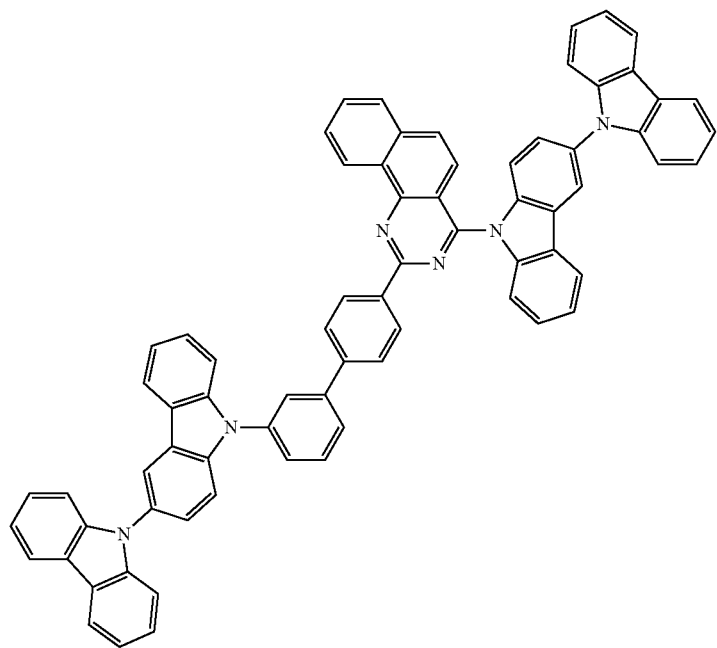

-continued
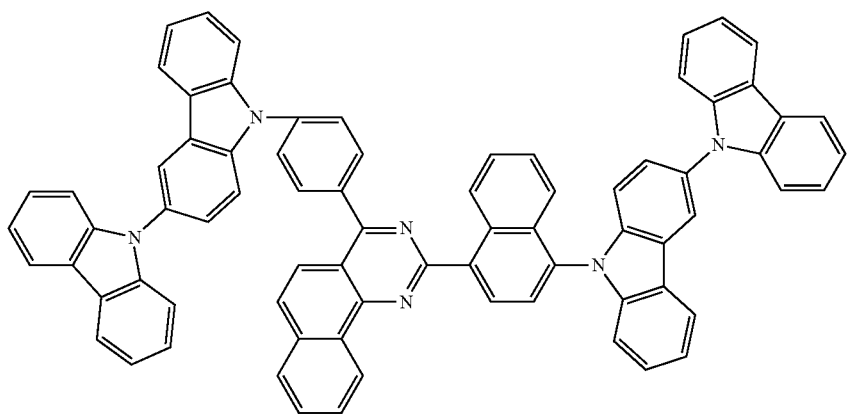
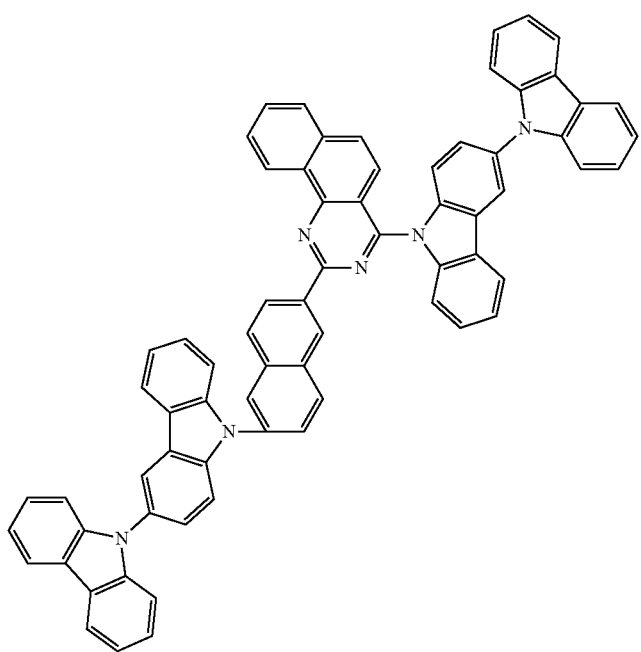

-continued
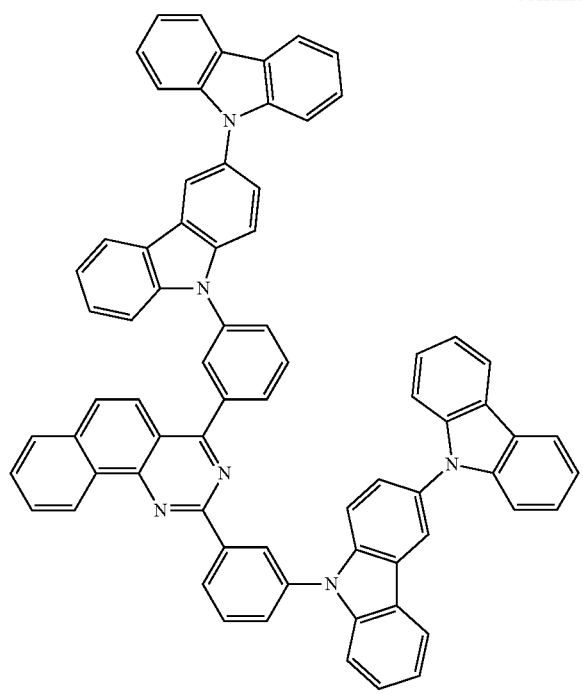
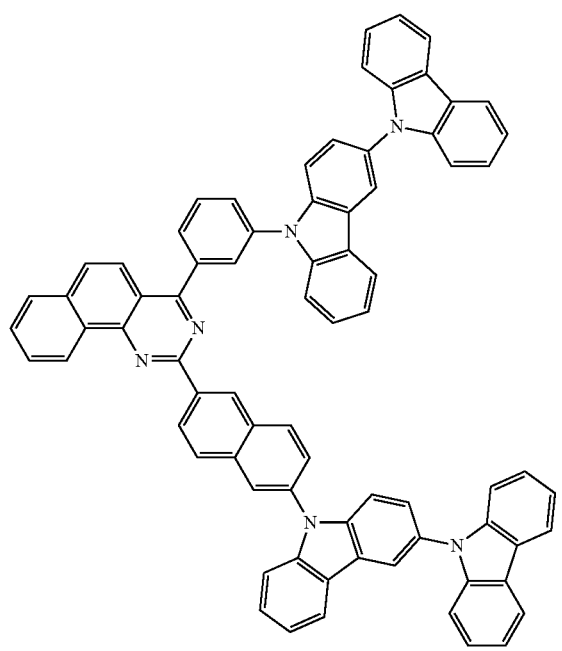

-continued
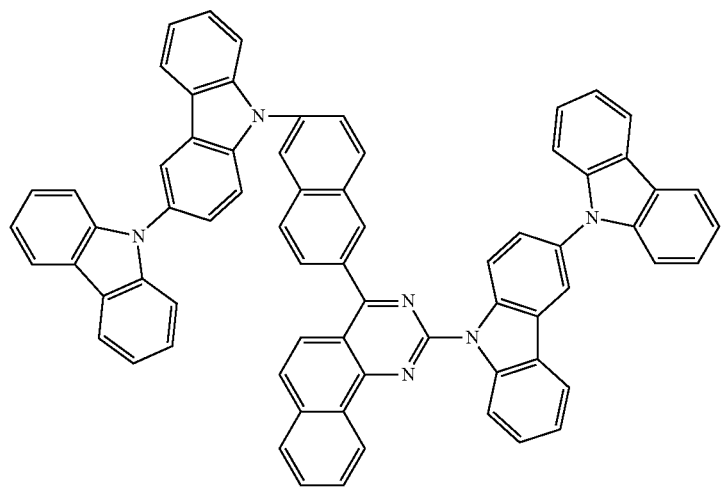
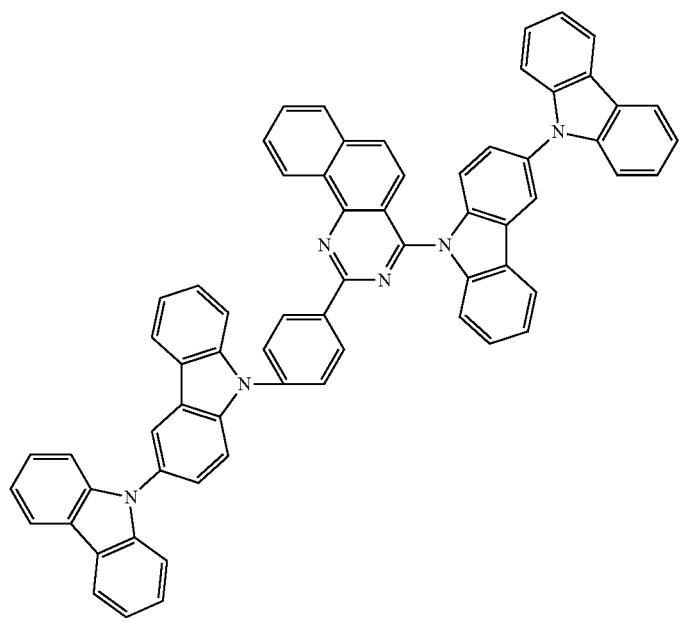
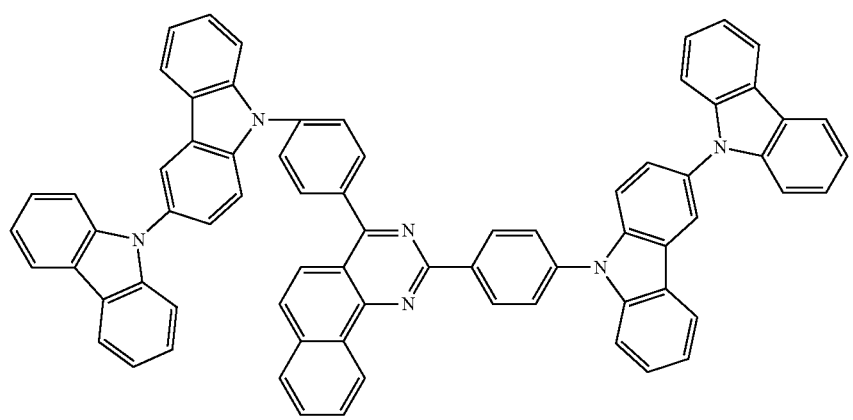

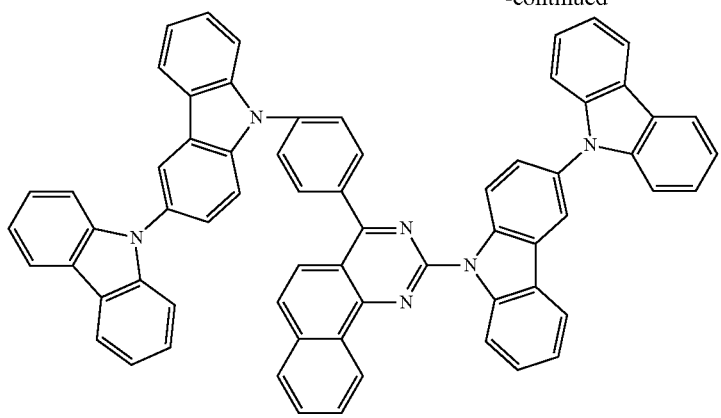
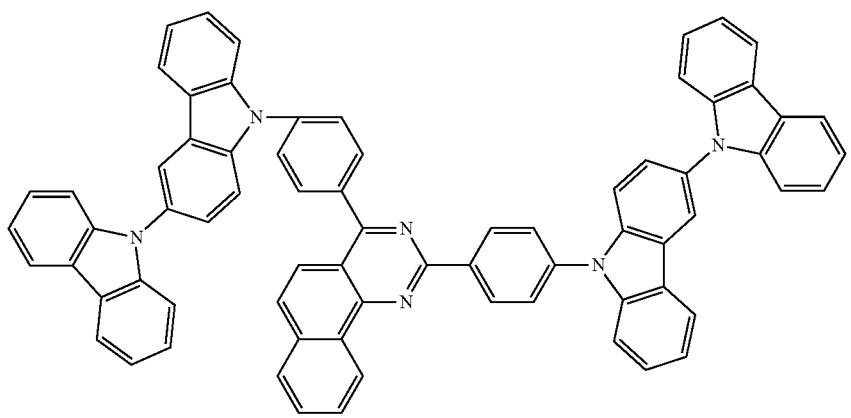
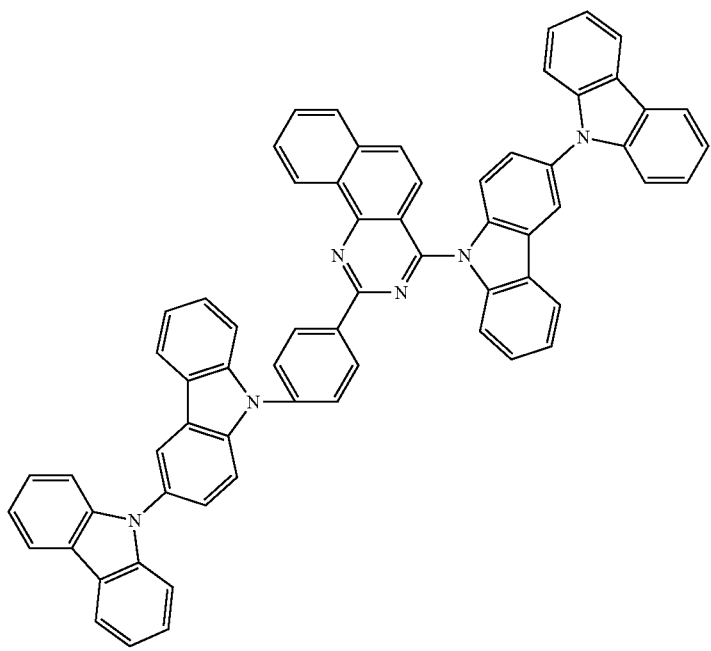

-continued
251
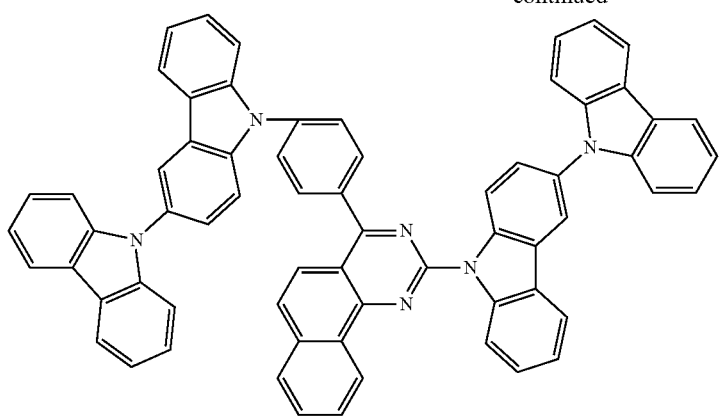
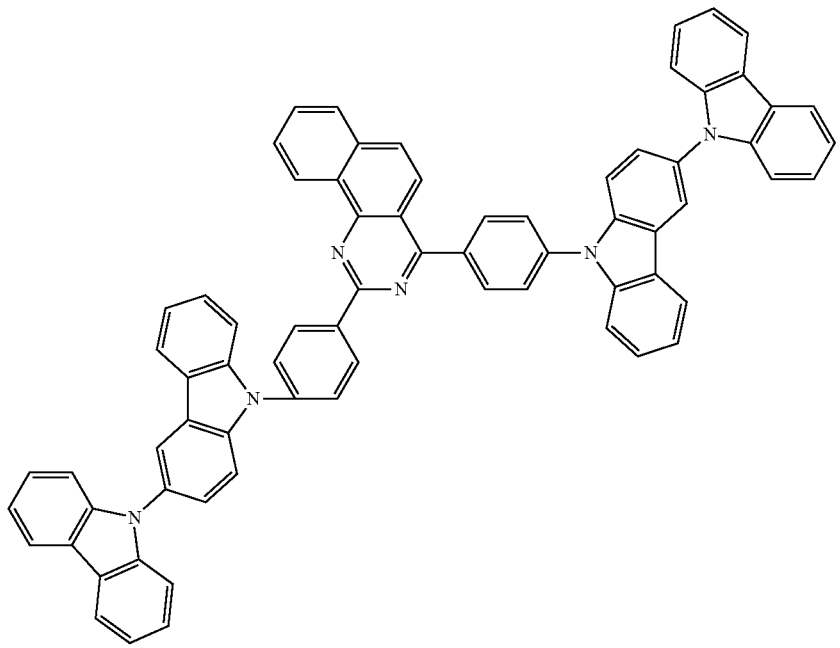
252
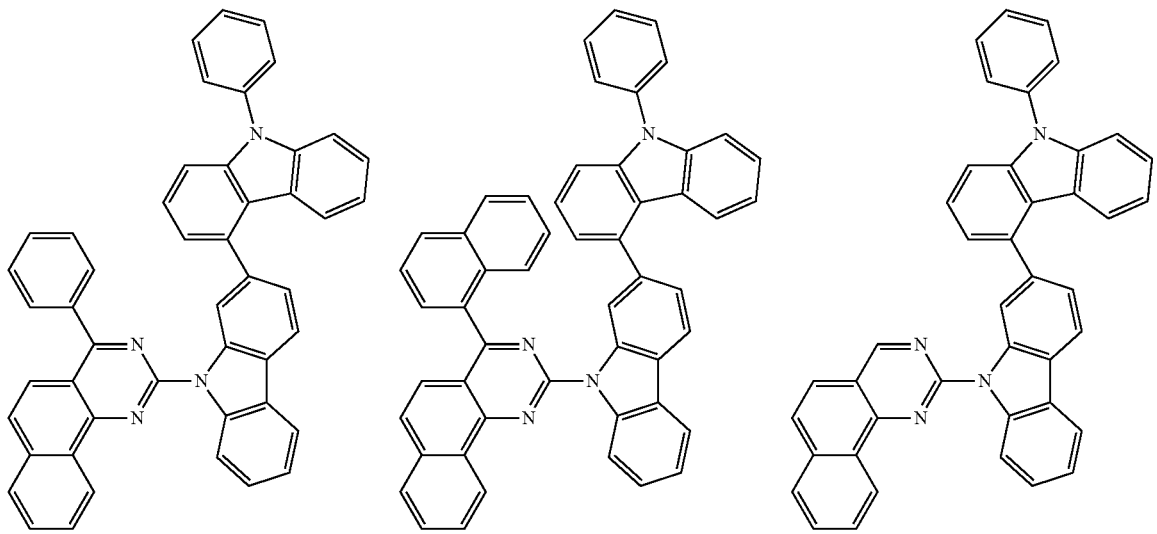

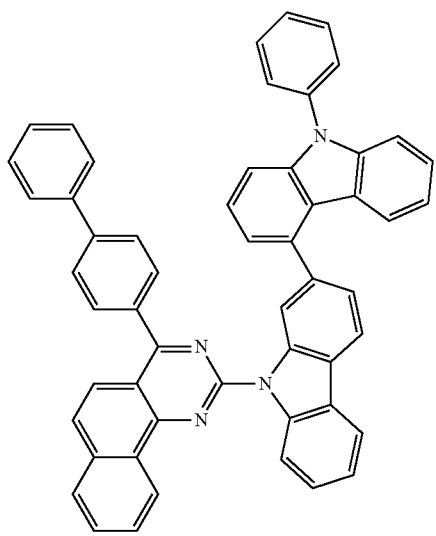
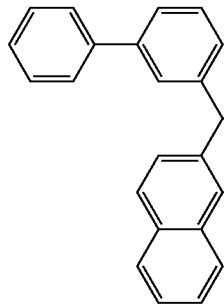
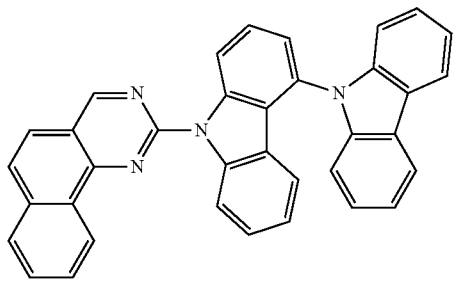
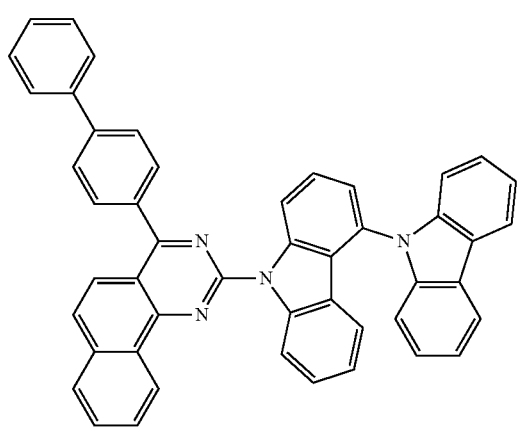
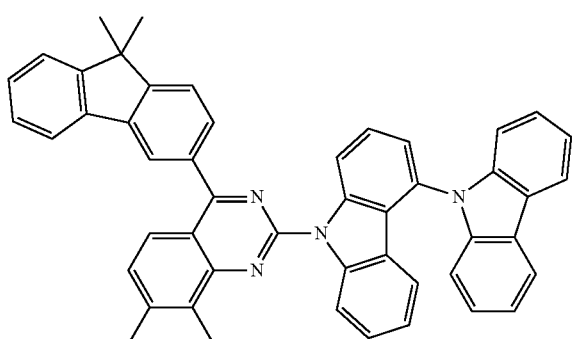
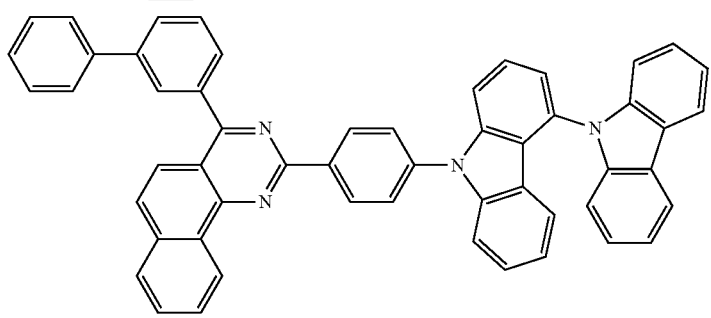

-continued
255
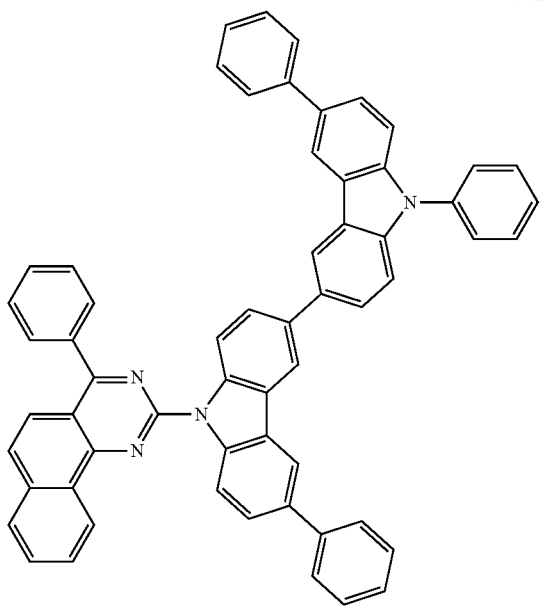
256
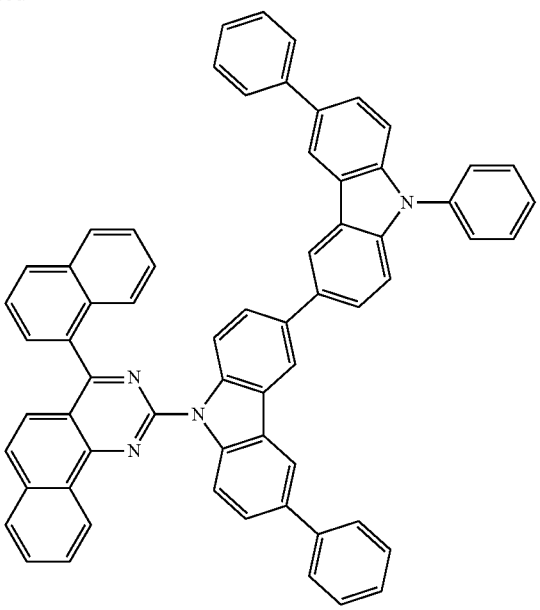
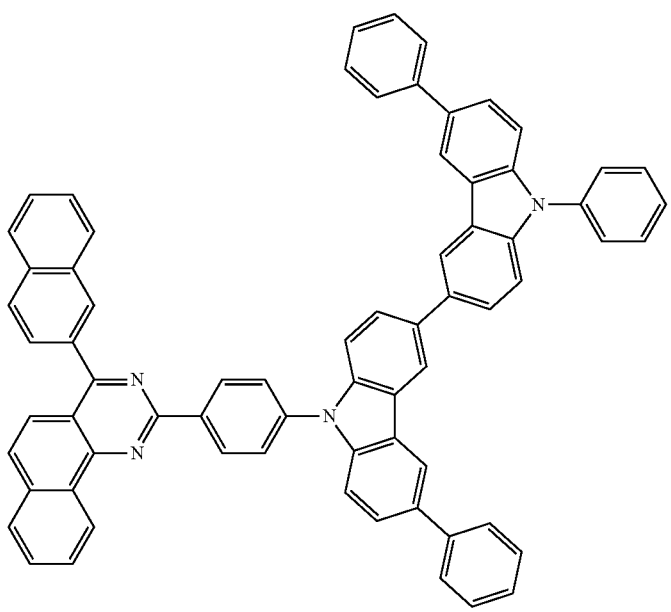

-continued
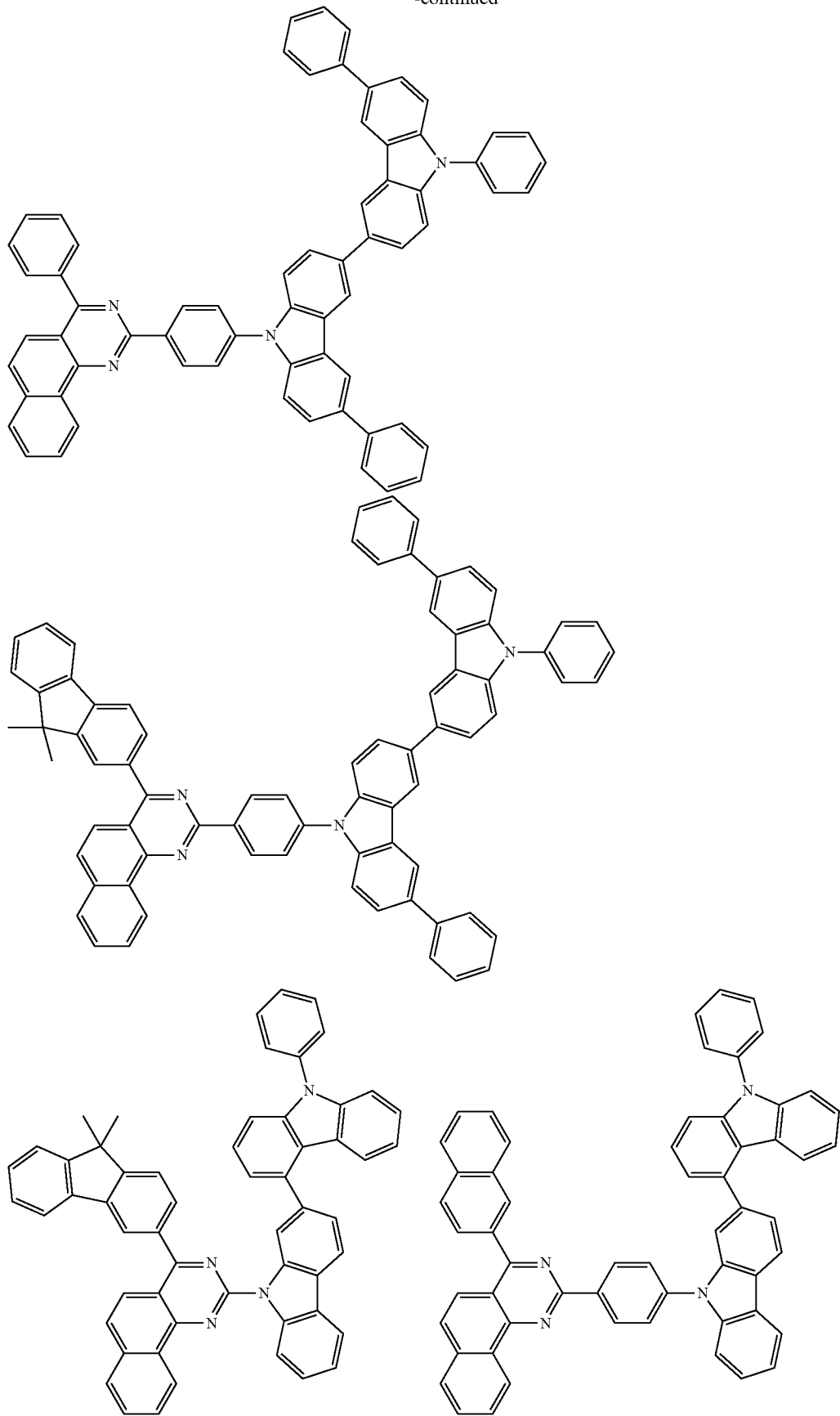

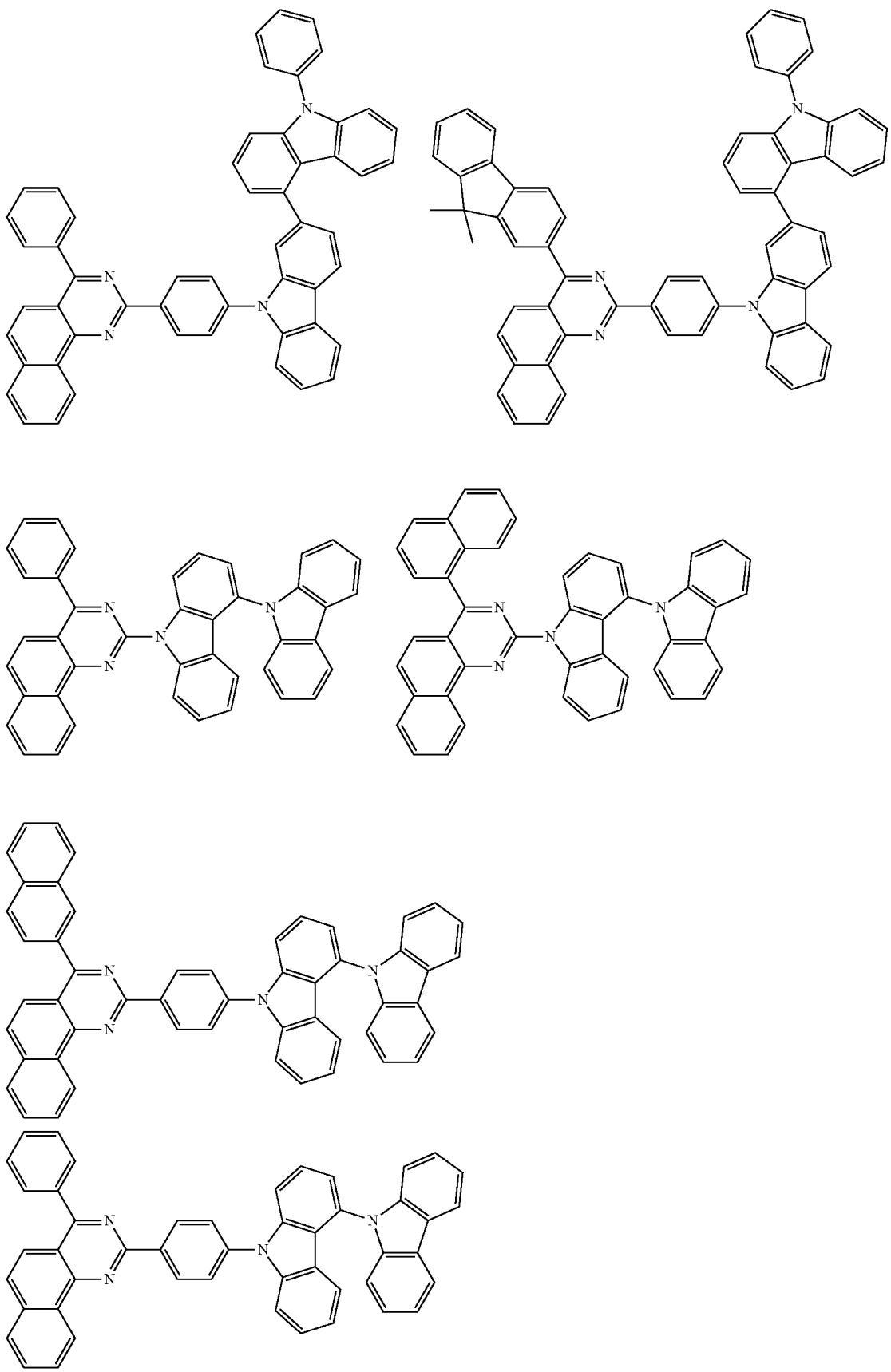

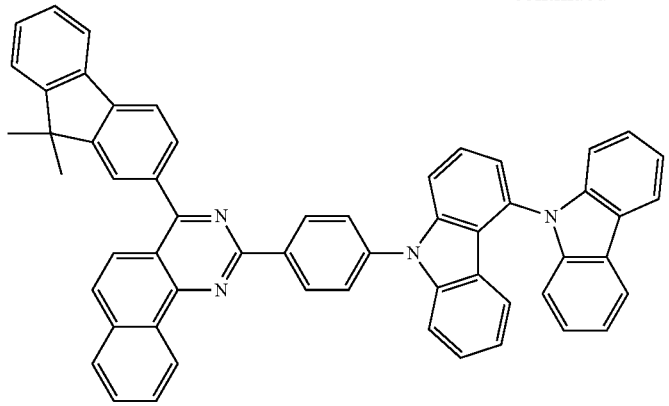
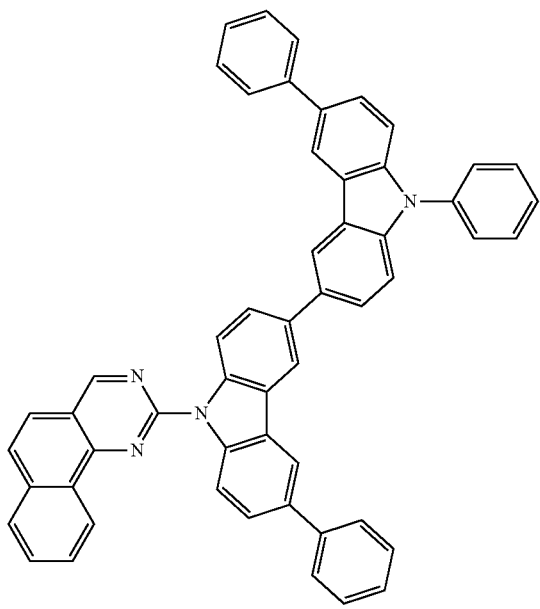
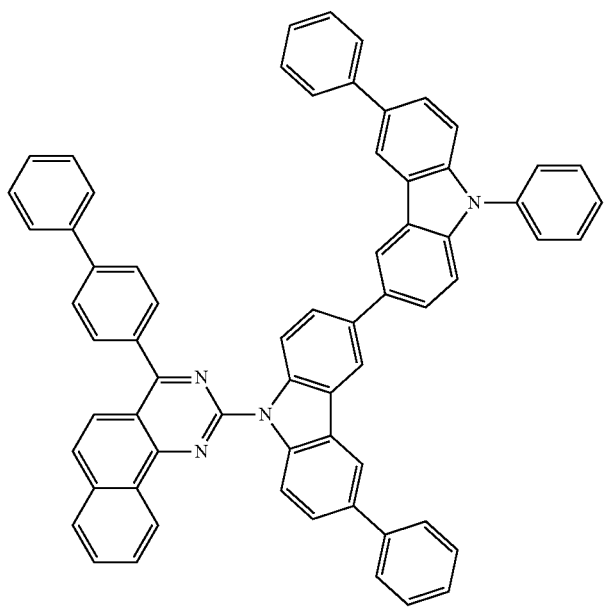

-continued
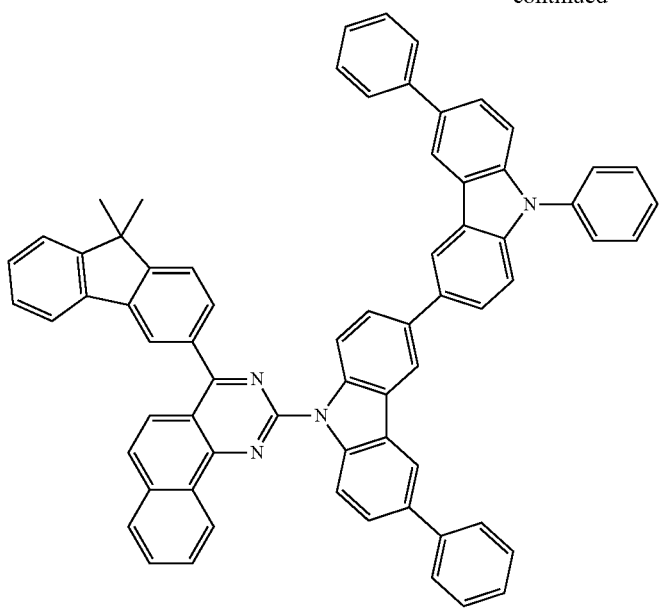
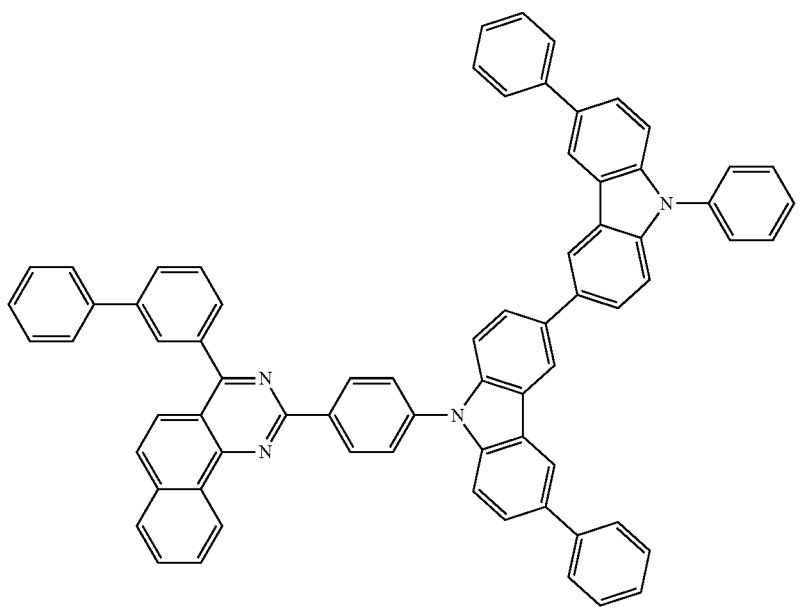
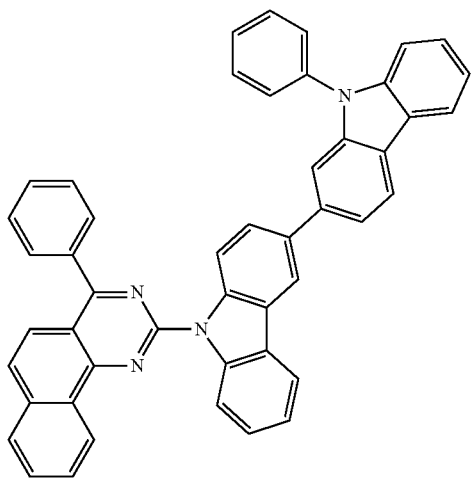
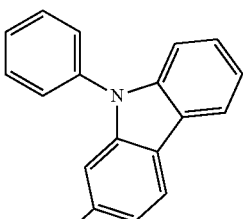
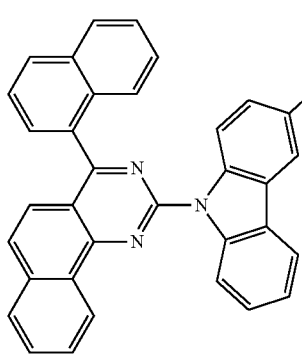

-continued
265
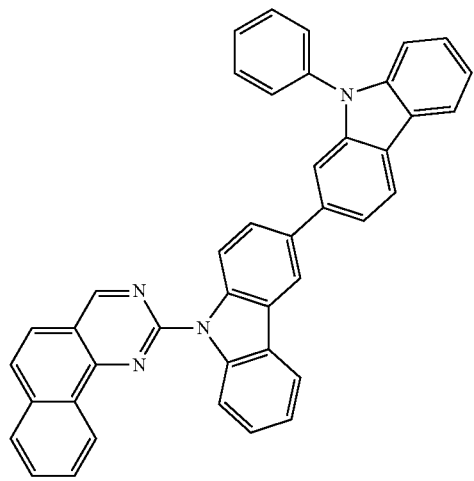
266
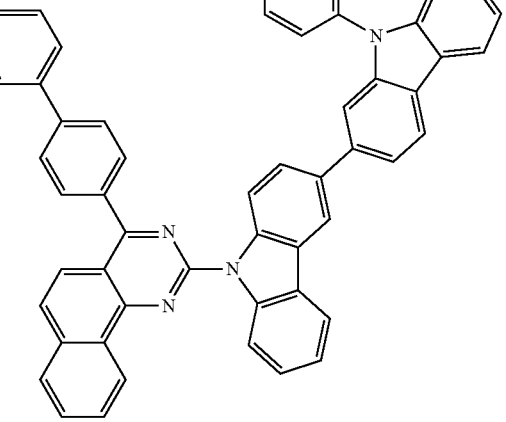
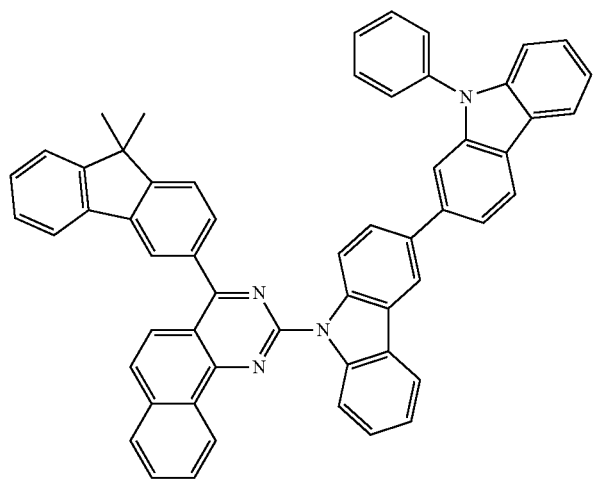
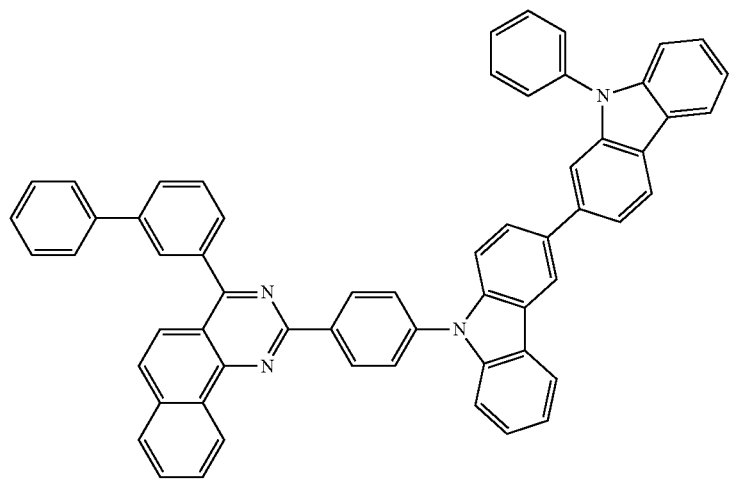

267 268
-continued
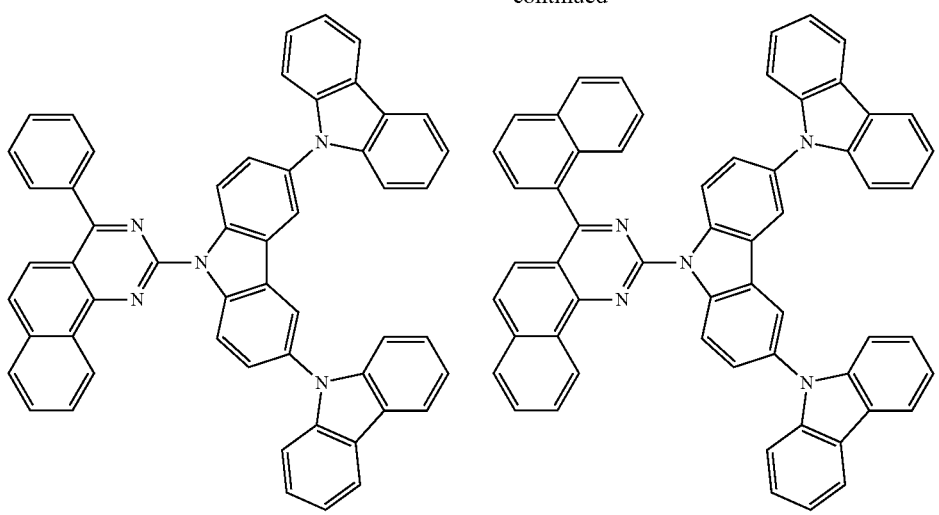
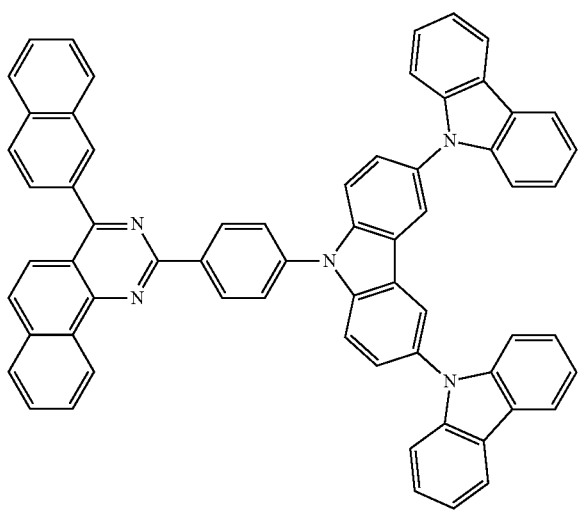
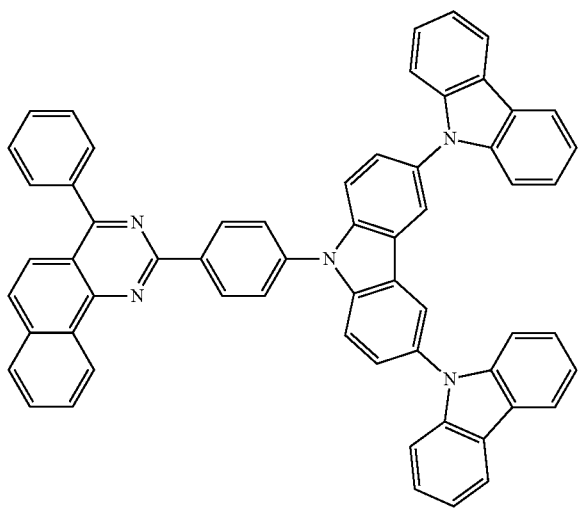

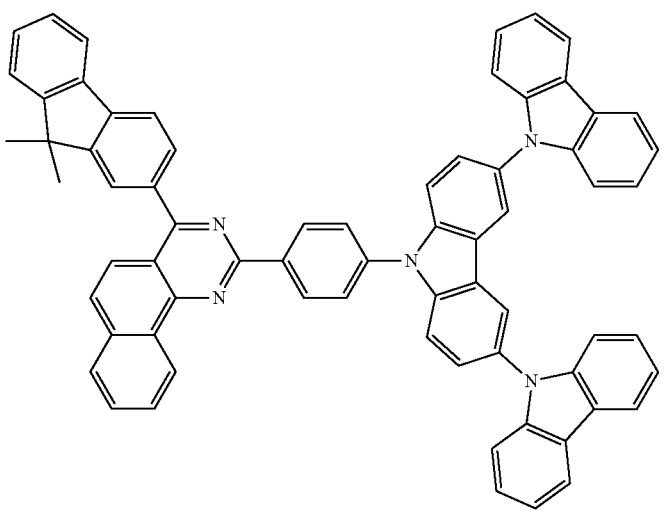
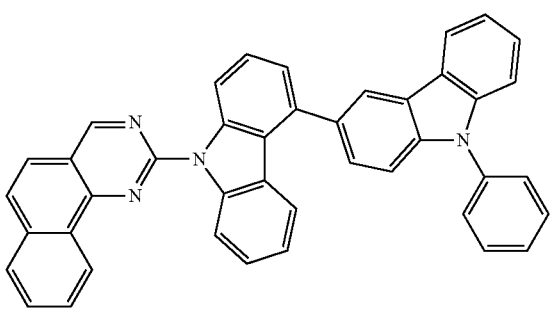
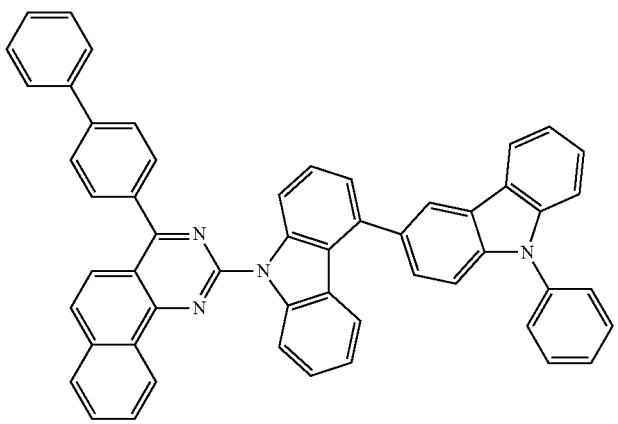
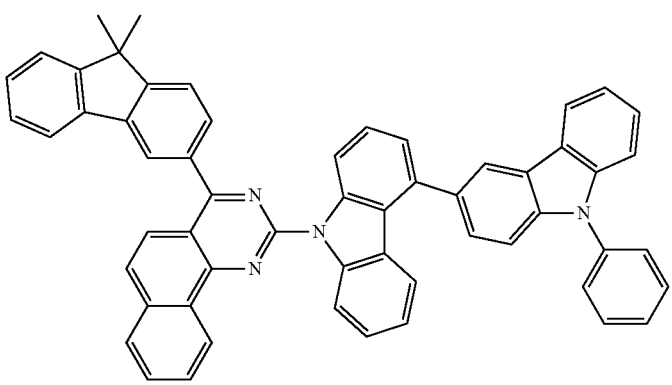

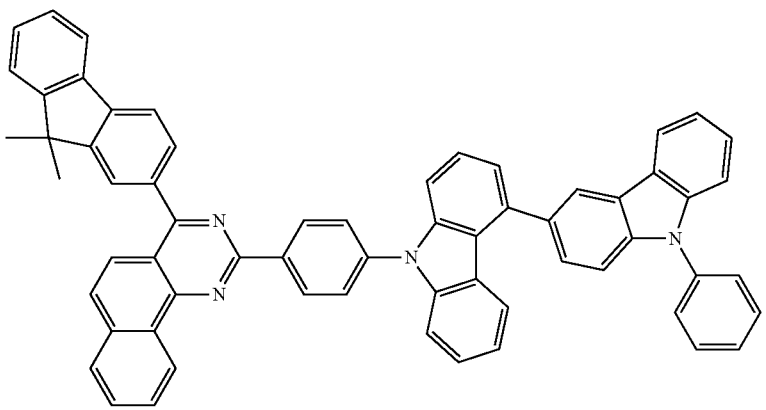
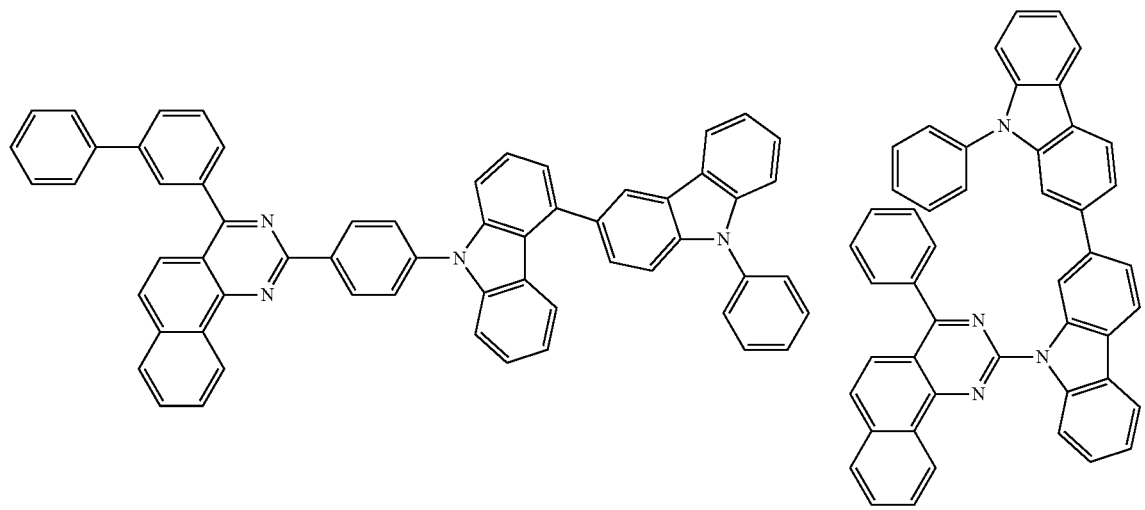
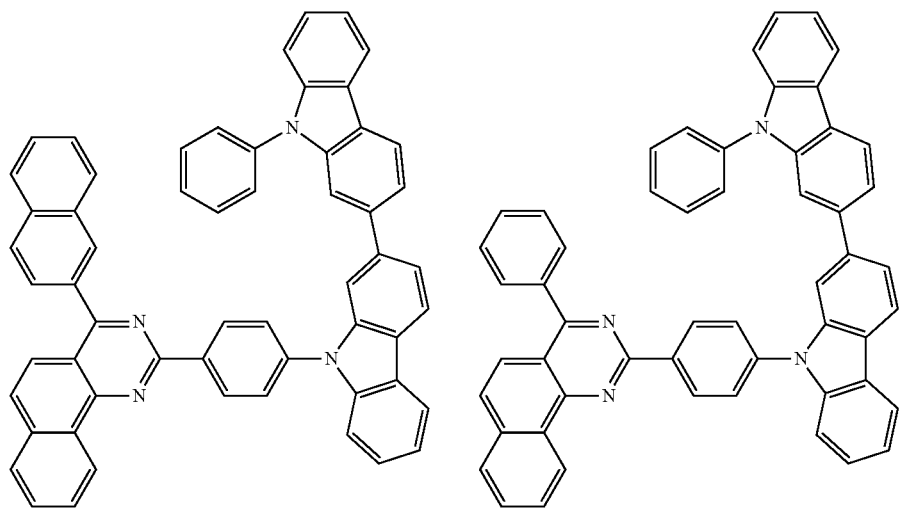

273
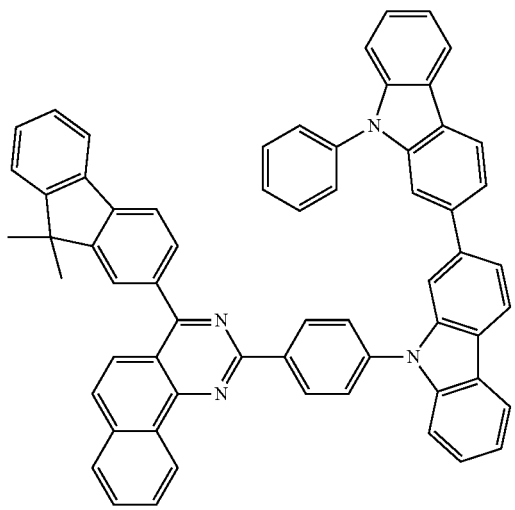
274
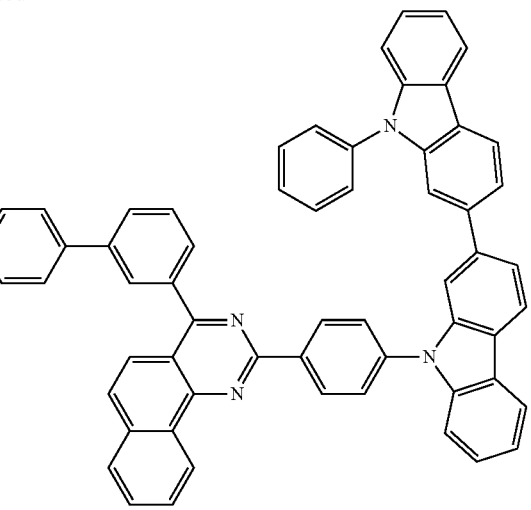
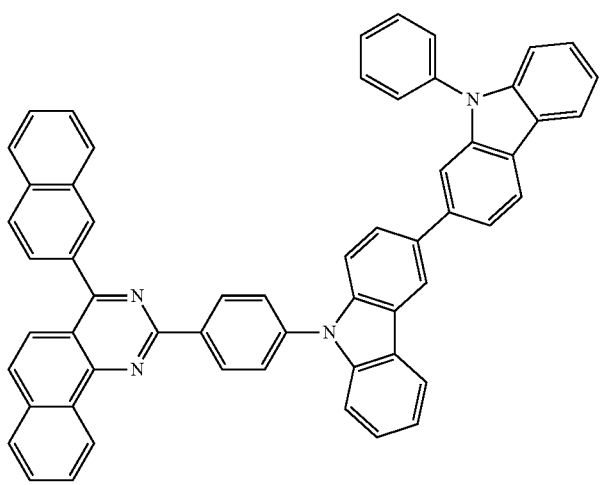
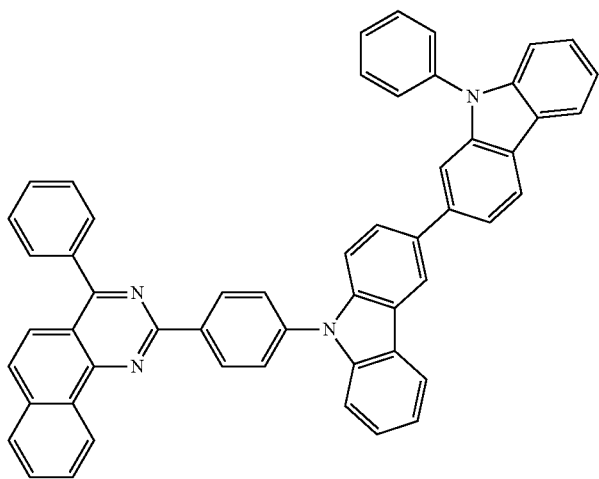

-continued
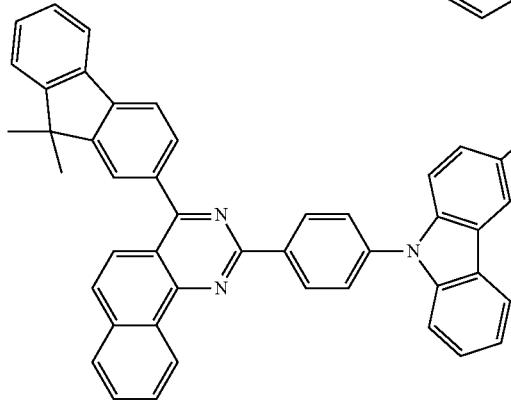
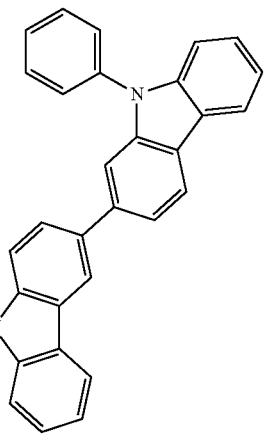
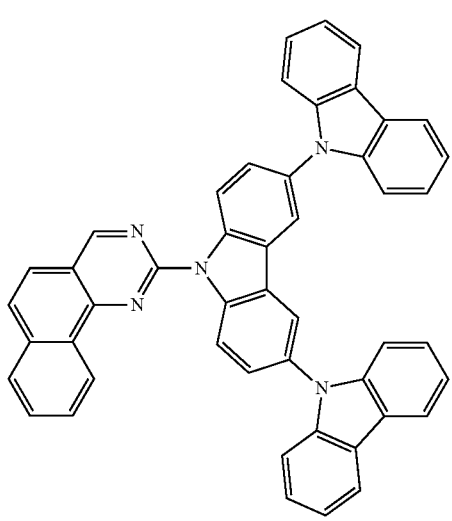
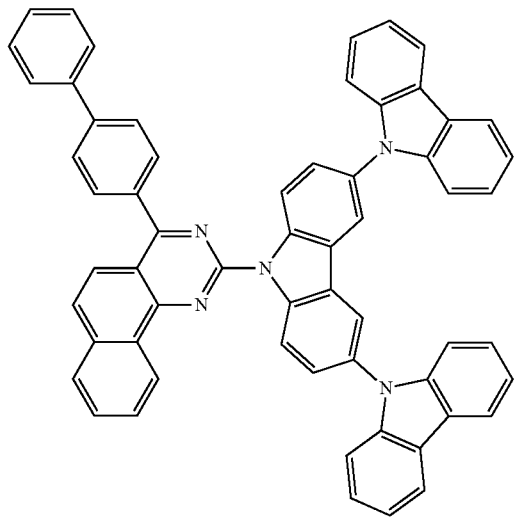
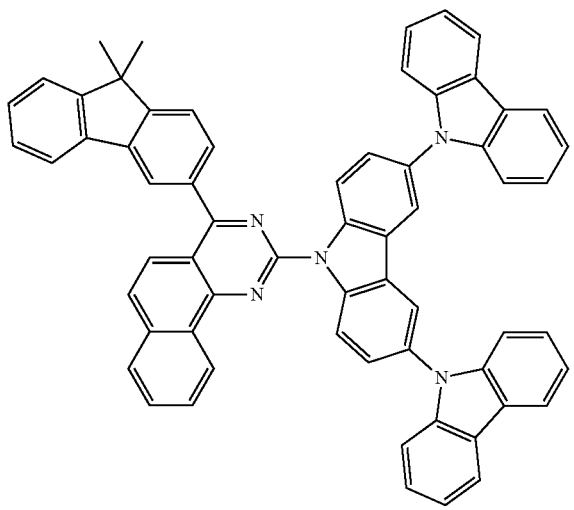

-continued
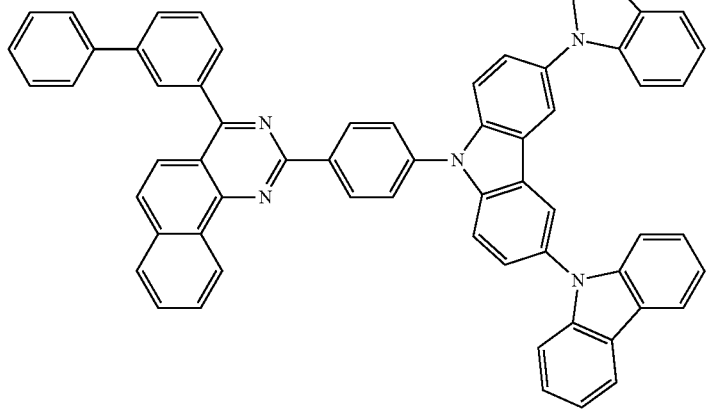
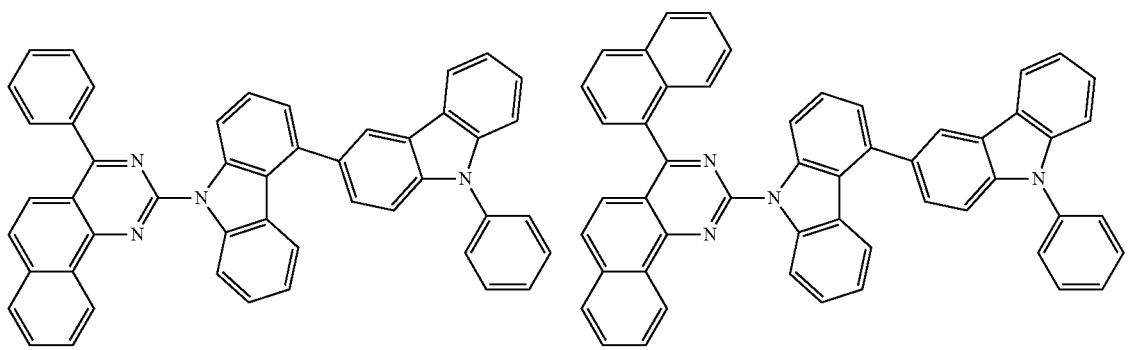
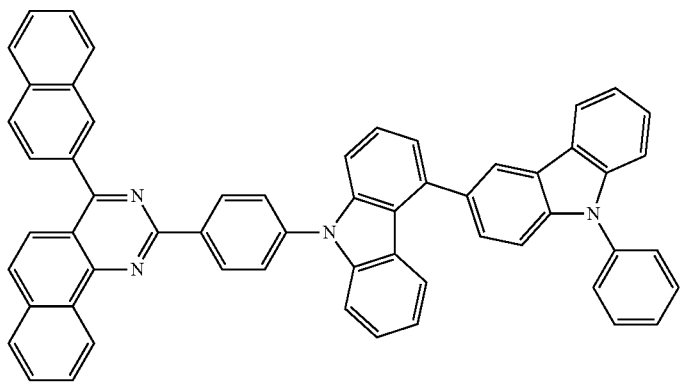
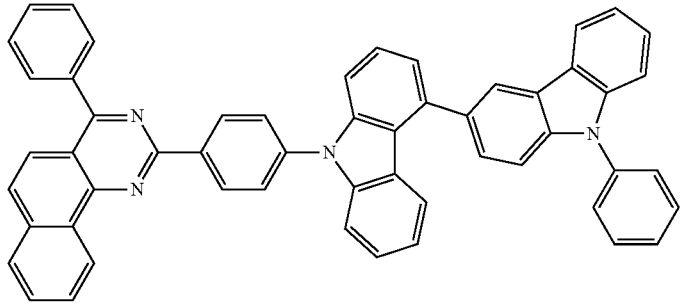

-continued
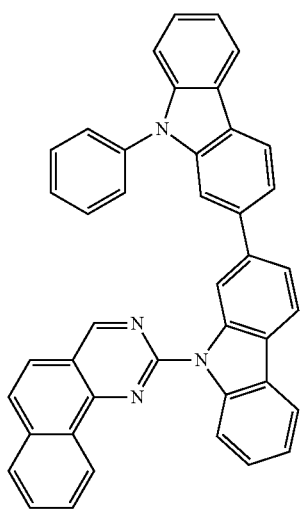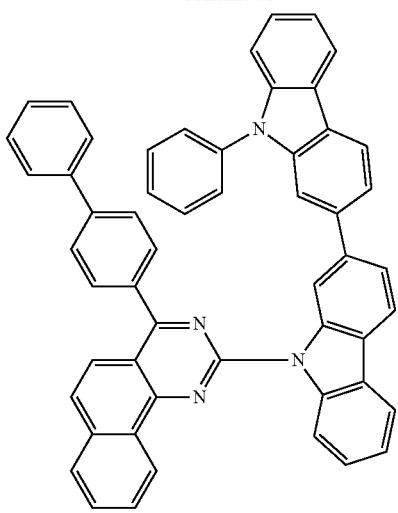
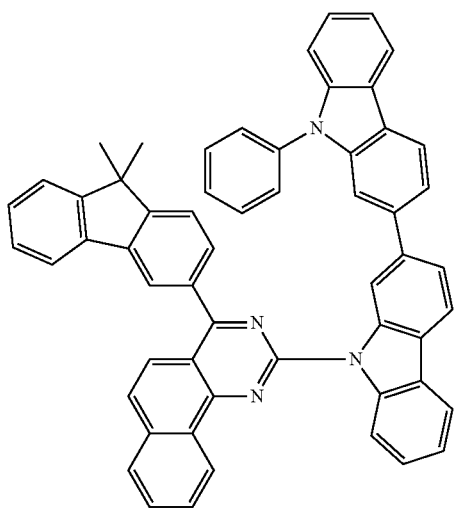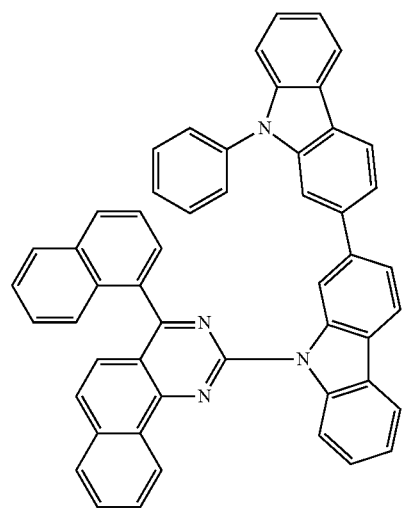
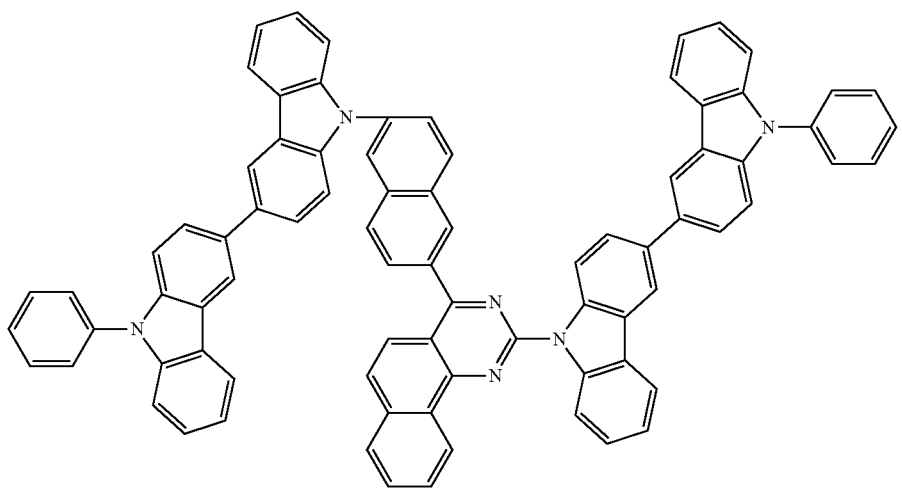

-continued
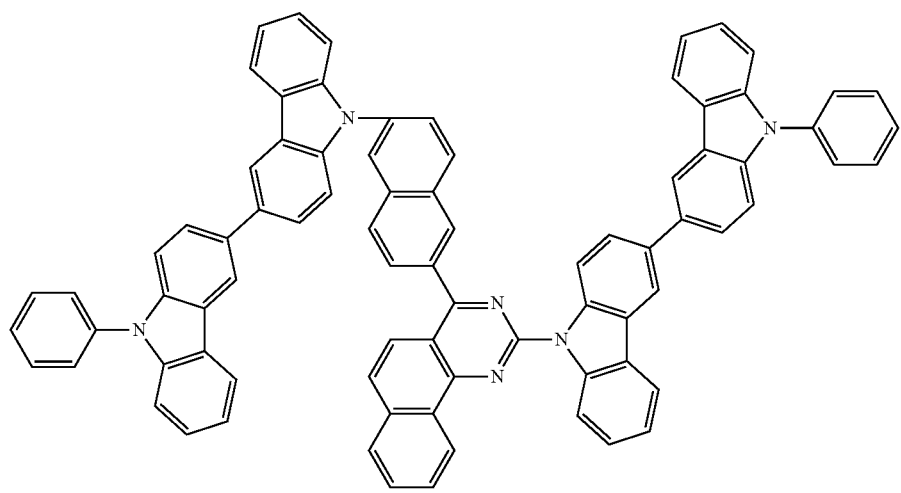
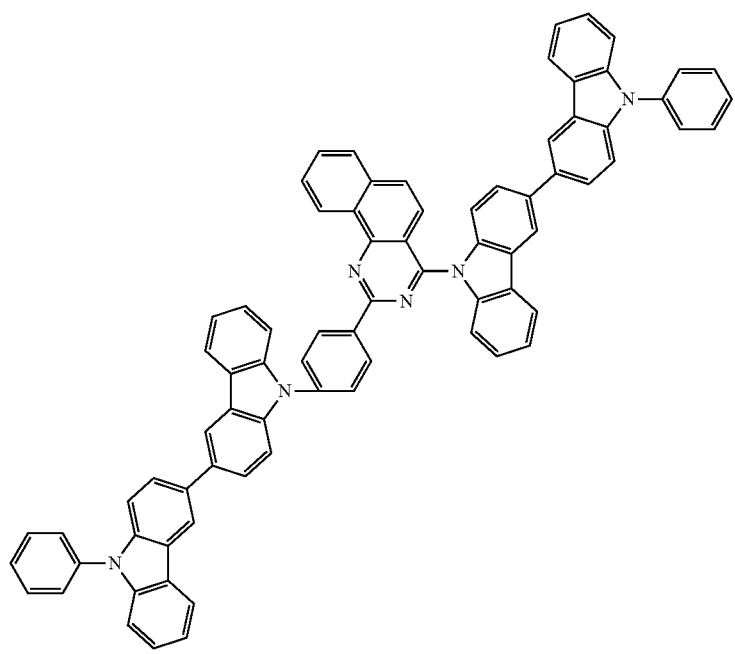

-continued
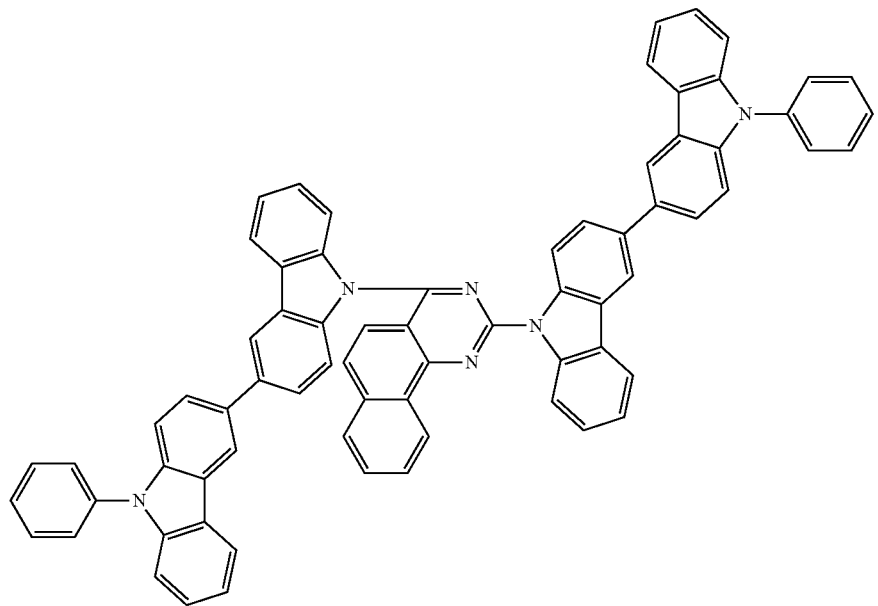
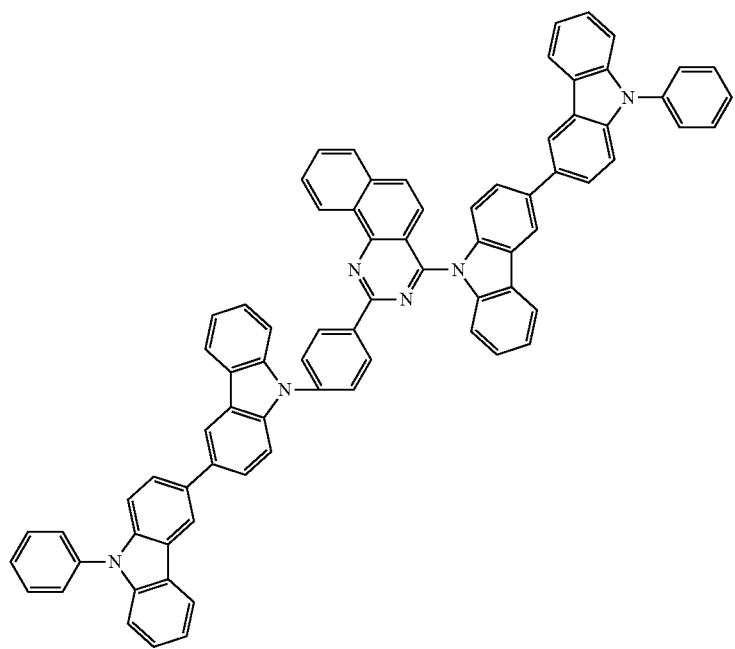

285 286
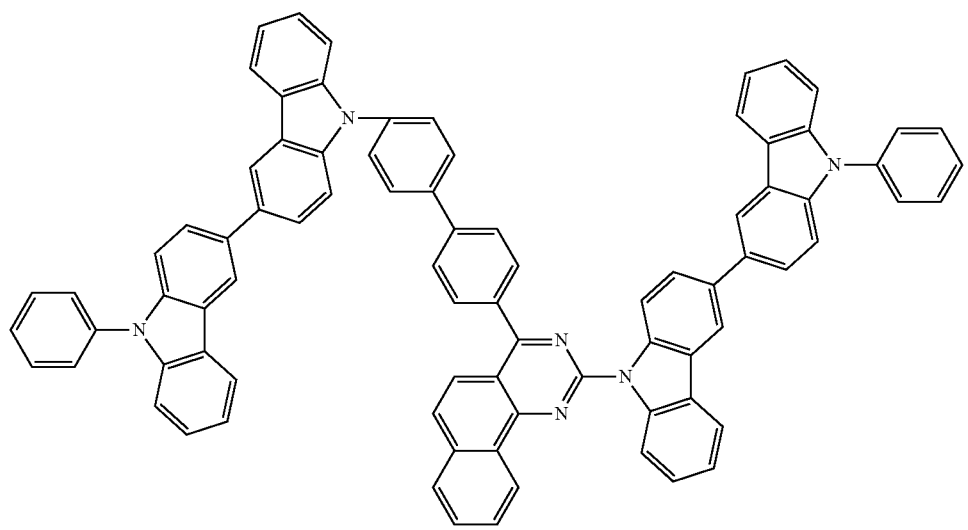
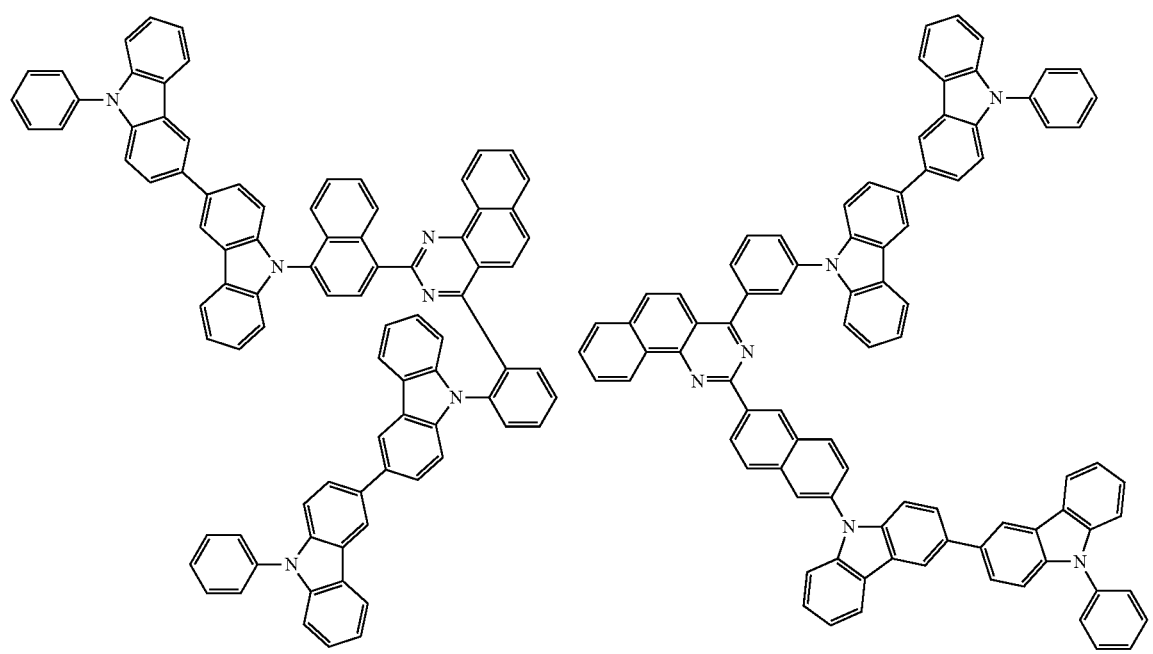

-continued
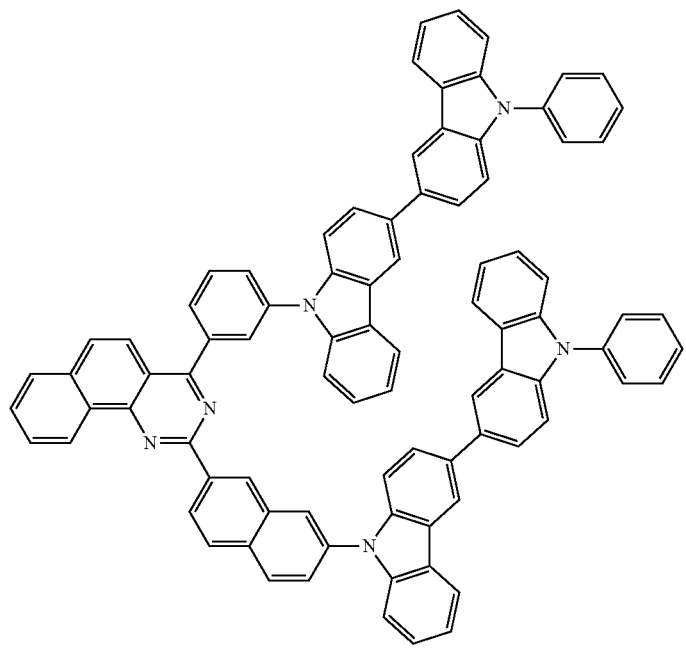
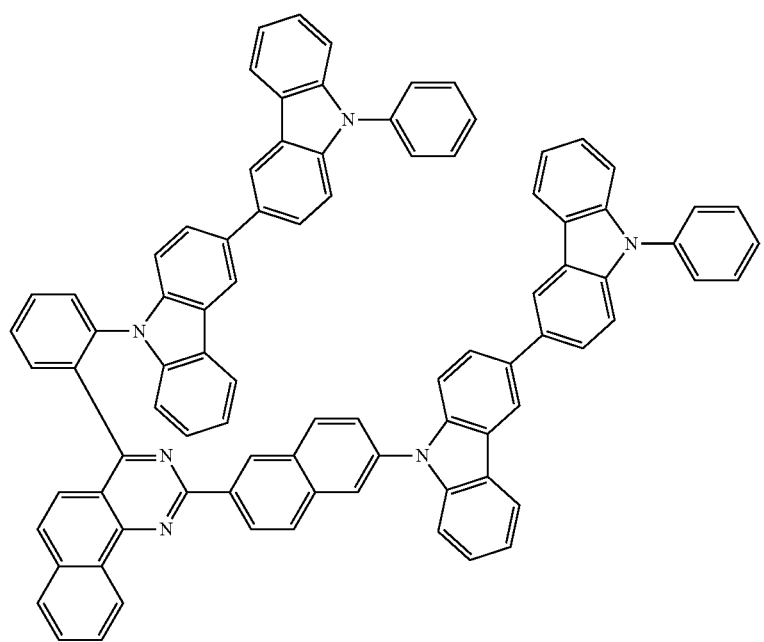

-continued
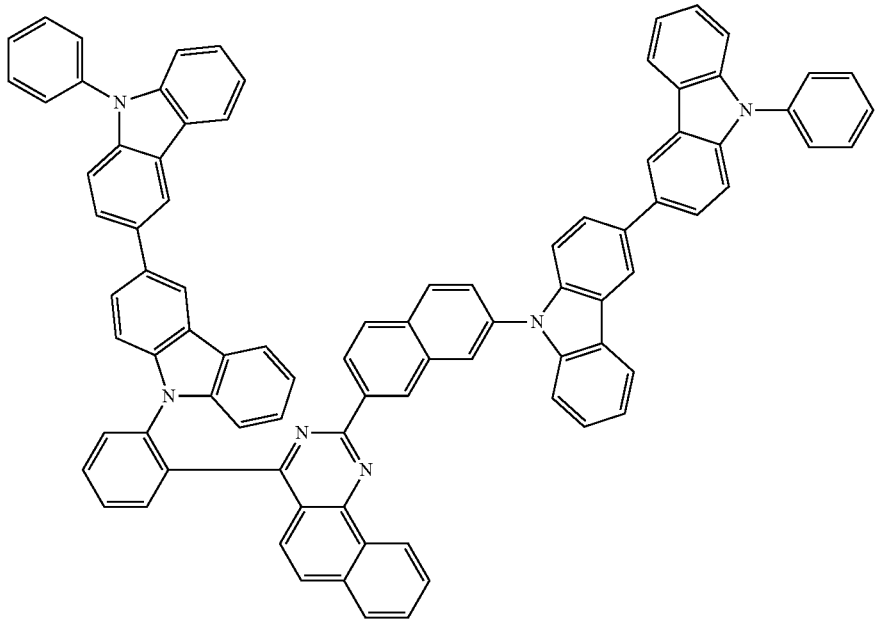
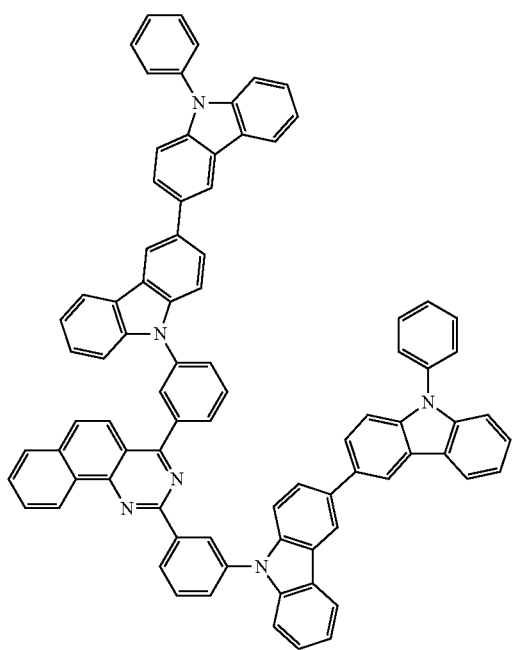

-continued
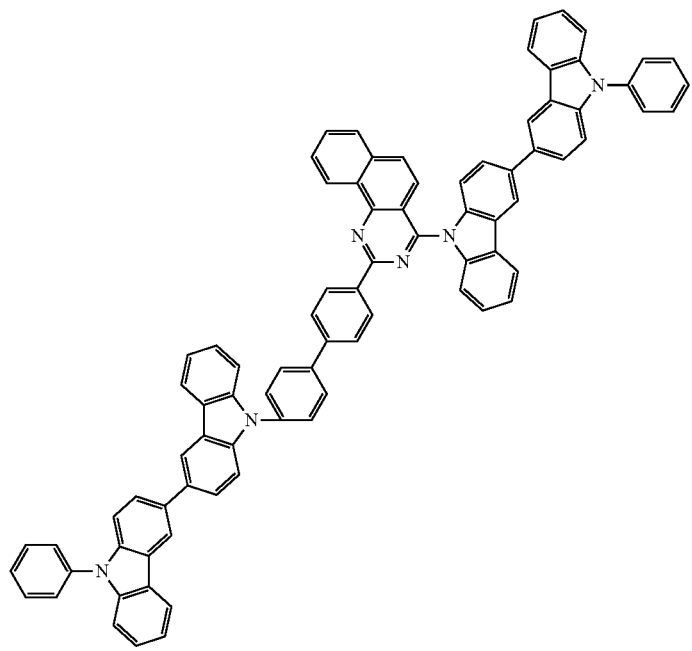
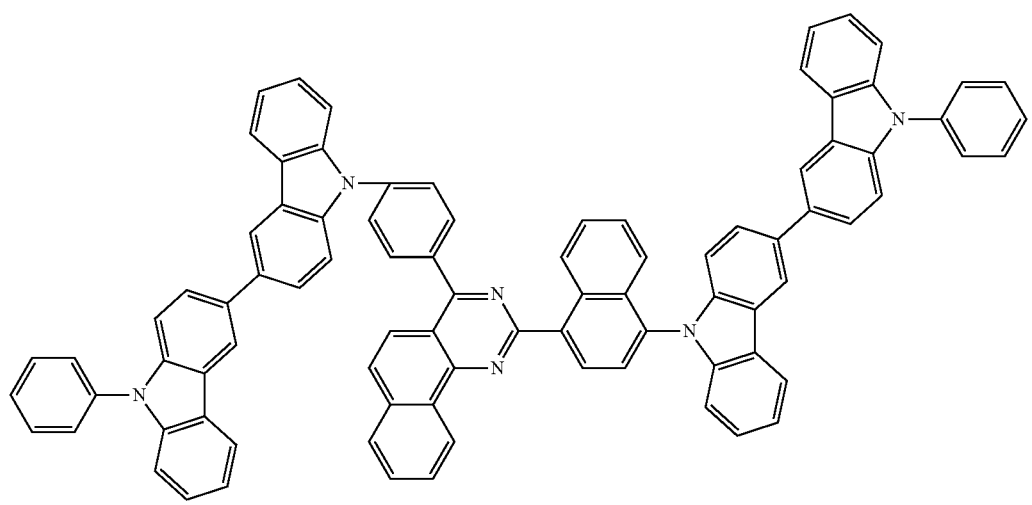

-continued
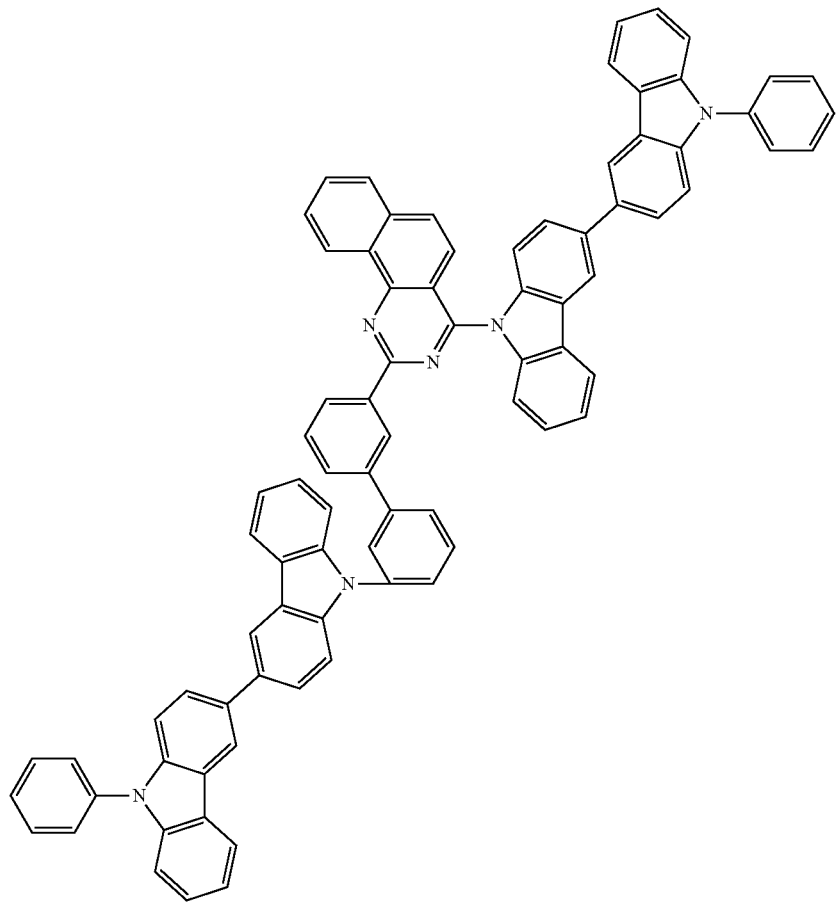
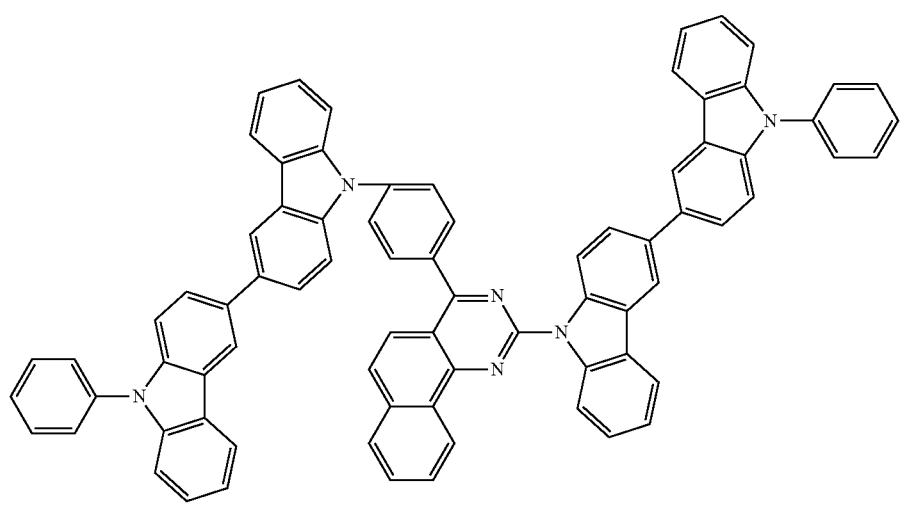

-continued
295
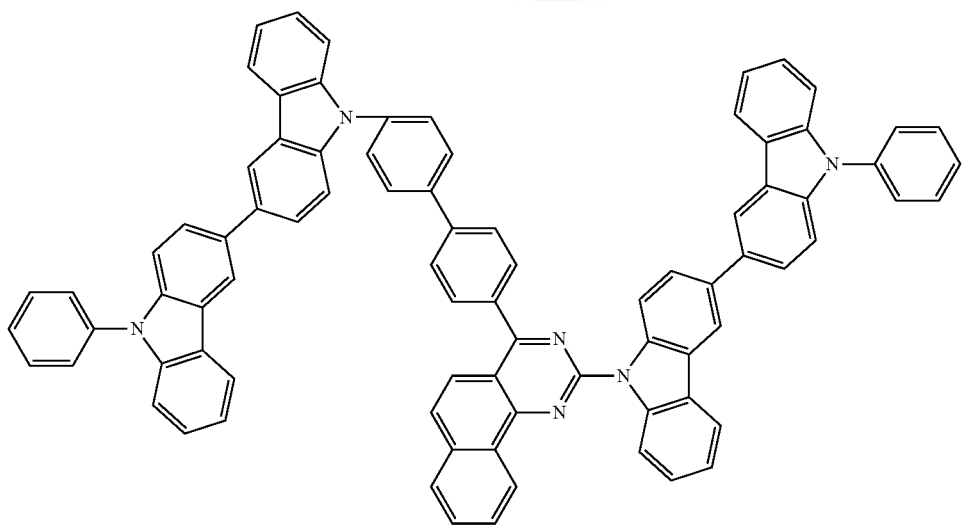
296
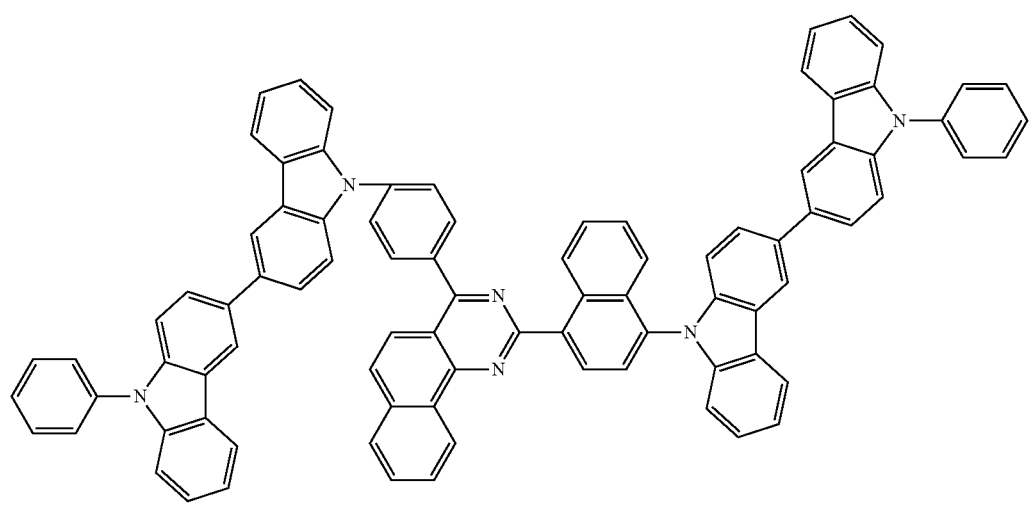

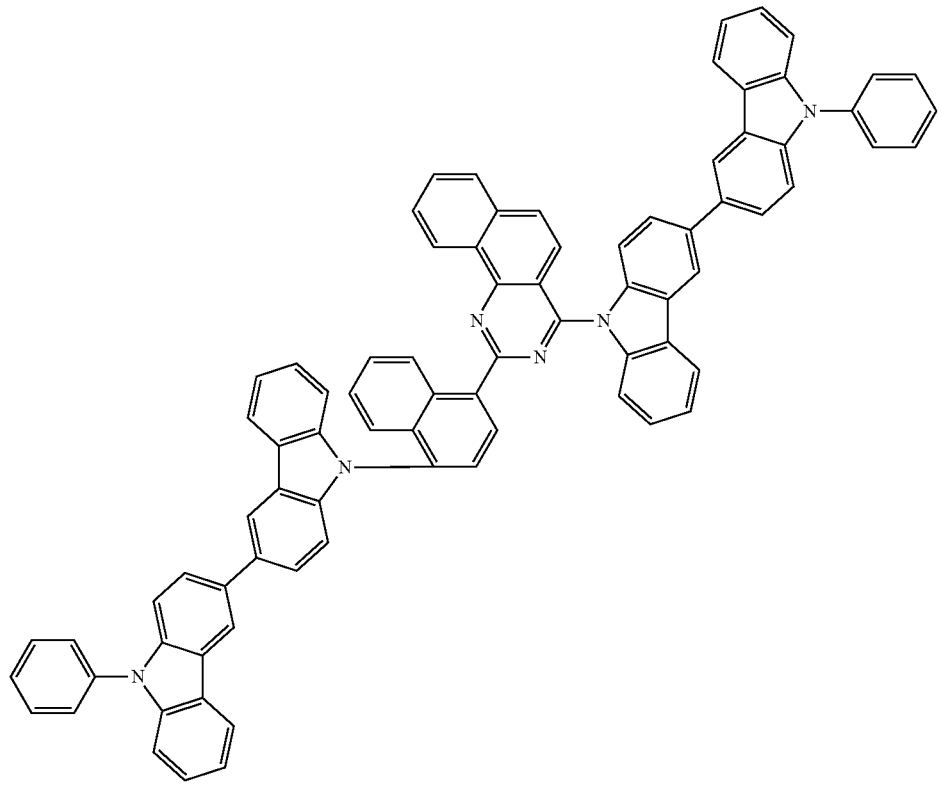
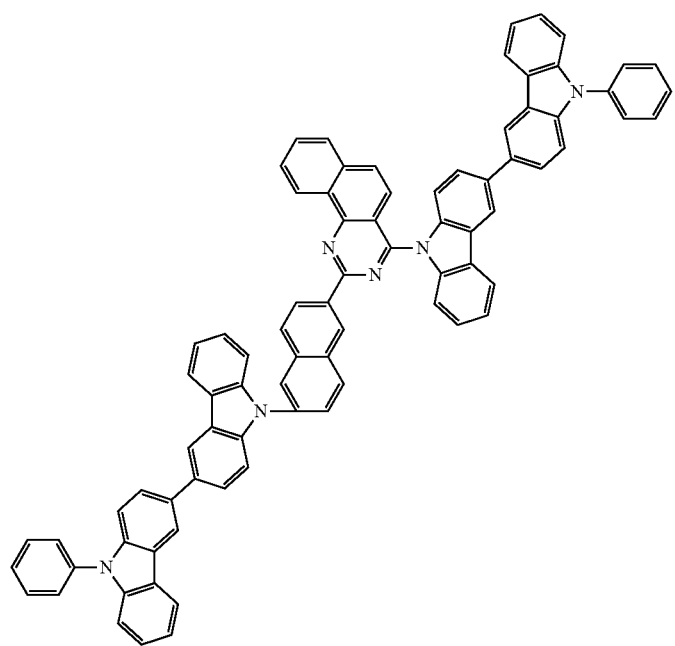

-continued
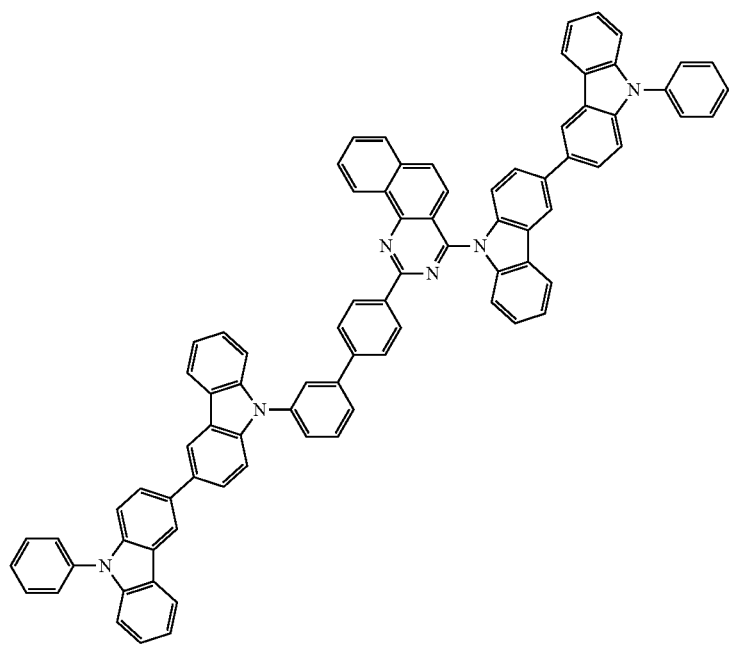
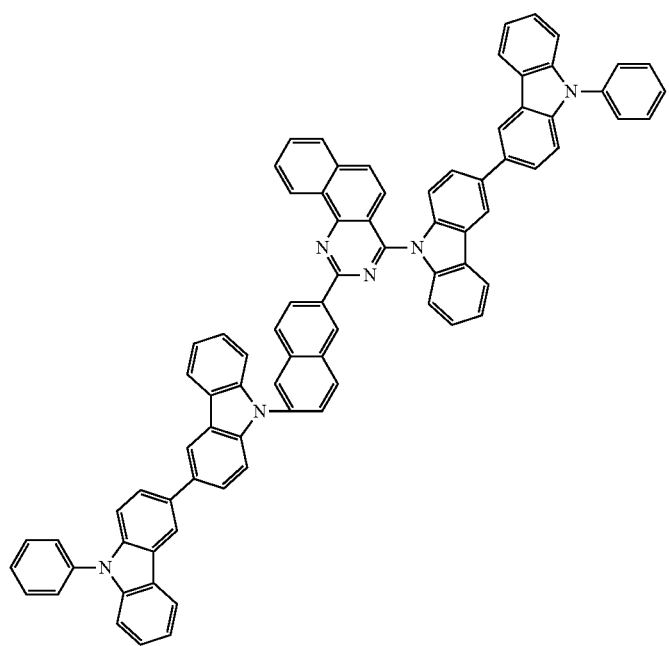

301                                                 302
-continued
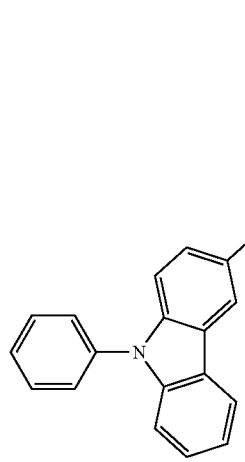
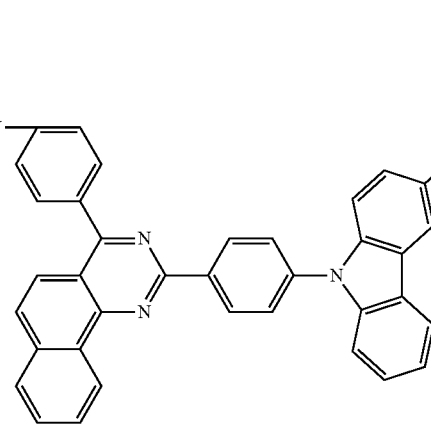
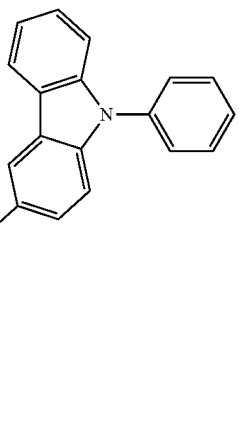
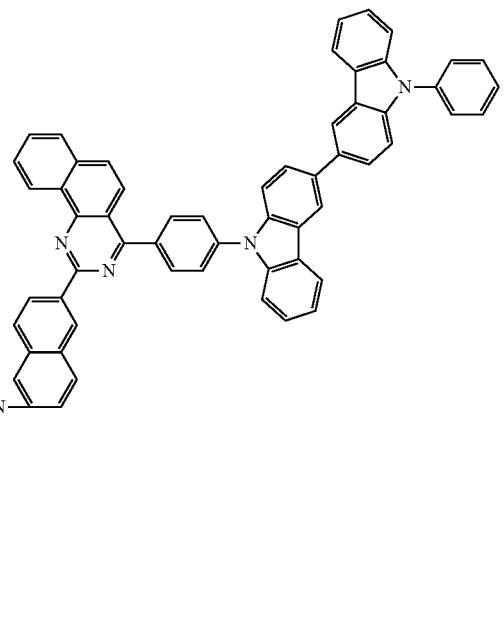
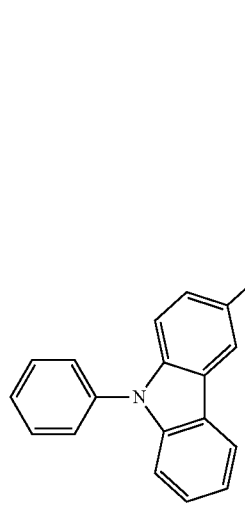
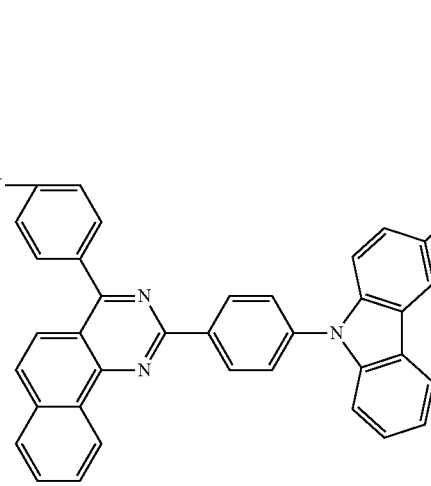
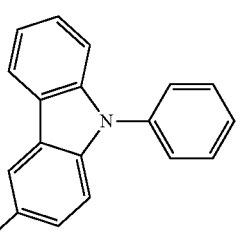

-continued
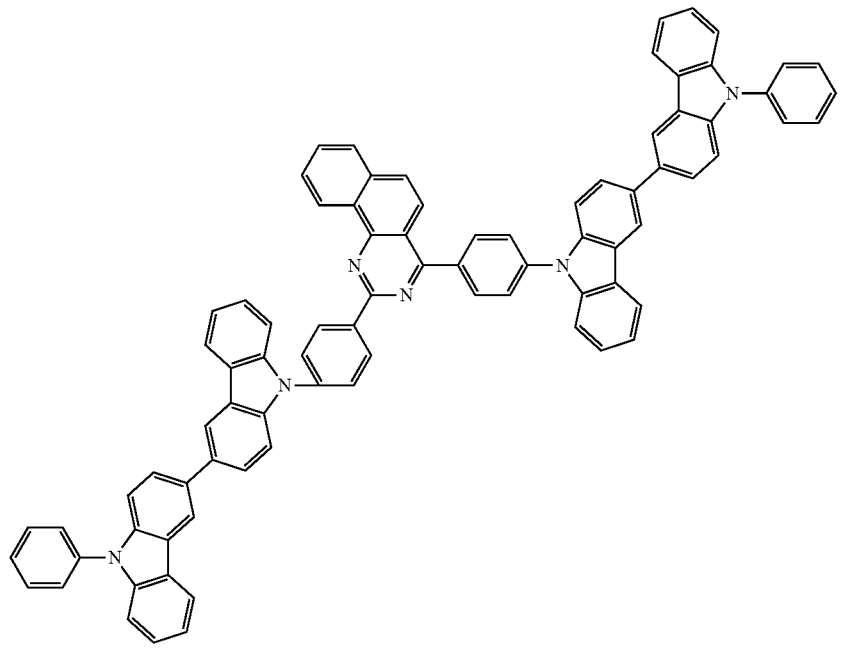
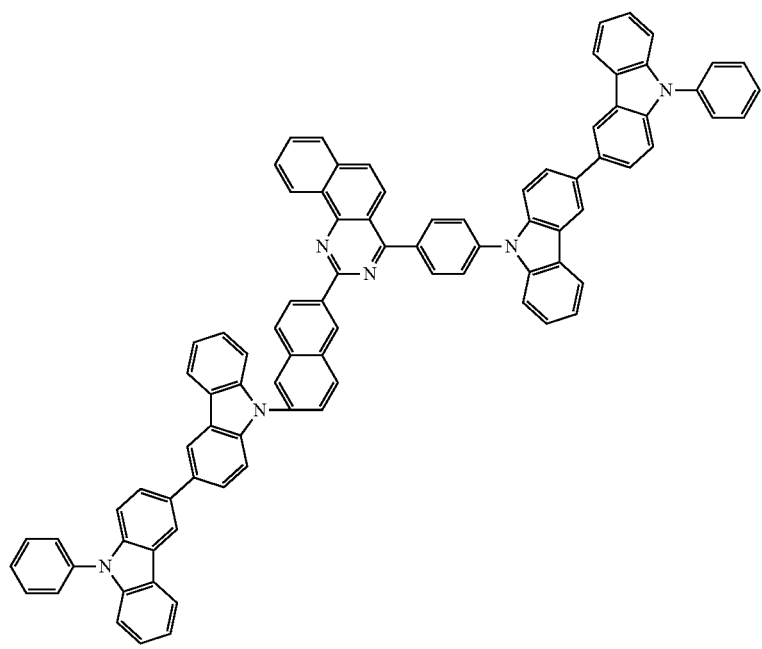

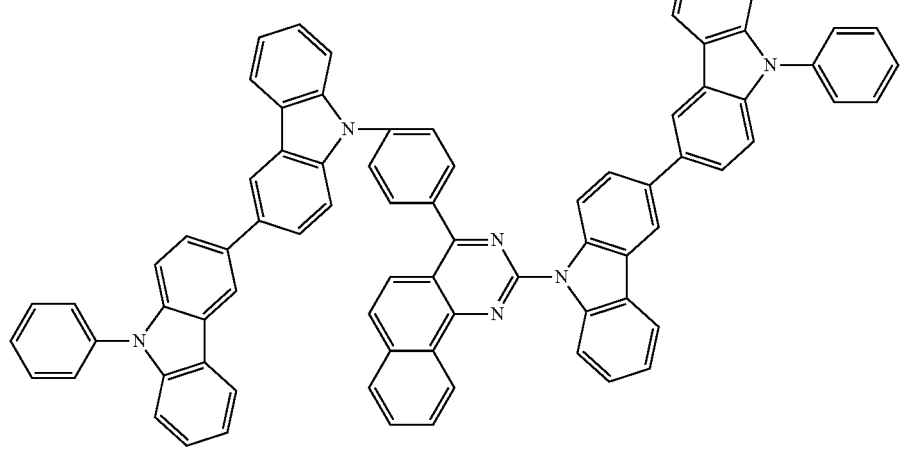
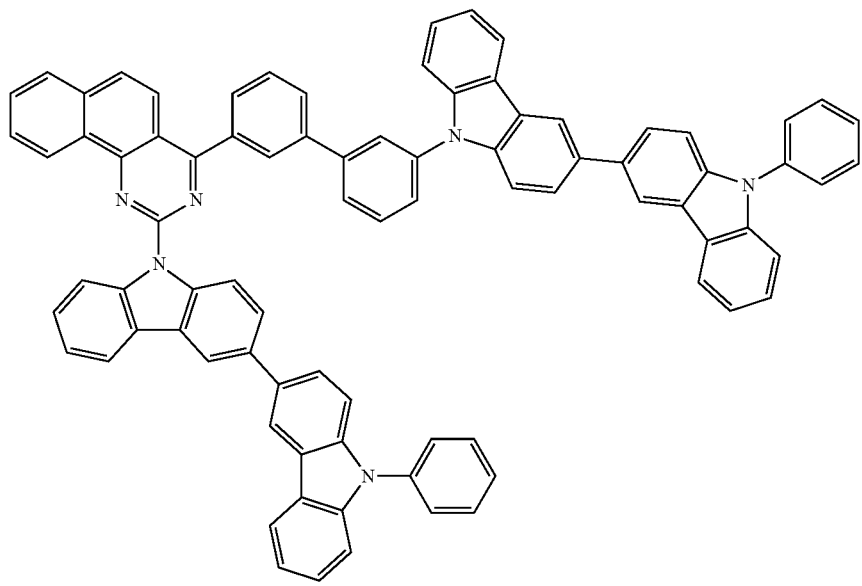
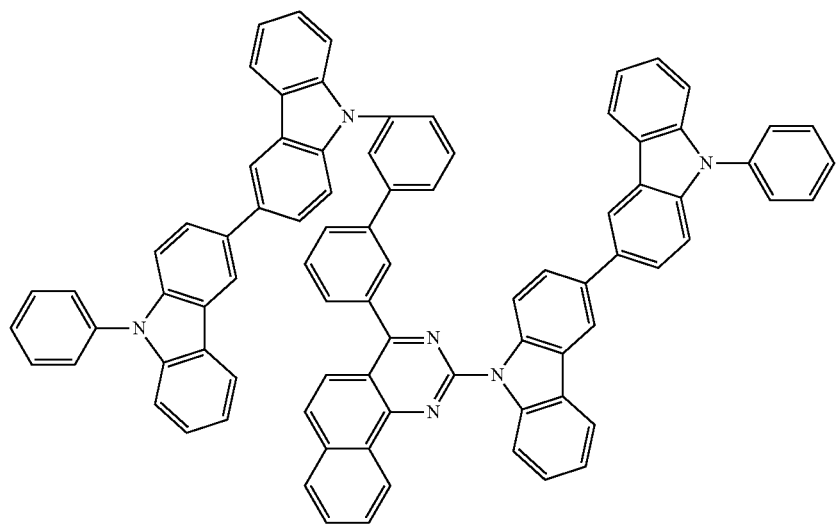

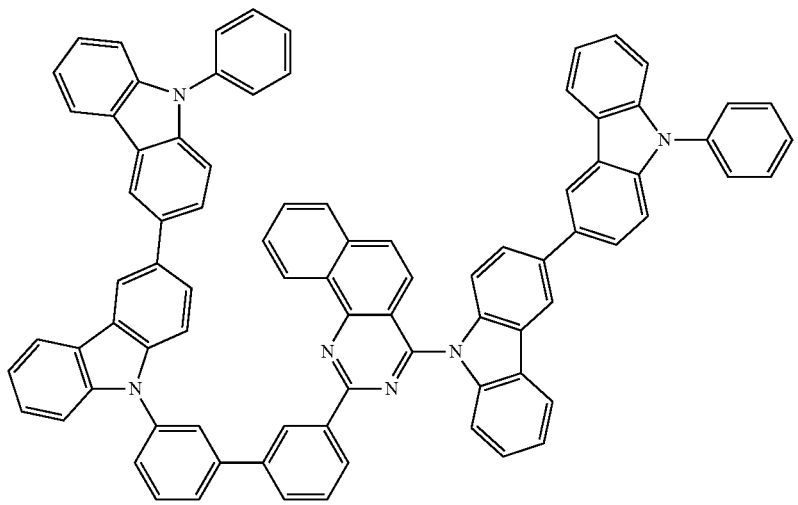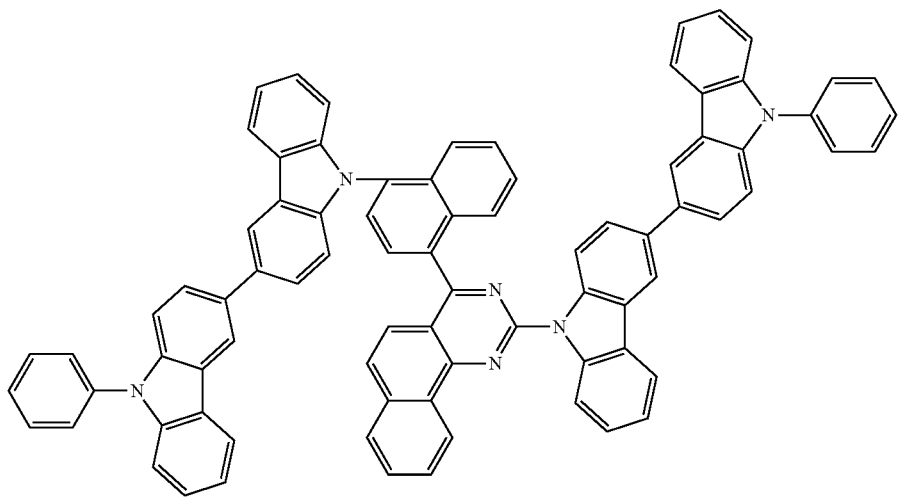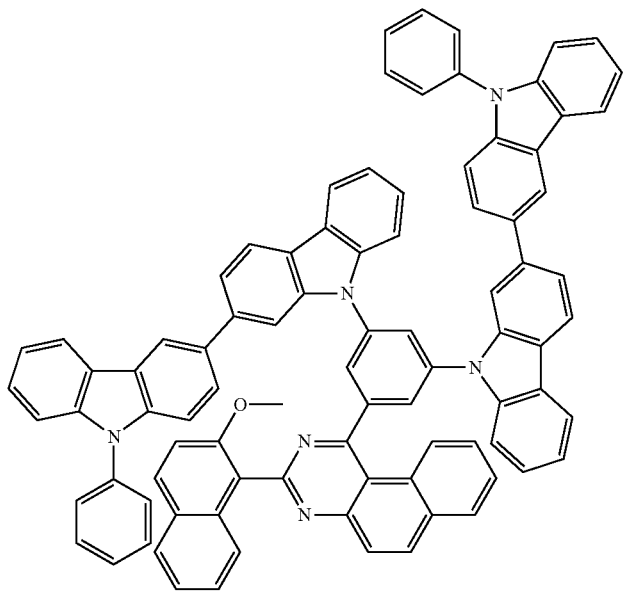

-continued
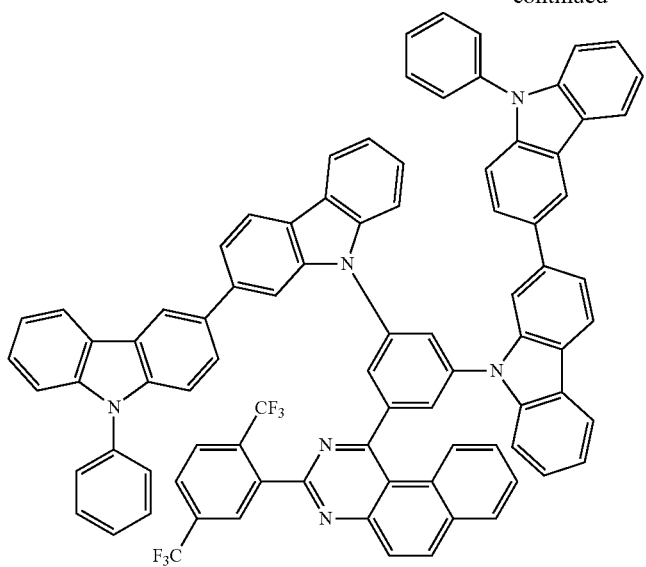
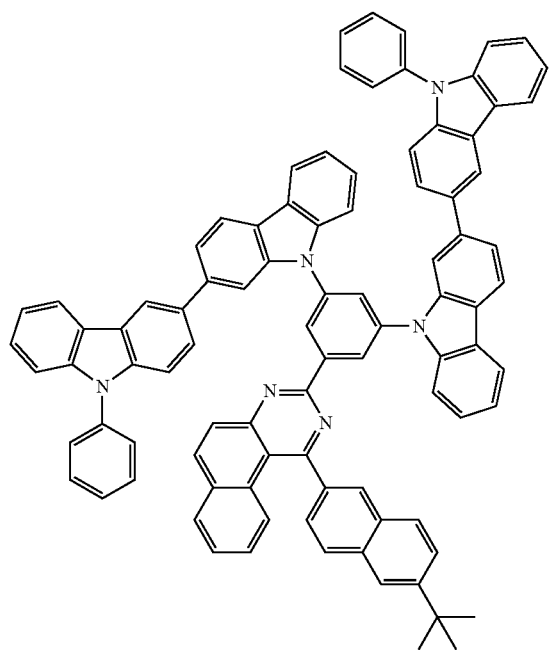

-continued
| 311 | 312 |
|---|---|
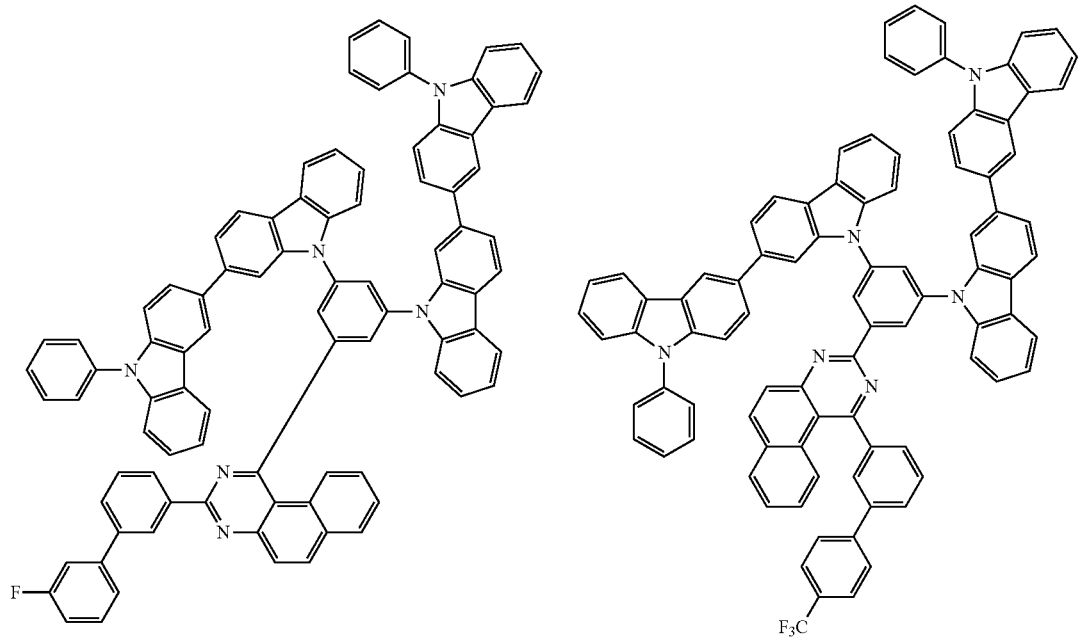
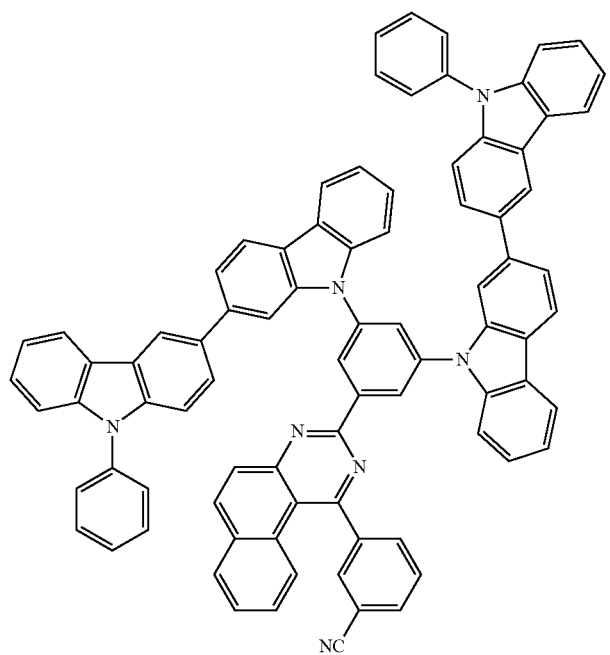

-continued
313 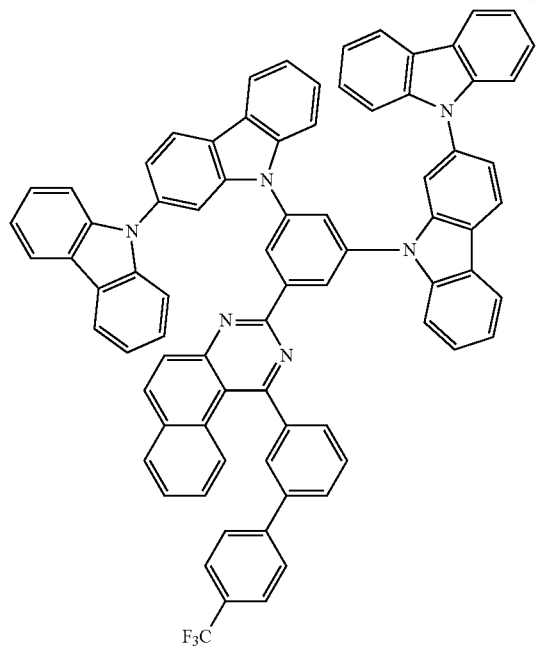
314 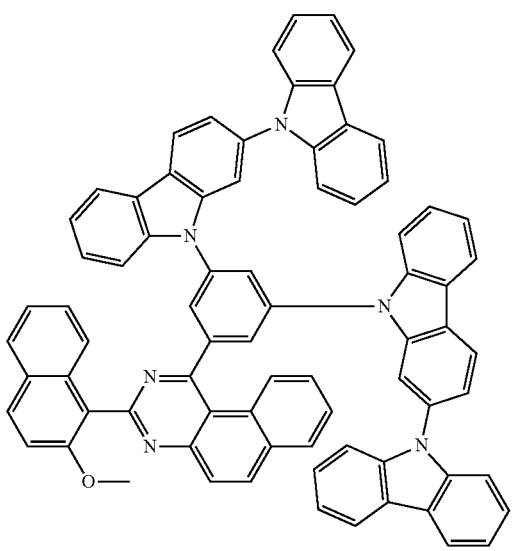
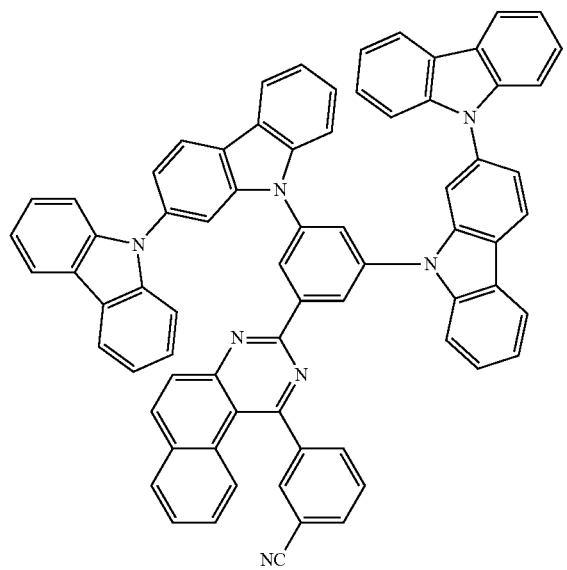

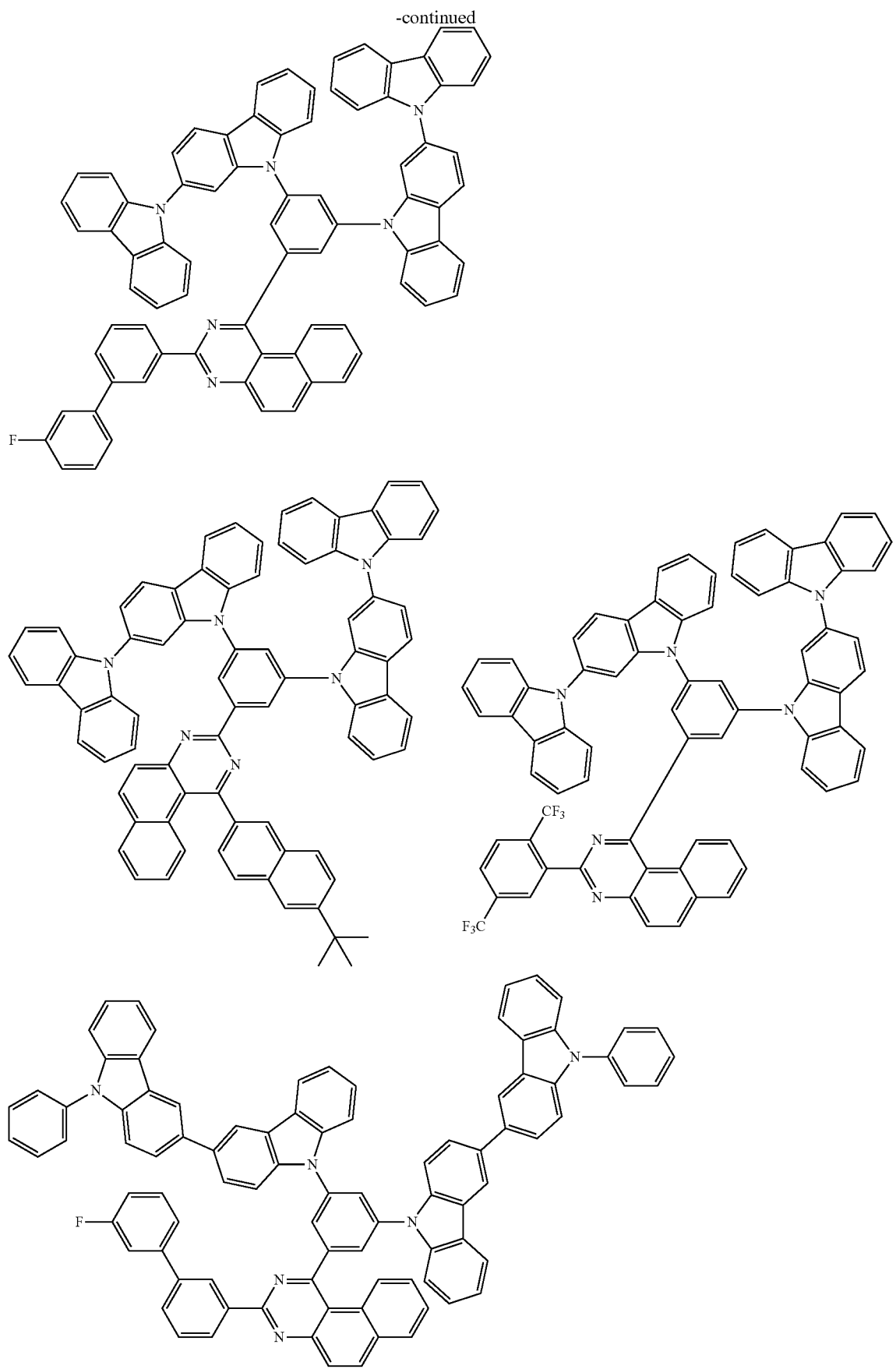

-continued
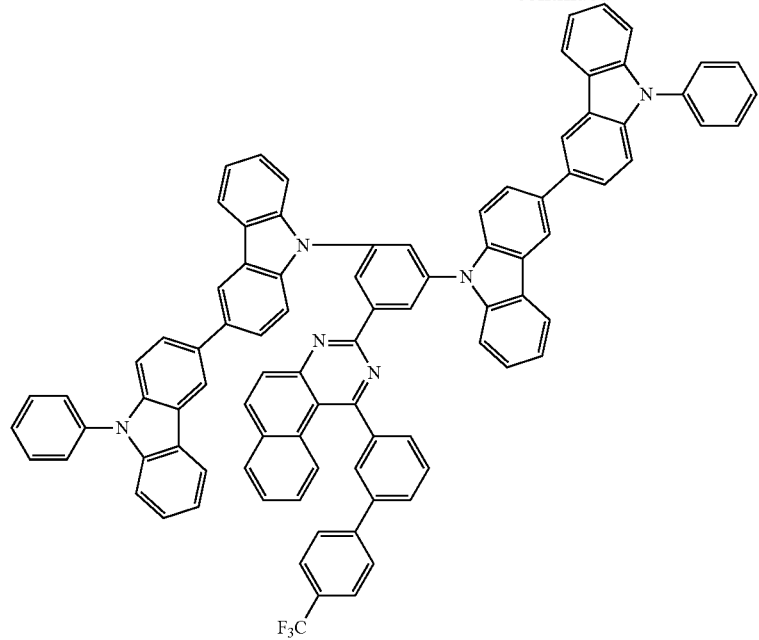
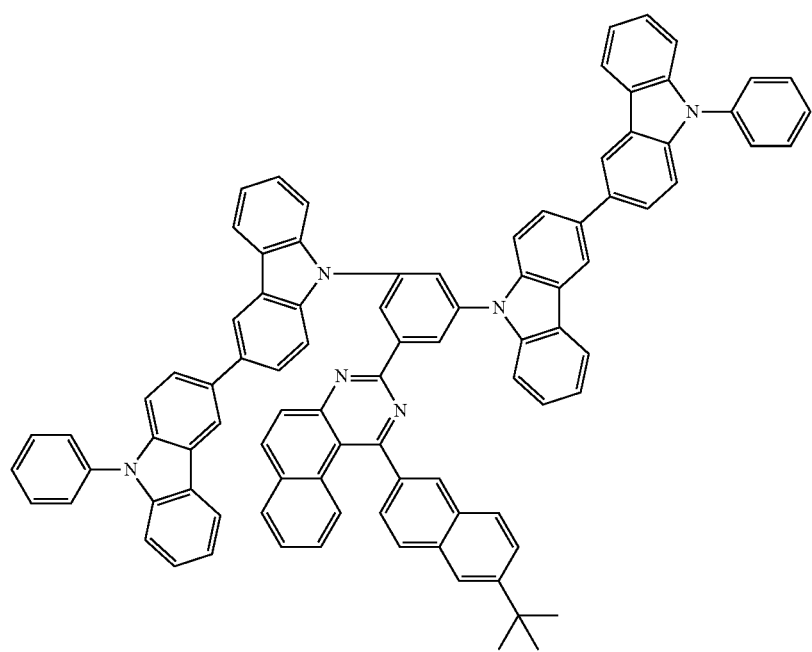

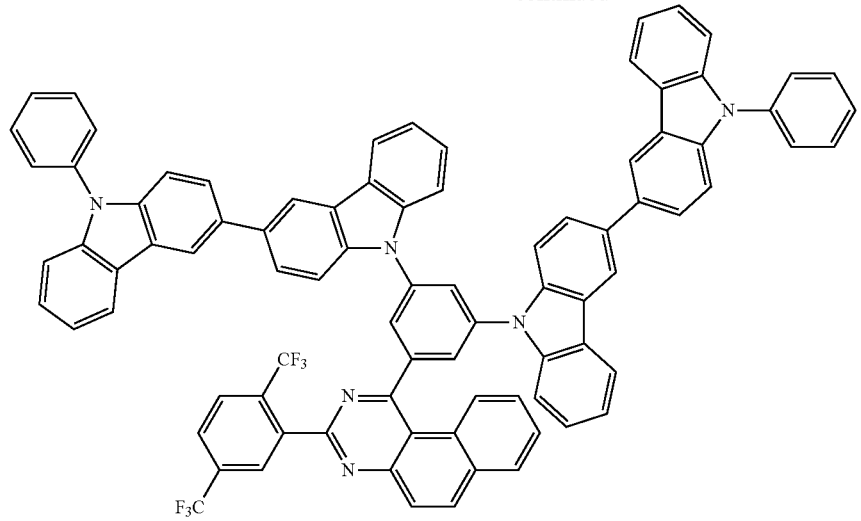
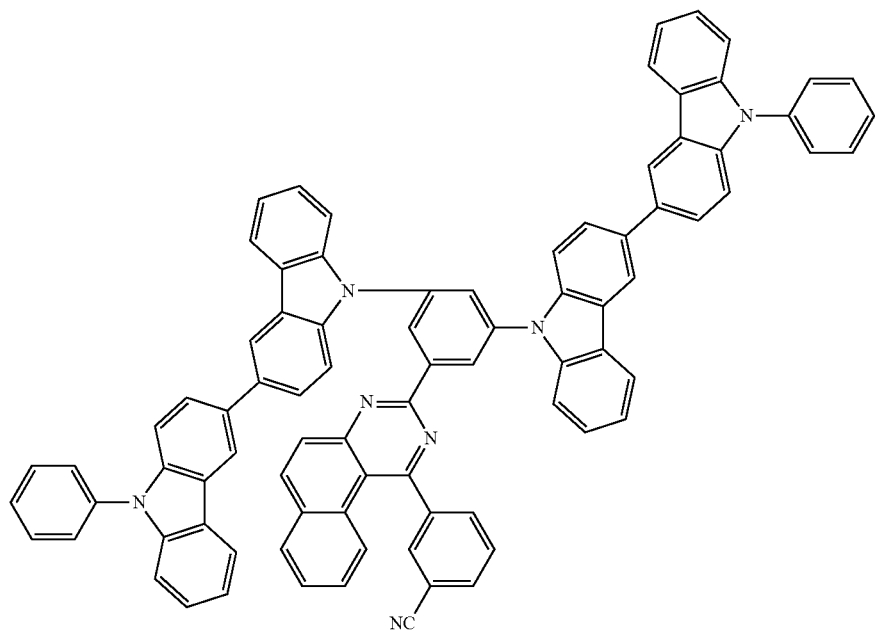
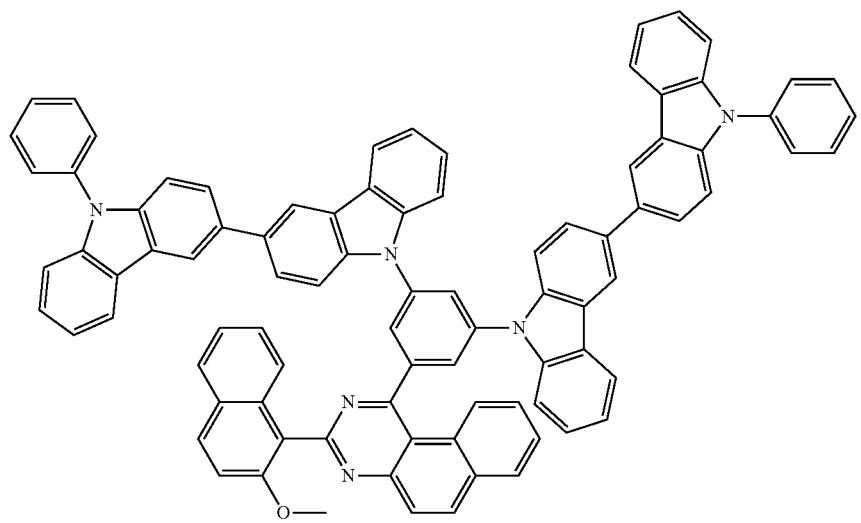

-continued
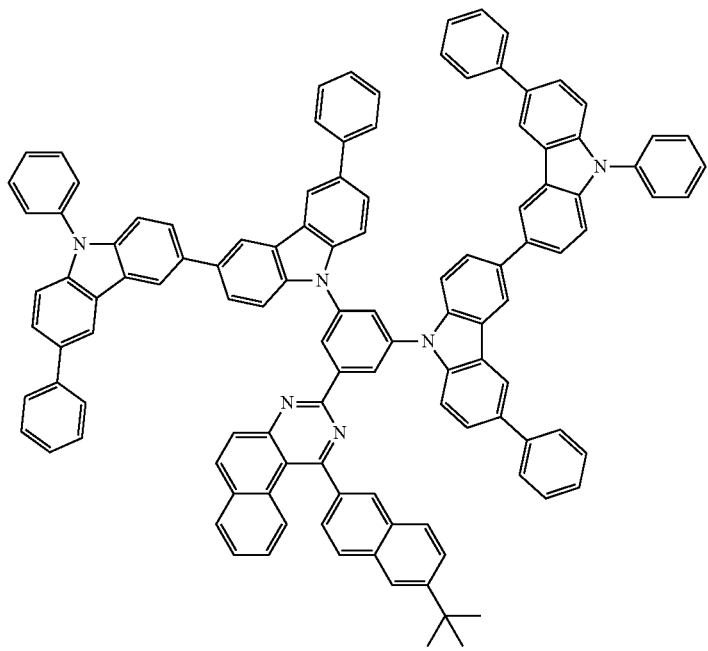
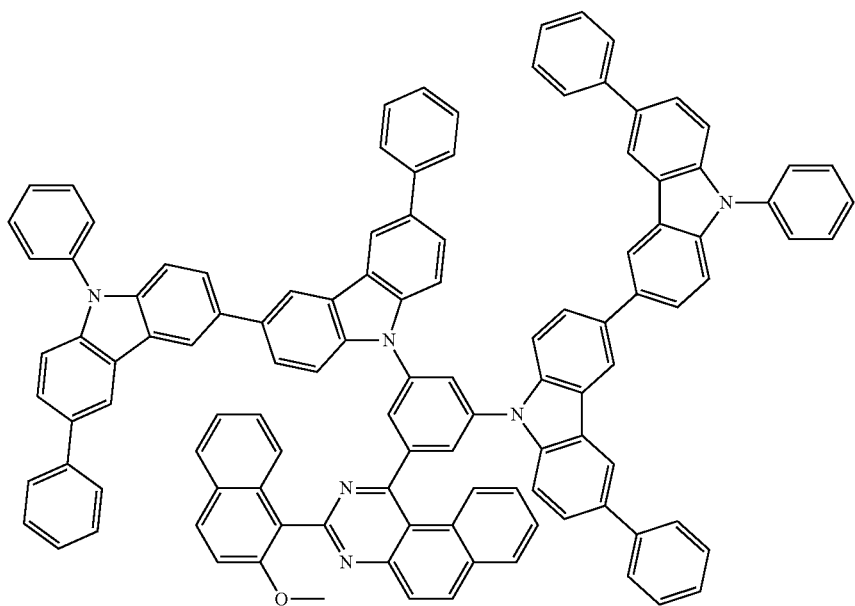

-continued
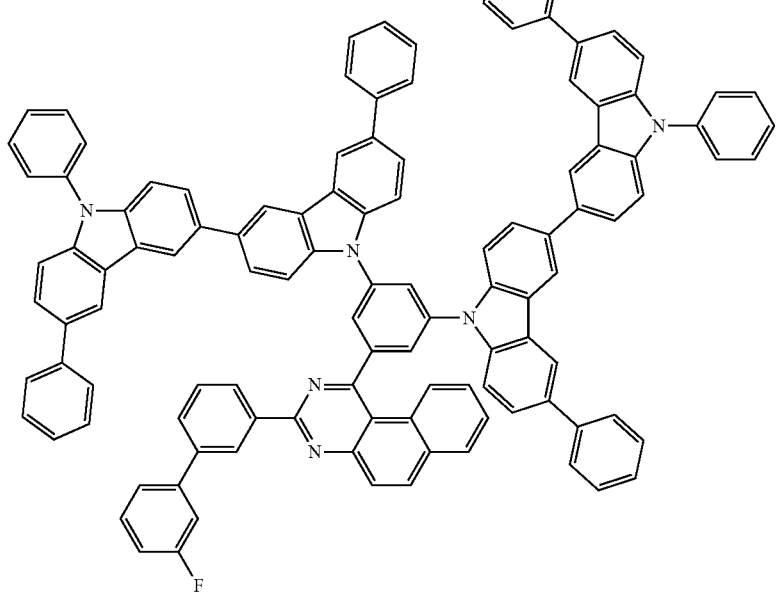
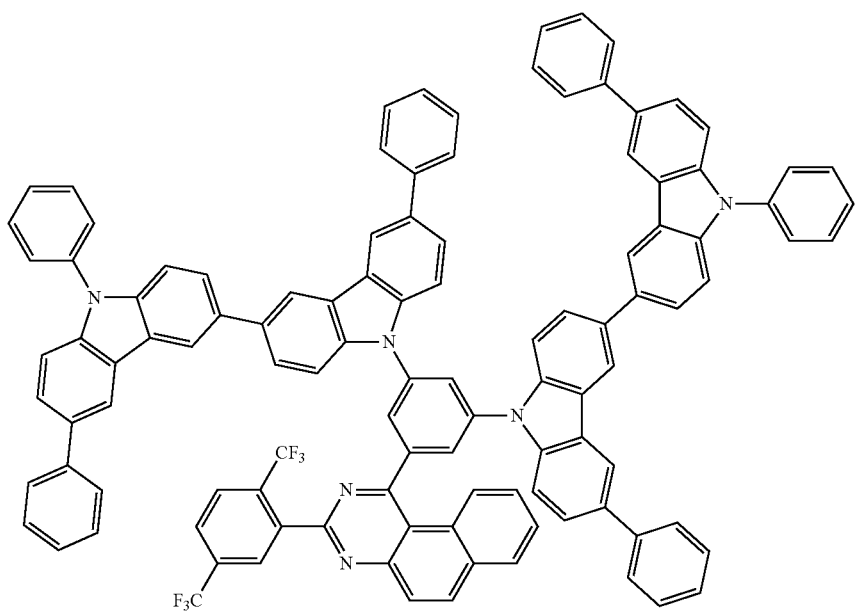

-continued
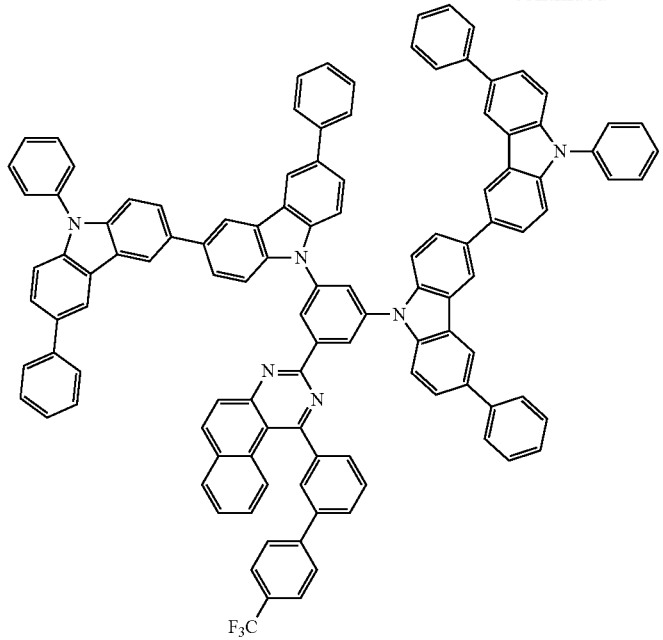
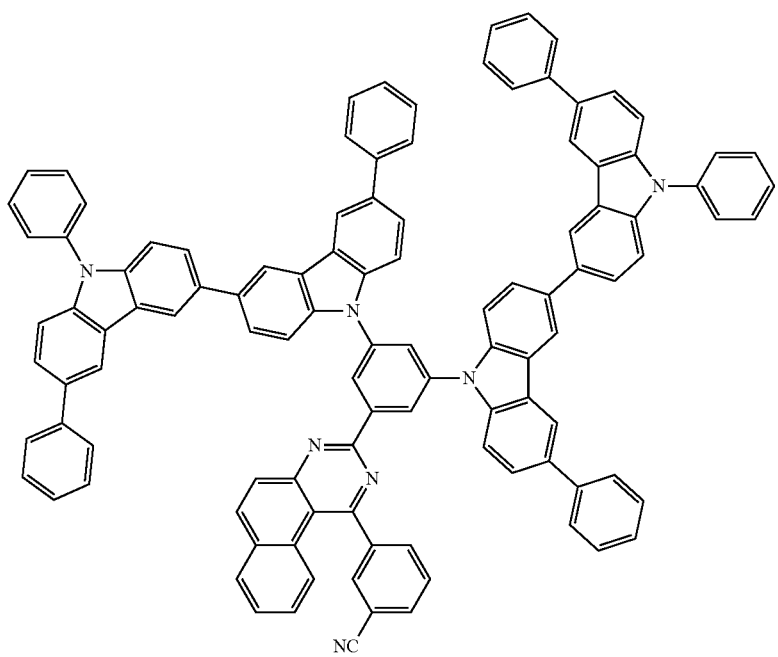

-continued
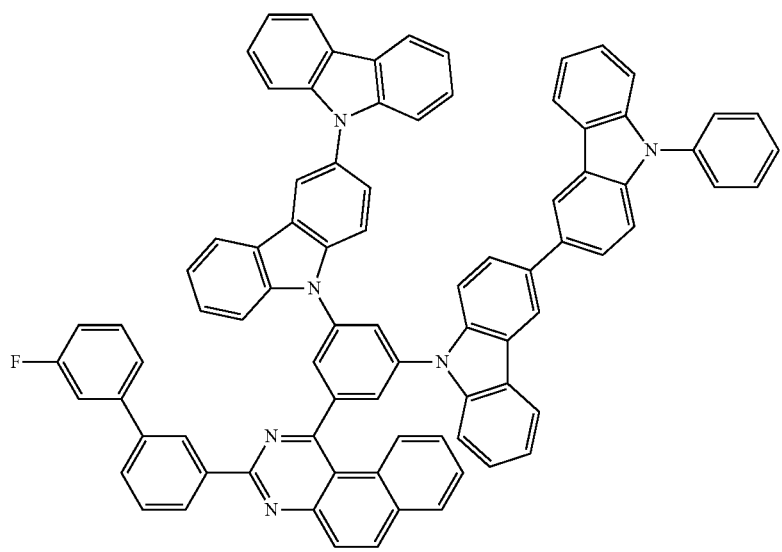
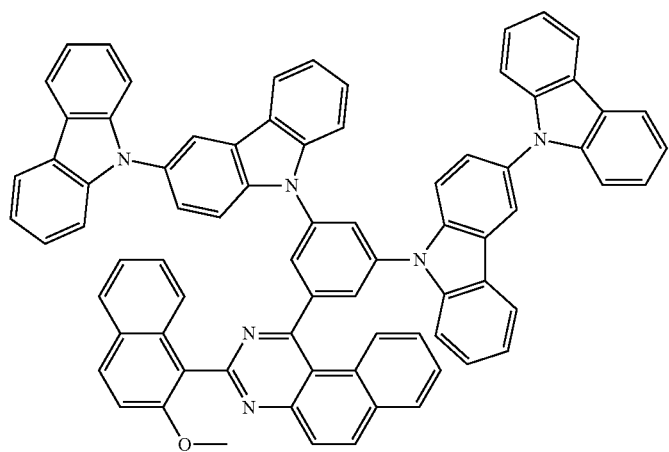
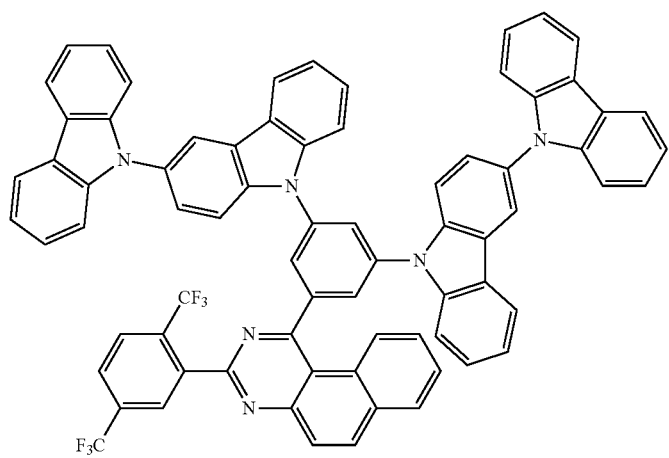

-continued
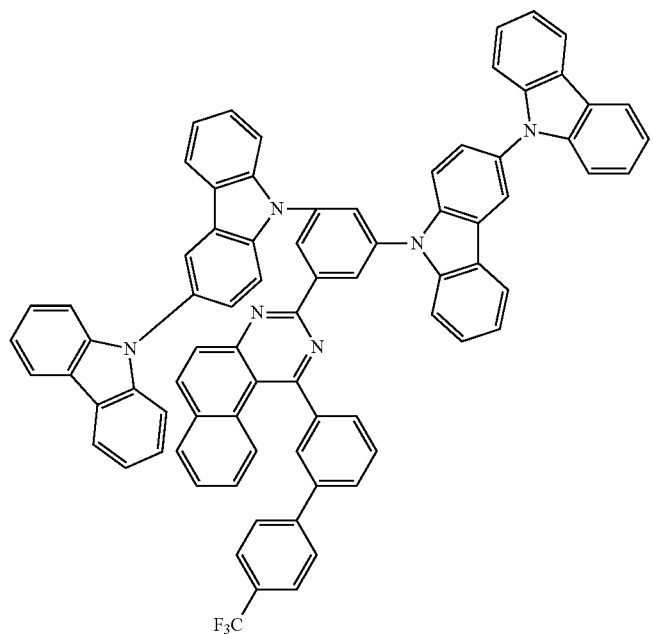
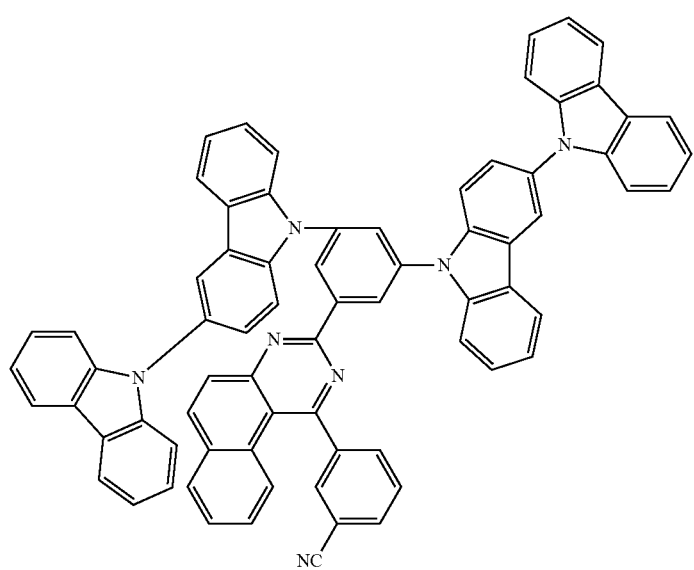

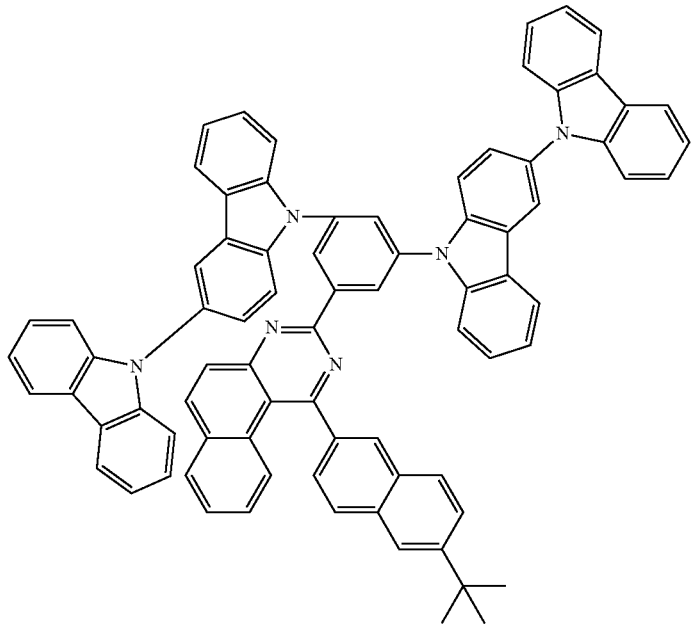

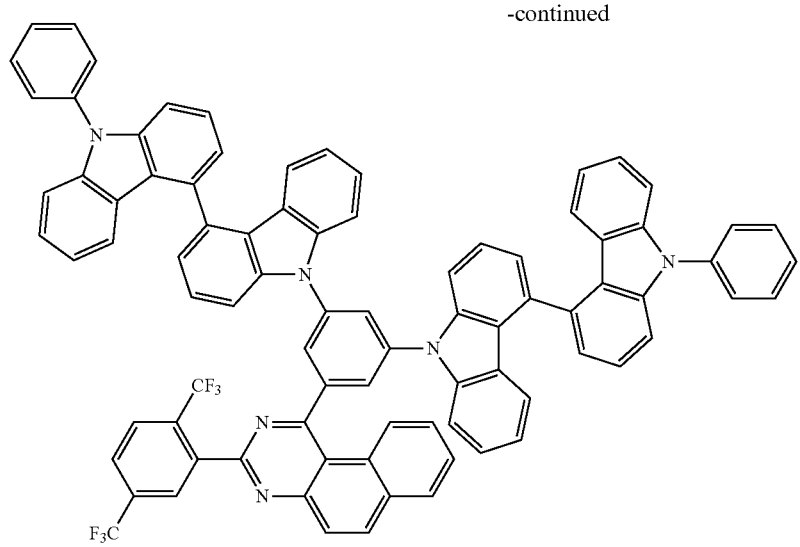
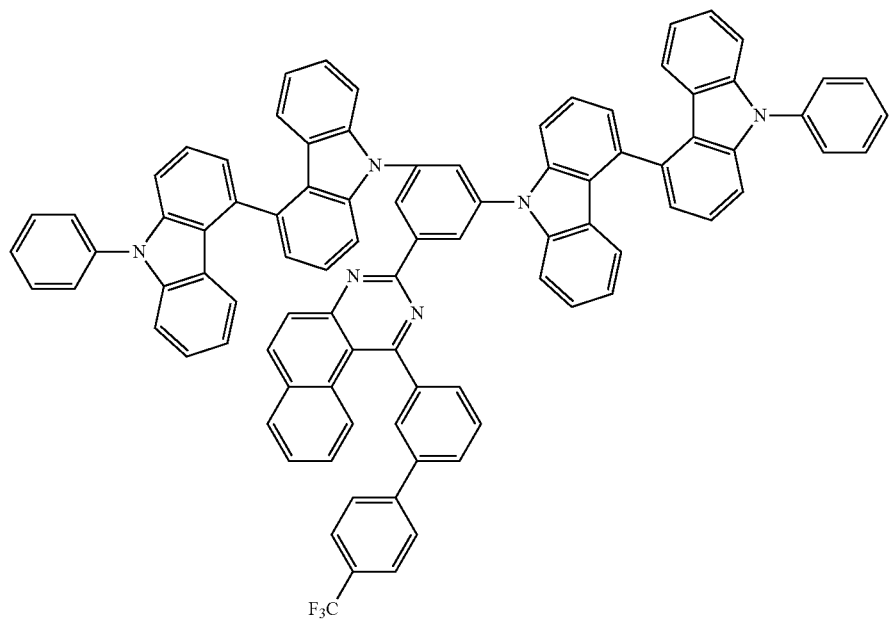
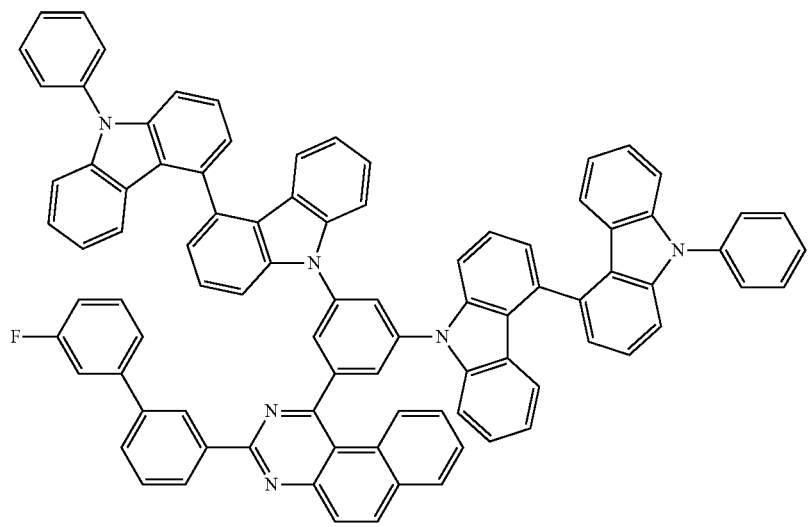

-continued

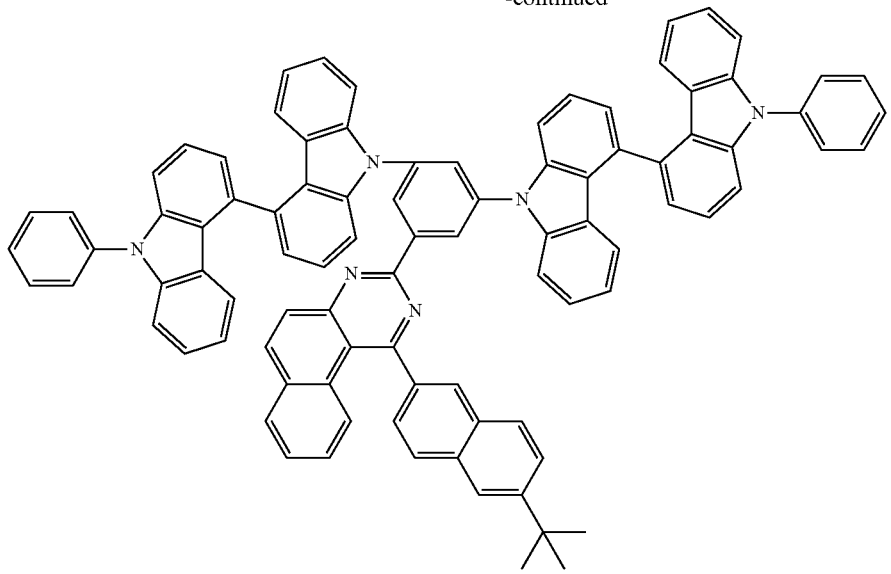

The compound represented by the formula (1) is suitable as a material for an organic EL device. The content of the compound in a material for an organic EL device is not particularly restricted. For example, the content may be 1 mass % or more, preferably be 10 mass % or more, more preferably 50 mass % or more, further preferably 80 mass % or more, and particularly preferably 90 mass % or more. The content of the compound may be 100 mass %. As for other materials than the above-mentioned compound, materials used in an emitting layer, an electron-transporting layer, a hole-transporting layer or the like mentioned later can be given.

The compound of the invention can be used as a host material and a dopant material in the emitting layer of a fluorescent emitting unit or as a host material in the emitting layer of a phosphorescent emitting unit. In any of a fluorescent emitting unit and a phosphorescent emitting unit, it can be useful as a material of an anode-side organic thin film layer provided between the anode and the emitting layer of an organic EL device or a material of a cathode-side organic thin film layer provided between the cathode and the emitting layer of an organic EL device; i.e. as materials for a hole-transporting layer, a hole-injecting layer, an electron-transporting layer, an electron-injecting layer, a hole-blocking layer, an electron-blocking layer, or the like.

In the meantime, the "emitting unit" means the minimum unit that includes one or more organic layers, one of which being an emitting layer, and can emit light by re-combination of holes and electrons injected.

An organic EL device as another aspect of the invention is characterized in that it has one or more organic thin film layers including an emitting layer between a cathode and an anode, and at least one of the organic thin film layers comprises the compound of the invention mentioned above.

As examples of the organic thin film layers in which the compound of the invention are included, an anode-side organic thin film layer provided between an anode and an emitting layer (hole-transporting layer, hole-injecting layer, etc.), an emitting layer, a cathode-side organic thin film layer provided between a cathode and an emitting layer (electron-transporting layer, electron-injecting layer, etc.), a spacing layer, a barrier layer, or the like can be given. The organic thin film layers are not limited thereto. The compound of the invention may be contained in any of the above-mentioned layers. For example, it can be used as a host material or a dopant material in the emitting layer of a fluorescent emitting unit, a host material in the emitting layer of a phosphorescent emitting unit, a hole-transporting layer of an emitting unit, an electron-transporting layer or the like.

The compound of the invention is preferable as a host material in the emitting layer of the phosphorescent emitting unit.

The organic EL device of the invention may be a fluorescent or phosphorescent monochromatic emitting device or may be a fluorescent/phosprecent hybrid white emitting device. It may be a simple emitting device having a single emitting unit or a tandem emitting device having plural emitting units. Among them, the organic EL device of the invention is preferably a phosprecent emitting device.

As the representative device configuration of a simple organic EL device, the following device configuration can be given.

(1) Anode/Emitting Unit/Cathode

The above-mentioned emitting unit may be a stacked unit having plural phosphorescent emitting layers and/or plural fluorescent emitting layers. In this case, between the emitting layers, a spacing layer may be provided in order to prevent diffusion of excitons formed in the phosphorescent emitting layer to the fluorescent emitting layer. The representative layer configurations of the emitting unit are given below.

(a) Hole-transporting layer/Emitting layer (/Electron-transporting layer)
(b) Hole-transporting layer/First phosphorescent emitting layer/Second phosphorescent emitting layer (/Electron-transporting layer)
(c) Hole-transporting layer/Phosphorescent emitting layer/Spacing layer/Fluorescent emitting layer (/Electron-transporting layer)
(d) Hole-transporting layer/First phosphorescent emitting layer/Second phosphorescent emitting layer/Spacing layer/Fluorescent emitting layer (/Electron-transporting layer)
(e) Hole-transporting layer/First phosphorescent emitting layer/Spacing layer/Second phosphorescent emitting layer/Spacing layer/Fluorescent emitting layer (/Electron-transporting layer)

(f) Hole-transporting layer/Phosphorescent emitting layer/Spacing layer/First fluorescent emitting layer/Second fluorescent emitting layer (/Electron-transporting layer)
(g) Hole-transporting layer/Electron barrier layer/Emitting layer (/Electron-transporting layer)
(h) Hole-transporting layer/Emitting layer/Hole barrier layer (/Electron-transporting layer)
(i) Hole-transporting layer/Fluorescent emitting layer/Triplet barrier layer (/Electron-transporting layer)

The phosphorescent or fluorescent emitting layer mentioned above emits different colors of light from each other. Specifically, in the above-mentioned stacked emitting layer (d), a layer configuration of a hole-transporting layer/first phosphorescent emitting layer (red emission)/second phosphorescent emitting layer (green emission)/spacing layer/fluorescent emitting layer (blue emission)/electron-transporting layer, or the like can be given.

Between each emitting layer and the hole-transporting layer or the spacing layer, an electron-barrier layer may be provided according to need. Further, between each emitting layer and the electron-transporting layer, a hole-barrier layer may be provided according to need. By providing an electron-barrier layer or a hole-barrier layer, it is possible to confine electrons or holes within the emitting layer, whereby possibility of re-combination of charges in the emitting layer can be improved, thus leading to a prolonged lifetime.

As the representative device configuration of a tandem organic EL device, the following device configuration can be given.
(2) Anode/First Emitting Unit/Intermediate Layer/Second Emitting Unit/Cathode As the first emitting unit and the second emitting unit, the same emitting unit as the above-mentioned emitting unit can be independently selected, for example.

In general, the intermediate layer as mentioned above is also referred to as an intermediate electrode, an intermediate conductive layer, a charge-generating layer, an electron-withdrawing layer, a connecting layer or an intermediate insulating layer. A known material configuration that supplies electrons to the first emitting unit and supplies holes to the second emitting unit can be used.

FIG. 1 shows a schematic configuration of one example of the organic EL device according to the invention. The organic EL device 1 has a substrate 2, an anode 3, a cathode 4, and an emitting unit 10 provided between the anode 3 and the cathode 4. The emitting unit 10 has an emitting layer 5 that includes at least one phosphorescent emitting layer containing a phosphorescent host material and a phosphorescent dopant. A hole-injecting and transporting layer 6 or the like may be formed between the emitting layer 5 and the anode 3, and an electron-injecting and transporting layer 7 or the like may be formed between the emitting layer 5 and the cathode 4. Further, an electron-barrier layer and a hole-barrier layer may respectively be provided on the anode 3 side of the emitting layer 5 and on the cathode 4 side of the emitting layer 5. As a result, it is possible to confine electrons or holes within the emitting layer 5, whereby possibility of generation of excitons in the emitting layer 5 can be increased.

In the specification, a host combined with a fluorescent dopant is called a fluorescent host and a host combined with a phosphorescent dopant is called a phosphorescent host. A fluorescent host and a phosphorescent host are not distinguished only by the molecular structure. That is, a phosphorescent host means a material that constitutes a phosphorescent emitting layer that contains a phosphorescent dopant, and does not mean it cannot be used as a material constituting a fluorescent emitting layer. The same can be applied to a fluorescent host.

The organic EL device of the invention is only required to have layers formed by using the compound of the invention mentioned above. As for other configurations, no specific restrictions are imposed, and known materials or the like can be used. Hereinbelow, a brief explanation will be made on elements constituting the device. Materials used in the organic EL device of the invention are not limited thereto.
(Substrate)

A substrate is used as a supporting body of an emitting device. As the substrate, glass, quarts, plastic or the like can be used, for example. A flexible substrate may be used. A flexible substrate means a substrate that can be bent (flexible), and a plastic substrate formed of polycarbonate or polyvinyl chloride, etc. can be given, for example.
(Anode)

In the anode formed on the substrate, it is preferable to use a metal having a large work function (specifically, 4.0 eV or more), alloys, electric conductive compounds, mixtures thereof, or the like. Specifically, indium oxide-tin oxide (ITO: Indium Tin Oxide), indium oxide-tin oxide that contains silicon or silicon oxide, indium oxide-zinc oxide, tungsten oxide, indium oxide that contains zinc oxide, graphene or the like can be given, for example. In addition, gold (Au), platinum (Pt), or a nitride of a metal material (titanium nitride, for example) or the like can be given.
(Hole-Injecting Layer)

A hole-injecting layer is a layer that contains a substance having high hole-injecting properties. As a substance having high hole-injecting properties, molybdenum oxides, titanium oxides, vanadium oxides, rhenium oxides, ruthenium oxides, chromium oxides, zirconium oxides, hafnium oxides, tantalum oxides, silver oxides, tungsten oxides, manganese oxides, aromatic amine compounds, or polymer compounds (e.g. oligomer, dendrimer, polymer, etc.) can also be used.
(Hole-Transporting Layer)

A hole-transporting layer is a layer that contains a substance having high hole-transporting properties. In the hole-transporting layer, an aromatic amine compound, a carbazole derivative, an anthracene derivative or the like can be used. A polymer compound such as poly(N-vinylcarbazole) (abbreviation: PVK) or poly(4-vinyltriphenylamine) (abbreviation: PVTPA) can be used. A substance other than these can be used as long as it has higher transporting properties of holes rather than electrons. In the meantime, as for a layer that contains a substance having high hole-transporting properties, it may be not only a single layer but also a stacked layer of two or more layers formed of the above-mentioned substance.
(Guest Material of Emitting Layer)

An emitting layer is a layer that contains a substance having high luminous properties, and various materials can be used. For example, as a substance having high luminous properties, a fluorescent compound that emits fluorescent light or a phosphorescent compound that emits phosphorescent light can be used. A fluorescent compound is a compound that can emit light from the singlet excited state, and a phosphorescent compound is a compound that can emit light from the triplet excited state.

As a blue fluorescent emitting material that can be used in the emitting layer, a pyrene derivative, a styrylamine derivative, a chrysene derivative, a fluoranthene derivative, a fluorene derivative, a diamine derivative, a triarylamine derivative or the like can be used. As a green fluorescent emitting material that can be used in the emitting layer, an aromatic amine derivative or the like can be used. As a red fluorescent emitting material that can be used in the emitting layer, a tetracene derivative, a diamine derivative or the like can be used.

As a blue phosphorescent emitting material that can be used in the emitting layer, a metal complex such as an iridium complex, an osmium complex and a platinum complex is used. As a green phosphorescent emitting material that can be used in the emitting layer, an iridium complex or the like can be used. As a red phosphorescent emitting material that can be used in the emitting layer, a metal complex such as an iridium complex, a platinum complex, a terbium complex, an europium complex or the like are used.

In the organic EL device of the invention, it is preferred that the emitting layer contain the compound of the invention as a host material. Further, it is preferred that the emitting layer be formed of a host material and a phosphorescent emitting material and that the host material be the compound of the invention.

It is preferred that the compound of the invention have a lowest excited triplet energy of 2.2 to 3.2 eV, more preferably 2.5 to 3.2 eV. The "triplet energy" means a difference in energy between the lowest excited triplet state and the ground state.

In respect of a high phosphorescent quantum yield and capability of further improving external quantum efficiency of an emitting device, the phosphorescent emitting material is preferably a compound having iridium (Ir), osmium (Os), ruthenium (Ru) or platinum (Pt). Further preferable are a metal complex such as an iridium complex, an osmium complex, a ruthenium complex and a platinum complex, among these an iridium complex and a platinum complex are more preferable, with an ortho-metalated complex of a metal atom sleeted from iridium, osmium (Os) and platinum (Pt) being most preferable. Specific examples of a metal complex such as an iridium complex, an osmium complex, a ruthenium complex, a platinum complex or the like are given below.

Abbreviations PQIr (iridium(III)bis(2-phenylquinolyl-N, $C^{2'}$)acetylacetonate) and Ir(ppy)$_3$(tris(2-phenylpyridinato-N,$C^{2'}$)iridium (III)) given below the specific examples are abbreviations of the organic metal complexes shown above the abbreviations.

Me is a methyl group.

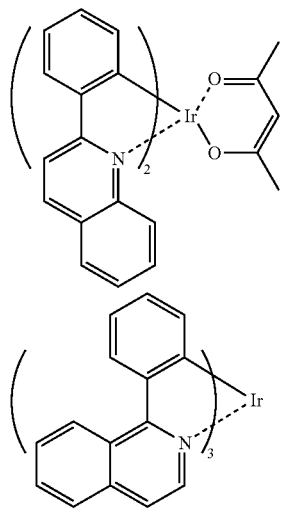

PQIr

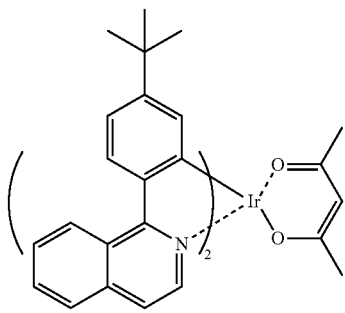

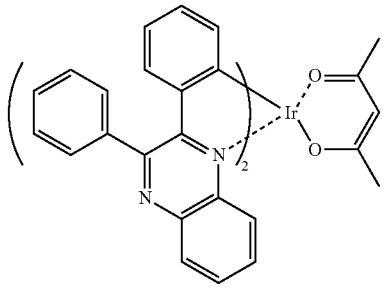

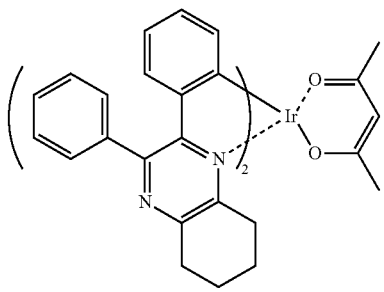

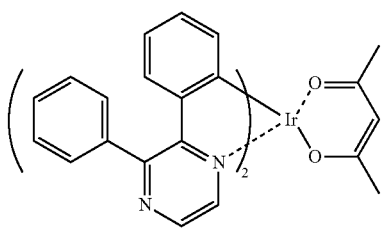

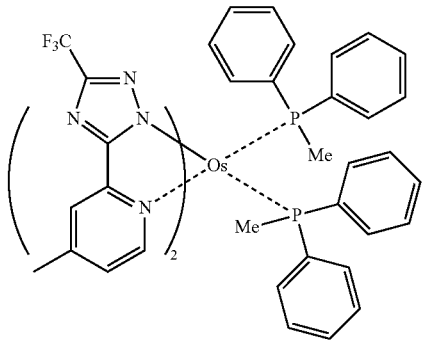

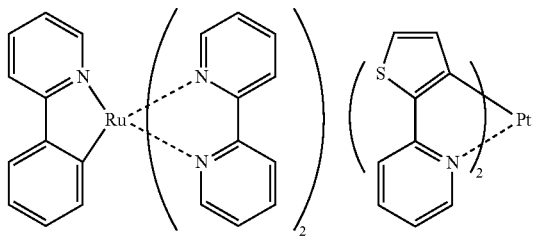

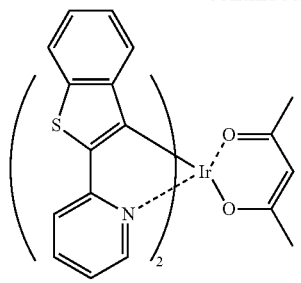
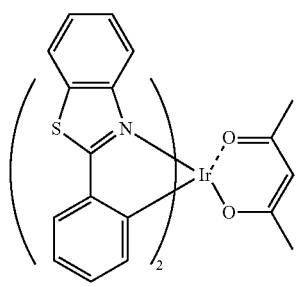
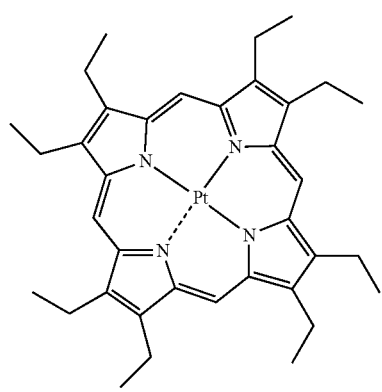
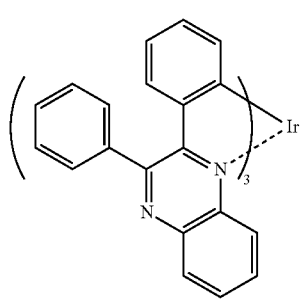
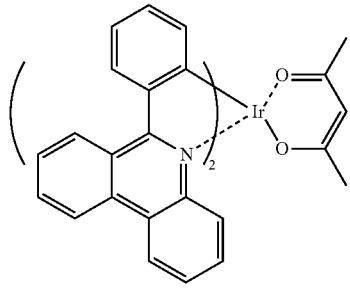
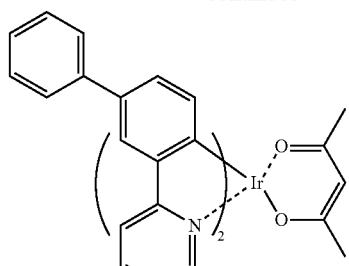
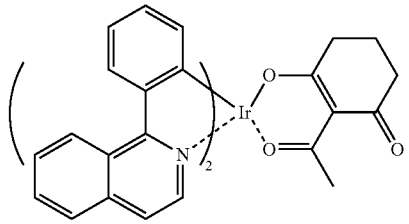
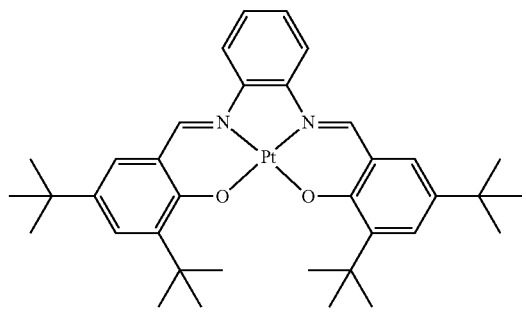
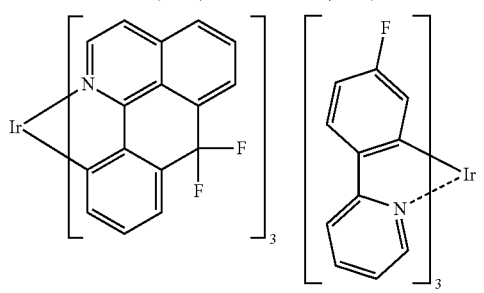
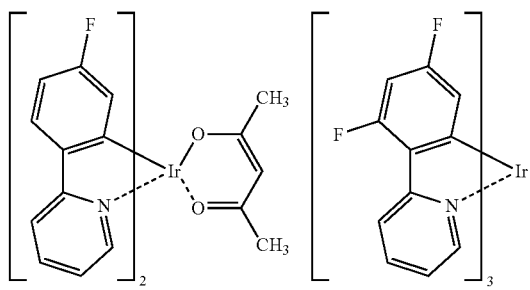
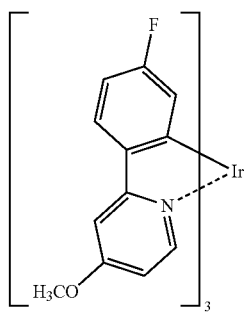

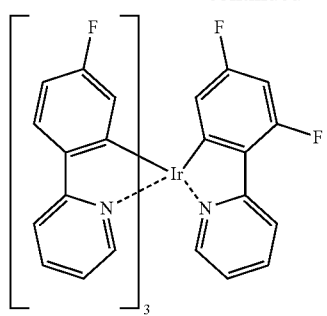
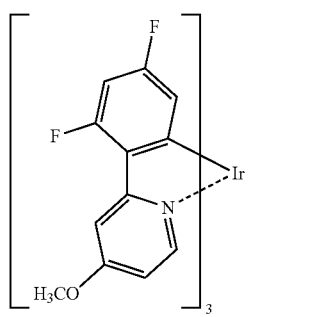
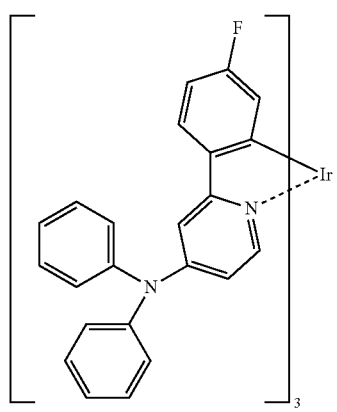
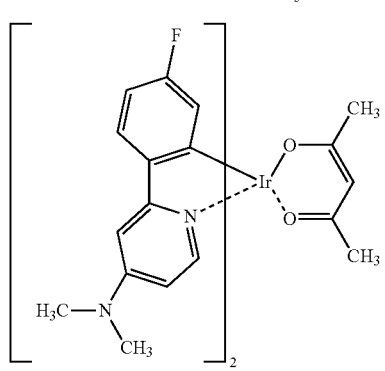
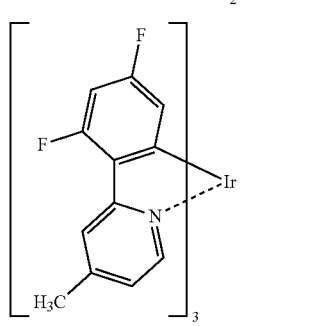
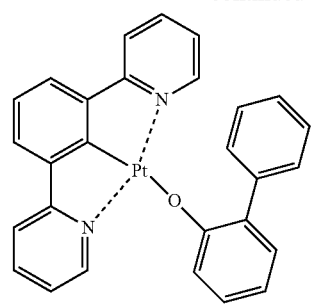
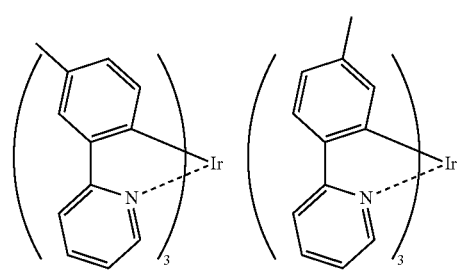
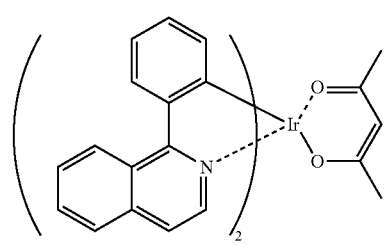
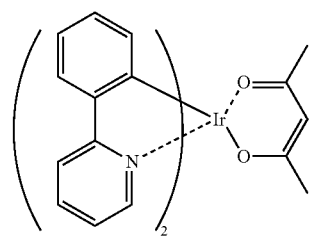
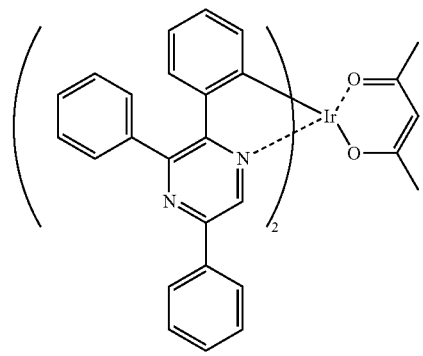
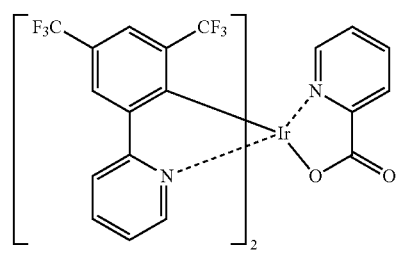

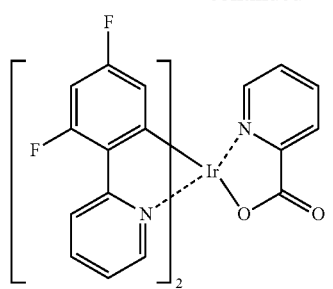
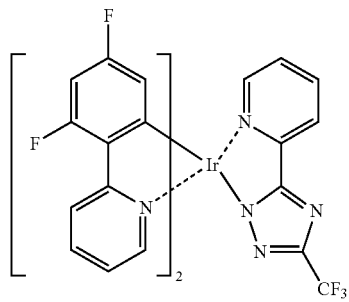
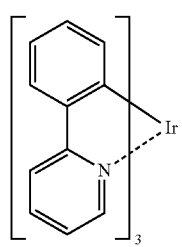
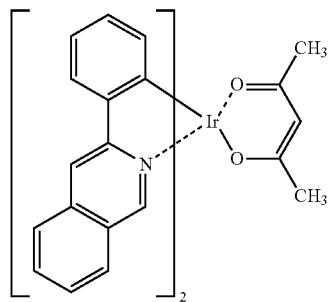
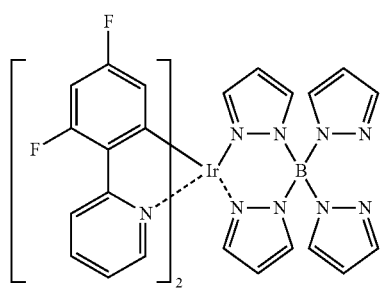
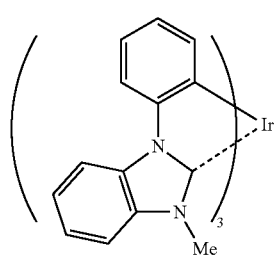
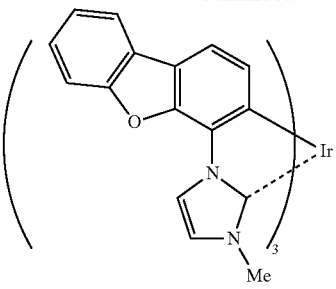
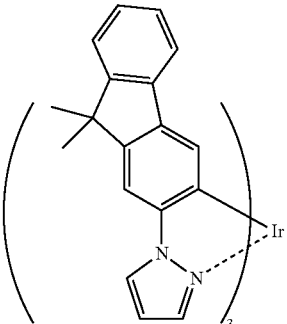
Ir(ppy)₃
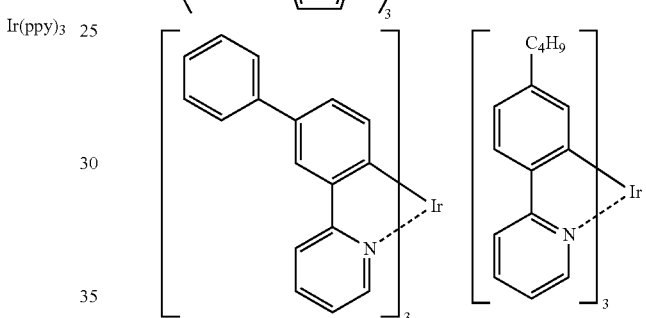
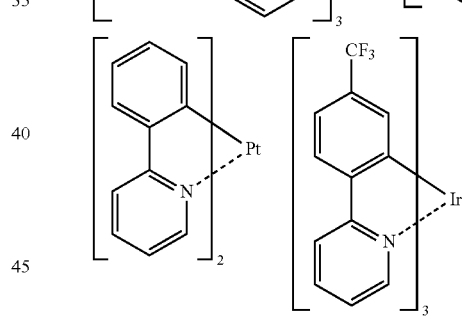
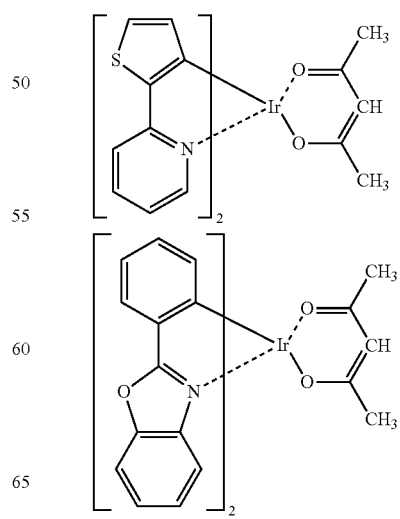

-continued

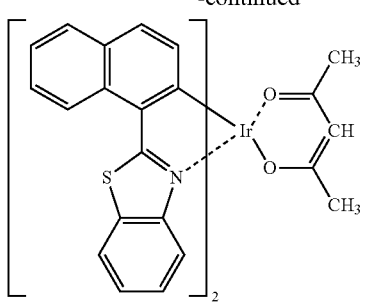

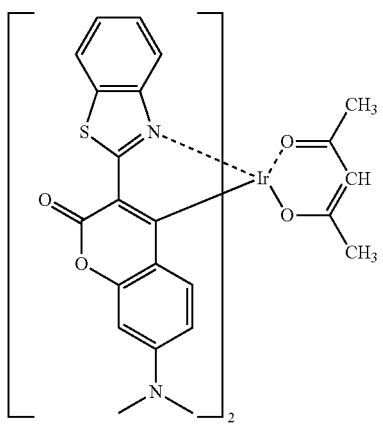

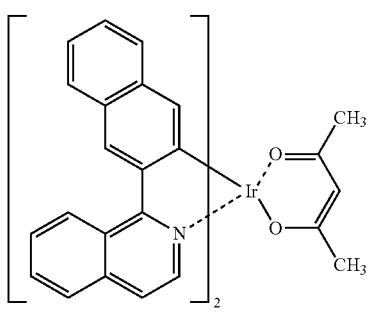

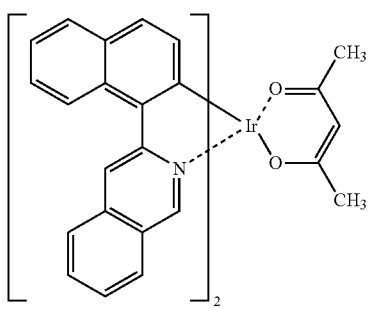

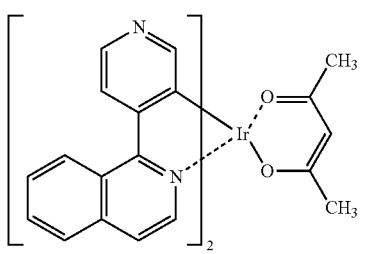

-continued

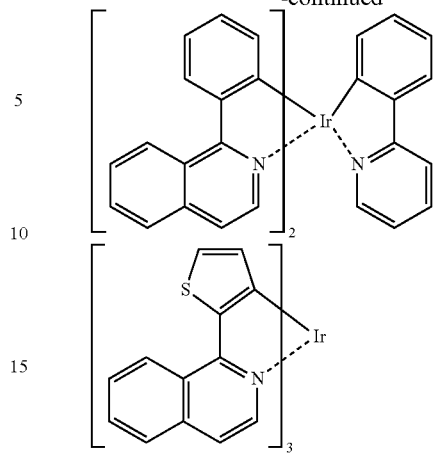

In the organic EL device of the invention, as a phosphorescent emitting material, a complex represented by the following formula (X) or (Y) is preferable.

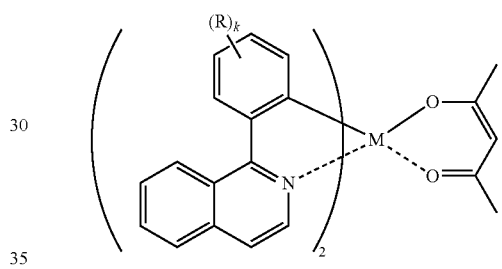

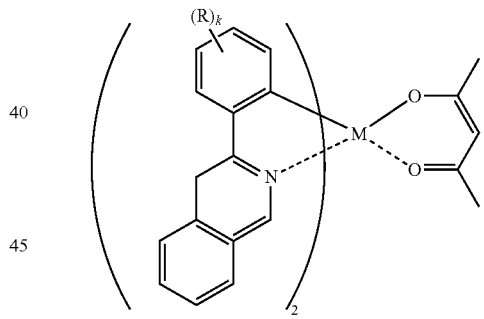

In the formulas (X) and (Y), R is a hydrogen atom or a substituent, k is an integer of 1 to 4, and M is Ir, Os or Pt.

As the substituent indicated by R, the same substituents as those exemplified above by $R_1$ or the like in the formula (1) can be given.

(Host Material of Emitting Layer)

The emitting layer may have a configuration in which the highly luminous substances (guest materials) mentioned above are dispersed in other substances (host materials). As a substance for dispersing a highly luminous substance, various substances can be used. It is preferable to use a substance that has a higher lowest unoccupied molecular orbit (LUMO) level and has a lower highest occupied molecular orbit (HOMO) level as compared with the highly luminous substance.

As the substance (host material) for dispersing a highly luminous substance, 1) a metal complex such as an aluminum complex, a beryllium complex or a zinc complex, 2) a heterocyclic compound such as an oxadiazole derivative, a benzimidazole derivative or a phenanthroline derivative, 3) a fused aromatic compound such as a carbazole derivative, an anthracene derivative, a phenanthrene derivative, a pyrene derivative or a chrysene derivative, or 3) an aromatic amine compound such as a triarylamine derivative or a fused polycyclic aromatic amine derivative can be given.

(Electron-Transporting Layer)

An electron-transporting layer is a layer that contains a substance having high electron-transporting properties. In the electron-transporting layer, 1) a metal complex such as an aluminum complex, a beryllium complex and a zinc complex, 2) a heteroaromatic compound such as an imidazole derivative, a benzimidazole derivative, an azine derivative, a carbazole derivative and a phenanthroline derivative, or 3) a polymer compound can be used.

(Electron-Injecting Layer)

An electron-injecting layer is a layer that contains a substance having high electron-injecting properties. In an electron-injecting layer, an alkali metal such as lithium (Li), lithium fluoride (LiF), cesium fluoride (CsF), calcium fluoride ($CaF_2$) and lithium oxide (LiOx) or a compound thereof can be used.

(Cathode)

In a cathode, it is preferable to use a metal having a small work function (specifically 3.8 eV or less), an alloy, an electric conductive compound, a mixture thereof or the like. As specific examples of such cathode material, an element belonging to the group 1 or 2 of the periodic table; i.e. an alkali metal such as lithium (Li) and cesium (Cs), an alkaline earth metal such as magnesium (Mg) and an alloy containing these (e.g. MgAg, AlLi) or the like can be given.

The method for forming each layer of the organic EL device of the invention is not specifically restricted. Each layer can be formed by a conventionally known method such as a vacuum deposition method, a spin coating method or the like. The organic thin layer that is used in the organic EL device of the invention and contains the compound of the invention can be formed by a known method such as a vacuum deposition method, a molecular beam epitaxy method (MBE) method, or by a coating method such as a dipping method, a spin coating method, a casting method, a bar coating method, a roll coating method, or the like, in which a solution obtained by dissolving the compound of the invention in a solvent is applied.

The thickness of each organic layer of the organic EL device of the invention is not particularly restricted. In general, if the film thickness is too small, defects such as formation of pinholes are likely to occur. On the other hand, if the film thickness is too large, a high voltage is required to be applied, leading to a poor efficiency. Therefore, normally, the film thickness is preferably in a range of several nm to 1 μm.

As the method for forming a layer containing the compound of the invention (in particular, an emitting layer), a method is preferable in which a solution containing the compound of the invention and, if need arises, other materials such as a dopant, is formed into a film.

As the film-forming method, a known coating method can be effectively utilized. For example, a spin coating method, a casting method, a micro gravure coating method, a gravure coating method, a bar coating method, a roll coating method, a slit coating method, a wire bar coating method, a dip coating method, a spray coating method, a screen printing method, a flexographic printing method, an offset printing method, an inkjet method, a nozzle printing method or the like can be given. When pattern formation is conducted, it is preferable to use a screen printing method, a flexographic printing method, an offset printing method and an inkjet printing method are preferable. Film formation by these methods can be conducted under conditions that are well known to a person skilled in the art.

After the film formation, it is only required to conduct heating (upper limit 250° C.) and drying in vacuum to remove the solvent. A polymerization reaction by exposure to light or heating at a high temperature exceeding 250° C. is not necessary. Therefore, it is possible to suppress deterioration in performance of a device by exposure to light or heating at a high temperature exceeding 250° C.

A solution for film formation is only required to contain at least one type of the compound of the invention. In addition, hole-transporting materials, electron-transporting materials, emitting materials, acceptor materials, a solvent and an additive such as a stabilizer other than those mentioned above can be used.

A solution for film formation may contain an additive for controlling viscosity and/or surface tension, e.g. a thickening agent (high-molecular weight compound, etc.), a viscosity depressant (low-molecular weight compound, etc.), a surfactant or the like. In order to improve storage stability, the solution may contain an anti-oxidant that does not affect adversely the performance of an organic EL device, the examples of which include a phenol-based anti-oxidant and a phosphorus-based anti-oxidant.

The content of the compound of the invention in the above-mentioned solution for film formation is preferably 0.1 to 15 mass %, more preferably 0.5 to 10 mass %, relative to the total of the solution for film formation, As the high-molecular weight compound that can be used as a thickening agent, insulating resins such as polystyrene, polycarbonate, polyarylate, polyester, polyamide, polyurethane, polysulfone, polymethyl methacrylate, polymethyl acrylate and cellulose, a copolymer thereof, photoconductive resins such as poly-N-vinylcarbazole and polysilane and conductive resins such as polythiophene and polypyrrole can be given.

As the solvent of the solution for film formation, for example, a chlorine-based solvent such as chloroform, methylene chloride, 1,2-dichloroethane, 1,1,2-trichloroethane, chlorobenzene, o-dichlorobenzene; an ether-based solvent such as tetrahydrofuran, dioxane, dioxorane and anisole; an aromatic hydrocarbon-based solvent such as toluene and xylene; an aliphatic hydrocarbon-based solvent such as cyclohexane, methylcyclohexane, n-pentane, n-hexane, h-heptane, n-octane, n-nonane and n-decane; a ketone-based solvent such as acetone, methyl ethyl ketone, cyclohexanone, benzophenone and acetophenone; an ester-based solvent such as ethyl acetate, butyl acetate, ethyl cellosolve acetate, methyl benzoate and phenyl acetate; a polyvalent alcohol such as ethylene glycol, ethylene glycol monobutyl ether, ethylene glycol monoethyl ether, ethylene glycol monomethyl ether, dimethoxyethane, propylene glycol, diethoxymethane, triethylene glycol monoethyl ether, glycerine and 1,2-hexanediol and derivatives thereof; an alcohol-based solvent such as methanol, ethanol, propanol, isopropanol and cyclohexanol; a sulfoxide-based solvent such as dimethylsulfoxide; and an amide-based solvent such as N-methyl-2-pyrrolidone and N,N-dimethylformamide can be given. These solvents may be used alone or in combination of two or more.

Among these solvents, in respect of solubility, homogeneity of film formation, viscosity properties or the like, an aromatic hydrocarbon-based solvent, an ether-based solvent, an aliphatic hydrocarbon-based solvent, an ester-based solvent and a ketone-based solvent are preferable. Toluene, xylene, ethylbenzene, diethylbenzene, trimethylbenzene, n-propylbenzene, isopropylbenzene, n-butylbenzene, isobutylbenzene, 5-butylbenzene, n-hexylbenzene, cyclohexylbenzene, 1-methylnaphthalene, tetralin, 1,3-dioxane, 1,4-dioxane, 1,3-dioxolane, anisole, ethoxy benzene, cyclohexane, bicyclohexyl, cyclohexenylcyclohexanone, n-heptylcyclohexane, n-hexylcyclohexane, decalin, methyl benzoate, cyclohexanone, 2-propylcyclohexanone, 2-heptanone, 3-heptanone, 4-heptanone, 2-octanone, 2-nonanone, 2-decanone, dicyclohexylketone, acetophenone, benzophenone are more preferable.

The organic EL device of the invention can be used as an emitting device in a panel module used in various displays.

The organic EL device of the invention can be used in a display device such as televisions, mobile terminals and personal computers and an electronic apparatus such as lightings.

EXAMPLES

In accordance with the following reactions, and by using known alternative reactions or raw materials that are suitable for obtaining an intended product, a compound that falls within the scope of the claims can be synthesized.

Synthesis of Compound

Example 1

Synthesis of Compound 1

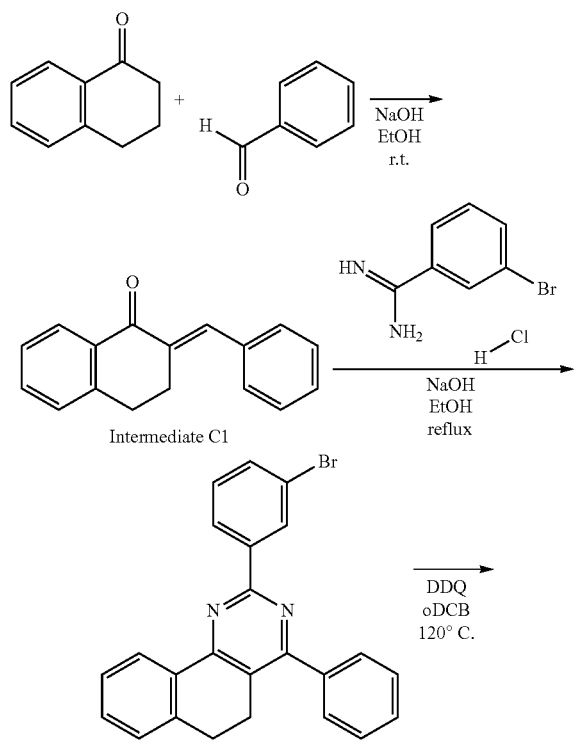

Intermediate C1

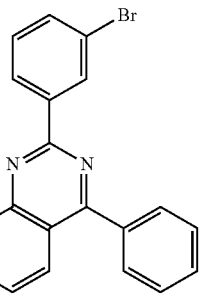

Intermediate B1

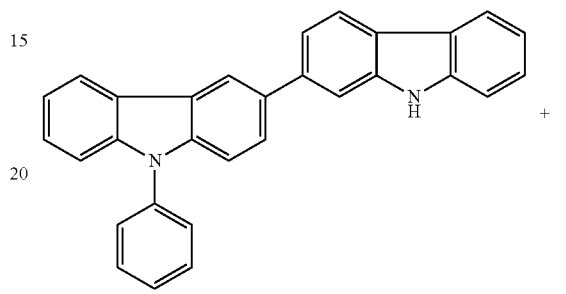

Intermediate A1

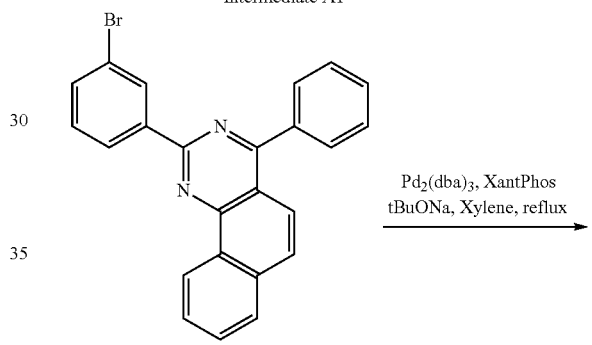

Intermediate B1

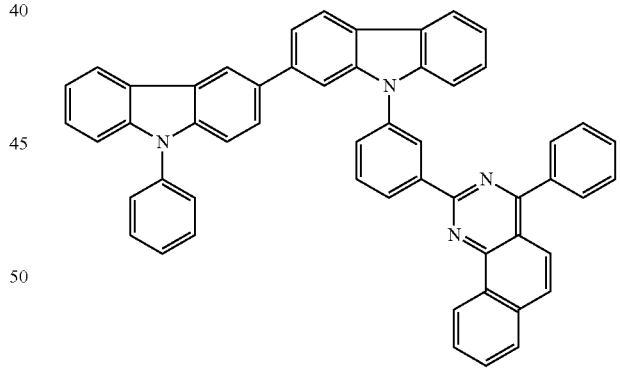

Compound 1

α-tetralone (3,4-dihydro-1(2H)-naphthalenone) (7.62 g, 52 mmol) and benzaldehyde (5.53 g, 52 mmol) were dissolved in ethanol (100 mL), sodium hydroxide (0.20 g, 5.0 mmol) was added, and the mixture was stirred at room temperature for 8 hours. The formed powder was collected by filtration, washed with methanol until the color of the liquid disappeared, followed by drying in vacuum, whereby chalcone intermediate C1 was obtained (9.13 g, yield 75%). This chalcone intermediate C1 (4.43 g, 18.9 mmol), 3-bromobenzamidine hydrochloride (4.45 g, 18.9 mmol) and sodium hydroxide (0.83 g, 20.8 mmol) were reacted in ethanol (190 mL) under reflux with heating for 8 hours. The formed powder was collected by filtration, washed with methanol, and dried in vacuum. In orthodichlorobenzene (100 mL), to this powder, 2,3-dichloro-5,6-dicyano-p-benzoquinone (DDQ) (4.90 g, 21.6 mmol) was added and the resultant was allowed to react at 120° C. for 5 hours. Then, after cooling to room temperature, purification was conducted with silica gel column chromatography, whereby benzoquinazoline intermediate B1 (5.45 g, yield 70%) was obtained.

In an argon atmosphere, biscarbazolyl intermediate A1 (1.29 g, 3.15 mmol), benzoquinazoline intermediate B1 (1.23 g, 3.00 mmol), tris (dibenzylideneacetone)dipalladium ($Pd_2(dba)_3$) (55 mg, 0.06 mmol), 4,5'-bis(diphenylphosphino)-9,9'-dimethylxanthene (XantPhos) (69 mg, 0.12 mmol), t-butoxy sodium (0.43 g, 4.5 mmol), and xylene anhydride (60 mL) were added in sequence. The resultant was heated under reflux for 12 hours. After cooling the reaction liquid to room temperature, insoluble matters were removed by filtration, and the organic solvent was distilled off under reduced pressure. The resulting residues were purified with silica gel column chromatography, whereby compound 1 was obtained (1.78 g, yield 80%).

HPLC (high-performance liquid chromatography): purity 99.45%

FD-MS (field desorption mass spectrometry): calcd for $C_{54}H_{34}N_4$=738.

found m/z=738 (M+, 100).

Example 2

Synthesis of Compound 2

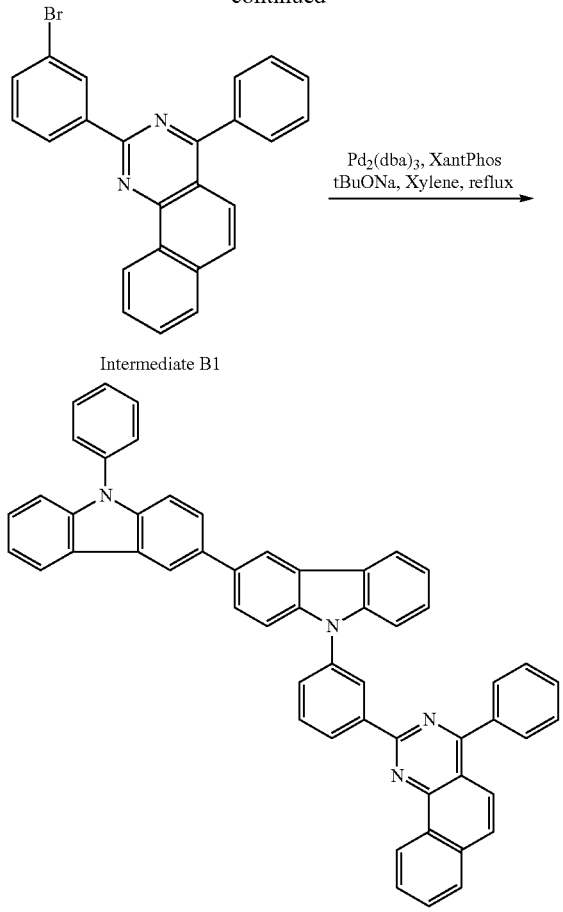

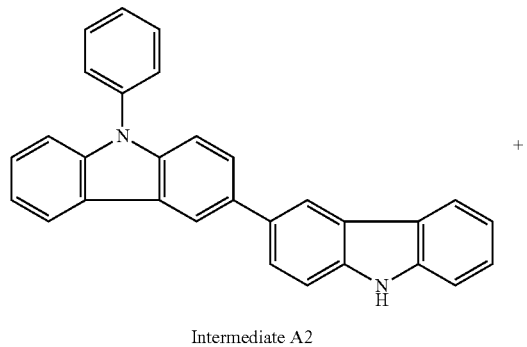

Intermediate A2

The same procedures as those in Example 1 were followed, except that biscarbazolyl intermediate A2 (1.29 g, 3.15 mmol) was used instead of the biscarbozolyl intermediate A1, whereby an intended compound 2 was obtained (1.64 g, yield 74%).

HPLC: purity 99.70%

FD-MS: calcd for $C_{54}H_{34}N_4$=738.

found m/z=738 (M+, 100).

Example 3

Synthesis of Compound 3

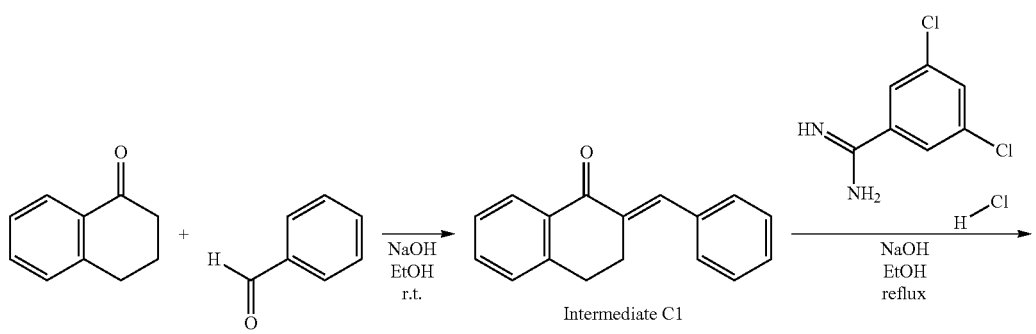

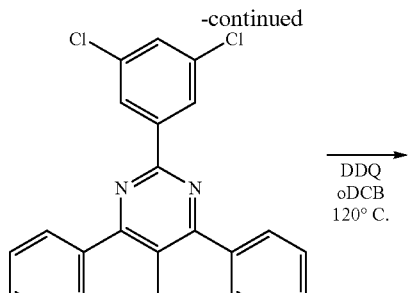
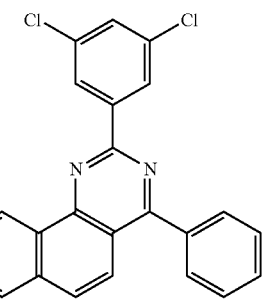

Intermediate B2

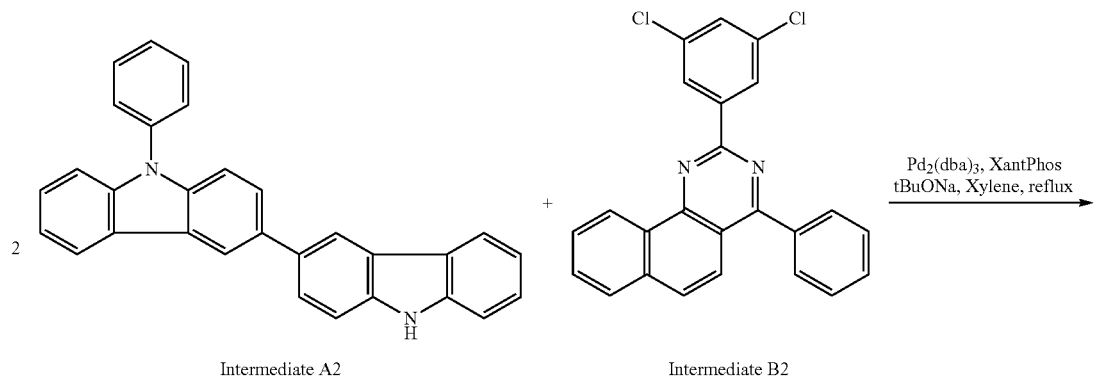

Intermediate A2     Intermediate B2

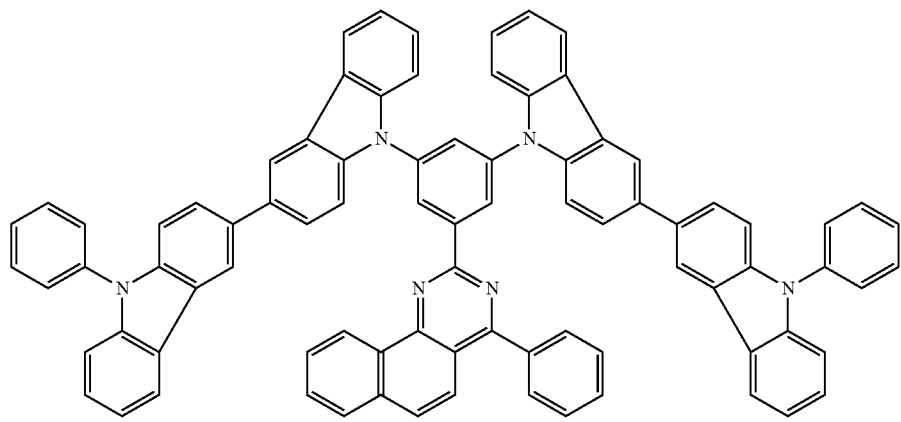

Compound 3

The chalcone intermediate C1 synthesized in Example 1 (4.69 g, 20.0 mmol), 3,5-dichlorobenzamidine hydrochloride (4.52 g, 20.0 mmol) and sodium hydroxide (0.88 g, 22 mmol) were reacted for 8 hours in ethanol (200 mL) under reflux with heating. The formed powder was collected by filtration, washed with methanol, and dried in vacuum. In orthodichlorobenzene (100 mL), to this powder, 2,3-dichloro-5,6-dicyano-p-benzoquinone (5.0 g, 22 mmol) was added and the resultant was allowed to react at 120° C. for 5 hours. Then, after cooling to room temperature, purification was conducted with silica gel column chromatography, whereby benzoquinazoline intermediate B2 (4.81 g, yield 60%) was obtained.

In an argon atmosphere, biscarbazolyl intermediate A2 (1.80 g, 4.40 mmol), benzoquinazoline intermediate B2 (0.84 g, 2.10 mmol), tris(dibenzylideneacetone)dipalladium (Pd$_2$(dba)$_3$) (39 mg, 0.04 mmol), 4,5'-bis(diphenylphosphino)-9,9'-dimethylxanthene (49 mg, 0.08 mmol), t-butoxy sodium (0.61 g, 6.3 mmol) and xylene anhydride (42 mL) were added in sequence, and the resultant was subjected to reflux with heating for 12 hours. After cooling the reaction liquid to room temperature, insoluble matters were removed by filtration, and the organic solvent was distilled off under reduced pressure. The resulting residues were purified by silica gel column chromatography, whereby compound 3 (2.02 g, yield 84%) was obtained.

HPLC: purity 99.20%

FD-MS: calcd for $C_{64}H_{52}N_6$=1144.

found m/z=1144 (M+, 100).

Example 4

Synthesis of Compound 4

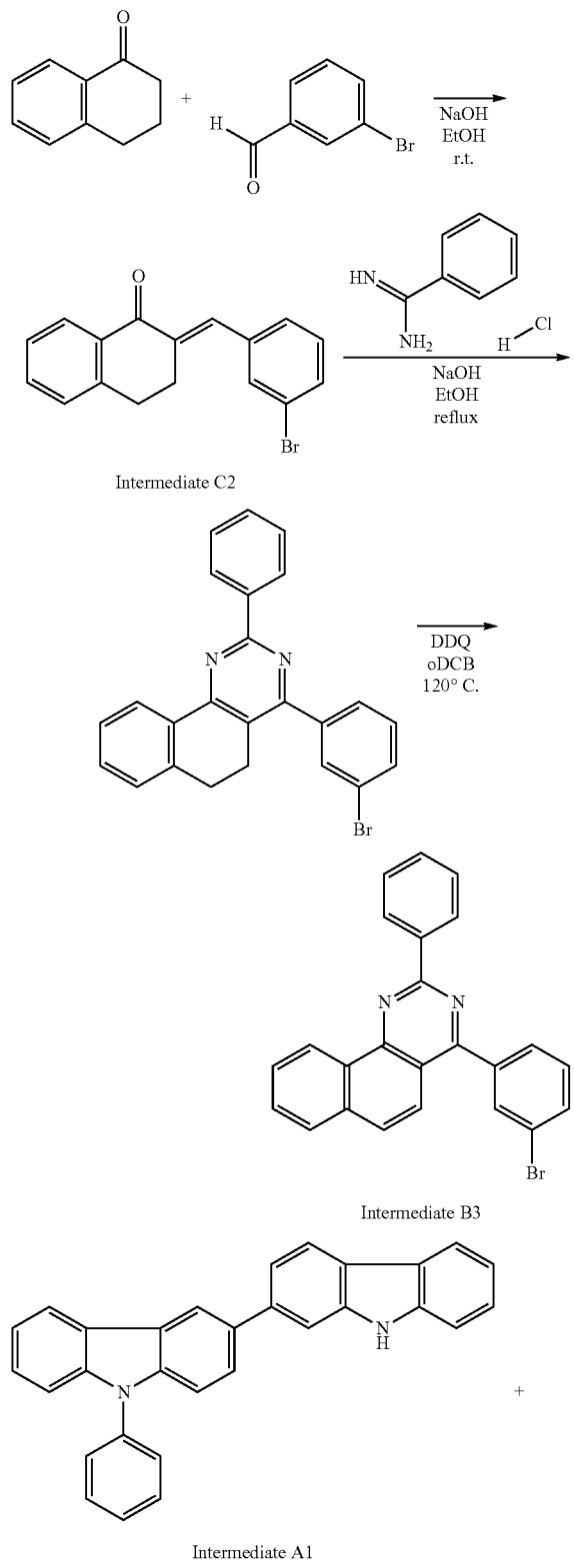

Intermediate C2

Intermediate B3

Intermediate A1

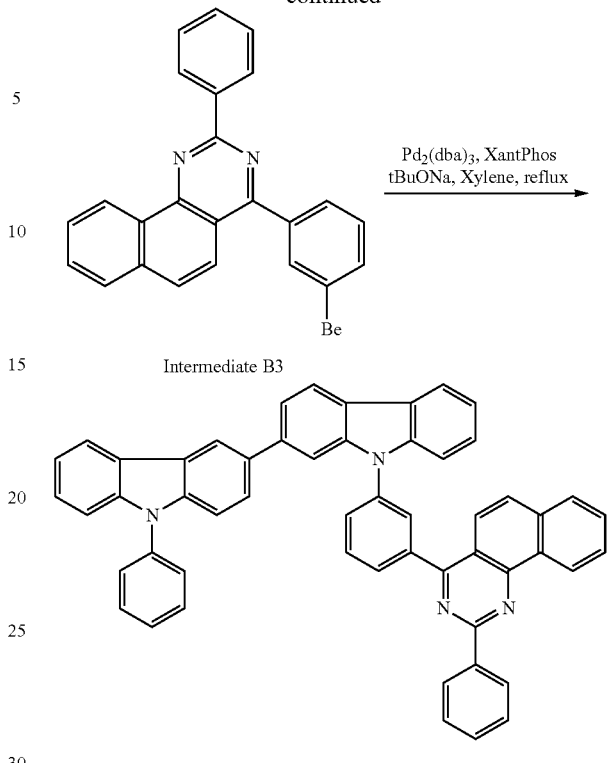

Intermediate B3

Compound 4

α-tetralone (3,4-dihydro-1(2H)-naphthalenone) (7.50 g, 51.3 mmol), and 3-bromobenzaldehyde (9.49 g, 51.3 mmol) were dissolved in ethanol (100 mL), sodium hydroxide (0.20 g, 5 mmol) was added and the mixture was stirred for 8 hours at room temperature. The formed powder was collected by filtration, washed with methanol until the color of the liquid disappeared, followed by drying in vacuum, whereby chalcone intermediate C2 was obtained (14.10 g, yield 88%).

The chalcone intermediate C2 (6.26 g, 20.0 mmol), benzamidine hydrochloride (3.13 g, 20.0 mmol) and sodium hydroxide (0.88 g, 22 mmol) were allowed to react in ethanol (100 mL) under reflux with heating for 8 hours. The formed powder was collected by filtration, washed with methanol, and dried in vacuum. In orthodichlorobenzene (100 mL), to this powder, 2,3-dichloro-5,6-dicyano-p-benzoquinone (5.0 g, 22 mmol) was added and the resultant was allowed to react at 120° C. for 5 hours. Then, after cooling to room temperature, purification was conducted with silica gel column chromatography, whereby benzoquinazoline intermediate B3 (5.52 g, yield 67%) was obtained.

In an argon atmosphere, biscarbazolyl intermediate A1 (1.29 g, 3.15 mmol), benzoquinazoline intermediate B3 (1.23 g, 3.00 mmol), tris(dibenzylideneacetone)dipalladium (55 mg, 0.06 mmol), 4, 5'-bis(diphenylphosphino)-9,9'-dimethylxanthene (69 mg, 0.12 mmol), t-butoxy sodium (0.43 g, 4.5 mmol) and xylene anhydride (60 mL) were added in sequence, and the resultant was subjected to reflux with heating for 12 hours. After cooling the reaction liquid to room temperature, insoluble matters were removed by filtration, and the organic solvent was distilled off under reduced pressure. The resulting residues were purified by silica gel column chromatography, whereby compound 4 (1.64 g, yield 74%) was obtained.

HPLC: purity 99.76%

FD-MS: calcd for $C_{54}H_{34}N_4$=738.

found m/z=738 (M+, 100).

Example 5

Synthesis of Compound 5

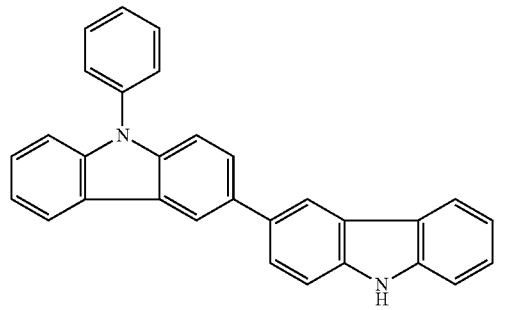

Intermediate A2

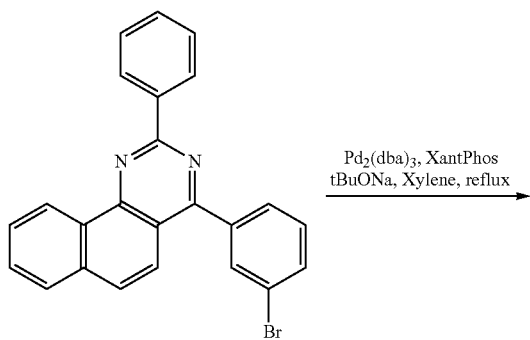

Intermediate B3

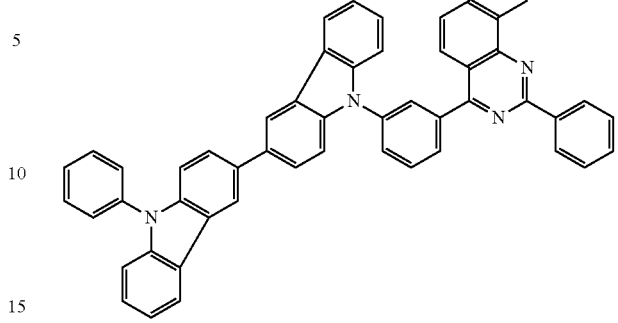

Compound 5

The same procedures as those in Example 4 were followed, except that biscarbazolyl intermediate A2 (1.29 g, 3.15 mmol) was used instead of the biscarbozolyl intermediate A1, whereby an intended compound 5 was obtained (1.81 g, yield 82%).

HPLC: purity 99.23%

FD-MS: calcd for $C_{54}H_{34}N_4$=738.

found m/z=738 (M+, 100).

Example 6

Synthesis of Compound 6

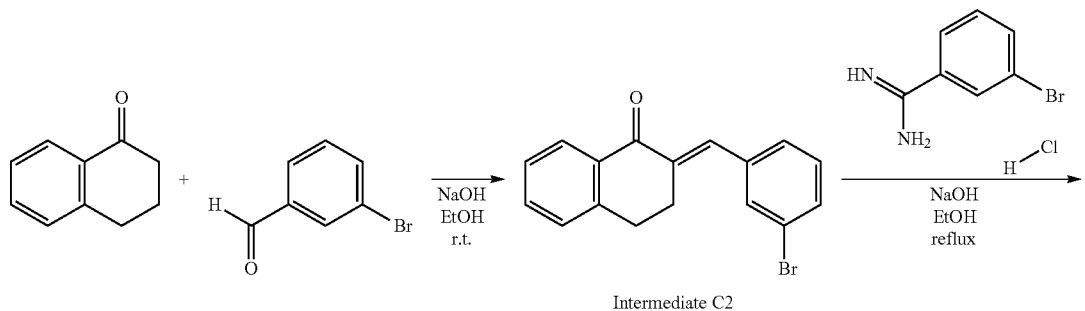

Intermediate C2

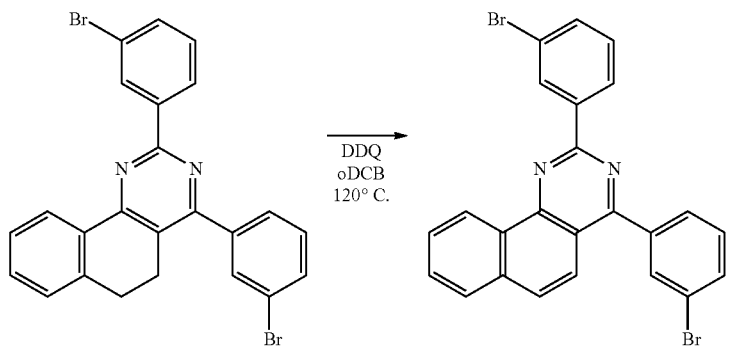

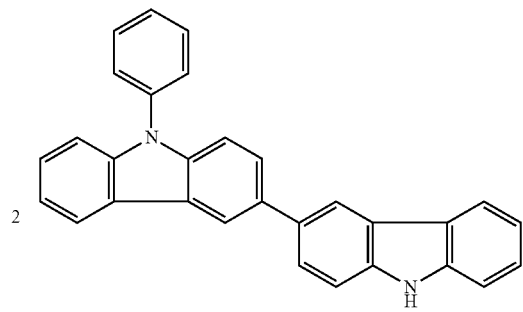 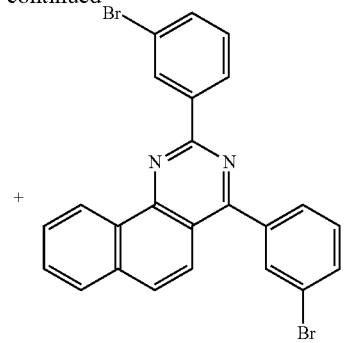

Intermediate A2    Intermediate B4

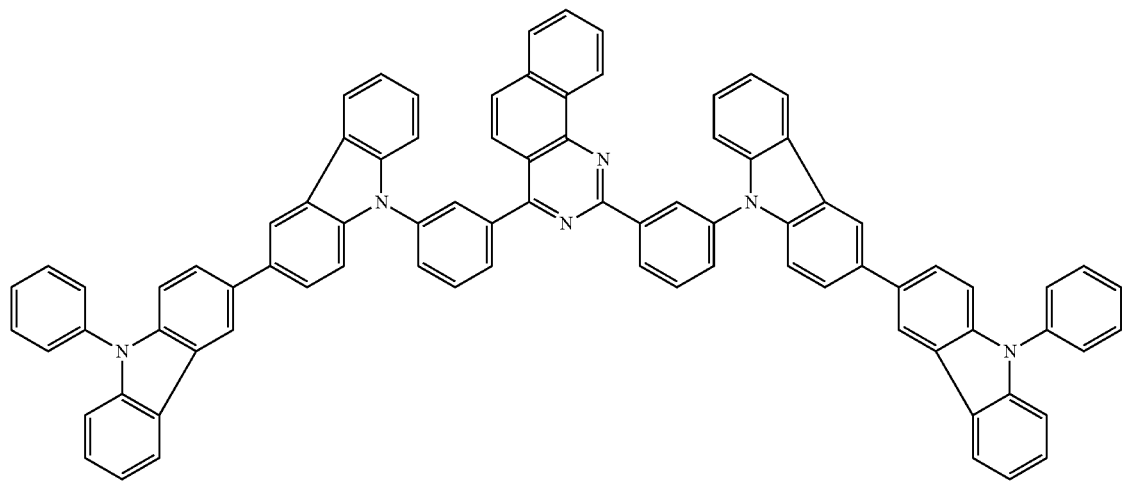

Compound 6

The chalcone intermediate C2 synthesized in Example 4 (6.26 g, 20.0 mmol), 3-bromobenzamidine hydrochloride (4.71 g, 20.0 mmol) and sodium hydroxide (0.88 g, 22 mmol) were reacted for 8 hours in ethanol (100 mL) under reflux with heating. The formed powder was collected by filtration, washed with methanol, and dried under vacuum. In orthodichlorobenzene (100 mL), to this powder, 2,3-dichloro-5,6-dicyano-p-benzoquinone (5.0 g, 22 mmol) was added and the resultant was allowed to react at 120° C. for 5 hours. Then, after cooling to room temperature, purification was conducted with silica gel column chromatography, whereby benzoquinazoline intermediate B4 (5.59 g, yield 57%) was obtained.

In an argon atmosphere, biscarbazolyl intermediate A2 (1.80 g, 4.40 mmol), benzoquinazoline intermediate B4 (1.03 g, 2.10 mmol), tris (dibenzylideneacetone)dipalladium (39 mg, 0.04 mmol), 4,5'-bis(diphenylphosphino)-9,9'-dimethylxanthene (49 mg, 0.08 mmol), t-butoxy sodium (0.61 g, 6.3 mmol), and xylene anhydride (42 mL) were added in sequence. The resultant was heated under reflux for 12 hours. After cooling the reaction liquid to room temperature, insoluble matters were removed by filtration, and the organic solvent was distilled off under reduced pressure. The resulting residues were purified with silica gel column chromatography, whereby compound 6 was obtained (2.12 g, yield 88%).

HPLC: purity 99.07%

FD-MS: calcd for $C_{84}H_{52}N_6$=1144.

found m/z=1144 (M+, 100).

Example 7
Synthesis of Compound 7
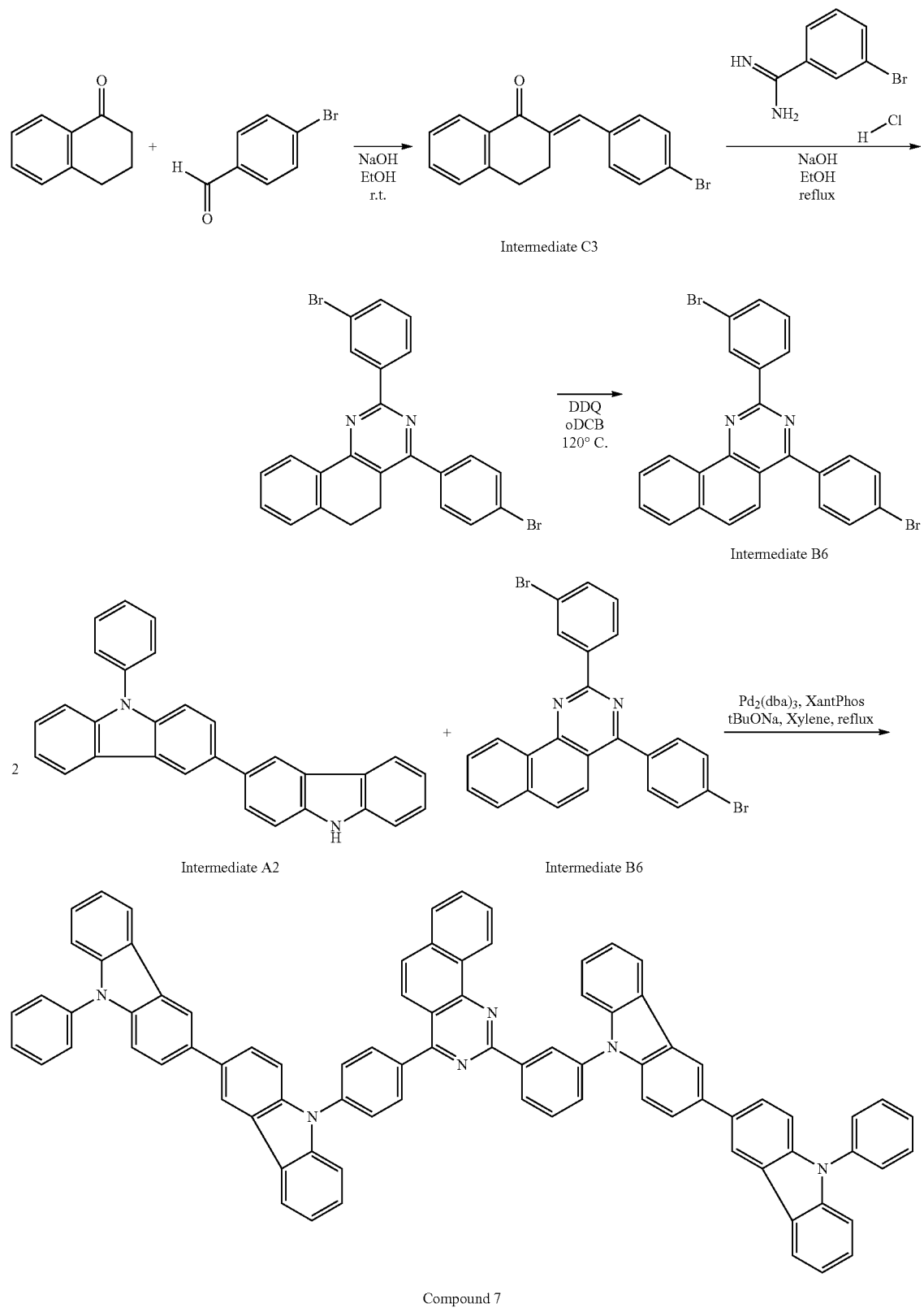
Compound 7

The same procedures as those in Example 4 were followed, except that 4-bromobenzaldehyde was used instead of 3-bromobenzaldehyde, whereby benzoquinazoline intermediate B6 was obtained.

The same procedures as those in Example 6 were followed by using the biscarbazolyl intermediate A2 (1.80 g, 4.40 mmol) and the benzoquinazoline intermediate B6 (1.03 g, 2.10 mmol), whereby compound 7 (2.02 g, yield 84%) was obtained.

HPLC: purity 99.97%

FD-MS: calcd for $C_{84}H_{52}N_6$=1144.

found m/z=1144 (M+, 100).

Example 8

Synthesis of Compound 8

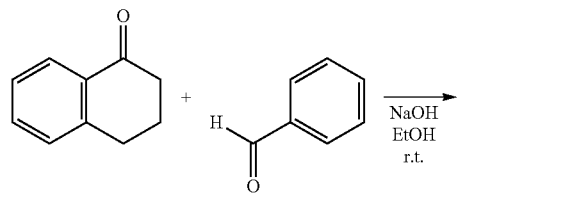

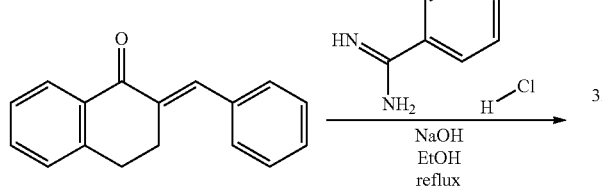

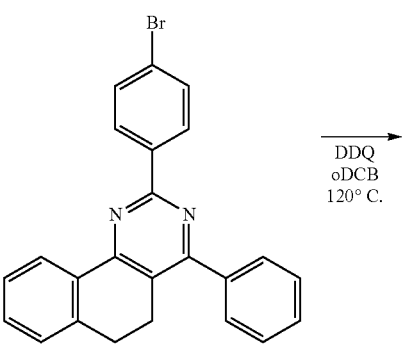

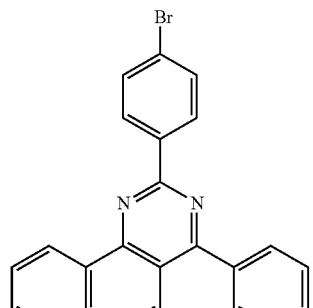

Intermediate B7

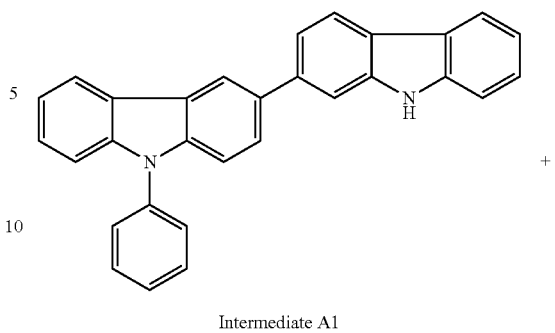

Intermediate A1

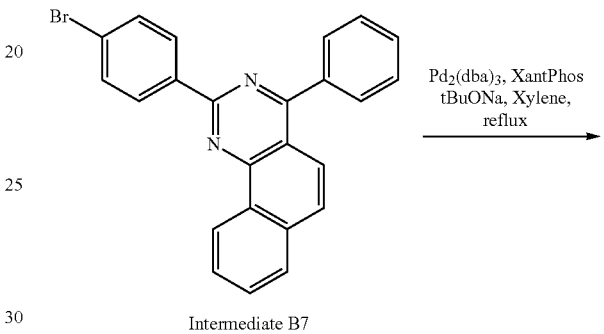

Intermediate B7

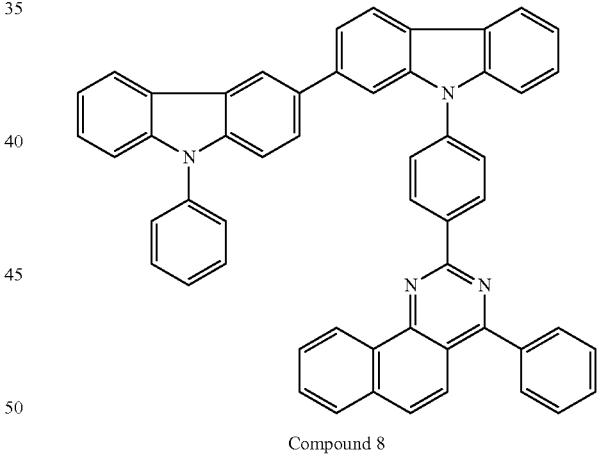

Compound 8

The same procedures as those in Example 1 were followed, except that 4-bromobenzaldehyde was used instead of 3-bromobenzamidine hydrochloride, whereby benzoquinazoline intermediate B7 was obtained.

The same procedures as those in Example 1 were followed by using the biscarbazolyl intermediate A1 (1.29 g, 3.15 mmol) and benzoquinazoline intermediate B7 (1.23 g, 3.00 mmol), whereby compound 8 was obtained (1.68 g, yield 76%).

HPLC: purity 99.52%

FD-MS: calcd for $C_{54}H_{34}N_4$=738.

found m/z=738 (M+, 100).

Example 9

Synthesis of Compound 9

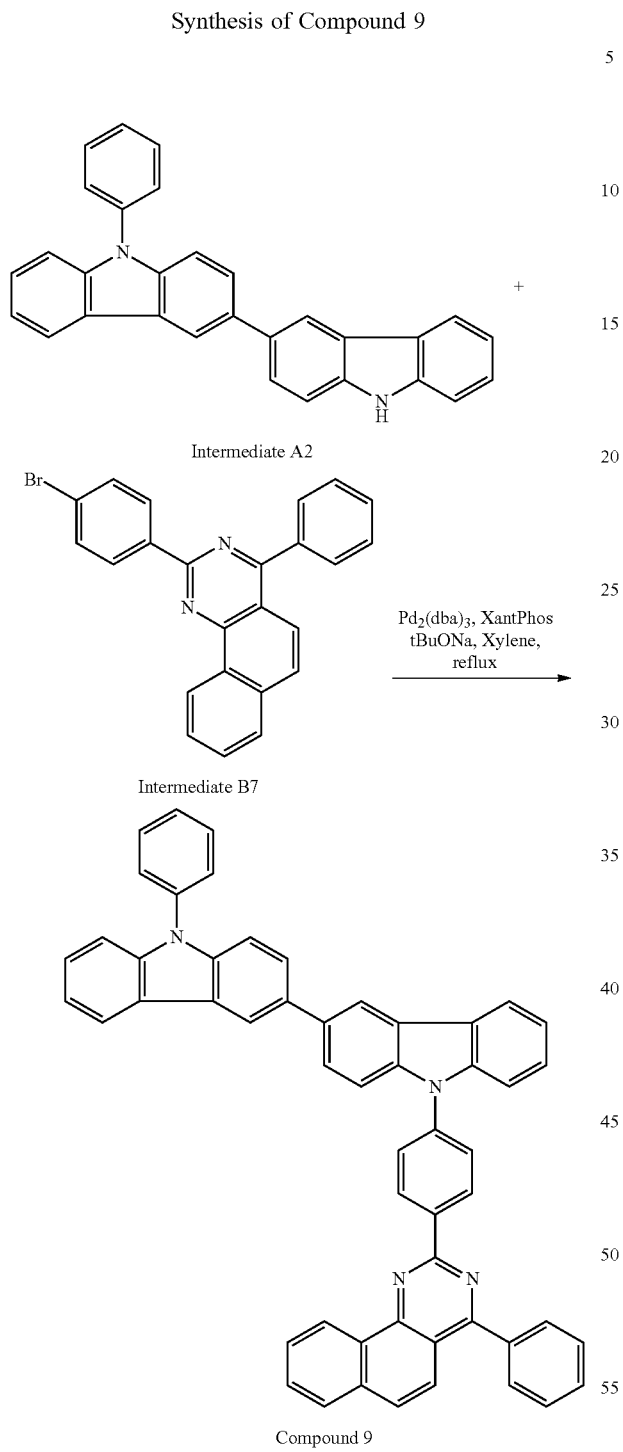

Intermediate A2

Intermediate B7

Compound 9

The same procedures as those in Example 8 were followed, except that the biscarbazolyl intermediate A2 was used instead of the biscarbazolyl intermediate A1, whereby compound 9 was obtained (1.95 g, yield 88%).

HPLC: purity 99.71%

FD-MS: calcd for $C_{54}H_{34}N_4$=738.

found m/z=738 (M+, 100).

Example 10

Synthesis of Compound 10

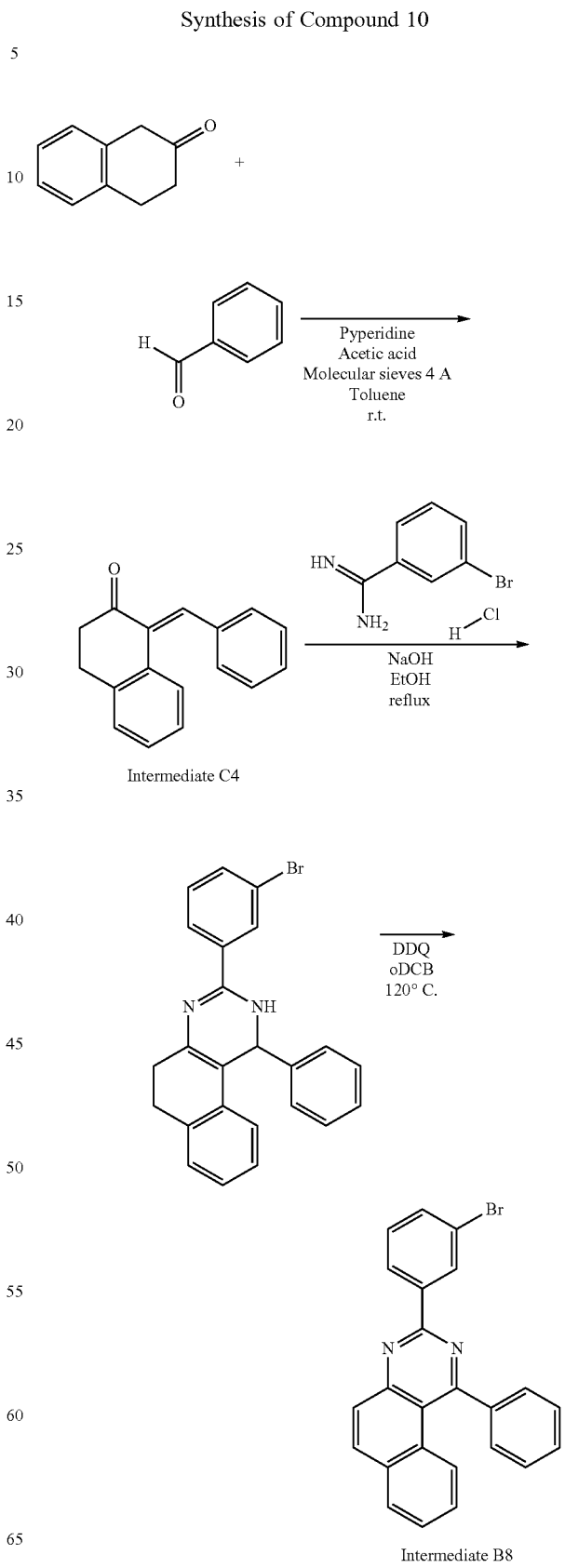

Intermediate C4

Intermediate B8

-continued

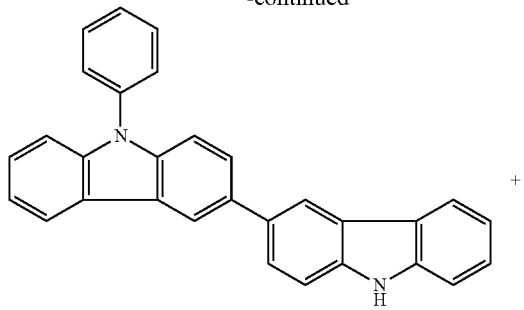

Intermediate A2

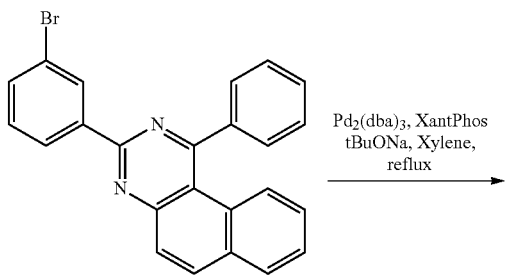

Intermediate B8

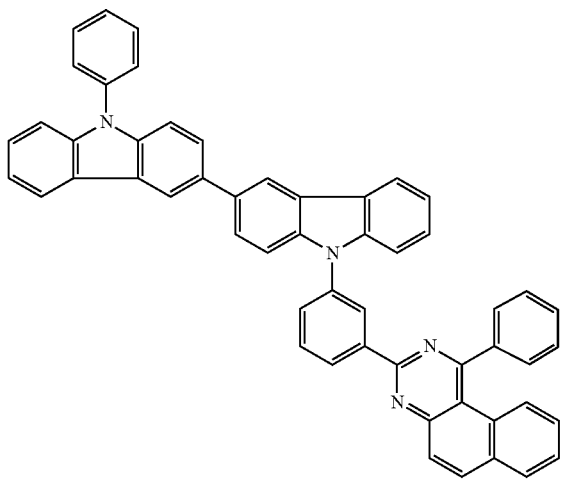

Compound 10

β-tetralone (7.31 g, 50 mmol) and benzaldehyde (5.31 g, 50 mmol) were dissolved in toluene (150 mL), piperidine (250 mg), acetic acid (250 mg) and molecular sieves 4 A (12.5 g) were added, and the resultant was stirred at room temperature for 12 hours. The reaction liquid was filtrated through celite, diluted with ethyl acetate, and then washed with an aqueous solution of saturated sodium sulfate. An organic phase was separated, dried with magnesium sulfide, and purified by silica gel chromatography after distilling off the solvent, whereby intermediate C4 was obtained (8.19 g, yield 70%). This intermediate C4 (4.69 g, 20 mmol), 3-bromobenzamidine hydrochloride (4.71 g, 20 mmol) and sodium hydroxide (0.88 g, 22 mmol) were reacted under reflux with heating for 8 hours in ethanol (200 mL). The formed powder was collected by filtration, washed with methanol and dried under vacuum. In orthodichlorobenzene (80 mL), to this powder, 2,3-dichloro-5,6-dicyano-p-benzoquinone (DDQ) (9.08 g, 40 mmol) was added and the resultant was allowed to react at 120° C. for 5 hours. Then, after cooling to room temperature, purification was conducted with silica gel column chromatography, whereby benzoquinazoline intermediate B8 (5.14 g, yield 63%) was obtained.

The same procedures as those in Example 1 were followed by using the biscarbazolyl intermediate A2 (1.29 g, 3.15 mmol) and the benzoquinazoline intermediate B8 (11.23 g, 3.00 mmol), whereby compound 10 (1.78 g, yield 80%) was obtained.

HPLC: purity 99.76%

FD-MS: calcd for $C_{54}H_{34}N_4$=738.

found m/z=738 (M+, 100).

Example 11

Synthesis of Compound 11

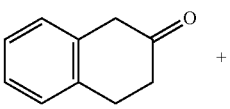

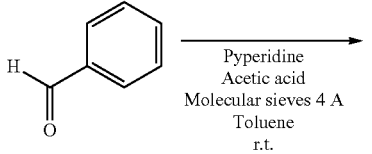

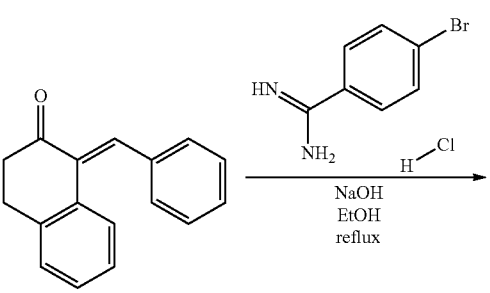

Intermediate C4

-continued

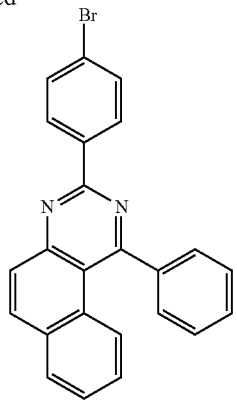

Intermediate B9

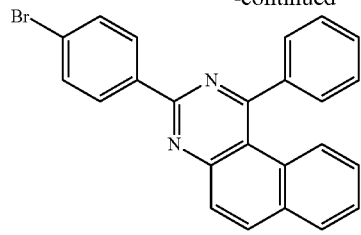

Intermediate B9

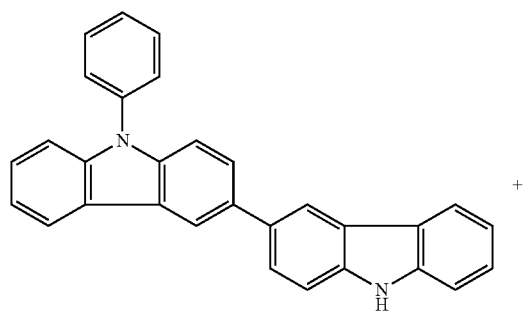

Intermediate A2

+

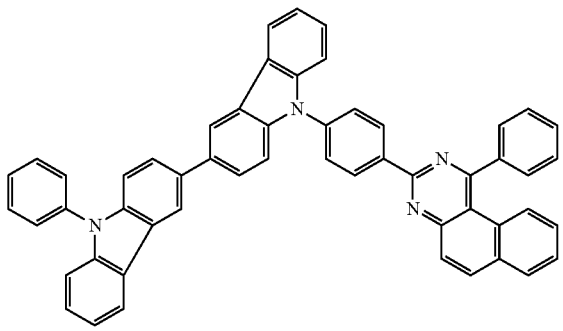

Compound 11

The same procedures as in Example 10 were followed, except that 4-bromobenzamidine hydrochloride was used instead of the 3-bromobenzamidine hydrochloride, whereby benzoquinazoline intermediate B9 was obtained (4.32 g, yield 52%).

The same procedures as those in Example 1 were followed by using biscarbazolyl intermediate A2 (1.29 g, 3.15 mmol) and benzoquinazoline intermediate B9 (1.23 g, 3.00 mmol), whereby compound 11 (1.82 g, yield 82%) was obtained.

HPLC: purity 99.65%

FD-MS: calcd for $C_{54}H_{34}N_4$=738.

found m/z=738 (M+, 100).

Example 12

Synthesis of Compound 12

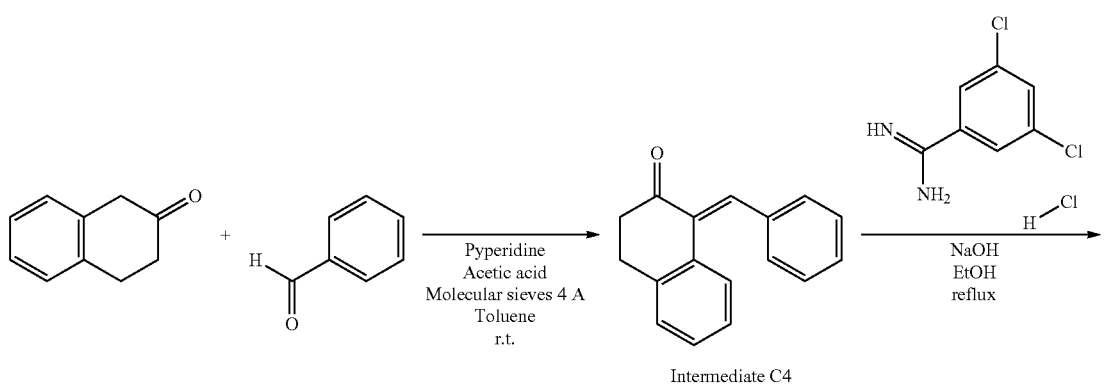

Intermediate C4

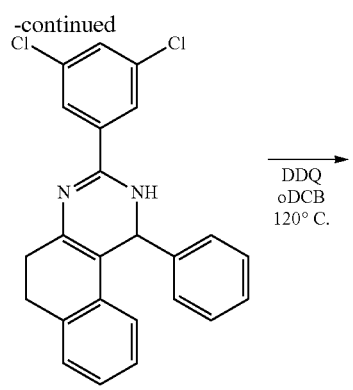
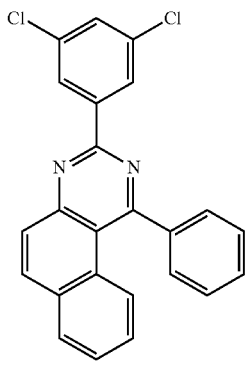

Intermediate B10

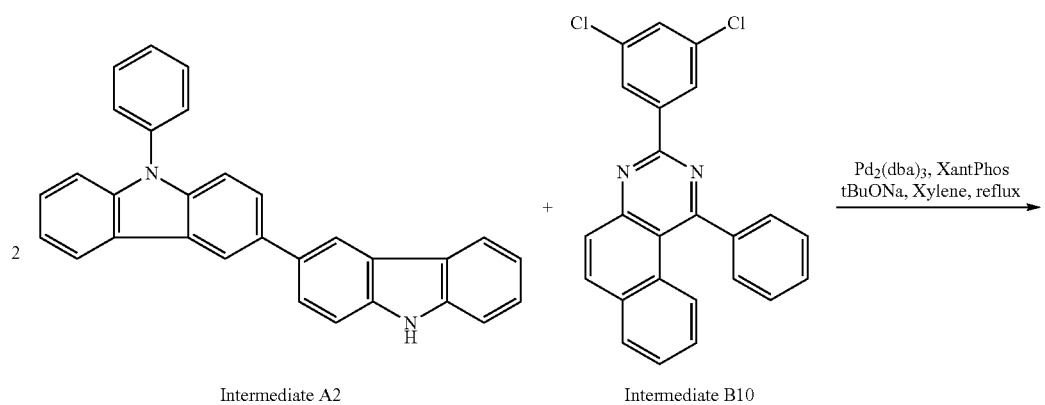

Intermediate A2     Intermediate B10

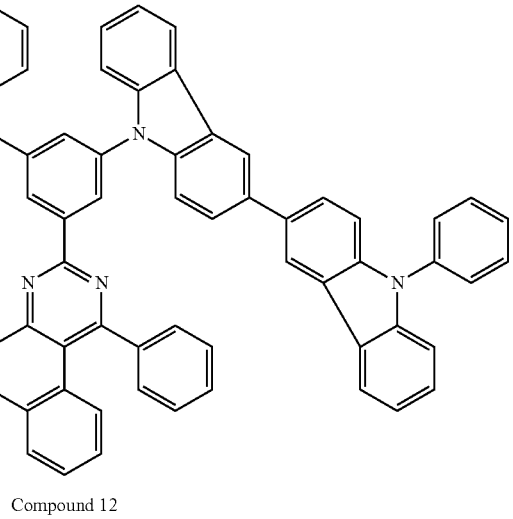

Compound 12

The same procedures as in Example 10 were followed, except that 3,5-dichlorobromobenzamidine hydrochloride (4.52 g, 20 mmol) was used instead of 3-bromobenzamidine hydrochloride, whereby benzoquinazoline intermediate B10 (4.10 g, yield 51%) was obtained.

The same procedures as in Example 3 were followed by using biscarbazolyl intermediate A2 (1.80 g, 4.40 mmol) and the benzoquinazoline intermediate B10 (0.84 g, 2.10 mmol), whereby compound 12 was obtained (2.00 g, yield 83%).

HPLC: purity 99.23%

FD-MS: calcd for $C_{84}H_{52}N_6$=1144.

found m/z=1144 (M+, 100).

Example 13
Synthesis of Compound 13
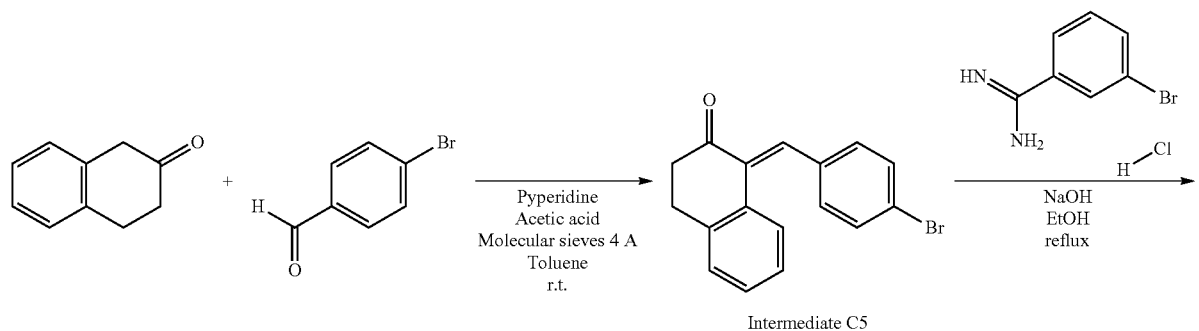
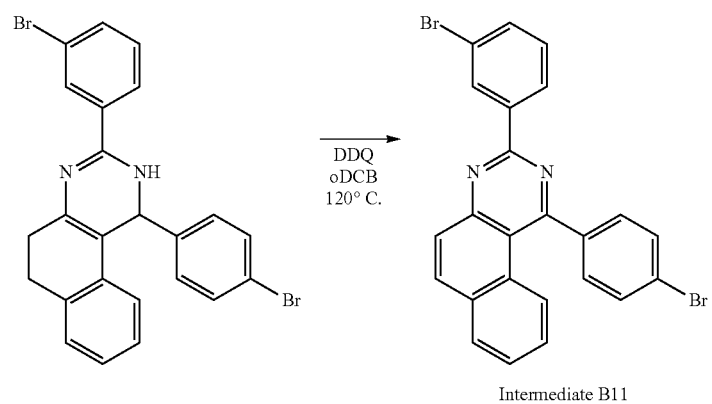
Intermediate B11
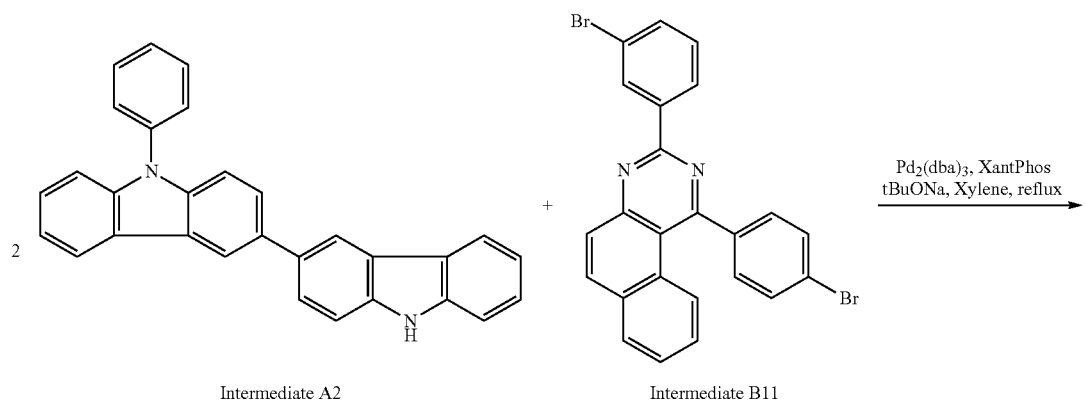
Intermediate A2      Intermediate B11

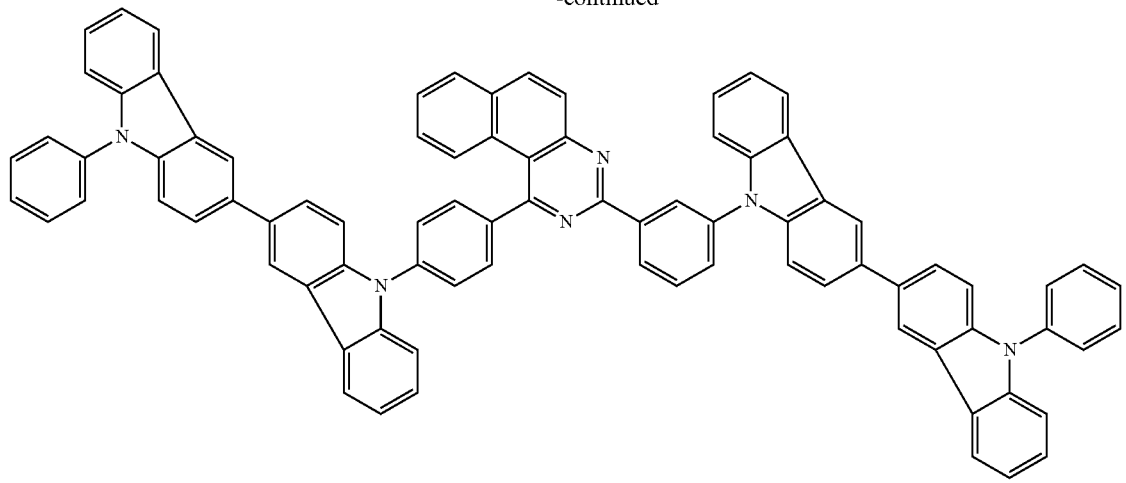

Compound 13

The same procedures as those in Example 10 were followed, except that 4-bromobenzaldehyde (9.25 g, 50 mmol) was used instead of benzaldehyde, whereby intermediate C5 (9.65 g, yield 31%) was obtained. The same procedures as those in Example 10 were followed by using this intermediate C5 (6.26 g, 20 mmol) and 3-bromobenzamidine hydrochloride (4.71 g, 20 mmol), whereby benzoquinazoline intermediate B11 (6.76 g, yield 69%) was obtained.

The same procedures as those in Example 3 were followed by using biscarbazolyl intermediate A2 (1.80 g, 4.40 mmol) and benzoquinazoline intermediate B11 (1.03 g, 2.10 mmol), whereby compound 13 (2.05 g, yield 85%) was obtained.

HPLC: purity 99.68%

FD-MS: calcd for $C_{84}H_{52}N_6$=1144.

found m/z=1144 (M+, 100).

Example 14

Synthesis of Compound 14

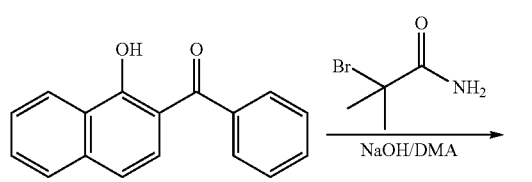

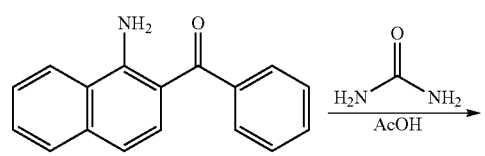

Intermediate C6

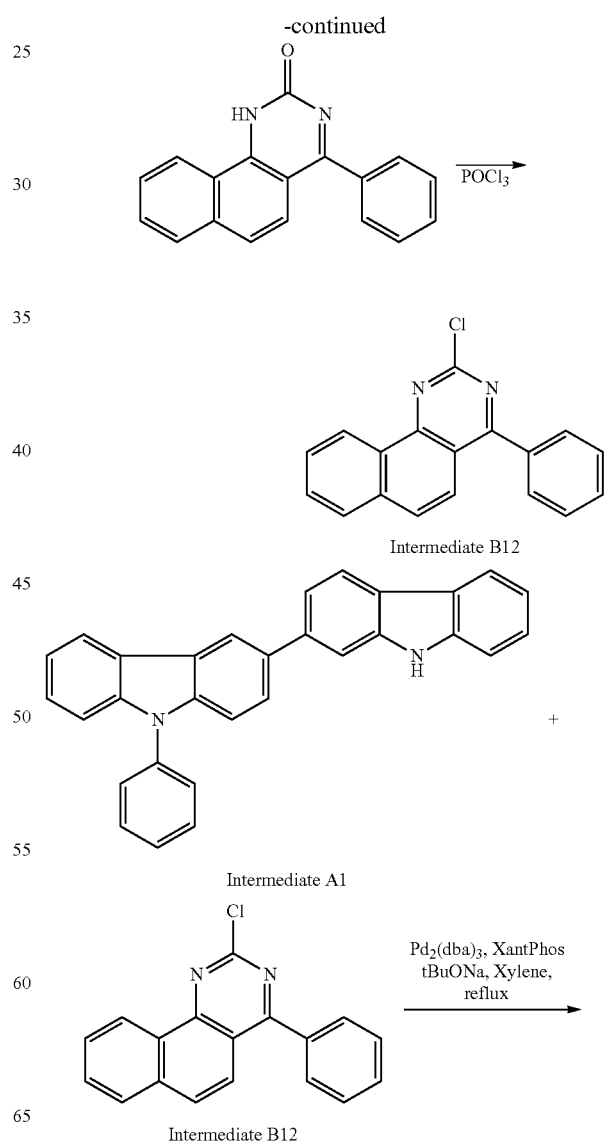

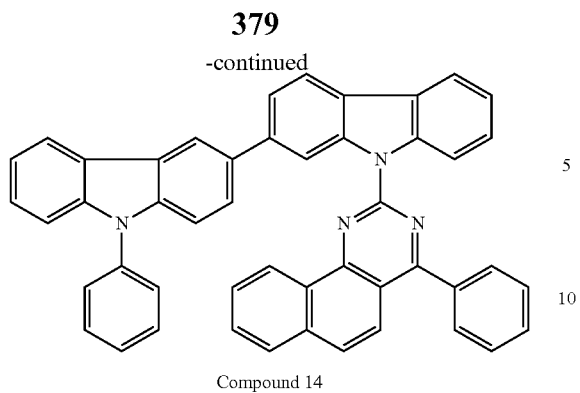

Compound 14

2-benzoyl-1-naphthol (12.44 g, 50 mmol) and sodium hydroxide (6.0 g, 150 mmol) were dissolved in 75 mL of N,N-dimethylacetamide (DMA), followed by stirring at room temperature for 1 hour. Then, 2-bromoisobutylamide (24.9 g, 150 mmol) was added, and further stirred at room temperature for 5 hours. Sodium hydroxide (18.0 g, 450 mmol) was added to the reaction liquid, and the liquid was heated to 50° C. to proceed the reaction for 1 hour. Thereafter, water (75 mL) was added, and the resultant was further heated and subjected to reflux with heating for 1 hour. The reaction liquid was cooled to room temperature, extracted with ethyl acetate and dried with magnesium sulfate. After distilling off the solvent, purification was conducted by silica gel chromatography, whereby intermediate C6 (11.62 g, yield 94%) was obtained. This intermediate C6 (9.89 g, 40 mmol) and urea (4.80 g, 40 mmol) were reacted in acetic acid (20 mL) for 5 hours under reflux with heating. After cooling to 100° C. or less, water (80 mL) was added, and formed powder was collected by filtration, washed with water, and dried under vacuum. This powder was added to phosphorus oxychloride (20 mL), and the resultant was reacted under reflux with heating for 5 hours. After cooling to room temperature, the resultant was added to 200 mL of ice water, and formed powder was washed with water. Purification was conducted with silica gel column chromatography, whereby benzoquinazoline intermediate B12 (7.21 g, yield 62%) was obtained.

The same procedures as those in Example 1 were followed by using biscarbazolyl intermediate A1 (1.29 g, 3.15 mmol) and benzoquinazoline intermediate B12 (0.87 g, 3.00 mmol), whereby compound 14 was obtained (1.78 g, yield 90%).

HPLC: purity 99.58%
FD-MS: calcd for $C_{48}H_{30}N_4$=662.
found m/z=662 (M+, 100).

Example 15

Synthesis of Compound 15

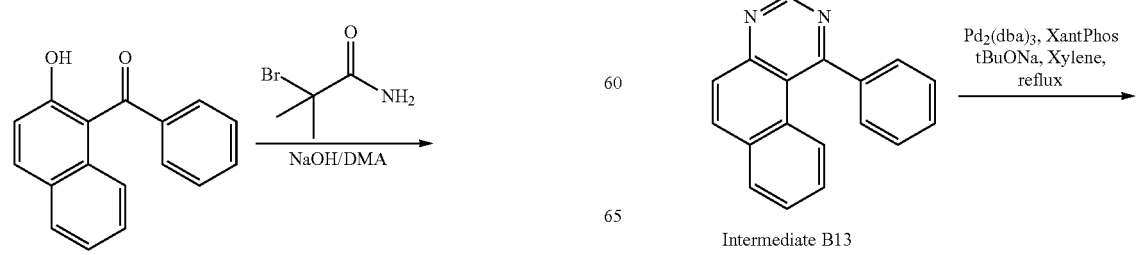

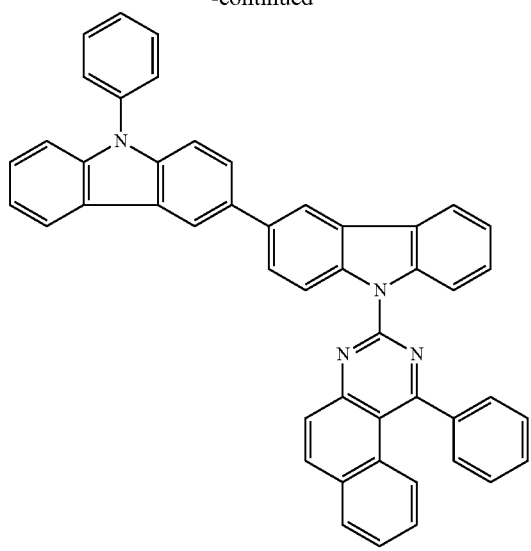

Compound 15

The same procedures as those in Example 14 were followed, except that 1-benzoyl-2-naphthol was used instead of 2-benzoyl-1-naphthol, whereby intermediate C7 (10.75 g, yield 87%) was obtained. By using this intermediate C7 (9.89 g, 40 mmol), the same procedures as those in Example 14 were followed, whereby benzoquinazoline intermediate B13 (6.86 g, yield 59%) was obtained.

The same procedures as those in Example 1 were followed by using biscarbazolyl intermediate A2 (1.29 g, 3.15 mmol) and benzoquinazoline intermediate B13 (0.87 g, 3.00 mmol), whereby compound 15 (1.82 g, yield 92%) was obtained.

HPLC: purity 99.49%

FD-MS: calcd for $C_{48}H_{30}N_4$=662.

found m/z=662 (M+, 100).

Example 16

Synthesis of Compound 16

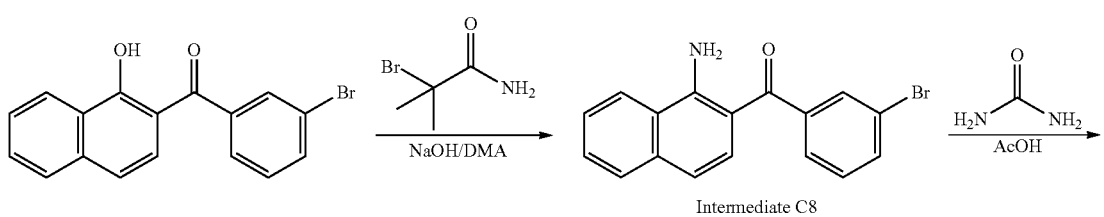

Intermediate C8

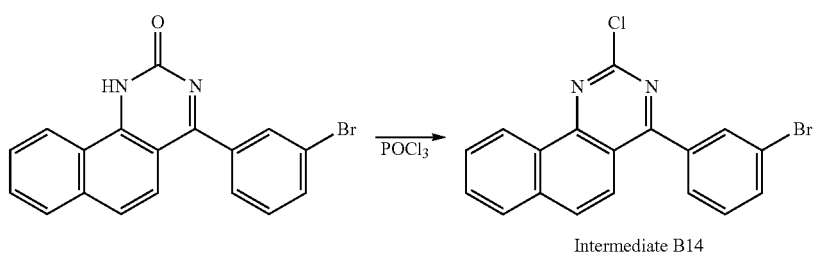

Intermediate B14

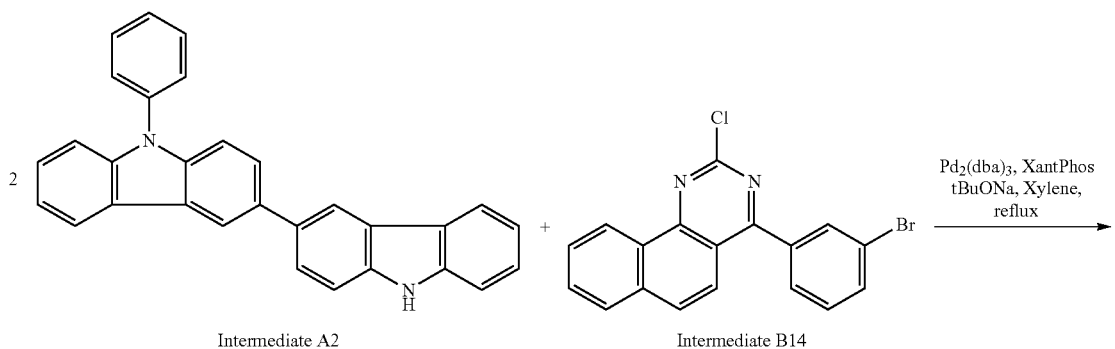

Intermediate A2     Intermediate B14

-continued

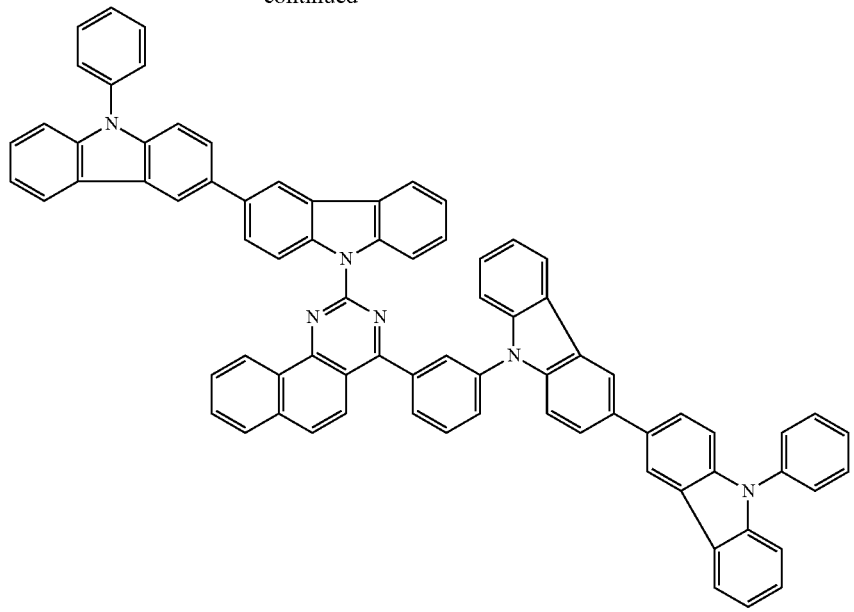

Compound 16

The same procedures as those in Example 14 were followed, except that 2-(3-bromobenzoyl)-1-naphthol (16.36 g. 50 mmol) was used instead of 2-benzoyl-1-naphthol, whereby intermediate C8 (13.86 g, yield 85%) was obtained. The same procedures as those in Example 14 were followed by using this intermediate C8 (13.05 g, 40 mmol), whereby benzoquinazoline intermediate B14 was obtained (9.31 g, yield 63%).

The same procedures as those in Example 3 were followed by using biscarbazolyl intermediate A2 (1.80 g, 4.40 mmol) and benzoquinazoline intermediate B14 (0.78 g, 2.10 mmol), whereby compound 16 (1.91 g, yield 85%) was obtained.

HPLC: purity 99.78%
FD-MS: calcd for $C_{78}H_{48}N_6$=1069.
found m/z=1069 (M+, 100).

Fabrication of Organic EL Device

Example 17

A glass substrate of 25 mm by 75 mm by 1.1 mm thick with an ITO transparent electrode (manufactured by GEO-MATEC Co., Ltd.) was subjected to ultrasonic cleaning with isopropyl alcohol for 5 minutes, and then subjected to UV-ozone cleaning for 30 minutes.

The cleaned glass substrate with the ITO transparent electrode lines (130 nm) was mounted in a substrate holder of a vacuum vapor deposition apparatus. On the surface where the transparent electrode lines were formed, the following compound HT-1 was deposited as a first hole-transporting material so as to cover the transparent electrode, whereby a 45 nm-thick first hole-transporting layer was formed. Subsequent to the formation of the first hole-transporting layer, the following compound HT-2 was deposited as a second hole-transporting material, whereby a 10 nm-thick second hole-transporting layer was formed.

Further, on this second hole-transporting layer, as a host material, compound 4 obtained in Example 4 and the following compound RD-1 as a phosphorescent emitting material were co-deposited, whereby a 40 nm-thick phosphorescent emitting layer was formed. The concentration of the compound RD-1 in the emitting layer was 5.0 mass %. This co-deposited film functions as an emitting layer. The all operations for forming the emitting layer were conducted in a glove box in a nitrogen atmosphere.

Subsequent to the formation of this emitting layer, the following compound ET-1 was formed into a 40 nm-thick film. This compound ET-1 film functions as a first electron-transporting layer.

Subsequently, LiF was formed into a 1 nm-thick film at a speed of 0.1 Å/min as an electron-injecting electrode (cathode). Metal Al was deposited on this LiF film, whereby an 80 nm-thick metal cathode was formed. After completion of all deposition processes, sealing was conducted in a glove box in a nitrogen atmosphere by using couterbored glass, whereby an organic EL device was fabricated.

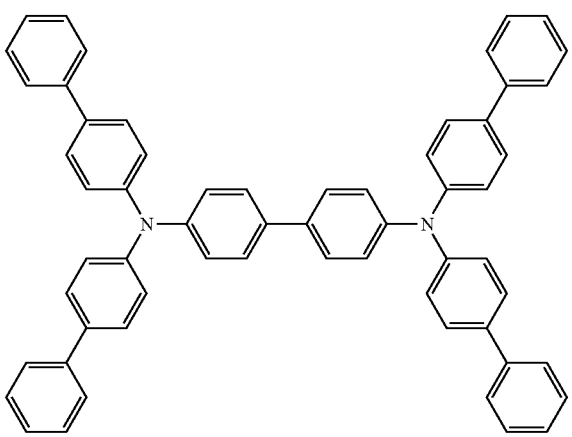

HT-1

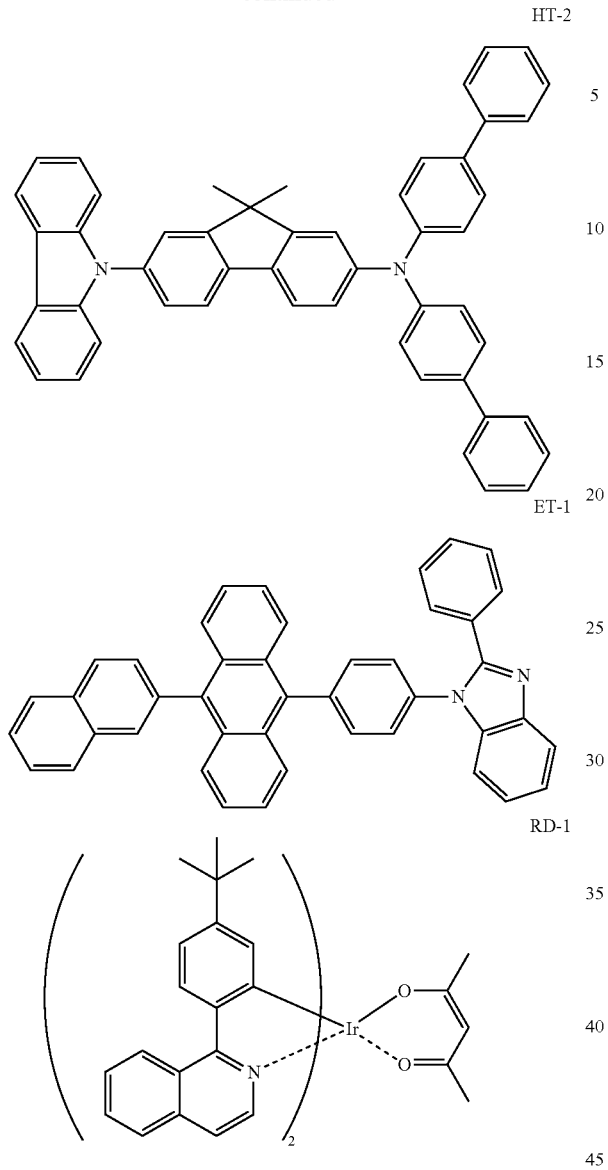

The results of measuring the external quantum efficiency of the organic EL devices fabricated in each of the above examples are shown in Table 1.

Example 18

An organic EL device was fabricated in the same manner as in Example 17, except that compound 5 obtained in Example 5 was used as the host material of the emitting layer instead of the compound 4 in Example 17.

Examples 19 to 27

An organic EL device was fabricated in the same manner as in Example 17, except that compounds shown in Table 1 were used as the host material of the emitting layer instead of the compound 4 in Example 17.

Comparative Example 1

An organic EL device was fabricated in the same manner as in Example 17, except that the following comparative compound 1 was used as the host material of the emitting layer instead of the compound 4 in Example 17.

TABLE 1

|  | Host material of emitting layer | Luminous efficiency (EQE) (%) |
| --- | --- | --- |
| Ex. 17 | Compound 4 | 15.9 |
| Ex. 18 | Compound 5 | 16.1 |
| Ex. 19 | Compound 1 | 15.5 |
| Ex. 20 | Compound 2 | 16.4 |
| Ex. 21 | Compound 6 | 16.0 |
| Ex. 22 | Compound 8 | 16.2 |
| Ex. 23 | Compound 9 | 15.9 |
| Ex. 24 | Compound 10 | 16.0 |
| Ex. 25 | Compound 11 | 15.6 |
| Ex. 26 | Compound 14 | 16.1 |
| Ex. 27 | Compound 15 | 16.3 |
| Comp. Ex. 1 | Comp. Compound 1 | 14.0 |

Example 28

A glass substrate of 25 mm by 25 mm by 1.1 mm thick with an ITO transparent electrode (manufactured by GEO-MATEC Co., Ltd.) was subjected to ultrasonic cleaning with isopropyl alcohol for 5 minutes, and then subjected to UV-ozone cleaning for 5 minutes.

By using CLEVIOUS A14083 (manufactured by Heraeus Holding) as a hole-transporting material, a 30 nm-thick hole-transporting layer was formed on the ITO substrate by a spin coating method. After the film formation, an unnecessary part was removed with acetone, and the film was sintered in air on a hot plate of 200° C. for 10 minutes, whereby a base substrate was prepared.

By using compound 3 obtained in Example 3 as the host material and the compound RD-1 as the dopant material, a 1.6 mass % toluene solution was prepared in a mixing ratio such that the amount ratio of compound 3 and the compound RD-1 became 95:5 in terms of weight ratio. This toluene solution was applied to the base substrate by a spin coating method such that a 50 nm-thick film was stacked. After application, an unnecessary part was removed with toluene, and the film was dried by heating on a hot plate of 150° C., whereby a stacked-structure substrate on which an emitting layer was formed was prepared. All operations for forming the emitting layer were conducted in a glove box in a nitrogen atmosphere.

The stacked substrate was conveyed to a deposition chamber, and, as an electron-transporting material, the compound ET-1 was deposited in a thickness of 50 nm, whereby an electron-transporting layer was formed.

Further, lithium fluoride and aluminum were stacked by deposition in thicknesses of 1 nm and 80 nm, respectively. After completion of all deposition processes, sealing was conducted in a glove box in a nitrogen atmosphere by using counterbored glass, whereby an organic EL device was fabricated.

Examples 29 to 32

Organic EL devices were fabricated in the same manner as in Example 28, except that the emitting layer was formed by using the compounds shown in Table 2 instead of the compound 3 as the host material.

An organic EL device was fabricated in the same manner as in Example 28, except that the following comparative compound 2 was used instead of the compound 3 as the host material.

The results of measuring the external quantum efficiency of the organic EL devices fabricated in each of the above examples are shown in Table 2.

TABLE 2

|  | Host material of emitting layer | Luminous efficiency (EQE) (%) |
|---|---|---|
| Ex. 28 | Compound 3 | 5.1 |
| Ex. 29 | Compound 7 | 5.2 |
| Ex. 30 | Compound 12 | 4.9 |
| Ex. 31 | Compound 13 | 5.6 |
| Ex. 32 | Compound 16 | 5.8 |
| Comp. Ex. 2 | Comp. Compound 2 | 3.5 |

As compared with the comparative compound in which the quinazoline structure is substituted by biscarbazole, the compounds of Examples have improved carrier balance. As a result, an organic EL device obtained by using the compounds of Examples as a host material for the emitting layer had improved luminous efficiency.

Although only some exemplary embodiments and/or examples of this invention have been described in detail above, those skilled in the art will readily appreciate that many modifications are possible in the exemplary embodiments and/or examples without materially departing from the novel teachings and advantages of this invention. Accordingly, all such modifications are intended to be included within the scope of this invention.

The specification of a Japanese application on the basis of which the present application claims Paris Convention priority is incorporated herein by reference in its entirety.

The invention claimed is:

1. A compound represented by the following formula (1):

wherein in the formula, $L_1$ is a single bond or a linking group, A is a group represented by the following formula (A), B is a group represented by the following formula (B), m is an integer of 1 to 3, and n is an integer of 1 to 4;

when m is 2 or more, plural Bs may be the same as or different from each other;

when n is 2 or more, plural $L_1$s may be the same as or different from each other, and plural Bs may be the same as or different from each other; and when $L_1$ is a single bond, it means that A and B are directly bonded, and m is 1;

Comp. compound 2

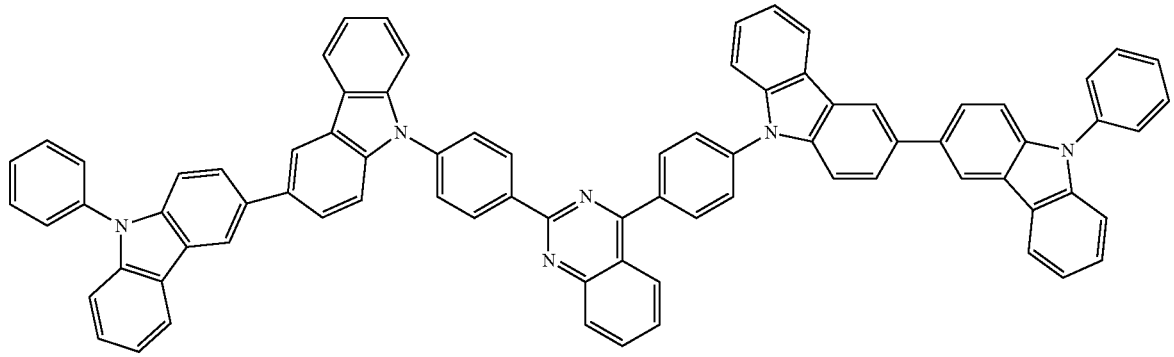

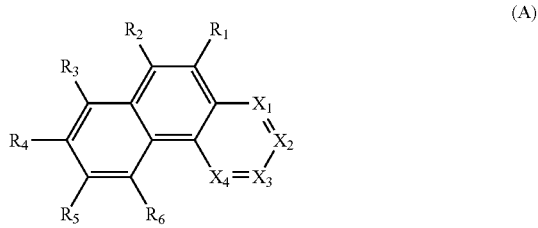

wherein in the formula (A), $X_1$ to $X_4$ are independently a nitrogen atom (N) or CRa, and two of $X_1$ to $X_4$ are a nitrogen atom;

"n" of Ra and $R_1$ to $R_6$ are a single bond that allows a carbon atom in the formula (A) for which they are substituted to be directly bonded to $L_1$ (or B when $L_1$ is a single bond); and among Ra and $R_1$ to $R_6$, Ra and $R_1$ to $R_6$ that are not a single bond are independently a hydrogen atom or a substituent;

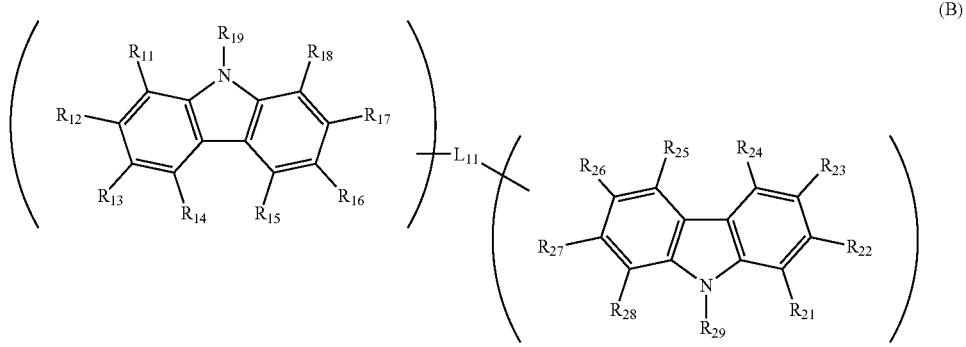

wherein in the formula (B), $L_{11}$ is a single bond or a linking group;

one of $R_{11}$ to $R_{19}$ is a single bond that allows a carbon atom in the formula (B) for which it is substituted to be directly bonded to $L_1$ (or A when $L_1$ is a single bond) and the other one of $R_{11}$ to $R_{19}$ is a single bond that allows a carbon atom in the formula (B) for which it is substituted to be directly bonded to $L_{11}$;

among $R_{11}$ to $R_{19}$, $R_{11}$ to $R_{19}$ that are not a single bond are independently a hydrogen atom or a substituent;

one of $R_{21}$ to $R_{29}$ is a single bond that allows a carbon atom in the formula (B) for which it is substituted to be directly bonded to $L_{11}$;

among $R_{21}$ to $R_{29}$, $R_{21}$ to $R_{29}$ that are not a single bond are independently a hydrogen atom or a substituent; and when $L_{11}$ is a single bond, one of $R_{11}$ to $R_{19}$ and one of $R_{21}$ to $R_{29}$ are independently a single bond that allows carbon atoms in the formula (B) for which they are substituted to be directly bonded with each other.

2. The compound according to claim 1 that is a compound represented by the following formula (2):

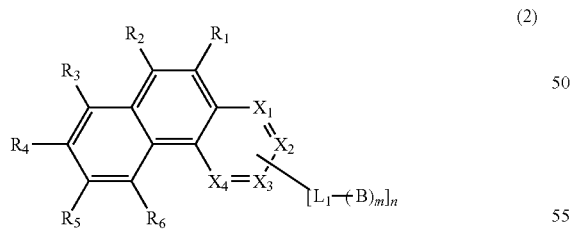

wherein $R_1$ to $R_6$, $X_1$ to $X_4$, $L_1$, B and m are as defined in the formula (1); n is 1 or 2, and "n" of the Ra is (are) a single bond that allows a carbon atom in the formula (2) for which it (they) is (are) substituted to be directly bonded to $L_1$ (or B when $L_1$ is a single bond).

3. The compound according to claim 1, wherein the A is a group represented by the following formula (A1):

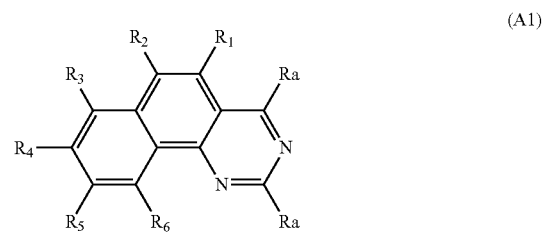

wherein in the formula, Ra and $R_1$ to $R_6$ are as defined in the formula (A).

4. The compound according to claim 3 that is represented by the following formula (A1-1) or (A1-2):

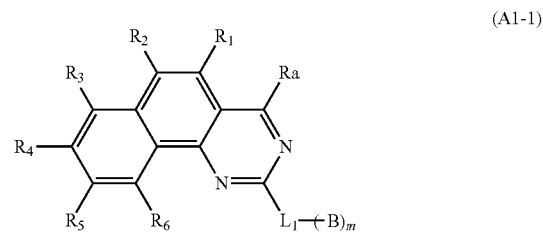

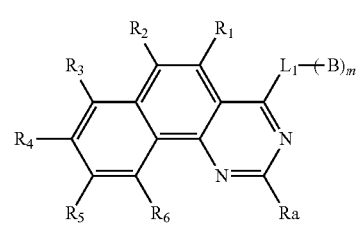

wherein in the formula, Ra, $R_1$ to $R_6$, $L_1$, B and m are as defined in the formulas (1) and (A1).

5. The compound according to claim 3 that is a compound represented by the following formula (A1-3):

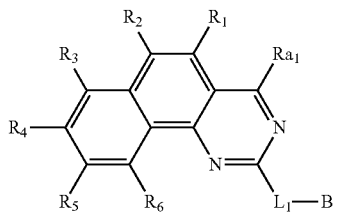
(A1-3)

wherein in the formula, $R_1$ to $R_6$, $L_1$ and B are as defined in the formulas (1) and (A1); and $Ra_1$ is a substituted or unsubstituted aryl group including 6 to 60 ring carbon atoms or a substituted or unsubstituted heteroaryl group including 5 to 60 ring atoms.

6. The compound according to claim 3 that is a compound represented by the following formula (A1-4):

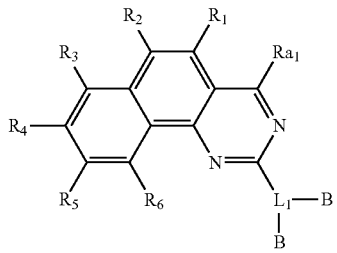
(A1-4)

wherein in the formula, $R_1$ to $R_6$, $L_1$ and B are as defined in the formulas (1) and (A1); two Bs may be the same as or different from each other; and $Ra_1$ is a substituted or unsubstituted aryl group including 6 to 60 ring carbon atoms or a substituted or unsubstituted heteroaryl group including 5 to 60 ring atoms.

7. The compound according to claim 3 that is a compound represented by the following formula (A1-5):

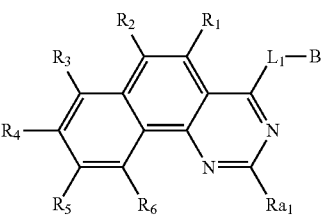
(A1-5)

wherein in the formula, $R_1$ to $R_6$, $L_1$ and B are as defined in the formulas (1) and (A1); and $Ra_1$ is a substituted or unsubstituted aryl group including 6 to 60 ring carbon atoms or a substituted or unsubstituted heteroaryl group including 5 to 60 ring atoms.

8. The compound according to claim 3 that is a compound represented by the following formula (A1-6):

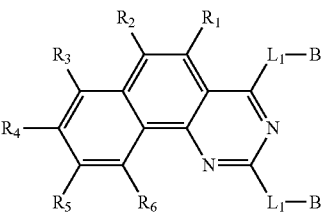
(A1-6)

wherein in the formula, $R_1$ to $R_6$, $L_1$ and B are as defined in the formulas (1) and (A1); and two Bs may be the same as or different from each other.

9. The compound according to claim 4 that is represented by the formula (A1-7) or (A1-8):

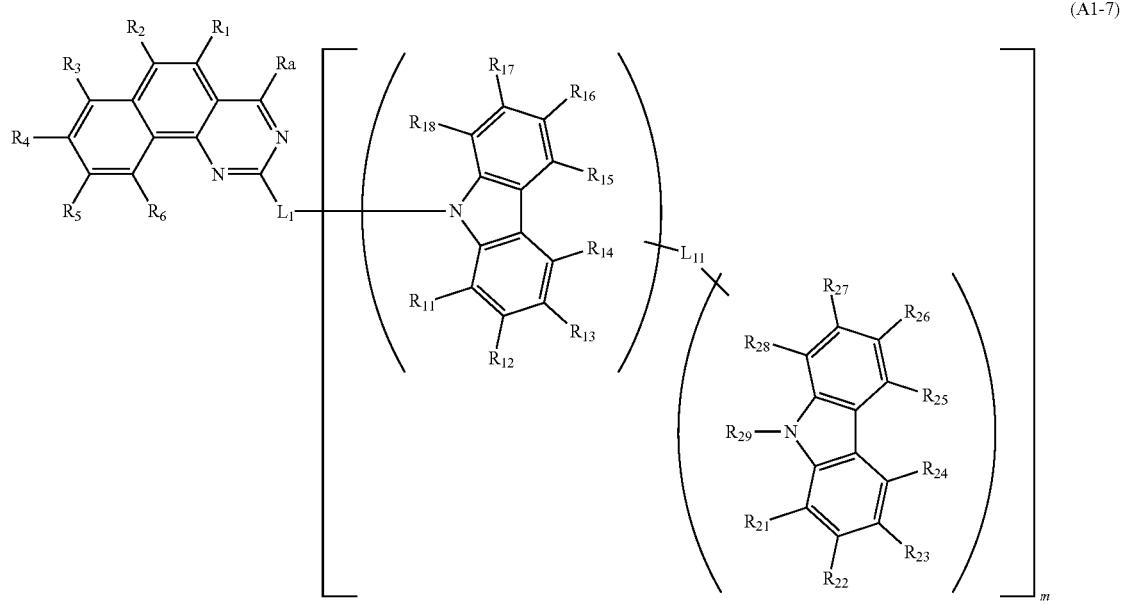
(A1-7)

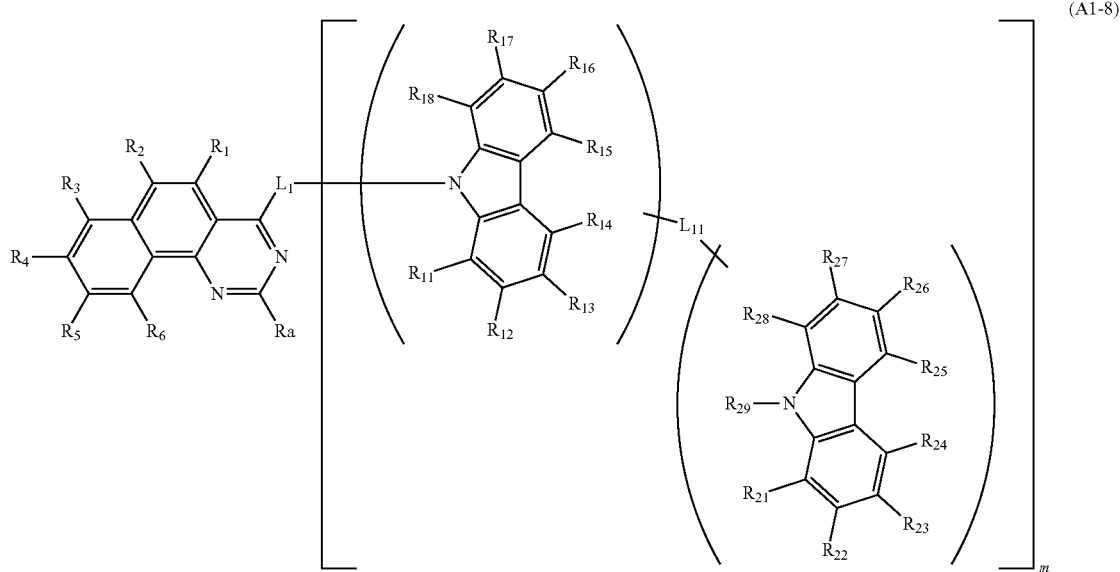
wherein in the formula, $L_1$, m, Ra, $R_1$ to $R_6$, $R_{11}$ to $R_{18}$, $R_{21}$ to $R_{29}$ and $L_{11}$ are as defined in the formula (1).
10. The compound according to claim 9 that is represented by the following formula (A1-9) or (A1-10):
wherein in the formula, $L_1$, m, Ra, $R_1$ to $R_6$, $R_{11}$ to $R_{18}$, $R_{21}$ to $R_{29}$ and $L_{11}$ are as defined in the formula (1).
11. The compound according to claim 9 that is represented by the following formula (A1-11) or (A1-12):
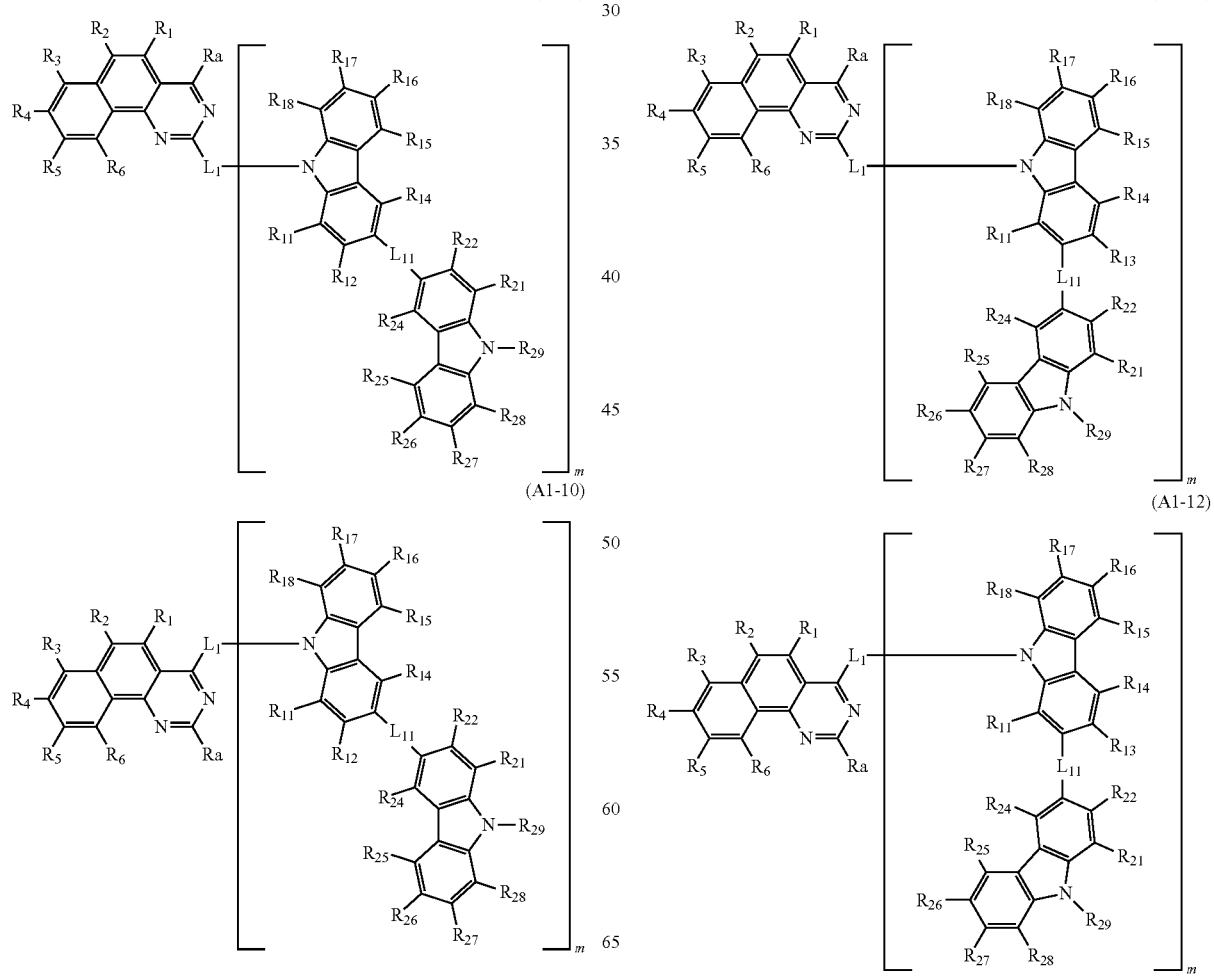

wherein in the formula $L_1$, m, Ra, $R_1$ to $R_6$, $R_{11}$ to $R_{18}$, $R_{21}$ to $R_{29}$, and $L_{11}$ are as defined in the formula (1).

12. The compound according to claim 1, wherein the A is a group represented by the following formula (A2):

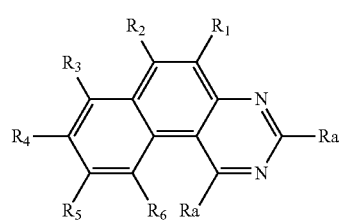

(A2)

wherein in the formula, Ra and $R_1$ to $R_6$ are as defined in the formula (A).

13. The compound according to claim 12 that is represented by the following formula (A2-1) or (A2-2):

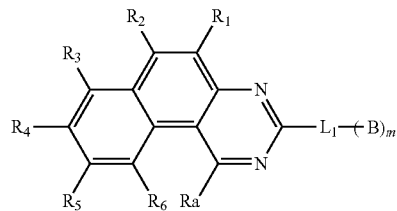

(A2-1)

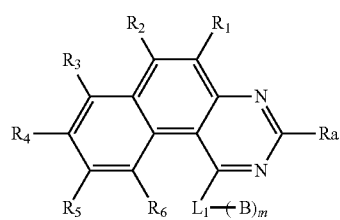

(A2-2)

wherein in the formula, Ra, $R_1$ to $R_6$, $L_1$, B and m are as defined in the formulas (1) and (A2).

14. The compound according to claim 13 that is represented by the following formula (A2-3) or (A2-4):

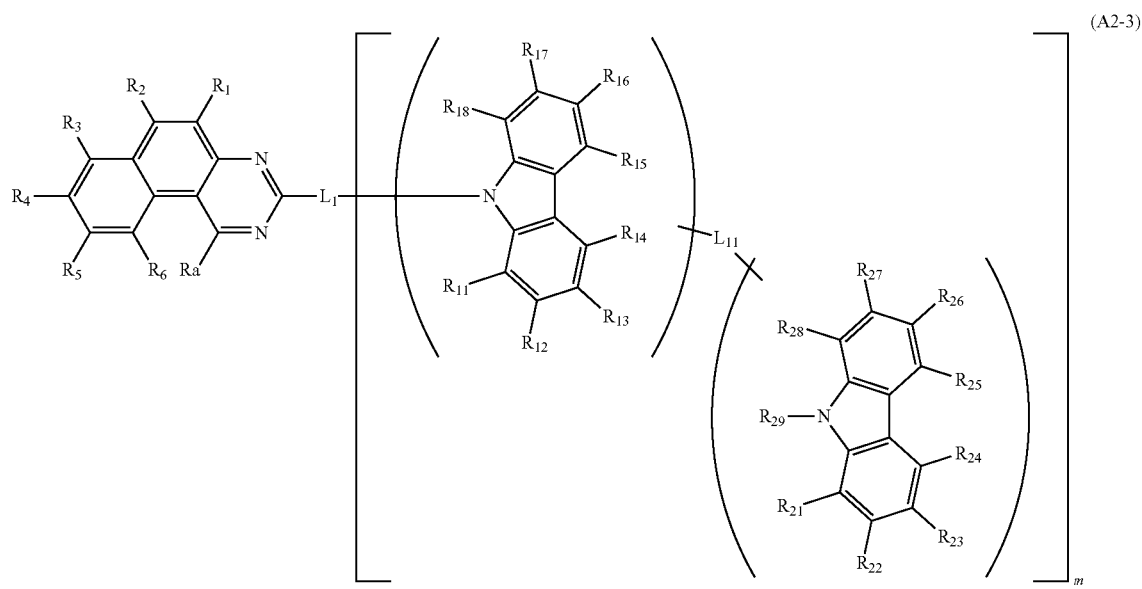

(A2-3)

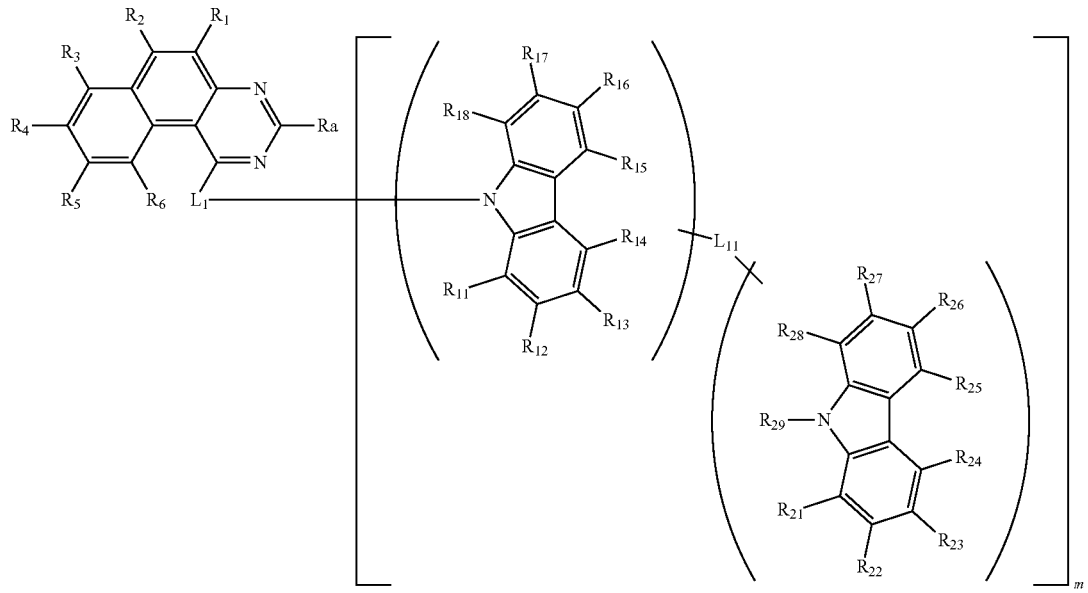

wherein in the formula, $L_1$, m, Ra, $R_1$ to $R_6$, $R_{11}$ to $R_{18}$, $R_{21}$ to $R_{29}$ and $L_{11}$ are as defined in the formula (1).

15. The compound according to claim 14 that is represented by the following formula (A2-5) or (A2-6):

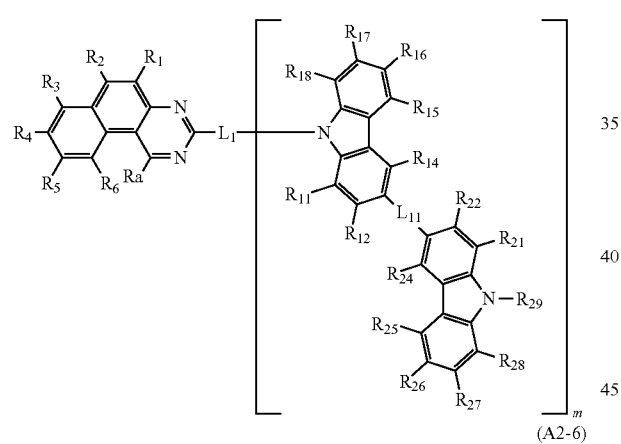

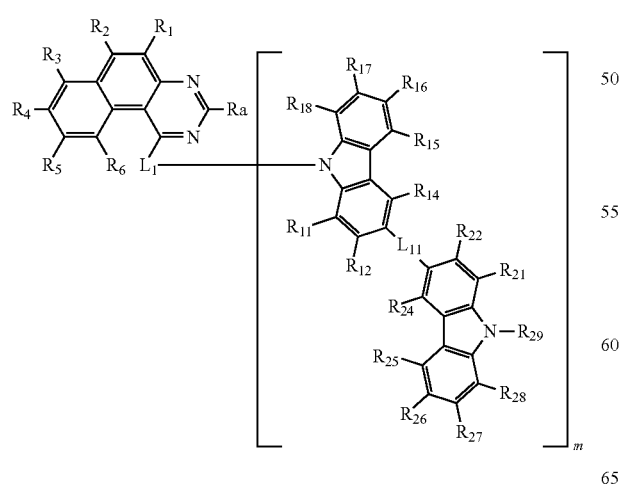

wherein in the formula, $L_1$, m, Ra, $R_1$ to $R_6$, $R_{11}$ to $R_{18}$, $R_{21}$ to $R_{29}$ and $L_{11}$ are as defined in the formula (1).

16. The compound according to claim 14 that is represented by the following formula (A2-7) or (A2-8):

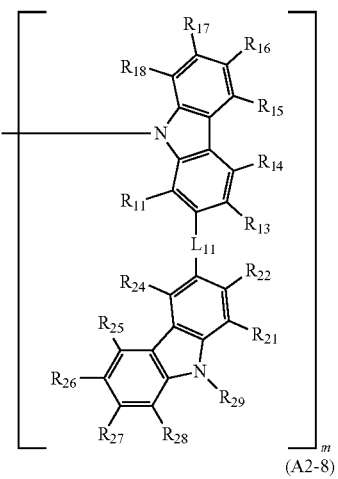

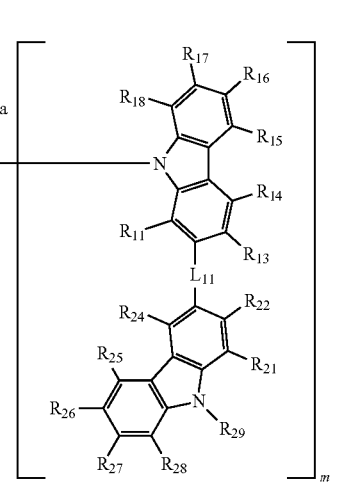

wherein in the formula, $L_1$, m, Ra, $R_1$ to $R_6$, $R_{11}$ to $R_{18}$, $R_{21}$ to $R_{29}$ and $L_{11}$ are as defined in the formula (1).

17. The compound according to claim 1, wherein the B is represented by the following formula (B'):

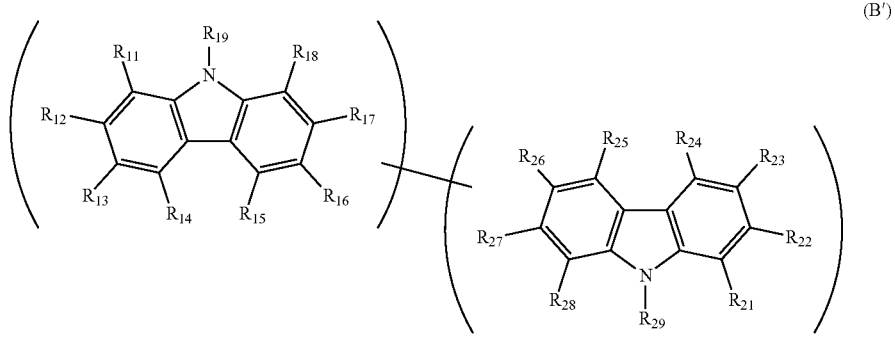

wherein in the formula, $R_{11}$ to $R_{19}$ and $R_{21}$ to $R_{29}$ are as defined in the formula (B).

18. The compound according to claim 1, wherein the $L_1$ is a substituted or unsubstituted arylene group including 6 to 30 ring carbon atoms.

19. The compound according to claim 1, wherein the $L_1$ is a phenylene group, a biphenylene group or a naphthylene group.

20. The compound according to claim 1, wherein the $L_1$ is m-phenylene.

21. The compound according to claim 1, wherein the substituents represented by the Ra, $R_1$ to $R_6$, $R_{11}$ to $R_{19}$ and $R_{21}$ to $R_{29}$ are independently a group selected from the group consisting of a substituted or unsubstituted alkyl group including 1 to 50 carbon atoms, a substituted or unsubstituted cycloalkyl group including 3 to 50 ring carbon atoms, a substituted or unsubstituted aryl group including 6 to 60 ring carbon atoms, a substituted or unsubstituted aralkyl group including 7 to 51 carbon atoms, an amino group, a mono- or di-substituted amino group having a substituent selected from a substituted or unsubstituted alkyl group including 1 to 50 carbon atoms and a substituted or unsubstituted aryl group including 6 to 60 ring carbon atoms, a substituted or unsubstituted alkoxy group including 1 to 50 carbon atoms, a substituted or unsubstituted aryloxy group including 6 to 50 ring carbon atoms, a mono-, di- or tri-substituted silyl group having a substituent selected from a substituted or unsubstituted alkyl group including 1 to 50 carbon atoms and a substituted or unsubstituted aryl group including 6 to 60 ring carbon atoms, a substituted or unsubstituted heteroaryl group including 5 to 60 ring atoms, a substituted or unsubstituted haloalkyl group including 1 to 50 carbon atoms, a halogen atom, a cyano group, a nitro group, a sulfonyl group having a substituent selected from a substituted or unsubstituted alkyl group including 1 to 50 carbon atoms and a substituted or unsubstituted aryl group including 6 to 60 ring carbon atoms, a di-substituted phosphoryl group having a substituent selected from a substituted or unsubstituted alkyl group including 1 to 50 carbon atoms and a substituted or unsubstituted aryl group including 6 to 60 ring carbon atoms, an alkylsulfonyloxy group, an arylsulfonyloxy group, an alkylcarbonyloxy group, an arylcarbonyloxy group, a boron-containing group, a zinc-containing group, a tin-containing group, a silicon-containing group, a magnesium-containing group, a lithium-containing group, a hydroxy group, an alkyl-substituted carbonyl group, an aryl-substituted carbonyl group, a carboxyl group, a vinyl group, a (meth)acryloyl group, an epoxy group and an oxetanyl group.

22. The compound according to claim 21, wherein the substituent is a substituted or unsubstituted aryl group or a substituted or unsubstituted heteroaryl group, wherein
the aryl group is an aryl group selected from the group consisting of a phenyl group, a naphthyl group, a naphthylphenyl group, a biphenylyl group, a terphenylyl group, an acenaphthylenyl group, an anthryl group, a benzoanthryl group, an aceanthryl group, a phenanthryl group, a benzophenanthryl group, a phenalenyl group, a fluorenyl group, a 9,9'-spirobifluorenyl group, a benzofluorenyl group, a dibenzofluorenyl group, a picenyl group, a pentaphenyl group, a pentacenyl group, a pyrenyl group, a chrysenyl group, a benzochrysenyl group, an s-indacenyl group, an as-indacenyl group, a fluoranthenyl group, a benzofluoranthenyl group, a tetracenyl group, a triphenylenyl group, a benzotriphenylenyl group, a perylenyl group, a coronyl group and a dibenzoanthryl group; and
the heteroaryl group is a heteroaryl group selected from the group consisting of a pyrrolyl group, a furyl group, a thienyl group, a pyridyl group, a pyridazinyl group, a pyrimidinyl group, a pyrazinyl group, a triazinyl group, an imidazolyl group, an oxazolyl group, a thiazolyl group, a pyrazolyl group, an isoxazolyl group, an isothiazolyl group, an oxadiazolyl group, a thiadiazolyl group, a triazolyl group, a tetrazolyl group, an indolyl group, an isoindolyl group, a benzofuranyl group, an isobenzofuranyl group, a benzothiophenyl group, an isobenzothiophenyl group, an indolizinyl group, a quinolizinyl group, a quinolyl group, an isoquinolyl group, a cinnolyl group, a phthalazinyl group, a quinazolinyl group, a quinoxalinyl group, a benzimidazolyl group, a benzoxazolyl group, a benzothiazolyl group, an indazolyl group, a benzisoxazolyl group, a benzisothiazolyl group, a dibenzofuranyl group, a dibenzothiophenyl group, a carbazolyl group, a phenanthridinyl group, an acridinyl group, a phenanthrolinyl group, a phenazinyl group, a phenothiazinyl group, a phenoxazinyl group, an azatriphenylenyl group, a diazatriphenylenyl group, a xanthenyl group, an azacarbazolyl group, an azadibenzofuranyl group, an azadibenzothiophenyl group, a benzofuranobenzothiophenyl group, a benzothienobenzothiophenyl group, a dibenzofuranonaphthyl group, a dibenzothienonaphthyl group and a dinaphthothienothiophenyl group.

23. The compound according to claim 1, wherein a substituent represented by the Ra is a substituted or unsubstituted aryl group, and
the aryl group is an aryl group selected from the group consisting of a phenyl group, a naphthyl group, a naphthylphenyl group, a biphenylyl group, a terphenylyl group, an acenaphthylenyl group, an anthryl group, a benzoanthryl group, an aceanthryl group, a phenanthryl group, a benzophenanthryl group, a phenalenyl group, a fluorenyl group, a 9,9'-spirobifluorenyl group, a benzofluorenyl group, a dibenzofluorenyl group, a picenyl group, a pentaphenyl group, a pentacenyl group, a pyrenyl group, a chrysenyl group, a benzochrysenyl group, an s-indacenyl group, an as-indacenyl group, a fluoranthenyl group, a benzofluoranthenyl group, a tetracenyl group, a triphenylenyl group, a benzotriphenylenyl group, a perylenyl group, a coronyl group and a dibenzoanthryl group.

24. An organic electroluminescence device that comprises an anode and a cathode and one or more organic thin film layers including an emitting layer between the anode and the cathode, wherein at least one of the organic thin film layers comprises the compound according to claim 1.

25. The organic electroluminescence device according to claim 24, wherein the emitting layer comprises the compound.

26. The organic electroluminescence device according to claim 24, wherein the emitting layer comprises a phosphorescent emitting material.

27. The organic electroluminescence device according to claim 26, wherein the phosphorescent emitting material is an ortho-metalated complex of a metal atom selected from iridium (Ir), osmium (Os) and platinum (Pt).

28. The organic electroluminescent device according to claim 27, wherein the phosphorescent emitting material is a complex represented by the following formula (X) or (Y):

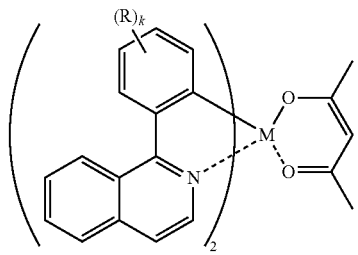

(X)

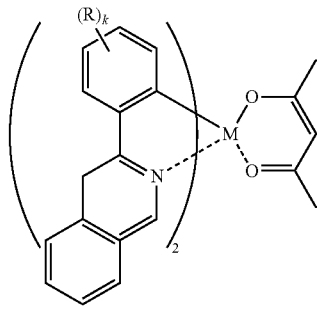

(Y)

wherein in the formulas (X) and (Y), R is a hydrogen atom or a substituent, k is an integer of 1 to 4, and M is Ir, Os or Pt.

29. An electronic apparatus that is provided with the organic electroluminescence device according to claim 24.